(12) United States Patent
Arbit et al.

(10) Patent No.: US 7,429,564 B2
(45) Date of Patent: *Sep. 30, 2008

(54) ORAL INSULIN THERAPY

(75) Inventors: Ehud Arbit, Tarrytown, NY (US); Richat Abbas, Audubon, PA (US); Michael Goldberg, Tarrytown, NY (US); T. Cooper Woods, New York, NY (US); Steven Dinh, Tarrytown, NY (US); Vivien Wong, Scarsdale, NY (US)

(73) Assignee: Emisphere Technologies, Inc., Cedar Knolls, NJ (US)

( * ) Notice: Subject to any disclaimer, the term of this patent is extended or adjusted under 35 U.S.C. 154(b) by 344 days.

This patent is subject to a terminal disclaimer.

(21) Appl. No.: 10/500,822

(22) PCT Filed: Jan. 7, 2003

(86) PCT No.: PCT/US03/00337

§ 371 (c)(1),
(2), (4) Date: Mar. 14, 2005

(87) PCT Pub. No.: WO03/057170

PCT Pub. Date: Jul. 17, 2003

(65) Prior Publication Data

US 2006/0234913 A1 Oct. 19, 2006

Related U.S. Application Data

(60) Provisional application No. 60/389,364, filed on Jun. 17, 2002, provisional application No. 60/374,979, filed on Apr. 23, 2002, provisional application No. 60/368,617, filed on Mar. 29, 2002, provisional application No. 60/347,312, filed on Jan. 9, 2002, provisional application No. 60/346,746, filed on Jan. 7, 2002.

(51) Int. Cl.
*A61K 38/28* (2006.01)
(52) U.S. Cl. ........................................ 514/4
(58) Field of Classification Search ........... None
See application file for complete search history.

(56) References Cited

U.S. PATENT DOCUMENTS

| 4,849,227 | A | 7/1989 | Cho |
| 5,698,515 | A | 12/1997 | Plate et al. |
| 6,399,090 | B1 | 6/2002 | Shehadeh |
| 6,540,982 | B1 | 4/2003 | Adjei et al. |
| 6,610,649 | B2 | 8/2003 | Wahren et al. |
| 7,060,675 | B2 | 6/2006 | Ekwuribe et al. |
| 7,084,114 | B2 | 8/2006 | Ekwuribe et al. |
| 7,115,663 | B2 | 10/2006 | Moye-Sherman et al. |
| 7,118,762 | B2 | 10/2006 | Byrd |
| 7,137,951 | B2 | 11/2006 | Pilarski |
| 2001/0056063 | A1* | 12/2001 | Weiner et al. .......... 514/3 |
| 2002/0003179 | A1 | 1/2002 | Verhoff et al. |
| 2002/0147135 | A1 | 10/2002 | Schnell |

FOREIGN PATENT DOCUMENTS

WO WO 02/02509 * 1/2002

OTHER PUBLICATIONS

Miller J. L., "Bedtime Insulin Added to Daytime Sulfonylureas Improves Glycemic Control in Uncontrolled Type II Diabetes", Clinical Pharmacology and Theraputics, vol. 53, No. 3., pp. 380-384, Mar. 1993.

Mesiha Mounir S., "Oral Absorption of Insulin Encapsulated in Artificial Chyles of Bile Salt, Palmitic Acid and α-Tocopherol Dispersions", International Journal of Pharmaceutics, vol. 249, No. 1-2, pp. 1-5, 2002.

Hosny Ehab A., "Oral Delivery of Insulin from Enteric-coated Capsules Containing Sodium Salicylate: Effect on Relative Hypoglycemia of Diabetic Beagle Dogs", International Journal of Pharmaceutics, vol. 237, No. 1-2, pp. 71-76, 2002.

Yki-Jarvinen H., "Comparison of Bedtime Insulin Regimens in Patients with Type II Diabetes Mellitus. A randomized, controlled trial.", Annals of Internal Medicine, vol. 130, No. 5, pp. 389-396, Mar. 2, 1999.

Clement Stephen, "Oral Insulin Product Hexyl-Insulin Monoconjugate 2 (HIM2) in Type 1 Diabetes Mellitus: The Glucose Stabilization Effects of HIM2", Diabetes Technology & Therapeutics, V. 4, No. 4, pp. 459-466, Aug. 2002.

* cited by examiner

*Primary Examiner*—Cecilia Tsang
*Assistant Examiner*—Christina Marchetti Bradley
(74) *Attorney, Agent, or Firm*—Pearl Cohen Zedek Latzer, LLP

(57) ABSTRACT

Pharmaceutical dosage forms for oral administration to a patient for the treatment of diabetes, comprising insulin and a delivery agent that facilitates insulin transport in a therapeutically effective amount to the bloodstream and that result in a lower incidence of vascular diseases associated with the repeated administration of insulin are disclosed. Also disclosed is a method of attenuating the undesirable incidence of diseases associated with chronic dosing of insulin is provided whereby the oral administration to a patient of insulin along with a suitable delivery agent that facilitates the absorption of insulin from the gastrointestinal tract of the patient in a therapeutically effective amount, for treatment of diabetes.

68 Claims, 25 Drawing Sheets

ORAL INSULIN THERAPY

FIELD OF THE INVENTION

This invention relates to the oral delivery of therapeutic proteins in a therapeutically effective amount to the bloodstream. This invention further relates to oral administration of proteins as active agents as part of a therapeutic regimen. This invention further relates to the oral administration of insulin in a therapeutically effective amount for the treatment of diabetes. This invention further relates to compositions of a delivery agent and insulin for oral administration that facilitates insulin transport in a therapeutically effective amount to the bloodstream for the treatment of diabetes. This invention further provides methods for the preparation of a composition comprising insulin for oral administration.

The present invention further relates to methods for reducing adverse effects on the vascular system that are associated with insulin therapy. More specifically, the present invention relates to methods that reduce the incidence of diseases associated with systemic hyperinsulinemia. The present invention is also directed to oral pharmaceutical dosage forms that are administrable on a chronic basis to diabetics, in part to achieve such results.

BACKGROUND OF THE INVENTION

Proteins, carbohydrates and other biological molecules ("biological macromolecules") are finding increasing use in many diverse areas of science and technology. For example, proteins are employed as active agents in the fields of pharmaceuticals, vaccines and veterinary products. Unfortunately, the use of biological macromolecules as active agents in pharmaceutical compositions is often severely limited by the presence of natural barriers of passage to the location where the active agent is required. Such barriers include the skin, lipid bi-layers, mucosal membranes, severe pH conditions and digestive enzymes.

Oral delivery of active agents is a particularly desirable route of administration, because of safety and convenience considerations and because oral delivery replicates the physiologic mode of insulin delivery. In addition, oral delivery provides for more accurate dosing than multidose vials and can minimize or eliminate the discomfort that often attends repeated hypodermic injections.

There are many obstacles to successful oral delivery of biological macromolecules. For example, biological macromolecules are large and are amphipathic in nature. More importantly, the active conformation of many biological macromolecules may be sensitive to a variety of environmental factors, such as temperature, oxidizing agents, pH, freezing, shaking and shear stress. In planning oral delivery systems comprising biological macromolecules as an active agent for drug development, these complex structural and stability factors must be considered.

In addition, in general, for medical and therapeutic applications, where a biological macromolecule is being administered to a patient and is expected to perform its natural biological function, delivery vehicles must be able to release active molecules, at a rate that is consistent with the needs of the particular patient or the disease process.

One specific biological macromolecule, the hormone insulin, contributes to the normal regulation of blood glucose levels through its release by the pancreas, more specifically by the B-cells of a major type of pancreatic tissue (the islets of Langerhans). Insulin secretion is a regulated process which, in normal subjects, provides stable concentrations of glucose in blood during both fasting and feeding. Diabetes is a disease state in which the pancreas does not release insulin at levels capable of controlling glucose levels. Diabetes is classified into two types. The first type is diabetes that is insulin dependent and usually appears in young people. The islet cells of the pancreas stop producing insulin mainly due to autoimmune destruction and the patient must inject himself with the missing hormone. These Type 1 diabetic patients are the minority of total diabetic patients (up to 10% of the entire diabetic population). The second type of diabetes (type 2) is non-insulin dependent diabetes, which is caused by a combination of insulin resistance and insufficient insulin secretion. This is the most common type of diabetes in the Western world. Close to 8% of the adult population of various countries around the world, including the United States, have Type 2 diabetes, and about 30% of these patients will need to use insulin at some point during their life span due to secondary pancreas exhaustion.

Diabetes is the sixth leading cause of death in the United States and accounted for more than 193,000 deaths in 1997. However, this is an underestimate because diabetes contributes to substantially many deaths that are ultimately ascribed to other causes, such as cardiovascular disease. Complications resulting from diabetes are a major cause of morbidity in the population. For example, diabetic retinopathy is the leading cause of blindness in adults aged 20 through 74 years, and diabetic kidney disease accounts for 40% of all new cases of end-stage renal disease. Diabetes is the leading cause for amputation of limbs in the United States. Heart disease and strokes occur two to four times more frequently in adults with diabetes than in adult non-diabetics. Diabetes causes special problems during pregnancy, and the rate of congenital malformations can be five times higher in the children of women with diabetes.

The main cause of mortality with Diabetes Mellitus is long term micro- and macro-vascular disease. Cardiovascular disease is responsible for up to 80% of the deaths of Type II diabetic patients. See, for example, Kirpichnikov et al., *Trends Endocrinol Metab* 12, 225-30 (2001); Garcia et al., *Diabetes* 23, 105-11 (1974); Haffner et al., *N Engl J Med* 339, 229-34 (1998); Sowers, *Arch Intert Med* 158, 617-21 (1998); Khaw, K. T. et al., *Bmj* 322, 15-8 (2001). Diabetics have a two- to four-fold increase in the risk of coronary artery disease, equal that of patients who have survived a stroke or myocardial infarction. See, for example, Haffner et al., *N Engl J Med* 339, 229-34 (1998); Sowers, *Arch Intern Med* 158, 617-21(1998). This increased risk of coronary artery disease combined with an increase in hypertensive cardiomyopathy manifests itself in an increase in the risk of congestive heart failure. Stratton et al., *Bmj* 321, 405-12 (2000); Shindler, D. M. et al., *Am J Cardiol* 77, 1017-20 (1996). These vascular complications lead to neuropathies, retinopathies and peripheral vascular disease. See Kirpichnikov et al., *Trends Endocrinol Metab* 12, 225-30 (2001). There is a need for diabetes treatments that will decrease the prevalence of such vascular disease in diabetes patients.

The beneficial effects of tight glycemic control on the chronic complications of diabetes are widely accepted in clinical practice. However, only recently it has been firmly established that elevated blood glucose levels are a direct cause of long-term complications of diabetes. The Diabetes Control and Complications Trial (DCCT) and the United Kingdom Prospective Diabetes Study (UKPDS) both showed that control of blood glucose at levels as close to normal as possible prevents and retards development of diabetic retinopathy, nephropathy, neuropathy, and microvascular disease. Drug therapy of diabetes type II has consisted of oral antidiabetic agents and insulin if and when the oral agents fail. Insulin therapy in type I diabetes is essential and is intended to replace the absent endogenous insulin with an exogenous insulin supply. Because insulin is a protein drug (MW approx. 6000 Da) that is not absorbed in the gastrointestinal tract, it ordinarily C requires parenteral administration such as by subcutaneous injection.

The problem of providing bioavailable unmodified human insulin, in a useful form, to the ever increasing population of diabetics has occupied physicians and scientists for almost 100 years. Many attempts have been made to solve some of the problems of stability and biological delivery of this small protein. Most diabetic patients self-administer insulin by daily subcutaneous injections. However, the limitations of multiple daily injections, such as inconvenience, poor patient acceptability, compliance and the difficulty of matching postprandial insulin availability to postprandial requirements, are some of the better known shortcomings of insulin therapy.

Despite studies demonstrating the beneficial effects of tight glycemic control on chronic complications of diabetes, clinicians are not particularly keen on aggressive insulin therapy, particularly in the early stages of the disease, and this is widely accepted in clinical practice. The unmet challenge of achieving tight glycemic control is due, in part, to the shortcomings of the available subcutaneous route of insulin administration and the fear of hypoglycemia. In addition to the practical limitations of multiple daily injections discussed above, the shortcomings of the commonly available subcutaneous route of insulin administration have resulted in the generally inadequate glycemic control associated with many of the chronic complications associated with diabetes. Elevated systemic levels of insulin lead to increased glucose uptake, glycogen synthesis, glycolysis, fatty acid synthesis and triacylglycerol synthesis, leading to the expression of key genes that result in greater utilization of glucose.

In the field of insulin delivery, where multiple repeated administrations are required on a daily basis throughout the patient's life, it would be desirable to create compositions of insulin that maintain protein tertiary structure so as not to alter physiological clinical activity and stability and do not require injections. It would also be desirable to provide compositions of insulin that could be orally administrable, e.g., absorbed from the gastrointestinal tract in adequate concentrations, such that insulin is bioavailable and bioactive after oral administration. Oral absorption allows delivery directly to the portal circulation.

A method of providing insulin without the need for injections has been a goal in drug delivery. Insulin absorption in the gastrointestinal tract is prevented by its large size and enzymatic degradation. It would be desirable to create an oral pharmaceutical formulation of a drug such as insulin (which is not normally orally administrable due to, e.g., insufficient absorption from the gastrointestintal tract), which formulation would provide sufficient absorption and pharmacokinetic/pharmacodynamic properties to provide the desired therapeutic effect.

Insulin exemplifies the problems confronted in the art in designing an effective oral drug delivery system for biological macromolecules. The medicinal properties of insulin can be readily altered using any number of techniques, but its physicochemical properties and susceptibility to enzymatic digestion have precluded the design of a commercially viable oral or alternate delivery system.

Accordingly, there is a need for a method of administering insulin to patients in need of insulin wherein those patients are not subject to systemic hyperinsulinema, which by itself can increase the risk of vascular disease (that is normally associated with such chronic insulin treatments, as discussed above). In other words, it is desirable to provide compositions and methods for treating diabetes without the drawbacks of systemic hyperglycemia to decrease the incidence of vascular complications and other detrimental effects.

SUMMARY OF THE INVENTION

It is one object of the present invention to provide useful oral pharmaceutical formulations of drugs that are not considered orally administrable due, e.g., to insufficient absorption of the drugs from the gastrointestinal tract, which formulations are therapeutically effective.

It is a further object of the present invention to provide useful pharmaceutical formulations of insulin for oral administration which are therapeutically effective.

It is a further object of the present invention to provide delivery agents that may be orally administered together with a drug that is not considered orally administrable due to, e.g., insufficient absorption of the drug from the gastrointestinal tract, so that the drug is absorbed in adequate amounts from the gastrointestinal tract to provide the desired therapeutic effect, such as insulin.

It is an object of the present invention to provide compositions comprising a delivery agent and insulin for oral administration.

It is an object of the present invention to provide compositions of a delivery agent and insulin for oral administration that facilitates insulin transport in a therapeutically effective amount to the bloodstream for the treatment of diabetes, for the treatment of impaired glucose tolerance, for the purpose of achieving glucose homeostasis, for the treatment of early stage diabetes, for the treatment of late stage diabetes, and/or to serve as replacement for type I diabetic patients.

It is an object of the present invention to provide methods for the preparation of a composition comprising insulin and delivery agent for oral administration, which result in an orally administrable unit dose that provides a desired therapeutic effect.

It is an object of the present invention to provide a delivery agent(s) that can be utilized in an amount that facilitates the preparation of an oral unit dosage form of a drug that is not considered orally administrable by itself due to poor absorption, etc., and results in an orally administrable unit dose that provides a desired therapeutic effect.

It is an object of the invention to reduce the risk of disease states associated with chronic systemic hyperinsulinemia of conventional insulin therapy.

It is another object of the invention to provide a method for reducing the incidence in vascular diseases associated with chronic systemic hyperinsulinemia caused by parenteral insulin therapy in diabetics.

It is another object of the invention to delay the time to onset of vascular diseases associated with chronic systemic hyperinsulinemia caused by parenteral insulin therapy in diabetics.

It is another object of the invention to reduce the severity of vascular diseases associated with chronic systemic hyperinsulinemia caused by parenteral insulin therapy in diabetics.

It is another object of the invention to reduce the exposure of the non-portal vasculature to hyperinsulinemic conditions.

It is another object of the invention to attenuate the complex series of systemic processes resulting from the reaction to insulin treatment.

It is a further object of the invention to provide a method and a pharmaceutical formulation which can reduce systemic blood insulin concentrations while providing therapeutically effective treatment of diabetes.

It is a further object of the invention to provide a method and a pharmaceutical formulation which may help decrease the instances and severity of the vascular complications and resultant conditions (such as, e.g., retinopathy, neuropathy, nephropathy) associated with Diabetes Mellitus.

It is a further object of the invention to lower the exposure of the systemic vasculature to insulin during insulin treatment.

It is a further object of the invention to reduce the incidence and/or severity of macro- and micro-vascular complications associated with insulin therapy in diabetics, which leads to neuropathies, retinopathies, peripheral vascular disease, cardiac complications and cerebrovascular complications.

In accordance with the above objects and others, the invention is directed in part to an oral solid dosage form comprising a dose of unmodified insulin that achieves a reduction in blood glucose concentration in human diabetic patients comparable to a subcutaneous insulin injection in those patients, while providing a lower (e.g., 20% or greater) totals dose of insulin in the peripheral blood circulation under acute, sub-acute and chronic conditions as compared to the peripheral blood insulin concentration obtained via the subcutaneous injection.

The invention is also directed in part to an oral solid dosage form comprising a dose of unmodified insulin that achieves a therapeutically effective reduction in blood glucose after oral administration to a human diabetic patient, and which maintains a physiological (portal/peripheral) gradient, and in certain embodiments provides a ratio of portal vein insulin concentration to peripheral blood insulin concentration from about 2.5:1 to about 6:1, and preferably from about 4:1 to about 5:1.

The invention is further directed in part to an oral dosage form comprising a dose of unmodified insulin that achieves a therapeutically effective reduction in blood glucose after oral administration to human diabetic patients, the oral solid dosage form providing an insulin $t_{max}$ at a time point from about 0.25 to about 1.5 hours after oral administration to said patients, at least about 80% of the blood glucose concentration reduction caused by said dose of insulin occurring within about 2 hours after oral administration of said dosage form.

The invention is further directed in part to an oral dosage form comprising a therapeutically effective amount of unmodified insulin, said dosage form upon pre-prandial oral administration to human diabetic patients causing the post prandial mean plasma glucose concentration in said patients to be reduced for the first hour after oral administration relative to a mean baseline (fasted) plasma glucose concentration (in the absence of sufficient insulin) in said patients.

The invention is further directed in part to an oral dosage form comprising a therapeutically effective amount of unmodified insulin, said oral dosage form upon pre-prandial oral administration provides a mean plasma glucose concentration which does not vary by more than about 40% (and more preferably not more than 30%) for the first hour after oral administration, relative to a mean baseline (fasted) plasma glucose concentration in said patients, where a meal is eaten by said patients within about one half hour of oral administration of said dosage form.

In preferred embodiments of the oral dosage forms of the invention described above, the oral dosage form is solid, and is preferably provided incorporated within a gelatin capsule or is contained in a tablet.

In certain preferred embodiments, the dose of unmodified insulin contained in the dosage form is from about 50 Units to about 600 Units (from about 2 to about 23 mg), preferably from about 100 Units (3.8 mg) to about 450 Units (15.3 mg) insulin, and most preferably from about 150 Units (5.75 mg) to about 300 Units (11.5 mg), based on the accepted conversion of factor of 26.11 Units per mg.

In certain preferred embodiments, the dosage forms of the invention provide a tram for insulin at about 0.1 to about 1.5 hours, and more preferably by about 0.25 to about 0.5 hours, after oral administration. In certain preferred embodiments, the $t_{max}$ for insulin occurs at less than about 100 minutes after oral administration of the composition, preferably at less than about 45 minutes, more preferably at less than about 40 minutes, and still more preferably at about 22 minutes after oral administration of the composition. In certain preferred embodiments, the composition provides a $t_{max}$ for glucose reduction at about 0.25 to about 1.5 hours, more preferably by about 0.75 to about 1.0 hours, after oral administration. In certain preferred embodiments, the $t_{max}$ for glucose reduction occurs preferably at less than about 120 minutes, more preferably at less than about 80 minutes, and most preferably at about 45 minutes, after oral administration of the composition.

In certain preferred embodiments of the invention, the dosage forms begin delivering insulin into the portal circulation (via absorption through the mucosa of the stomach) to achieve peak levels within about 30 minutes or less.

In certain embodiments of the dosage forms described above, in the absence of a delivery agent, the dose of unmodified insulin is not adequately absorbed from the gastrointestinal tract when administered orally to render a desired effect. In certain preferred embodiments, in the absence of a delivery agent, the dose of insulin is not sufficiently absorbed when orally administered to a human patient to provide a desirable therapeutic effect but said dose provides a desirable therapeutic effect when administered to said patient by another route of adminstration. The invention in such embodiments is further directed to an oral dosage form comprising a dose of unmodified insulin together with a pharmaceutically acceptable delivery agent in an amount effective to facilitate the absorption of said insulin, such that a therapeutically effective amount of said dose of insulin is absorbed from the gastrointestinal tract of human diabetic patients.

In certain preferred embodiments, the pharmaceutical composition comprises from about 1 mg to about 800 mg of said delivery agent, preferably about 50 to about 600, more preferably from about 100 to about 400, most preferably about 200. In certain embodiments, the composition provides a peak plasma delivery agent concentration $C_{max}$ from about 1,000 and about 150,000 ng/ml, and a $t_{max}$ at about 0.25 to about 1.5 hours, and more preferably by about 0.25 to about 0.75 hours, most preferably 0.5 hours, after oral administration.

For purposes of the present invention, a preferred delivery agent is identified via chemical nomenclature as 4-[(4-chloro, 2-hydroxybenzoyl)amino]butanoic acid. In certain preferred embodiments, the delivery agent is a sodium salt, preferably monosodium salt. Alternatively, the same compound is identified by the alternative nomenclature monosodium N-(4-chlorosalicyloyl)-4-aminobutyrate, or by the short name "4-CNAB".

The invention is further directed in part to a method of treatment of diabetes in humans, comprising administering one or more unit doses of the dosage forms described above and in further sections of the present specification.

The invention is further directed in part to a method of treatment of impaired glucose tolerance, achieving glucose homeostasis, early stage diabetes, and late stage diabetes in humans, comprising administering one or more unit doses of the dosage forms described above and in further sections of the present specification on a chronic basis.

The invention is also related to a method of orally treating mammals with an active agent (i.e., insulin) that is not sufficiently absorbed when orally administered to provide a desirable therapeutic effect but that provides a desirable therapeutic effect when administered by another route of adminstration, comprising orally administering said active agent together with a delivery agent which facilitates the absorption of insulin from the gastrointestinal tract, having one or more of the further characteristics set forth above.

The invention is further directed to a method of providing a therapeutically effective orally administrable unit dose of unmodified insulin, comprising combining from about 2 to about 23 mg of unmodified insulin with from about 100 to about 600 mg of a pharmaceutically acceptable delivery agent which facilitates absorption of said insulin from the gastrointestinal tract of human diabetic patients, and orally administering said unit dose to a human diabetic patient to provide a therapeutic effect. In preferred embodiments, the total weight of the unit dose is from about 102 mg to about 800 mg.

The present invention is also directed in part to a method of treating human diabetic patients comprising orally administering to human diabetic patients on a chronic basis an oral insulin treatment comprising a dose of unmodified insulin together with a delivery agent that facilitates the absorption of the dose of insulin from the gastrointestinal tract to provide a therapeutically effective reduction in blood glucose and a blood plasma insulin concentration that is reduced relative to the systemic blood insulin concentration of an equivalent therapeutically effective reduction in blood glucose concentration achieved by subcutaneous injection of insulin.

The invention is also directed to a method of reducing the incidence and/or severity of one or more disease states associated with chronic administration of insulin, comprising treating human diabetic patients via oral administration on a chronic basis with a therapeutically effective dose of a (preferably solid) pharmaceutical composition comprising a dose of unmodified insulin and a delivery agent that facilitates the absorption of said unmodified insulin from the gastrointestinal tract in an effective amount such that the pharmaceutical composition provides therapeutically effective control of mean blood glucose concentration and a mean systemic blood insulin concentration in diabetic patients that is reduced on a chronic basis relative to the mean systemic blood insulin concentration provided by chronic subcutaneous administration of insulin in an amount effective to achieve equivalent control of mean blood glucose concentration in a population of human diabetic patients.

The invention is further directed to a method of treating diabetes and reducing the incidence of systemic hyperinsulinemia associated with chronic dosing of insulin, comprising orally administering on a chronic basis to a diabetic patient a dose of insulin and a delivery agent that facilitates the absorption of the dose of insulin from the gastrointestinal tract to provide a therapeutically effective reduction and/or control in blood glucose and a mean systemic blood insulin concentration of the diabetic patient that is reduced relative to the mean systemic blood insulin concentration provided by subcutaneous injection of insulin in an amount effective to achieve equivalent reduction and/or control in a population of human diabetic patients.

The mean values of insulin concentration determination obtained in patients who have been administered subcutaneous insulin are well known to those skilled in the art.

The following terms will be used throughout the application as defined below:

Diabetic patient—refers to humans suffering from a form of diabetes.

IGT—means impaired glucose tolerance.

Diabetes—is deemed to encompass type 1 and type 2 diabetes, unless specifically specified otherwise.

Biological macromolecule—biological polymers such as proteins and polypeptides. For the purposes of this application, biological macromolecules are also referred to as macromolecules.

Delivery agent—refers to carrier compounds or carrier molecules that are useful in the oral delivery of therapeutic agents. "Delivery agent" may be used interchangeably with "carrier".

Therapeutically effective amount of insulin—an amount of insulin included in the oral dosage forms of the invention which are sufficient to achieve a clinically significant control of blood glucose concentrations in a human diabetic patient either in the fasting state or in the fed state effective, during the dosing interval.

Effective amount of delivery agent—an amount of the delivery agent that promotes the absorption of a therapeutically effective amount of the drug from the gastrointestinal tract.

Organic solvents—any solvent of non-aqueous origin, including liquid polymers and mixtures thereof. Organic solvents suitable for the present invention include: acetone, methyl alcohol, methyl isobutyl ketone, chloroform, 1-propanol, isopropanol, 2-propanol, acetonitrile, 1-butanol, 2-butanol, ethyl alcohol, cyclohexane, dioxane, ethyl acetate, dimethylformamide, dichloroethane, hexane, isooctane, methylene chloride, tert-butyl alchohol, toluene, carbon tetrachloride, or combinations thereof.

Peptide—a polypeptide of small to intermediate molecular weight, usually 2 or more amino acid residues and frequently but not necessarily representing a fragment of a larger protein.

Protein—a complex high polymer containing carbon, hydrogen, oxygen, nitrogen and usually sulfur and composed of chains of amino acids connected by peptide linkages. Proteins in this application refer to glycoproteins, antibodies, non-enzyme proteins, enzymes, hormones and peptides. The molecular weight range for proteins includes peptides of 1000 Daltons to glycoproteins of 600 to 1000 kiloDaltons.

Reconstitution—dissolution of compositions or compositions in an appropriate buffer or pharmaceutical composition.

Unit-Dose Forms—refers to physically discrete units suitable for human and animal subjects and packaged individually as is known in the art. It is contemplated for purposes of the present invention that dosage forms of the present invention comprising therapeutically effective amounts of insulin may include one or more unit doses (e.g., tablets, capsules) to achieve the therapeutic effect.

Unmodified insulin—means insulin prepared in any pharmaceutically acceptable manner or from any pharmaceutically acceptable source which is not conjugated with an oligomer such as that described in U.S. Pat. No. 6,309,633 and/or which not has been subjected to amphiphilic modification such as that described in U.S. Pat. Nos. 5,359,030; 5,438,040; and/or 5,681,811.

As used herein, the phrase "equivalent therapeutically effective reduction" means that a maximal reduction of blood glucose concentration achieved by a first method of insulin administration (e.g. oral administration of insulin in a patient(s)) is not more 20%, and preferably not more than 10% and even more preferably not more than 5% different from a maximal reduction of blood glucose concentration after administration by a second method (e.g., subcutaneous injection) in the same patient(s) or a different patient requiring the same reduction in blood glucose level.

The term "AUC" as used herein, means area under the plasma concentration-time curve, as calculated by the trapezoidal rule over the complete dosing interval, e.g., 24-hour interval.

The term "$C_{max}$" as it is used herein is the highest plasma concentration of the drug attained within the dosing interval.

The term "$t_{max}$" as it is used herein is the time period which elapses after administration of the dosage form at which the plasma concentration of the drug attains the $C_{max}$ within the dosing interval.

The term "multiple dose" means that the human patient has received at least two doses of the drug composition in accordance with the dosing interval for that composition.

The term "single dose" means that the human patient has received a single dose of the drug composition and the drug plasma concentration has not achieved steady state.

Unless specifically designated as "single dose" or at "steady-state" the pharmacokinetic parameters disclosed and claimed herein encompass both single dose and steady-state conditions.

The term "mean", when preceding a pharmacokinetic value (e.g., mean $t_{max}$) represents the arithmetic mean value of the pharmacokinetic value unless otherwise specified.

The term "Bioavailability" as used herein means the degree or ratio (%) to which a drug or agent is absorbed or otherwise available to the treatment site in the body. This is calculated by the formula $$Rel.\ Bioavailability(\%) = \frac{Dose\ SC}{Dose\ Oral} \times \frac{AUC_{INS}Oral}{AUC_{INS}SC} \times 100$$

The term "Biopotency" as used herein means the degree or ratio (%) to which a drug or agent is effective to the treatment site in the body. This is calculated by the formula $$Rel.\ Biopotency(\%) = \frac{Dose\ SC}{Dose\ Oral} \times \frac{AUC_{GIR}Oral}{AUC_{GIR}SC} \times 100$$

The term "$F_{rel}$" as used herein means the relative bioavailability of insulin calculated by comparing dose corrected oral insulin AUC with the dose corrected SC insulin AUC.

$K_{el}$ is the terminal elimination rate constant calculated by linear regression of the terminal linear portion of the log concentration vs. time curve The term "$AUC_{(0-x)}$" as used herein means the area under the plasma concentration-time curve using linear trapezoidal summation from time 0 to time x hours post-dose.

The term "$AUC_{(0-t)}$" as used herein means the area under the plasma concentration-time curve using linear trapezoidal summation from time zero to time t post-dose, where t is the time of the last measurable concentration ($C_t$).

The term "$AUC_{(0-inf)}$" as used herein means the area under the plasma concentration-time curve from time 0 to infinity, $AUC_{(0-inf)} = AUC_{(0-t)} + Ct/K_{el}$.

The term "$AUC_{\%\ Extrap}$" as used herein means the percentage of the total $AUC_{(0-inf)}$ obtained by extrapolation.

The term "$AUEC_{(0-x)}$" as used herein means the area under the effect-time curve calculated using the linear trapezoidal summation from time 0 to the concentration at time x hours post-dose.

The term "$AUEC_{(0-t)}$" as used herein means the area under the effect-time curve calculated using the linear trapezoidal summation from time 0 to the concentration at time t hours post-dose, where t is the time of the last measurable effect (E).

The term "$AURC_{(0-x)}$" as used herein means the area under the response-time curve calculated using the linear trapezoidal summation from time zero to the concentration at time x (Baseline Subtracted AUEC).

The term "$AURC_{(0-t)}$" as used herein means the area under the response-time curve calculated using the linear trapezoidal summation from time zero to the concentration at time t (Baseline Subtracted AUEC), where t is the time of the last measurable response (R).

The term "$C^b$" as used herein means the maximum observed plasma insulin concentration prior to intervention for hypoglycemia.

The term "CL/F" as used herein means the apparent total body clearance calculated as Dose/$AUC_{(0-inf)}$.

The term "$E^b$" as used herein means the maximum observed effect (baseline subtracted) prior to intervention for hypoglycemia.

The term "$E_{max}$" as used herein means the maximum observed effect (baseline subtracted).

The term "MRT" as used herein means the mean residence time calculated as the ratio of the Area Under the first moment of the plasma concentration-time curve (AUMC) and the area under the plasma concentration-time curve, (AUMC)/$AUC_{(0-inf)}$.

The term "$R_{max}$" as used herein means the maximum observed response (total response), i.e., minimum glucose concentration.

The term "$R^b$" as used herein means the maximum observed response (total response) prior to hypoglycemic intervention.

The term "$t^b$" as used herein means the time to reach insulin/glucose plasma concentration prior to hypoglycemic intervention.

The term "$t^c$" as used herein means the time to reach glucose concentration change from baseline prior to hypoglycemic intervention.

The term "$t_{Rmax}$" as used herein means the time to reach maximum response.

The term "$t_{Emax}$" as used herein means time of the maximum effect (obtained without interpolation).

The term "$t_{1/2}$" as used herein means the terminal half-life calculated as $\ln(2)/K_{el}$.

The term "$V_d/F$" as used herein means the apparent volume of distribution calculated as $(CL/F)/K_{el}$.

As used herein and in the appended claims, the singular forms "a," "an," and "the," include plural referents unless the context clearly indicates otherwise. Thus, for example, reference to "a molecule" includes one or more of such molecules, "a reagent" includes one or more of such different reagents, reference to "an antibody" includes one or more of such different antibodies, and reference to "the method" includes reference to equivalent steps and methods known to those of ordinary skill in the art that could be modified or substituted for the methods described herein.

Unless defined otherwise, all technical and scientific terms used herein have the same meaning as commonly understood by one of ordinary skill in the art to which the invention belongs. Although any methods, compositions, reagents, cells, similar or equivalent to those described herein can be used in the practice or testing of the invention, the preferred methods and materials are described herein. All publications mentioned herein are incorporated herein, including all figures, graphs, equations, illustrations, and drawings, to describe and disclose specific information for which the reference was cited in connection with.

The publications discussed above are provided solely for their disclosure before the filing date of the present application. Nothing herein is to be construed as an admission that the invention is not entitled to antedate such disclosure by virtue of prior invention. Throughout this description, the preferred embodiment and examples shown should be considered as exemplars, rather than as limitations on the present invention.

DETAILED DESCRIPTION

Figure 1:
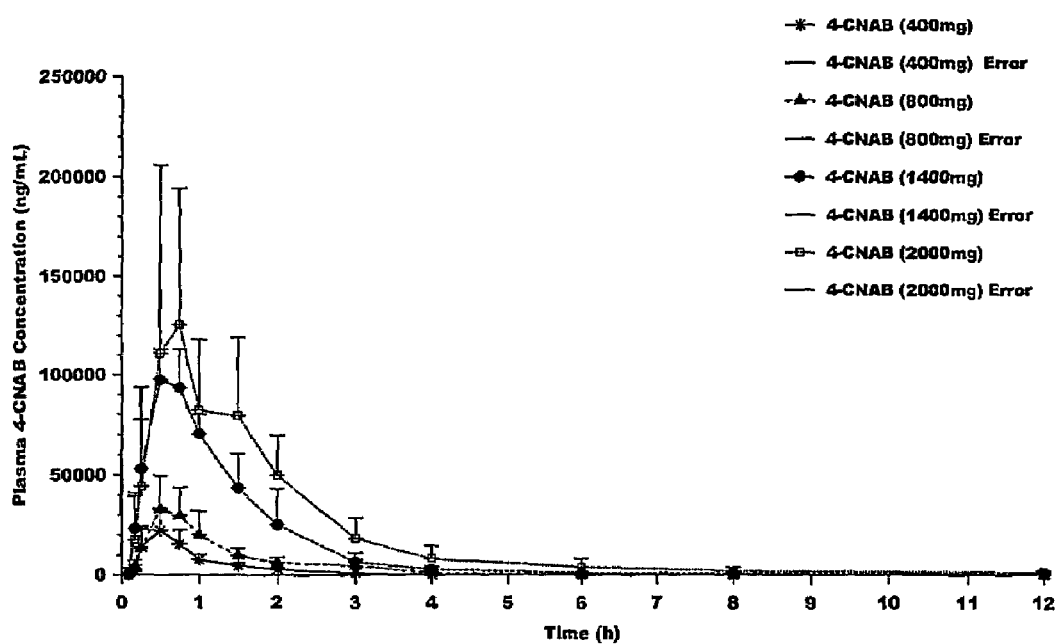
FIG. 1 shows mean (+SD) plasma concentration/time profiles of 4-CNAB following the administration of 4-CNAB alone to healthy male volunteers.

Hyperinsulinemia (elevated blood concentrations of insulin) is caused by the administration of insulin in a location (and manner) which is not consistent with the normal physiological route of delivery. In normal healthy humans, insulin is released from the pancreas into the portal vein, which transfers the insulin to the liver. The liver utilizes a large portion of the insulin which it receives from the portal circulation. Glucose is the principal stimulus to insulin secretion in humans. Glucose enters the β cell by facilitated transport, and is then phosphorylated by glucokinase. Expression of glucokinase is primarily limited to cells and tissues involved in the regulation of glucose metabolism, such as the liver and the pancreatic β cells. The capacity of sugars to undergo phosphorylation and subsequent glycolysis correlates closely with their ability to stimulate insulin release. Insulin circulates in blood as the free monomer, and its volume distribution approximates the volume of extracellular fluid. Under fasting conditions, the concentration of insulin in portal blood is, e.g., about 2-4 ng/ml, whereas the systemic (peripheral) concentration of insulin is, e.g., about 0.5 ng/ml, in normal healthy humans, translating into, e.g., a 5:1 ratio.

Insulin is administered parenterally, usually by subcutaneous injection. In human diabetics who receive insulin via subcutaneous injection, the ratio is changed to about 0.75:1. Thus, in such diabetic patients, the liver does not receive the necessary concentrations of insulin to adequately control blood glucose.

It has been an unmet goal in the art to imitate normal insulin levels in the portal and systemic circulation via oral administration of insulin. By virtue of the present invention, the ratio of portal (unmodified) insulin concentration to systemic (unmodified) insulin concentration approaches in human diabetic patients approaches that which is obtained in normal healthy humans. The chronic administration of oral dosage forms of the present invention result in a higher portal insulin concentration and lower systemic insulin concentration over time than that obtained with an equi-effective dose of insulin administered subcutaneously (i.e., which provide similar control of blood glucose levels). By virtue of the present invention, lower levels of hyperinsulinemia are obtained, e.g., systemic insulin concentrations are at least about 20% lower when compared to a comparably effective subcutaneous dose of insulin. Transient peaks in insulin levels which may occur by virtue of the oral administration of insulin in accordance with the present invention is not believed to be associated with vascular diseases.

Typically, insulin is not absorbed to any extent through the gastrointestinal tract, presumably due to its size and potential for enzymatic degradation. The present invention provides pharmaceutical compositions that are useful as delivery agents in the oral delivery of an active agent that is not generally considered by those skilled in the art to be administrable via the oral route, such as insulin. Such compositions serve to make insulin bioavailable and absorbable through the gastrointestinal mucosa when orally administered.

In normal, healthy human subjects, insulin secretion is a tightly regulated process which provides stable blood concentrations of glucose regardless of whether or not the subject has ingested a meal (i.e., fasting and fed states). Insulin is secreted by the beta cells of the islets of Langerhans of the pancreas and has three basic effects: enhanced rate of glucose metabolism; decreased blood glucose concentration; and increased glycogen stores in the tissues. Diabetes mellitus results from a dual defect of insulin resistance and "burn out" of the beta cells of the pancreas. Insulin facilitates (and increases the rate of) glucose transport through the membranes of many cells of the body, particularly skeletal muscle and adipose tissue. In very basic terms, the liver plays a key role in the metabolism of glucose as follows: in the presence of excess insulin, excess glucose, or both, the liver takes up large quantities of glucose from the blood; and in the absence of insulin or when the blood glucose concentration falls very low, the liver gives glucose back to the blood. Thus, the liver acts as a key blood glucose buffer mechanism by keeping blood glucose concentrations from rising too high or from falling too low. When evoked by the presence of glucose (e.g., after a solid meal is ingested), insulin secretion is biphasic: the first phase reaches a peak after 1 to 2 minutes and is short-lived, whereas a second phase of secretion has a delayed onset but a longer duration. Thus, secretion of insulin rises rapidly in normal human subjects as the concentration of blood glucose rises above base levels (e.g., 100 mg/100 ml of blood) and the turn-off of insulin secretion is also rapid, occurring within minutes after reduction in blood glucose concentrations back to the fasting level. The exact mechanism by which insulin release is stimulated by increased glucose levels is not fully understood, but the entry of glucose into the beta cells of the pancreas and its metabolism is required.

Insulin treatment of diabetics is typically accomplished in such a manner so as to administer enough insulin so that the patient will have normal carbohydrate metabolism. For example, the diabetic patient may administer a single dose of one of the long-acting insulins each day subcutaneously, with an action lasting about 24 hours. Additional quantities of regular insulin, with a duration of action of, e.g., 5-6 hours, may be subcutaneously administered at those times of the day when the patient's blood glucose level tends to rise too high, such as at meal times.

The oral insulin formulations of the present invention provide an advantageous result over the subcutaneously administered insulin which is currently the state of the art, beyond the benefit of ease of administration, pain-free administration, and the potential for improved patient compliance. By administration of the oral insulin formulations of the present invention, the blood levels of insulin which occur upon the first (initial) phase of insulin secretion by the pancreas can be simulated. The first phase of insulin secretion, while of short duration, has an important role in priming the liver to the metabolic events ahead (meal). Because subcutaneously administered insulin does not undergo portal circulation, this result is not possible with subcutaneously administered insulin.

Thus, in certain preferred embodiments of the present invention, the oral insulin formulations of the invention may be administered to a patient at meal time, and preferably slightly before (e.g., about 0.5 hours before) ingestion of a solid meal, such that the peak insulin levels are attained at the time of the meal. As a further advantage in certain preferred embodiments, the administration of a relatively short-acting insulin (e.g., such as the insulin used to prepare the capsules administered in the clinical studies reported in the appended Examples (human regular insulin (Humulino® R from Eli Lilly and Company)) will further result in blood insulin levels returning to baseline levels within about 4 hours (and preferably within about 3 hours or less) after oral administration of the oral insulin formulations of the present invention. By virtue, e.g., of the lowered C-peptide levels obtained via treatment of human diabetic patients with the oral insulin formulations of the invention, the oral formulations and methods of the invention may be considered to be beta cell-sparing.

The present invention provides a method of administering insulin and pharmaceutical compositions useful for administering insulin such that the insulin is bioavailable and absorbable from the gastrointestinal tract and such that the incidence of vascular diseases normally associated with chronic dosing of insulin is attenuated. The delivery agents of the invention enable insulin to be orally absorbable through the mucosa of the stomach. Following oral administration of the pharmaceutical compositions of the present invention, the delivery agent passes though the mucosal barriers of the gastrointestinal tract and is absorbed into the blood stream where it can be detected in the plasma of subjects. The level of delivery agent in the bloodstream as measured in the plasma is dose-dependent. The delivery agent facilitates the absorption of insulin administered therewith (either in the same dosage form, or simultaneously therewith), or sequentially (in either order, as long as both the delivery agent and insulin are administered within a time period which provides both in the same location, e.g., the stomach, at the same time). As disclosed below, oral administration of insulin, in particular using the delivery agents disclosed herein, effectively reduces the incidence of vascular and other disease states that are associated with traditional dosing of insulin, i.e., subcutaneously.

The preferred pharmaceutical compositions of the invention comprise a combination of insulin and a delivery agent in a suitable pharmaceutical carrier or excipient as understood by practitioners in the art. The means of delivery of the pharmaceutical composition can be, for example, a capsule, compressed tablet, pill, solution, freeze-dried powder ready for reconstitution or suspension suitable for administration to the subject.

The pharmaceutical compositions and method of the present invention provide a number of advantages in addition to convenience, acceptance and patient compliance. Insulin absorbed in the gastrointestinal tract mimics the physiology of insulin secreted by the pancreas because both are released into the portal vein and carried directly to the liver. Absorption into the portal circulation maintains a peripheral-portal insulin gradient that regulates insulin secretion. The present invention comprises pharmaceutical compositions and method for oral insulin delivery that enable achieving low blood glucose without having high levels of systemic insulin.

Preferably, the pharmaceutical composition includes insulin as the active agent. As used herein, "insulin" refers to insulin from a variety of sources. Naturally occurring insulin and structurally similar bioactive equivalents (insulin analogues including short acting and analogues with protracted action) can be used. Insulin useful in the invention can be isolated from different species of mammal. For example, animal insulin preparations extracted from bovine or porcine pancreas can be used. Insulin analogues, derivatives and bioequivalents thereof can also be used with the invention. In addition to insulin isolated from natural sources, the present invention can use insulin chemically synthesizing using protein chemistry techniques such as peptide synthesis. Analogues of insulin are also suitable for the present invention.

The insulin used in the present invention may be obtained by isolating it from natural sources or by chemically synthesizing it using peptide synthesis, or by using the techniques of molecular biology to produce recombinant insulin in bacteria or eucaryotic cells. Analogs of insulin are also provided by the present invention. Insulin from other species of mammal may also be used in the present invention. The physical form of insulin may include crystalline and/or amorphous solid forms. In addition, dissolved insulin may be used. Other suitable forms of insulin, including, but not limited to, synthetic forms of insulin, are described in U.S. Pat. Nos. 4,421,685, 5,474,978, and 5,534,488, the disclosure of each of which is hereby incorporated by reference in its entirety.

The most preferred insulin useful in the pharmaceutical compositions and methods of the present invention is human recombinant insulin. Human recombinant insulin can be prepared using genetic engineering techniques that are well known in the art. Recombinant insulin can be produced in bacteria or eucaryotic cells. Functional equivalents of human recombinant insulin are also useful in the invention. Recombinant human insulin can be obtained from a variety of commercial sources. For example, insulin (Zinc, human recombinant) can be purchased from Calbiochem (San Diego, Calif.). Alternatively, human recombinant Zinc-Insulin Crystals: Proinsulin Derived (Recombinant DNA Origin) USP Quality can be obtained from Eli Lilly and Company (Indianapolis, Ind.). All such forms of insulin, including insulin analogues (including but not limited to Insulin Lispro, Insulin Aspart, Insulin Glargine, Insulin Detemir) are deemed for the purposes of this specification and the appended claims are considered to be encompassed by the term "insulin."

The present invention provides compositions of recombinant human zinc insulin and a delivery agent as a drug for oral administration of insulin in humans.

In yet further embodiments of the invention, the active agent is not insulin but instead is an active agent of a biological nature suitable for use in the present invention including, but not limited to, proteins; polypeptides; peptides; hormones; polysaccharides, and particularly mixtures of mucopolysaccharides; carbohydrates; lipids; other organic compounds; and particularly compounds which by themselves do not pass (or which pass as only a fraction of the administered dose) through the gastrointestinal mucosa and/or are susceptible to chemical cleavage by acids and enzymes in the gastrointestinal tract; or any combination thereof. Further examples of active agents of a biological nature include, but are not limited to, the following, including synthetic, natural or recombinant sources thereof: growth hormones, including human growth hormones (hGH), recombinant human growth hormones (rhGH), bovine growth hormones, and porcine growth hormones; growth hormone-releasing hormones; interferons, including a, D and y; interleukin-1; interleukin-2; insulin, including porcine, bovine, human, and human recombinant, optionally having counter ions including sodium, zinc, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor, antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); parathyroid hormone (PTH), including its fragments; antimicrobials, including anti-fungal agents; vitamins; analogs, fragments, mimetics or polyethylene glycol (PEG)-modified derivatives of these compounds; or any combination thereof.

In one embodiment of this invention, the protein active agents have a molecular weight of less than or equal to 10,000

Daltons. In another embodiment of this invention, protein active agents have a molecular weight of about 6,000 Daltons. In another embodiment of this invention, protein active agents have a molecular weight of greater than or equal to 10,000 Daltons. According to an alternate embodiment of the present invention, protein active agents have a molecular weight that is greater than or equal to 20,000 Daltons. In a further embodiment, protein active agents have a molecular weight that is greater than or equal to 30,000 Daltons. According to an alternate embodiment, protein active agents have a molecular weight that is greater than or equal to 40,000 Daltons. According to another alternate embodiment, protein active agents have a molecular weight that is greater than or equal to 50,000 Daltons.

Insulin entry into the bloodstream produces a decrease in plasma glucose levels. Therefore, oral absorption of insulin may be verified by observing the effect on a subject's blood sugar following oral administration of the composition. In a preferred embodiment of the invention, the oral dosage forms of the invention facilitate the oral delivery of insulin, and after insulin is absorbed into the bloodstream, the composition produces a maximal decrease in blood glucose in treated patients from about 20 to about 60 minutes after oral administration. In another embodiment of the present invention, the pharmaceutical composition produces a maximal decrease in blood glucose in treated patients from about 30 to about 50 minutes post oral administration. More particularly, the pharmaceutical composition produces a maximal decrease in blood glucose in treated patients at about 40 minutes after oral administration.

The magnitude of the decrease in blood glucose produced by insulin absorbed into the bloodstream following entry into the gastrointestinal tract varies with the dose of insulin. In certain embodiments of the invention, human diabetic patients show a maximal decrease in blood glucose by at least 10% within one hour post oral administration. In another embodiment, human diabetic patients show a maximal decrease in blood glucose by at least 20% within one hour post oral administration, alternatively, at least 30% within one hour post oral administration.

Normal levels of blood glucose vary somewhat throughout the day and in relation to the time since the last meal. One goal of the present invention is to provide oral compositions of insulin that facilitate achieving close to normal levels of blood glucose throughout the 24-hour daily cycle. In a preferred embodiment of the invention, wherein the pharmaceutical composition includes insulin or an insulin analog as the active agent and a delivery agent in an amount effective to achieve a fasting blood glucose concentration from about 90 to about 110 mg/dl. In another preferred embodiment of the invention, wherein the pharmaceutical composition includes insulin or an insulin analog as the active agent and a delivery agent in an amount effective to achieve a fasting blood glucose concentration from about 95 to about 105 mg/dl, more preferably, the subject manifests fasting blood glucose concentrations at about 100 mg/dl.

In the time after a meal is consumed, blood glucose concentration rises in response to digestion and absorption into the bloodstream of carbohydrates derived from the food eaten. The present invention provides oral compositions of insulin that prevent or control very high levels of blood glucose from being reached and/or sustained. More particularly, the present invention provides compositions which facilitate achieving normal levels of blood glucose after a meal has been consumed, i.e., post-prandial. In a preferred embodiment of the invention, the pharmaceutical composition includes insulin as the active agent and a delivery agent in an amount effective to achieve a post-prandial blood glucose concentration from about 130 to about 170 mg/dl. In another preferred embodiment of the invention, the pharmaceutical composition includes insulin or an insulin analog as the active agent and a delivery agent in an amount effective to achieve a post-prandial blood glucose concentration from about 140 to about 160 mg/dl, more preferably, the subject manifests fasting blood glucose concentrations at less than about 160 mg/dl.

The present invention provides pharmaceutical compositions for oral administration which includes insulin or an insulin analog as the active agent and a delivery agent in an amount effective to achieve pre-prandial (before a meal is consumed) blood glucose concentration from about 95 to about 125 mg/dl. In a preferred embodiment, the present invention provides pharmaceutical compositions for oral administration which includes insulin or an insulin analog as the active agent and a delivery agent in an amount effective to achieve pre-prandial blood glucose concentration from about 100 to about 120 mg/dl.

The present invention provides pharmaceutical compositions for oral administration which include insulin as the active agent and a delivery agent in an amount effective to achieve blood glucose concentrations within the normal range during the evening period from about 70 to about 120 mg/dl. In a preferred embodiment, the present invention provides pharmaceutical compositions for oral administration which include insulin or an insulin analog as the active agent and a delivery agent in an amount effective to achieve blood glucose concentrations at 3 AM from about 80 to about 120 mg/dl.

In certain preferred embodiments, the methods and pharmaceutical compositions provide the pharmacokinetic parameters set forth in U.S. Provisional Applications Nos. 60/346,746 and 60/347,312, the disclosure of each of which is incorporated herein by reference.

The amount of delivery agent necessary to adequately deliver insulin into the blood stream of a subject needing the therapeutic effect of insulin can vary depending on one or more of the following; chemical structure of the particular delivery agent; the nature and extent of interaction of insulin and the delivery agent; the nature of the unit dose, i.e., solid, liquid, tablet, capsule, suspension; the concentration of delivery agent in the GI tract, the feeding state of the subject, the diet of the subject, the heath of the subject and the ratio of delivery agent to insulin.

In preferred embodiments, the oral dosage forms of the present invention comprise a mixture of insulin and a delivery agent, e.g., monosodium N-(4-chlorosalicyloyl)-4-aminobutyrate (4-CNAB), a novel compound discovered by Emisphere Technologies, Inc., or separately containing insulin and the delivery agent.

In further embodiments of the present invention, the oral dosage forms described herein are orally administered as described herein in combination with an additional therapy to treat diabetes, impaired glucose tolerance, or to achieve glucose homeostasis, said additional therapy comprising, for example, an additional drug such as sulfonylurea, a biguanide, an alpha-glucosidase, insulin delivered via a different pathway (e.g., parenteral insulin), and/or an insulin sensitizer.

In further embodiments of the invention, the oral dosage forms described herein reduce the likelihood of hypoglycemic events, mainly because of two reasons: (a) one cannot hyperinsulinize the liver, because even under hyperinsulinemia the liver uptake of glucose will be unchanged. Unlike the peripheral tissue, the liver will only cease producing endogenous insulin and not sequester additional glucose; and (b)

the short peak of insulin (e.g., as shown in the appended examples) shows that even if insulin were to reach high peripheral levels, the peak drops precipitously.

The effect of absorption of insulin is manifested in human patients treated with the pharmaceutical compositions of the present invention by observing reductions in C-peptide concentration following oral treatment. For example, in one embodiment of the invention, the pharmaceutical composition comprises insulin as the active agent and the compound 4-CNAB as a delivery agent to facilitate the oral delivery of insulin, and, after insulin is absorbed into the bloodstream, the composition produces a maximal decrease in C-peptide concentration in treated patients from about 80 and about 120 minutes post oral administration. More particularly, the composition produces a decrease in C-peptide concentration post administration, e.g., a maximal decrease in C-peptide concentration in treated patients from about 90 and about 110 minutes post oral administration.

Absorption of insulin can be detected in subjects treated with the pharmaceutical compositions of the present invention by monitoring the plasma levels of insulin after treatment. The time it takes for an active agent to reach a peak in the bloodstream ($t_{max}$) may depend on many factors such as the following: the nature of the unit dose, i.e., solid, liquid, tablet, capsule, suspension; the concentration of active agent and delivery agent in the GI tract; the feeding state of the subject; the diet of the subject; the health of the subject and the ratio of active agent to the delivery agent. In a preferred embodiment of the invention, wherein the pharmaceutical composition includes the compound 4-CNAB as the delivery agent and insulin as the active agent, the composition provides a peak plasma insulin concentration from about 0.1 to about 1 hour after oral administration. In another embodiment, the composition provides a peak plasma insulin concentration from about 0.2 to about 0.6 hours after oral administration. In a preferred embodiment, the composition provides a peak plasma insulin concentration from about 0.3 to about 0.4 hours after oral administration. In another embodiment, the composition provides a peak plasma insulin concentration within about 1 hour after oral administration. In certain preferred embodiments of the invention, the pharmaceutical composition comprises insulin as the active agent and the compound 4-CNAB as a delivery agent to facilitate the oral delivery of insulin, and after insulin is absorbed into the bloodstream, the plasma insulin levels in treated patients peak at about 20 minutes post oral administration with a second peak at about 105 minutes.

In preferred embodiments, the compositions of the present invention include an active agent (e.g., insulin) and a delivery agent that serves to render the active agent orally absorbable through the mucosa of the stomach. Accordingly, the present invention solves the problem of oral absorption of macromolecules by providing delivery agents that facilitate transport of such biomolecules through the gastrointestinal system and into the bloodstream where the active agent can perform its necessary biological role. As a result of the present invention, effective oral drug delivery methods are provided to increase the oral bioavailability and absorption of drugs that are currently administered parenterally.

In other preferred embodiments, the delivery agents used in the invention have the following structure:

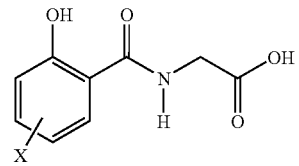

wherein X is one or more of hydrogen, halogen, hydroxyl or $C_1$-$C_3$ alkoxy, and R is substituted or unsubstituted $C_1$-$C_3$ alkylene, substituted or unsubstituted $C_1$-$C_3$ alkenylene.

In certain preferred embodiments, the delivery agents of the invention preferably have the following structure:

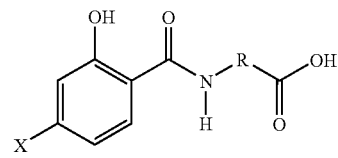

wherein X is halogen, and R is substituted or unsubstituted $C_1$-$C_3$ alkylene, substituted or unsubstituted $C_1$-$C_3$ alkenylene.

In a preferred embodiment of the present invention, the pharmaceutical composition includes a delivery agent wherein X is chlorine and R is $C_3$ alkylene. In another preferred embodiment of the present invention, the pharmaceutical composition includes the compound 4-[(4-chloro, 2-hydroxybenzoyl)amino]butanoic acid as a delivery agent for the oral delivery of insulin, preferably the monosodium salt thereof.

The delivery agents may be in the form of the carboxylic acid or salts thereof. Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

Other suitable delivery agents that can be used in the present invention include those delivery agents described U.S. Pat. Nos. 5,650,386, 5,773,647, 5,776,888, 5,804,688, 5,866,536, 5,876,710, 5,879,681, 5,939,381, 5,955,503, 5,965,121, 5,989,539, 5,990,166, 6,001,347, 6,051,561, 6,060,513, 6,090,958, 6,100,298, 5,766,633, 5,643,957, 5,863,944, 6,071,510 and 6,358,504, the disclosure of each of which is incorporated herein by reference. Additional suitable delivery agents are also described in International Publications Nos. WO 01/34114, WO 01/21073, WO 01/41985, WO 01/32130, WO 01/32596, WO 01/44199, WO 01/51454, WO 01/25704, WO 01/25679, WO 00/50386, WO 02/02509, WO 00/47188, WO 00/07979, WO 00/06534, WO 98/25589, WO 02/19969, WO 00/59863, WO 95/28838, WO 02/20466 and WO 02/19969, and International Patent Applications Nos. PCT/US02/06610 and PCT/US02/06295, the disclosure of each of which is incorporated herein by reference.

Salts of the delivery agent compounds of the present invention may be prepared by methods known in the art. For example, sodium salts may be prepared by dissolving the delivery agent compound in ethanol and adding aqueous sodium hydroxide.

The compounds described herein may be derived from amino acids and can be readily prepared from amino acids by methods known by those with skill in the art based upon the present disclosure and the methods described in International Publications Nos. WO 96/30036, WO 97/36480, WO 98/34632 and WO 00/07979, and in U.S. Pat. Nos. 5,643,957 and 5,650,386, the disclosure of each of which is incorporated herein by reference. For example, the compounds may be prepared by reacting the single amino acid with the appropriate acylating or amine-modifying agent, which reacts with a free amino moiety present in the amino acid to form amides. Protecting groups may be used to avoid unwanted side reactions as would be known to those skilled in the art.

The delivery agents may also be prepared by the methods of International Patent Application No. PCT/US01/21073, the disclosure of which is incorporated herein by reference.

The delivery agents may also be prepared by alkylation of the appropriate salicylamide according to the methods of International Publication No. WO 00/46182, the disclosure of which is incorporated herein by reference. The salicylamide may be prepared from salicylic acid via the ester by reaction with sulfuric acid and ammonia.

In addition, poly amino acids and peptides comprising one or more of these compounds may be used. An amino acid is any carboxylic acid having at least one free amine group and includes naturally occurring and synthetic amino acids. Poly amino acids are either peptides (which are two or more amino acids joined by a peptide bond) or are two or more amino acids linked by a bond formed by other groups which can be linked by, e.g., an ester or an anhydride linkage. Peptides can vary in length from dipeptides with two amino acids to polypeptides with several hundred amino acids.

The delivery agent compound may be purified by recrystallization or by fractionation on one or more solid chromatographic supports, alone or linked in tandem. Suitable recrystallization solvent systems include, but are not limited to, ethanol, water, heptane, ethyl acetate, acetonitrile, methanol and tetrahydrofuran and mixtures thereof. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Following oral administration of the pharmaceutical compositions of the present invention, the delivery agent passes though the mucosal barriers of the GI tract and is absorbed into the blood stream where it can be detected in the plasma of subjects. The level of delivery agent in the bloodstream as measured in the plasma is dose-dependent. The delivery agent facilitates the absorption of the drug (active agent) administered therewith (either in the same dosage form, or simultaneously therewith), or sequentially (in either order, as long as both the delivery agent and the drug are administered within a time period which provides both in the same location, e.g., the stomach, at the same time).

In certain preferred embodiments of the invention, a peak plasma concentration ($C_{max}$) of the delivery agent achieved after oral administration is preferably from about 10 to about 250,000 ng/ml, after oral administration, preferably from about 100 to about 125,000, and preferably the peak plasma concentration of the delivery agent is from about 1,000 to about 50,000 ng/ml, after oral administration. More preferably, the peak plasma concentration of the delivery agents of the present invention is from about 5,000 to about 15,000 ng/ml, after oral administration.

The time it takes for the delivery agent to reach a peak in the bloodstream ($t_{max}$) may depend on many factors such as the following: the nature of the unit dose, i.e., solid, liquid, tablet, capsule, suspension; the concentration of delivery agent in the GI tract; the feeding state of the subject; the diet of the subject; the health of the subject and the ratio of delivery agent to the active agent. The delivery agents of the present invention are rapidly absorbed from the gastrointestinal tract when orally administered in an immediate release dosage form, and preferably provide a peak plasma concentration within about 0.1 to about 8 hours after oral administration, and preferably at about 0.1 to about 3 hours after oral administration.

In preferred embodiments, the $t_{max}$ of the delivery agent occurs at about 0.3 to about 1.5 hours after oral administration. In certain embodiments, the delivery agent achieves a $t_{max}$ within about 2 hours after oral administration, and most preferably, within about 1 hour after oral administration.

The amount of delivery agent necessary to adequately deliver an active agent into the blood stream of a subject needing the therapeutic effect of that active agent may vary depending on one or more of the following; the chemical nature of the active agent; the chemical structure of the particular delivery agent; the nature and extent of interaction from about the active agent and delivery agent; the nature of the unit dose, i.e., solid, liquid, tablet, capsule, suspension; the concentration of delivery agent in the GI tract; the feeding state of the subject; the diet of the subject; the health of the subject and the ratio of delivery agent to the active agent. In a certain preferred embodiment of the invention, the amount of the delivery agent preferred for the pharmaceutical composition is from about 1 mg to about 2,000 mg delivery agent, more preferably from about 1 mg to about 800 mg of said delivery agent, more preferably from about 50 mg to about 700 mg of said delivery agent, even more preferably from about 70 mg to about 700 mg of said delivery agent, still more preferably from about 100 to about 600 mg.

Preferably, the delivery agent is 4-CNAB. Since the amount of delivery agent required to deliver a particular active agent is variable and the amount of active agent required to produce a desired therapeutic effect is also a variable, the ratio of active agent to delivery agent may vary for different active agent/delivery agent combinations. In certain preferred embodiments of the invention where the oral pharmaceutical composition includes insulin as the active agent and the delivery agent is the compound 4-CNAB, the amount of the delivery agent included in the pharmaceutical composition may be from about 100 mg to about 600 mg of said delivery agent.

In certain preferred embodiments of the invention, the pharmaceutical composition includes insulin as the active agent and the delivery agent is the monosodium salt of 4-CNAB, the ratio of insulin [Units] to delivery agent [mg] ranges from 10:1 [Units/mg] to 1:10 [Units/mg], preferably, the ratio of insulin [Units] to delivery agent [mg] ranges from 5:1 [Units/mg] to 0.5:1 [Units/mg].

Preferred insulin doses in a single administration are about 5 to about 1000 insulin units USP, preferably from about 50 to about 400, more preferably from about 150 to about 400, and still more preferably from about 150 to about 300 units.

The optimum ratio of insulin to delivery agent can vary depending on the delivery agent. Optimizing the ratio of insulin to delivery agent is within the knowledge of one skilled in the art.

In a preferred embodiment of the invention, wherein the pharmaceutical composition includes the compound 4-CNAB as the delivery agent and insulin as the active agent, the composition provides a peak plasma delivery agent concentration within about 0.1 to about 3 hours after oral administration. In certain preferred embodiments where the pharmaceutical composition includes the compound 4-CNAB as the delivery agent and insulin as the active agent, the peak plasma concentration of delivery agent attained is from about 8,000 to about 37,000 ng/ml.

The mechanism by which 4-CNAB facilitates the gastrointestinal absorption of insulin has not yet been fully elucidated. The current working hypothesis is that 4-CNAB interacts with insulin non-covalently, creating more favorable physicochemical properties for absorption. This working hypothesis is provided for explanation purposes only and is not intended to limit the present invention or the appended claims in any way.

A preferred embodiment of the invention provides methods for reducing the incidence of vascular disease associated with chronic dosing of insulin. The methods in a preferred embodiment comprise treating human diabetic patients on a chronic basis with an oral and a delivery agent or pharmaceutically acceptable salt thereof that facilitates the absorption of insulin from the gastrointestinal tract (i.e., bioavailable).

The delivery agent may be used directly by mixing one or more such agents with the active agent (e.g., unmodified insulin) prior to administration. The delivery agent and active agent may be mixed in dry powder form or wet granulated together. To this mixture, other pharmaceutically acceptable excipients may be added. The mixture may be then tableted or placed into gelatin capsules containing a unit dose of the active agent and the delivery agent. Alternatively, the delivery agent/active agent mixture may be prepared as an oral solution or suspension. The delivery agent and active agent do not need to be mixed together prior to administration, such that, in certain embodiments, the unit dose of active agent (with or without other pharmaceutically acceptable excipients) is orally administered without the delivery agents of this invention, and the delivery agent is separately orally administered (with or without other pharmaceutically acceptable excipients) before, after, or simultaneously with the active agent.

In certain preferred embodiments, the oral dosage forms of the present invention are solid. The unmodified insulin in dry powder form is stable, and in certain preferred embodiments is simply mixed in a desirable ratio with the delivery agent. The dry powder mixture may then be filled into gelatin capsules, with or without optional pharmaceutical excipients. Alternatively, the unmodified insulin in dry powder form may be mixed with the delivery agent together with optional pharmaceutical excipients, and the mixture may be tableted in accordance with standard tableting procedures known to those having ordinary skill in the art.

The present invention also provides methods for treating human diabetic patients with active agents that are not inherently bioavailable, such as for example treating diabetics with insulin. More particularly, the present invention provides method of treating humans with an oral dosage form of a pharmaceutical composition, wherein the pharmaceutical composition includes the following: first, an active agent or a pharmaceutically acceptable salt thereof, which is not orally bioavailable when dissolved or suspended in aqueous solution, wherein the active agent provide a therapeutic effect when administered to a subject by another means (e.g., via subcutaneous injection); and, second, an effective amount of a delivery agent or a pharmaceutically acceptable salt thereof, which renders the active agent orally absorbed (e.g., bioavailable). In certain embodiments, the method comprises the following steps: first, contacting the active agent (e.g., insulin) with said delivery agent, and thereafter orally administering the pharmaceutical composition. Alternatively, the method comprises administering the insulin and the delivery agent in such a manner that the insulin and delivery agent contact each other in-vivo (e.g., in the stomach), such that the delivery agent is available to facilitate absorption of the insulin through the stomach mucosa.

The dosage forms of the present invention may be produced by first dissolving the active agent and delivery agents into one solution or separate solutions. The solvent will preferably be an aqueous solution, but organic solvents or aqueous organic solvent mixtures may be used when necessary to solubilize the delivery agent. If two solutions are used, the proportions of each necessary to provide the correct amount of either active agent or delivery agent are combined and the resulting solution may be dried, by lyophilization or equivalent means. In one embodiment of the invention, the oral dosage form may be dried and rehydrated prior to oral administration.

The administration mixtures may be prepared, e.g., by mixing an aqueous solution of the delivery agent with an aqueous solution of the active ingredient, such as insulin, just prior to administration. Alternatively, the delivery agent and the biologically or chemically active ingredient can be admixed during the manufacturing process. The solutions may optionally contain additives such as phosphate buffer salts, citric acid, acetic acid, gelatin, and gum acacia.

Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

The amount of active agent, e.g., insulin, is an amount effective to accomplish the purpose of the particular active agent. The amount in the composition is a therapeutically effective dose, i.e., a pharmacologically or biologically effective amount. However, the amount can be less than a pharmacologically or biologically effective amount when the composition is used in a dosage unit form, such as a capsule, a tablet or a liquid, because the dosage unit form may contain a multiplicity of delivery agent/biologically or chemically active agent compositions or may contain a divided pharmacologically or biologically effective amount. The total effective amounts can then be administered in cumulative units containing, in total, pharmacologically or biologically or chemically active amounts of biologically or pharmacologically active agent.

The total amount of active agent, and particularly insulin, to be used can be determined by those skilled in the art. However, it has surprisingly been found that with some biologically or chemically active agents, the use of the presently disclosed delivery agents provides extremely efficient delivery.

The amount of delivery agent in the present composition is a delivery effective amount and can be determined for any particular delivery agent/active agent combination by methods known to those skilled in the art.

The oral dosage forms of the present invention, containing a mixture of the active agent, e.g., insulin and the delivery agent, e.g., 4-CNAB or separately containing the active agent and the delivery agent, may include additional materials known to those skilled in the art as pharmaceutical excipients. Any excipient or ingredient, including pharmaceutical ingredients or excipients. Such pharmaceutical excipients include, for example, the following: Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoro-methane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant); Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethyl-cellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolmaide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate, glycerin, mono- and di-acetylated monoglycerides, polyethylene glycol, propylene glycol, triacetin, triethyl citrate); Polymers (e.g., cellulose acetate, alkyl celloloses, hydroxyalkylcelloloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Table disintegrants (alginic acid, microcrystalline cellulose, croscarmellose sodium, corspovidone, polacrilin potassium, sodium starch glycolate, starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane); Vehicle: solid carrier (sugar spheres); Vehicle: sterile (bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol). This list is not meant to be exclusive, but instead merely representative of the classes of excipients and the particular excipients which may be used in oral dosage forms of the present invention.

In the case of insulin, oral delivery may have advantages beyond convenience, acceptance and compliance issues. Insulin absorbed in the gastrointestinal tract mimics the physiology of insulin secreted by the pancreas because both are released into the portal vein and carried directly to the liver. Absorption into the portal circulation maintains a peripheral-portal insulin gradient that regulates insulin secretion. In its first passage through the liver, roughly 60% of the insulin is retained and metabolized, thereby reducing the incidence of peripheral hyperinsulinemia, a factor in diabetes related systemic complications. A feared and not uncommon complication of insulin treatment and other oral antidiabetic agents is hypoglycemia.

The present invention relates in part to a method of treating human diabetics via the chronic oral administration of insulin together with a drug delivery agent that enhances the absorption of insulin (e.g., from the duodenum) such that a therapeutically effective control and/or reduction in blood glucose is achieved while effecting a reduction in the systemic blood insulin concentration (serum insulin level) on a chronic basis required to achieve the reduction in blood glucose concentration, e.g., relative to the serum insulin level required to achieve therapeutic efficacy via subcutaneous injection of insulin.

Whereas traditional subcutaneous insulin dosing shifts the point of entry of insulin into the circulation from the natural site (the portal vein) to the systemic circulation, the oral dosing method of the present invention shifts the site of insulin entry back to the portal vein. The effect of this route of dosing is two fold. First, by targeting the liver directly, a greater control of glucose may be achieved. Various studies have shown that intraportal delivery of insulin can yield a comparable control of glucose at infusion rates lower than those required by peripheral administration. (Stevenson, R. W. et al., Insulin infusion into the portal and peripheral circulations of unanaesthetized dogs, Clin Endocrinol (Oxf) 8, 335-47 (1978); Stevenson, R. W. at al., Effect of intraportal and peripheral insulin on glucose turnover and recycling in diabetic dogs, Am J Physiol 244, E190-5 (1983); Shishko, P. I. et al., I. U. Comparison of peripheral and portal (via the umbilical vein) routes of insulin infusion in IDDM patients, Diabetes 41, 1042-9 (1992). Because the insulin will undergo first-pass metabolism prior to entering the systemic circulation, a lower serum concentration is achieved. This may, in turn, alleviate any detrimental effects of insulin on non-target tissues.

In normal healthy humans, the physiologic ratio of blood insulin concentration in the portal vein as compared to systemic (peripheral) blood insulin concentration is greater than about 2:1. In contrast, administration of insulin to human diabetic patients has been found to shift this ratio of portal vein insulin blood concentration to systemic insulin blood concentration to about 0.75:1. By virtue of the present invention, the ratio of concentration of unmodified insulin in the portal circulation to systemic circulation approaches the normal physiological ratio, e.g., from about 2:1 to about 6:1.

One aspect of the physiological response to the presence of insulin is the stimulation of glucose transport into muscle and adipose tissue. It has been reported that hyperglycemia (elevated blood glucose levels) and/or hyperinsulinemia is a cause of vascular diseases associated with diabetes. Impairment to the vascular system is believed to be the reason behind conditions such as microvascular complications or diseases (retinopathy (lesions in the small blood vessels and capillaries supplying the retina of the eye); neuropathy (impairment of the function of the autonomic nerves, leading to abnormalities in the function of the gastrointestinal tract and bladder, and also loss of feeling in lower extremities); nephropathy (lesions in the small blood vessels and capillaries supplying the kidney, which may lead to kidney disease)); or macrovascular complications or diseases (e.g., cardiovascular disease; etc.).

The present invention provides a method of attenuating and/or reducing the incidence of diseases associated with exposure to systemic hyperinsulinemia by the oral administration to a patient a dosage form in accordance with the invention comprising unmodified insulin, preferably along with a suitable drug delivery agent that facilitates the absorption of insulin from the gastrointestinal tract of the patient in a therapeutically effective amount, for treatment of diabetes. Both the methods and pharmaceutical compositions useful for oral administration of insulin are within the scope of the invention.

The methods and oral compositions of the invention can attenuate and/or reduce the incidence of cardiovascular disease associated with chronic dosing of insulin. It is believed that orally administering insulin with the compositions of the invention will decrease the complications associated with vascular disease by lowering the systemic vasculature's exposure to insulin that is greater than normal physiological levels. With a first passage through the liver, roughly 50% of the insulin is retained and metabolized, thereby reducing the incidence of peripheral hyperinsulinemia.

In certain embodiments, the invention provides a method of treating diabetics comprising orally administering to diabetic patients on a chronic basis an oral insulin treatment comprising a dose of insulin together with a delivery agent which facilitates the absorption of the dose of insulin from the gastrointestinal tract to provide a therapeutically effective reduction in blood glucose and a peak serum insulin concentration that is reduced relative to the peak serum insulin concentration of an equivalent therapeutically effective reduction in blood glucose concentration achieved by subcutaneous injection of insulin. In certain embodiments, this method can result in the reduction of the incidence of a disease state associated with chronic insulin administration, which disease states include, for example, cardiovascular diseases. Cardiovascular diseases include, for example, congestive heart failure or coronary artery disease, neuropathy, nephropathy, retinopathy, arteriopathy, atherosclerosis, hypertensive cardiomyopathy and combinations thereof.

In some embodiments, the invention provides a method of reducing the incidence and/or severity of one or more disease states associated with chronic administration of insulin comprising treating diabetic patients via oral administration on a chronic basis of a therapeutically effective dose of a pharmaceutical composition which comprises insulin and a delivery agent that facilitates the absorption of insulin from the gastrointestinal tract, such that the pharmaceutical composition provides a therapeutically effective reduction in blood glucose and a peak serum insulin concentration of the diabetic patient that is reduced relative to the peak serum insulin concentration of an equivalent therapeutically effective reduction in blood glucose concentration achieved by subcutaneous injection of insulin. Disease states associated with chronic administration of insulin for which the incidence and/or severity can be reduced by the method described herein include, for example, cardiovascular diseases, such as congestive heart failure or coronary artery disease. Other disease states include, for example, neuropathy, nephropathy, retinopathy, arteriopathy, atherosclerosis, hypertensive cardiomyopathy and combinations thereof.

In some embodiments, the method of reducing the incidence and/or severity of one or more disease states associated with chronic administration of insulin can provide for a reduced expression of genes associated with vascular disease as compared to the level of expression of genes associated with vascular disease resulting from an equivalent reduction in blood glucose concentration achieved in a population of patients via subcutaneous injection of insulin. The genes associated with vascular disease can include, for example, early response genes, genes associated with cytokines, genes associated with adhesion molecules, genes associated with lipid peroxidation, genes associated with thrombosis and combinations thereof. Early response genes can include, for example, c-myc, jun B, Egr-1, Ets-1 and combinations thereof.

The methods provided herein relating to oral administration of insulin and oral administration of insulin on a chronic basis, in some embodiments, provide for obtaining plasminogen activator inhibitor concentrations that are lower as compared to the plasminogen activator inhibitor concentrations resulting from an equivalent therapeutically effective reduction in blood glucose concentration achieved by subcutaneous injection of insulin. These methods also can provide for obtaining pro-inflammatory cytokine concentrations that are lower than pro-inflammatory cytokine concentrations resulting from an equivalent therapeutically effective reduction in blood glucose concentration achieved by subcutaneous injection of insulin.

In some embodiments, the invention provides a method of treating diabetes and reducing the incidence and or severity of hyperinsulinemia associated with chronic dosing of insulin, comprising orally administering on a chronic basis to a diabetic patient a dose of insulin and a delivery agent that facilitates the absorption of the dose of insulin from the gastrointestinal tract to provide a therapeutically effective reduction in blood glucose and a peak serum insulin concentration of the diabetic patient that is reduced relative to the peak serum insulin concentration of an equivalent therapeutically effective reduction in blood glucose concentration achieved by subcutaneous injection of insulin.

In some embodiments, the invention provides a method of screening a drug for vascular injury associated with route of administering the drug, comprising administering a drug to a first test animal parenterally, administering the drug to a second test animal orally, and comparing the expression of early response genes selected from the group consisting of c-myc, c-fos, Jun B, Erg-1 and combinations thereof for the first and second test animal, wherein an increase in the expression of one or more early response genes is indicative of vascular injury. In some embodiments, the step of measuring the change in expression is done using gene chip analysis and can comprise measuring the changes in mRNA expression.

In some embodiments, the invention provides a method of reducing the incidence of and/or the severity of disease states or of vascular diseases associated with chronic insulin administration to diabetics, comprising orally administering an oral insulin treatment comprising a dose of insulin together with a delivery agent that facilitates the absorption of said insulin from the gastrointestinal tract on a chronic basis to diabetic patients to reduce blood glucose levels in said diabetic patients by a desired amount, such that the concentration of insulin circulating in the blood of said diabetic patients as a result of insulin treatment is reduced relative to the peak serum insulin concentration of an equivalent therapeutically effective reduction in blood glucose concentration achieved by subcutaneous injection of insulin.

In some embodiments, the invention provides a method for reducing the incidence of, the severity of, or the incidence and severity of vascular diseases associated with chronic insulin therapy in diabetics, comprising orally administering an oral insulin treatment comprising a dose of insulin together with a delivery agent that facilitates the absorption of said insulin from the gastrointestinal tract on a chronic basis to diabetic patients to reduce blood glucose levels in said diabetic patients by a desired amount, such that the concentration of insulin circulating in the blood of said diabetic patients as a result of insulin treatment is reduced relative to the peak serum insulin concentration of an equivalent therapeutically effective reduction in blood glucose concentration achieved by subcutaneous injection of insulin.

In some embodiments, the invention provides a method of attenuating processes resulting from the reaction to a mild injurious stimulus in multiple areas of the response to increases in mRNA during insulin treatment, comprising orally administering an oral insulin treatment comprising a dose of insulin together with a delivery agent that facilitates the absorption of said insulin from the gastrointestinal tract on a chronic basis to diabetic patients to reduce blood glucose levels in said diabetic patients by a desired amount, such that the concentration of insulin circulating in the blood of said diabetic patients as a result of insulin treatment is reduced relative to the peak serum insulin concentration of an equivalent therapeutically effective reduction in blood glucose concentration achieved by subcutaneous injection of insulin.

In some embodiments, the invention provides a method of treating diabetic patients, comprising orally administering an oral insulin treatment comprising a dose of insulin together with a delivery agent that facilitates the absorption of said insulin from the gastrointestinal tract on a chronic basis to diabetic patients to reduce blood glucose levels in said diabetic patients by a desired amount, such that the concentration of insulin circulating in the blood of said diabetic patients as a result of said oral insulin treatment is not substantially greater than normal physiological levels.

DETAILED DESCRIPTION OF PREFERRED EMBODIMENTS

In order that this invention may be better understood, the following examples are set forth. These examples are for the purpose of illustration only and are not to be construed as limiting the scope of the invention in any manner.

EXAMPLE 1

Plasma Delivery Agent Design and Efficiency

Delivery agents 1-3 were investigated for their ability to penetrate the GI mucosa. The plasma concentration of each delivery agent was measured in human subjects after oral administration of delivery agent loaded capsules as a measure of each delivery agent's penetration efficiency. See Tables 1 and 2.

TABLE 1

Structures of Delivery Agents 1-3

Delivery Agent 1 (SNAC)

Delivery Agent 2 (SNAD)

Delivery Agent 3 (4-CNAB)

TABLE 2

Delivery Agent Plasma Concentrations in Humans

| Delivery Agent | Variables | | Delivery Agent Dose (Mg) | AUC (ng · hr/ml) |
|---|---|---|---|---|
| | X | n | | |
| 1 (SNAC) | H | 7 | 750 | 3499 |
| 2 (SNAD) | H | 9 | 750 | 2037 |
| 3 (4-CNAB) | Cl | 3 | 800 | 47478 |

Blood sampling for plasma delivery agent concentration determination (2 mL in sodium heparin tube) were drawn 15 minutes before dosing, and at 5, 10, 15, 30, and 45 minutes and 1, 1.5, 2, 3, 4, 6, 8, and 12 hours post-dose (14 samples per treatment) for delivery agent measurements in all treatment groups.

Two 18-gauge IV lines were situated prior to dosing; one for blood sampling, and the other for potential infusion of 20% glucose for subjects in groups 2 and 3. The subjects in group 1 only had one cannula inserted. The blood samples were centrifuged at 3000 rpm for a period of fifteen minutes at a temperature from about 2° C. to 8° C., within one hour of sample collection. Using a plastic pipette and without disturbing the red cell layer, the plasma from the collection tube was pipetted in duplicate for each analysis, blood glucose, Human Insulin, C-peptide, delivery agent into pre-labeled polypropylene tubes. The samples were stored at −70° C. until analysis.

The indicated doses were ingested by healthy human volunteers and the plasma concentrations of the delivery agents were monitored over time and the area under the curve (AUC) calculated. Surprisingly, as provided in Table 2, oral administration of 800 mg delivery agent number 3 with X as chlorine and n equal to 3 alkyl produced an approximately 13.5 fold greater penetration of the GI mucosa in humans than did oral administration of 750 mg of delivery agent 1 having n equal 7 alkyl. Similarly, oral administration of 800 mg of delivery agent number 3 produced more than a 23 fold greater penetration of the GI mucosa in humans than did oral administration of 750 mg of delivery agent 2 having n equal to 9 alkyl.

Similar results were obtained when delivery agents 1-3 were administered orally to monkeys and the plasma concentrations of the delivery agents monitored over time and the AUC calculated. As provided in Table 3, oral administration of 300 mg of delivery agent number 3 with X as chlorine and n equal to 3 alkyl produced a more than 11 fold greater penetration of the GI mucosa in monkeys than did oral administration of 300 mg of delivery agent 1 having n equal to 7 alkyl. See Table 3. Further, 300 mg of delivery agent 3 displayed a more than 6 fold greater penetration of the GI mucosa in monkeys than did oral administration of 300 mg of delivery agent 2 having n equal to 9 alkyl. See Table 3.

TABLE 3

Delivery Agent Plasma Concentrations in Monkeys

| Delivery Agent | X | n | Delivery Agent Dose (Mg) | AUC (ng · hr/ml) |
|---|---|---|---|---|
| 1 (SNAC) | H | 7 | 300 | 45 |
| 2 (SNAD) | H | 9 | 300 | 82 |
| 3 (4-CNAB) | Cl | 3 | 300 | 499 |

EXAMPLE 2

Comparison of the Delivery Efficiency of Delivery Agents 1-3

Next, delivery agents 1-3 were compared for the ability to efficiently transport an active agent across the GI mucosa in a biologically active form by determining the relationship between delivery agent dose, dose of active agent and the glucose response. See Table 4. The effective dose of delivery agent necessary to deliver a therapeutic dose of active agent and produce a therapeutic effect was measured. See Table 4. For delivery agent 3, the active agent was insulin, and the therapeutic effect was determined by the ability of the delivery agent/insulin combination to lower serum glucose by at least 10% within one hour post administration. For delivery agents 1 and 2, the active agent was heparin, and the therapeutic effect was determined by [Emisphere: please fill in]

TABLE 4

Effective Clinical Dose of Delivery Agent in Humans

| Delivery Agent | X | N | Delivery Agent Dose (Mg) |
|---|---|---|---|
| 1 (SNAC) | H | 7 | 2400 |
| 2 (SNAD) | H | 9 | 1500 |
| 3 (4-CNAB) | Cl | 3 | 200 |

Again, as shown in Table 4, delivery agent 3 with X as chlorine and n equal to 3 alkyl was approximately 12 fold more efficient in facilitating insulin transit across the GI mucosa in a biologically active form than was delivery agent 1 having n equal to 7 alkyl. Similarly, delivery agent no. 3 was 7.5 fold more efficient in facilitating transport of insulin across the GI mucosa in a biologically active form than was delivery agent 2 having n equal to 9 alkyl. See Table 4.

Most importantly, only delivery agent 3 is efficient enough at facilitating transport of biologically active insulin to allow packaging of a therapeutically effective dose of insulin plus delivery agent into a single capsule.

EXAMPLE 3

Preparation of the Delivery Agent 4-CNAB

The compound corresponding to the following structure may be prepared as described below:

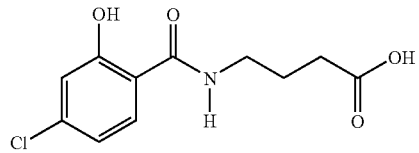

4-Chlorosalicylic acid (10.0 g, 0.0579 mol) was added to a one-neck 250 ml round-bottomed flask containing about 50 ml methylene chloride. Stirring was begun and continued for the remainder of the reaction. The coupling agent 1,1-carbonyldiimidazole (9.39 g, 0.0579 mol) was added as a solid in portions to the flask. The reaction was stirred at room temperature for approximately 20 minutes after all of the coupling agent had been added and then ethyl-4-aminobutyrate hydrochloride (9.7 g, 0.0579 mol) was added to the flask with stirring. Next, triethylamine (10.49 ml, 0.0752 mol) was added dropwise from an addition funnel. The addition funnel was rinsed with methylene chloride. The reaction was allowed to stir at room temperature overnight.

The reaction was poured into a separatory funnel and washed with 2N HCl and an emulsion formed. The emulsion was left standing for two days and was then filtered through celite in a fritted glass funnel. The filtrate was put back in a separatory funnel to separate the layers. The organic layer was dried over sodium sulfate, which was then filtered off and the filtrate concentrated by rotary evaporation. The resulting solid material was hydrolyzed with 2N NaOH, stored overnight under refrigeration, and then hydrolyzing resumed. The solution was acidified with 2N HCl and the solids that formed were isolated, dried under vacuum, and recrystallized twice using methanol/water. Solids precipitated out overnight and were isolated and dried. The solids were dissolved in 2N NaOH and the pH of the sample was brought to pH 5 with 2N HCl. The solids were collected and HPLC revealed a single peak. These solids were then recrystallized in methanol/water, isolated, and then dried under vacuum, yielding 4.96 g (33.0%) of 4-(4 chloro-2-hydroxybenzoyl)aminobutyric acid, ($C_{11}H_{12}ClNO_4$; Molecular weight 257.67). A melting point of 131-133° C. was determined. Combustion analysis revealed the following content: % C: 51.27 (calc.), 51.27 (found); % H, 4.69 (calc.), 4.55 (found); % N, 5.44 (calc.), 5.30 (found). Proton H NMR Analysis revealed: ($d_6$-DMSO): d 13.0, s, 1H (COOH); d 12.1, s, 1H (OH); d 8.9, t, 1H (NH); d 7.86, d, 1H (H ortho to amide); d 6.98, d, 1H (H ortho to phenol OH); d 6.96, d, 1H, (H meta to amide); d 3.33, m, 2H ($CH_2$ adjacent to NH); d 2.28, t, 2H ($CH_2$ adjacent to COOH); d 1.80, m, 2H (aliphatic $CH_2$ beta to NH and $CH_2$ beta to COOH).

4-CNAB Preparation for Human Studies

4-CNAB for the human dosings (Monosodium N-(4-chlorosalicyloyl)-4-amino-butyrate) was made under good manufacturing practices (GMP) conditions by Regis Technologies, Inc. (Morton Grove, Ill.) according to the methods of International Publication No. WO 00/46182 except that the starting material 4-chlorosalicylic acid (purchased from Ihara Chemical Industry Co. Inc, Ltd., Tokyo, Japan and Aapin Chemicals Ltd., Oxfordshire, UK) was used and converted to the amide via a methyl ester using 0.14 equivalents sulfuric acid in methanol and then about 4 equivalents ammonia in methanol. The alkylating agent used was ethyl-4-bromobutyrate.

The monosodium salt of 4-CNAB was made according to the following method on a 40 kilogram scale. 4-CNAB free acid (500 g, 1.94 mol, FW=257.67) was charged to a 22 L five neck round bottom flask. The flask was equipped with an overhead stirrer, a thermocouple temperature read out, a reflux condenser and a heating mantle, and was placed under nitrogen. Reagent grade acetone (13 L) was added to the reactor and the mixture was agitated. The 4-CNAB/acetone mixture was heated to 50° C. to dissolve any solids. A hazy brown solution was achieved.

The 50° C. solution was pumped through a warm pressure filter (dressed with Whatman #1 filter paper, ~5 microns, 18.5 sq. in. area) into a clean 22 L reactor to remove sodium chloride and other insolubles. The pressure dropped across the filter to about 20 psig at the end of filtration. The reactor containing the clear yellow filtrate was agitated and heated. At 50° C. the reactor was removed from heat.

The clear filtrate was charged with 50% sodium hydroxide solution (155 g, 1.94 mol) as rapidly as possible, while maintaining a vigorous agitation. (An overcharge will result in the undesirable formation insoluble disodium salts. A slight undercharge is preferable because the free acid is removed during the final filtration step.) The reaction mixture exothermed to approximately 52° C. Precipitates formed and the product gelled before becoming clear again.

After the base addition was completed and the temperature leveled, the solution became cloudy and increased in viscosity. The reaction was refluxed for 2 hours at 60° C., while agitating vigorously. The reaction mixture continued to thicken, forming solid chunks. The slurry became light pink and foamed. The reactor contents were cooled to ambient temperature over 3 to 4 hours. The ambient temperature was held for 30 minutes. The precipitated solids were isolated on a filter funnel. The isolated product was not washed. The resulting 4-CNAB monosodium salt was dried in vacuo at 40 to 50° C. for 16 to 24 hours to give 490 grams (1.75 mol, 90% yield, FW=279.65).

The insulin for the subcutaneous injection was HUMULIN® R injection insulin from Eli Lilly and Company (Indianapolis, Ind.).

All capsules containing 200 mg 4-CNAB and 150 insulin units USP were prepared as follows. First, the total amount of delivery agent material necessary for filling the delivery agent alone capsules and the delivery agent plus insulin composition capsules was prepared by weighing 3160 g of 4-CNAB. The 3160 g 4-CNAB was then milled in a Quadro comil, model 197S mill with screen number 2A 050 G 037 19 136 (1270 micron). Next, 1029 g of the milled 4-CNAB was passed through a #35 mesh screen. Then, the pass through screened material was transferred into a 4 quart shell and blended using for example, a V blender, at 25 rpm for 10.2 minutes. The resultant blended material was used to fill capsules. In this case, a Fast Cap Capsule Filler was used with a size 3 Fast Cap Encapsulation tray. The empty capsules weighed approximately 48 mg each and were filled with an average fill weight of 205.6 mg of 4-CNAB alone. Thus, the dose of the delivery agent alone capsules was 205.6 mg.

The insulin compositions were prepared by first dispensing 31.8 g of recombinant human zinc crystalline insulin (Potency 26.18 Units per mg) proinsulin derived (recombinant DNA origin) USP quality) from Eli Lilly and Company (Indianapolis, Ind.) into an appropriately sized plastic bag. Next, sequential 30 g additions of the milled and screened 4-CNAB were added to the bag until approximately 510 g had been added. The bag was thoroughly mixed after each 30 g addition of 4-CNAB by shaking and inversion. In order to add and mix the next 532.5 g of 4-CNAB, the 541.8 g mixture of insulin and 4-CNAB was transferred to a V blender and mixed again at 25 rpm for 10.2 minutes. Next, the remaining 4-CNAB was added to the blender and the entire mixture was mixed in the blender at 25 rpm for 10.2 minutes. Finally, the resulting composition was dispensed as described above into empty capsules. The final capsules contained an average of 5.7 mg insulin (equivalent to 150 units insulin) and 200.5 mg of 4-CNAB or a ratio of 1:57.3, insulin: 4-CNAB. Multiple samples of the final blend were ran on HPLC to verify uniformity and were found to be uniform.

EXAMPLE 4

Previous Non-clinical Studies with 4-CNAB and Insulin/4-CNAB

The present invention comprising compositions of insulin and the delivery agent 4-CNAB was evaluated for safety and toxicity in a nonclinical program that included pharmacological screening, pharmacokinetic profiling, and toxicity assessments in rats and monkeys. In general, animal physiological responses to 4-CNAB alone and to Insulin/4-CNAB were comparable. Pharmacokinetic studies in mice, rats and monkeys have shown that 4-CNAB is absorbed rapidly following oral administration, and subsequently cleared from the body. 4-CNAB did not demonstrate potential activity in any of the primary molecular targets evaluated in receptor binding screening assays. Four genotoxicity studies have been conducted with 4-CNAB, with no positive findings. Based on 14-day oral repeated dose toxicity studies, the NOAEL (No-Adverse Effect Level) was estimated to be 500 mg/kg in Sprague-Dawley rats, and 400 mg/kg in rhesus monkeys.

In toxicology studies, 4-CNAB doses from 400 mg to 2000 mg were evaluated. Following 14-day oral repeated dose toxicity studies in rats and monkeys, the estimated No Adverse Effect Level (NOAEL) for 4-CNAB was 500 mg/kg in Sprague-Dawley rats and 400 mg/kg in rhesus monkeys; therefore, the monkey appeared to be the most sensitive species. The highest proposed dose of 2000 mg 4-CNAB in man (<30 mg/kg) is 12-16 fold lower than the NOAEL in monkeys (i.e., NOAEL=400 mg/kg 4-CNAB alone and in combination with 15 U/kg insulin). The absolute bioavailability of insulin in monkeys was about 1% or less. In the toxicology studies, there were no findings in rats attributed to insulin at an oral dose level of 15 U/kg in combination with 4-CNAB doses as high as 2000 mg/kg. In monkeys, an insulin dose of 15 U/kg was associated with a single hypoglycemic episode in combination with a 4-CNAB dose of 1200 mg/kg in one monkey; there were no effects at 15 U/kg insulin in combination with lower doses.

Non-clinical studies in rats and monkeys demonstrated that, over the range tested, insulin absorption increases with increasing doses of 4-CNAB. Similarly, for a fixed oral dose of 4-CNAB, insulin absorption increases with increasing doses of insulin. Oral insulin absorption was evaluated in rats at varying doses of both insulin and 4-CNAB. Significant increases in serum insulin concentrations were observed following the administration of insulin at doses of 4.55, 6.5, 9.75, and 13 Units/kg in the presence of a fixed 4-CNAB dose (200 mg/kg). The mean peak serum insulin levels were 31, 44, 85, and 132 µU/mL respectively. Insulin absorption was dose dependent and increased as the dose of insulin increased. Oral administration of aqueous solutions of insulin alone (13 Units/kg) or 4-CNAB alone (200 mg/kg) did not result in any significant increases in serum insulin levels. Significant increases in serum insulin concentrations were also observed following the administration of 4-CNAB at doses of 50, 100, 200, and 300 mg/kg in the presence of a fixed insulin dose (13 Units/kg). The mean peak serum insulin levels were 9, 39, 103, and 157 µU/mL, respectively. Insulin absorption was dose dependent and increased as the dose of 4-CNAB increased.

Based on the above nonclinical information, the starting insulin dose of 150 insulin Units USP (which is about 7-fold lower than the 15 U/kg no effect dose in monkey) was selected.

EXAMPLE 5

A single center, double-blind, randomized placebo-controlled study undertaken in healthy human subjects in order to assess the safety and tolerability of escalating single oral doses of 4-CNAB capsules and insulin/4-CNAB capsules. A subcutaneous (SC) insulin treatment group was added to allow comparison of the combined treatment against an existing standard treatment, and an oral insulin alone treatment group was also included to further evaluate the effect of 4-CNAB on oral insulin absorption.

One objective of this study was to evaluate the safety and tolerability of single oral doses of 4-CNAB and of Insulin/4-CNAB capsules in healthy subjects. Other objectives of this study were to assess the PK of 4-CNAB when given alone and when given as part of the Insulin/4-CNAB combination, to assess the PK of insulin and the effect of increasing proportions of 4-CNAB on insulin PK and to assess the effects on blood glucose following single oral doses of 4-CNAB alone or Insulin/4-CNAB. The study allowed the investigation of the effect of 4-CNAB on oral insulin PK and PD to be studied across a range of doses and to be compared with SC and oral insulin alone treatments. Control treatments of 10 Units SC insulin, 150 USP Units oral insulin alone, oral placebo and SC placebo allowed the tolerability, PK and effects of 4-CNAB and Insulin/4-CNAB to be evaluated effectively. Simultaneous measurement of C-peptide protein allowed the correction for endogenous insulin. Food given at 6 h post-dose also allowed its effect on insulin and glucose to be observed. Parallel groups were used due to the number of treatments administered and also reduced the length of the study. The double-blind nature of subject and physician ensured minimal bias.

Male subjects aged between 18 and 50 years were recruited and were chosen to be representative of the general healthy population, which was deemed suitable for such a study. Selection criteria (inclusion and exclusion) were chosen to ensure that the subjects were healthy and therefore at minimal risk from the study procedures and to side effects of Insulin/4-CNAB. The subjects were in good health as determined based on medical history, physical examination and clinical laboratory studies at screening. The subjects were within the permissible deviations (+/−15%) of ideal weight according to the 1983 tables of desirable weights issued by the adjusted Metropolitan Life Insurance Co. All laboratory values (hematology, serum chemistries, and urinalysis) obtained during screening were generally within normal ranges. The laboratory tests were conducted in a fasted state and glucose measured. However, for clinical laboratory values outside of the normal range, the laboratory test was repeated once. The subjects had 12-lead ECG recorded within 14 days prior to the study start, and results indicated a normal recording or a non-clinically significant abnormality.

Within each treatment period in each group, eight subjects were planned to receive active treatment and two subjects to receive placebo. In Group 1, there were four escalating single doses of 4-CNAB (400, 800, 1400 and 2000 mg) and each subject received either all four of these escalating doses or three escalating single doses and one dose of placebo. In Group 2 there were three treatments (10 Units of SC insulin and 2 escalating oral doses of Insulin/4-CNAB; 150 Units/ 200 mg, 100 Units/600 mg) and each subject received either all three of these treatments or two of these treatments and one placebo treatment. In Group 3 there were three escalating oral doses of Insulin/4-CNAB (100 Units/300 mg, 100 Units/450 mg and 150 Units/100 mg) and one SC dose of 150 Units of insulin. Each subject received either all four of these treatments or three of these treatments and one placebo treatment. For all groups, there was a washout period of at least 72 hours between treatment periods.

Twenty-nine volunteers, divided among three groups (9 in group 1, and 10 in each of groups 2 and 3), participated in this study. Randomization was stratified such that any individual subject received placebo only on a single occasion or not at all. Two subjects in each group received placebo. Group 1 received four escalating oral doses of 4-CNAB capsules or placebo (see Table 5), with each subject receiving four active treatments or three active treatments and one placebo treatment. For each treatment, seven subjects received active treatment and two received placebo, according to the pre-prepared randomization code.

TABLE 5

Group 1 - 4-CNAB alone (4 escalating doses)

| Group 1:<br>4-CNAB only<br>Treatment: | # of Subjects &<br>4-CNAB Dose | # of Subjects on<br>placebo | # of Capsules |
|---|---|---|---|
| Treatment 1 | 7 subjects 400 mg | 2 | 2 |
| Treatment 2 | 7 subjects 800 mg | 2 | 4 |
| Treatment 3 | 7 subjects 1400 mg | 2 | 7 |
| Treatment 4 | 7 subjects 2000 mg | 2 | 10 |

Group 2 received three escalating oral doses of Insulin/4-CNAB capsules or placebo (see Table 6), with each subject receiving three active treatments or two active treatments and one placebo treatment. For each treatment, eight subjects received active treatment and two received placebo, according to the pre-prepared randomization code.

TABLE 6

Group 2 - Insulin/4-CNAB (2 escalating doses) and SC insulin alone (1 dose)

| Group 2<br>Insulin/4-CNAB<br>Treatment | # of Subjects &<br>Insulin/4-CNAB Dose<br>(Unit Insulin/mg 4-CNAB) | # of<br>Subjects<br>on placebo | # of<br>Capsules |
|---|---|---|---|
| Treatment 1 | 8 subjects 10 IU insulin subcutaneous/0 mg 4-CNAB | 2 | 0 |
| Treatment 2 | 8 subjects 150/200 | 2 | 1 |
| Treatment 3 | 8 subjects 100/600 | 2 | 4 |

Group 3 received three oral doses of Insulin/4-CNAB capsules or placebo and one oral dose of Insulin capsule alone or placebo (see Table 7), with each subject receiving four active treatments or three active treatments and one placebo treatment. For each treatment, eight subjects received active treatment and two received placebo, according to the pre-prepared randomization code.

TABLE 7

Group 3 - Insulin/4-CNAB (3 escalating doses) and Insulin alone (1 dose)

| Group 3<br>Insulin/4-CNAB<br>Treatment: | # of Subjects &<br>Insulin/4-CNAB Dose<br>(Unit Insulin/mg 4-CNAB) | # of<br>Subjects on<br>placebo | # of<br>Capsules |
|---|---|---|---|
| Treatment 1 | 8 subjects 100/300 | 2 | 2 |
| Treatment 2 | 8 subjects 100/450 | 2 | 3 |
| Treatment 3 | 8 subjects 150/100 | 2 | 1 |
| Treatment 4 | 8 subjects 150/0 | 2 | 1 |

The 4-CNAB alone and Insulin/4-CNAB capsules were prepared by AAIPharma Inc., Wilmington N.C. The 4-CNAB used for the capsules was manufactured under cGMP compliance. The Insulin used to prepare the capsules was Zinc-Insulin Crystals Human: Proinsulin Derived (Recombinant DNA Origin) USP Quality obtained from Eli Lilly and Company (Indianapolis, Ind.). Insulin used for the SC dosing was provided by Medeval Ltd. This insulin was zinc-insulin crystals human: proinsulin derived (recombinant DNA origin) equivalent to Humulin R (trade name Humulin S injection 100 Units/mL). Placebo capsules consisted of Size 3 hard gelatin capsules filled with 200 mg of Methocel E15 Premium LV. Each capsule was stored frozen at or below minus 10° C., was brought to room temperature (between 15 and 30° C.) before opening, and was not left at room temperature for more than 4 hours Capsules were administered with 240 mL water. For all groups, there was a washout period of at least 72 hours between treatment periods. After each dosing, safety data (i.e., vital signs, blood glucose, and available 4-CNAB plasma concentrations) were collected and evaluated before proceeding to the next dose level.

On day one of each study treatment period, study medication (capsules or SC dose) were administered at approximately 8:00 AM following an 8-hour minimum overnight fast. The capsules were administered with 240 mL of water with subjects in an upright position. The total administration time did not exceed 2.5 minutes. The SC dose of insulin solution or placebo (saline) was injected in the abdominal wall as a single bolus administration. Each treatment period lasted between 12 and 24 hours.

The appearance of the prepared active and placebo study treatments was identical, and, therefore, maintenance of blinding from treatment appearance was not an issue in this study. Administration of the medication was supervised, and, therefore, non-compliance was not an issue in this study.

Subjects fasted overnight for a minimum of 8 hours prior to morning dosing until 6 hours after dosing, after which each subject ate a full meal, including at least two slices of bread. Subjects were provided with standard high carbohydrate meals and snacks. Water was allowed ad libitum, except for 1 hour prior through to 1 hour after administration of each treatment (apart from that required for dosing). Subjects were asked to refrain from xanthine or xanthine related agents, grapefruit containing products, Seville oranges and marmalade during the 24 hours prior to dosing and throughout the study periods. No concomitant medication, apart from acetaminophen (paracetamol), was allowed during the study, and no alcohol was allowed for 24 hours prior to admission and while resident in the clinical unit. Non-smokers or smokers who smoked up to five cigarettes a day were recruited. Smoking was not allowed while resident in the Clinical Unit Subjects were asked to avoid strenuous physical activity and contact sports from 48 hours prior to Day-1 until the end of the residential period.

Dose escalation within each group continued until two subjects per treatment exhibited a blood glucose level of less than 54 mg/dl (3.0 mmol/L). Once this dose had been identified, there was an adaptable approach to exploring changing the ratios of insulin and 4-CNAB. The chosen insulin dose was no higher than the insulin dose that caused the blood glucose level of 54 mg/dL (3.0 mmol/L), and the dose of 4-CNAB was not higher than that already given.

Safety assessments included physical examinations, medical history, vital signs, 12-lead electrocardiogram (ECG) monitoring, laboratory evaluations and checking for adverse events. Activity parameters included blood glucose, insulin, C-peptide, and 4-CNAB plasma concentration measurements.

For insulin/4-CNAB treatment Groups 2 and 3, subjects' blood samples (1 drop per sample) were drawn at 15 minutes before dosing, and at 5, 10, 15, 20, 25, 30, 35, 40, and 50 minutes and at 1, 1.25, 1.5, 1.75, 2, 2.5, 3, 4, 6, 8 and 12 hours post-dose (21 samples per treatment for Insulin/4-CNAB dosing groups) for plasma glucose, insulin and C-peptide measurements. For the 4-CNAB alone treatment Group 1, blood samples were collected before dosing (−15 minutes), and at 30 minutes and at 2 hr post-dose for blood glucose measurements. For the insulin alone control group (minimum 3 subjects), blood samples (3 mL in sodium heparin tube) were drawn at 15 minutes before dosing, and at 10, 20, 30, 40, 50 minutes and 1, 1.25, 2, 2.5, 3 and 6 hr post-dose (12 samples per treatment). The blood samples for glucose were assayed in real time using a Glucometer®. These measurements were used for detection of onset of hypoglycemia, so rescue action could be taken where necessary. Plasma glucose, insulin and C-peptide measurements were done according to standard procedures.

Two 18-gauge IV lines were situated prior to dosing; one for blood sampling, and the other for potential infusion of 20% glucose for subjects in Groups 2 and 3, if required for the treatment of hypoglycemia. The subjects in Group 1 only had one cannula inserted. Blood samples for plasma glucose, insulin and C-peptide analyses were stored between 2° C. and 8° C. immediate after sampling and prior to centrifugation. Blood samples for were centrifuged at 3000 rpm for a period of 15 minutes at a temperature between 2° C. and 8° C. within one hour of sample collection. Using a plastic pipette and without disturbing the red cell layer, the plasma from the collection tube was pipetted into pre-labelled polypropylene tubes and stored at −70° C.

Total blood volume (including study screening and safety assessment) collected from each subject for the entire study did not exceed 625 mL for subjects in Group 3, and 487 mL for subjects in Group 2, and 380 mL for subjects in Group 1.

The concentration of 4-CNAB in plasma was determined using a combination of liquid chromatography and Mass spectrometry assay known as LC-MS/MS. The method involves protein precipitation followed by separation on liquid chromatography using a Hypersil BDS column and a mobile phase consisting of methanol and acetate buffer. The eluting peaks were quantified by MS/MS. The equipment used for the determination of 4-CNAB in plasma comprises of an Agilent 1100 modular HPLC system with a Micromass Quattro Micro MS/MS detector. HPLC and AR grade chemicals and reagents were used throughout the study.

Pharmacokinetic and Pharmacodynamic Assessments

Plasma glucose was measured based on a timed-endpoint method using a BECKMAN Synchron CX system that mixes exact proportions of reagents that catalyse the phosphorylation of glucose. The Synchron CX measures changes in the absorbance spectrum at 340 nm at a fixed time interval. The change in absorbance is directly proportional to the concentration of glucose in the sample.

Plasma C-peptide was measured using a DELFIA C-peptide kit, based on a solid phase, two-site fluoroimmunometric assay, which used the direct sandwich technique in which two monoclonal antibodies are directed against antigenic determinants on the C-peptide molecule. Reagent dissociates europium ions from the labeled antibody, which form fluorescent chelates with the reagent. The fluorescence is directly proportional to the concentration of C-peptide in the sample.

On the basis of plasma concentrations of 4-CNAB and insulin, PK analysis was performed using non-compartmental PK methods as implemented in WinNonlin™ Professional version 3.2. The profiles for insulin and C-peptide corrected insulin were evaluated up to 6 hours as food was given 6 hours following insulin treatment. The following parameters were derived for 4-CNAB: $C_{max}$, $t_{max}$, $AUC_{(0-t)}$, $AUC_{(0-inf)}$, $AUC_{\%Extrap}$, $K_{el}$, $t_{1/2}$, CL/F, Vd/F, $MRT_{(0-t)}$, $MRT_{(0-inf)}$ and and $F_{rel}$. The following parameters were derived for insulin and C-peptide corrected insulin: $C_{max}$, $t_{max}$, $AUC_{(0-2)}$, $AUC_{(0-6)}$, $AUC_{(0-t)}$ and concentrations ($C^b$) and corresponding time ($t^b$) immediately prior to intervention for hypoglycemia.

On the basis of plasma concentrations of glucose, PD analysis was performed using WinNonlin™ Professional version 3.2. The profiles for glucose, glucose change from baseline and glucose percentage change from baseline were evaluated up to 6 hours as food was given 6 hours following insulin treatment. The following PD parameters were computed for plasma glucose concentration: $AURC_{(0-2)}$, $AURC_{(0-t)}$ (total response), $R_{max}$ (minimum value), $t_{Rmax}$ and concentrations ($R^b$) and corresponding time ($t^b$) immediately prior to intervention for hypoglycemia. The following PD parameters were computed for plasma glucose concentration change from baseline: $AUEC_{(0-2)}$, $AUEC_{(0-t)}$ (baseline subtracted), $E_{max}$ (baseline subtracted), $t_{Emax}$ (obtained without interpolation), percent change from baseline and concentrations ($E^c$) and corresponding time ($t^c$) immediately prior to intervention for hypoglycemia.

The above parameters were to be summarized using descriptive statistics (mean, standard deviation (SD), coefficient of variation (CV %), standard error of the mean (SE), minimum (Min), median, maximum (Max), and sample size (N) by treatment group. Individual data was reported by dose, by subject.

For the PK analysis of insulin, analysis was conducted for both measured insulin and C-peptide corrected insulin concentrations. This was done using concentrations of the precursor C-peptide and the following equation:

Corrected Insulin Concentration=Insulin Concentration−(Baseline Ratio×C-peptide)

where $$\text{Baseline Ratio} = \frac{\text{Insulin Concentration}}{C-\text{peptide Concentration}}$$

at each time point

Similarly, in order to take into account baseline levels of glucose, PD analysis was conducted based on the percent change (decrease or increase) in glucose concentration from the baseline, where baseline was taken as the pre-dose concentration levels, rather than absolute values only. The glucose concentration percent change from baseline values were also calculated, and profiles were tabulated and plotted. Thus, $$\text{Glucose\% Change from Baseline} = \left(\frac{\text{Glucose Conc.}-\text{Baseline Glucose Conc.}}{\text{Baseline Glucose Conc.}}\right) \times 100$$

where Glucose Change from Baseline=(Glucose Conc.−Baseline Glucose Conc.).

The additional parameters $AUC_{(0-2)}$ for insulin and C-peptide corrected insulin and $AURC_{(0-2)}$ and $AUEC_{(0-2)}$ for glucose and glucose change from baseline, respectively, were calculated because the maximum change in insulin and glucose appeared to occur during the first 2 hours following dosing. For insulin no extrapolation was possible for the vast majority of subjects therefore elimination half-life rate constant $K_{el}$ and hence $AUC_{(0-inf)}$ could not be calculated. Since food was given at 6 hours following dosing, AUC, AURC and AUEC were calculated up to 6 hours for insulin and glucose respectively which gave a more accurate measure of the effect of Insulin/4-CNAB on insulin and glucose concentrations. For glucose change from baseline, $E_{max}$ was taken as the maximum reduction up to 6 hours post-dose.

The plasma concentration-time profiles for 4-CNAB were evaluated in those subjects who received 4-CNAB or Insulin/4-CNAB treatments. Insulin, C-peptide and glucose concentration-time profiles following administration of all treatments were evaluated for the 20 subjects in Groups 2 and 3. Pharmacokinetic ("PK") parameters for 4-CNAB, insulin and C-peptide corrected insulin, and pharmacodynamic ("PD") parameters for glucose concentration change from baseline, respectively were calculated for subjects whether they required hypoglycemic rescue or not. Concentrations from subjects who required food/drink due to hypoglycemia were excluded from descriptive statistics. PK and PD parameters were summarized separately for these subjects, except following SC insulin where descriptive statistics were provided for all eight subjects who required intervention with food/drink due to hypoglycemia.

A number of subjects experienced hypoglycemia during treatments and were given food (chocolate, fruit or orange juice) in order to raise blood glucose levels. These subjects were excluded from the concentration-time summary statistics and the summary PK and PD parameters were presented separately from subjects who did not require hypoglycemic rescue. For those subjects who experienced hypoglycemia, additional parameters of $C^b$ and $t^b$ values for insulin, $R^b$ and $t^b$ values for glucose and $E^c$ and $t^c$ values for glucose change from baseline were recorded that reflected the concentration and time immediately prior to hypoglycemic rescue.

4-CNAB Pharmacokinetics

Individual plasma-concentrations of 4-CNAB following all treatments were tabulated. Mean (+SD) plasma concentration/time profiles of 4-CNAB following the administration of 4-CNAB alone or insulin/4-CNAB capsules to healthy male volunteers are shown in FIGS. 1 (Group 1) and 2 (Groups 2 and 3).

The mean 4-CNAB concentration-time profiles following escalating oral doses of 4-CNAB alone (FIG. 1) showed rapid absorption with peak concentrations achieved at median times of approximately 0.62 h. After reaching the maximum concentration, 4-CNAB concentrations rapidly declined in a biphasic manner. The maximum concentrations $C_{max}$ and exposure (i.e. AUCs) clearly increased with increasing dose. When the combination capsules of Insulin/4-CNAB were administered (FIGS. 2A and 2B), 4-CNAB maximum levels were reached at approximately the same time as with 4-CNAB treatments alone and 4-CNAB peak concentrations clearly increased with increasing amounts of 4-CNAB in combination with insulin. The combined treatment of 100 Units Insulin/600 mg 4-CNAB which contained the highest dose of 4-CNAB, resulted in the highest mean peak concentration while the lowest mean peak concentration was observed following the administration of lowest dose of 150 Units Insulin/100 mg 4-CNAB.

Mean values±SD, and ranges in parenthesis for $t_{max}$, for each treatment for 4-CNAB in plasma following 4-CNAB alone and Insulin/4-CNAB treatments are given below together with descriptive statistics.

Pharmacokinetic parameters of 4-CNAB following oral administration of capsules of 4-CNAB alone are summarized in Table 8 below for (Group 1), and mean (+SD) plasma concentration/time profiles are shown in FIG. 1.

TABLE 8

PK Parameters of 4-CNAB alone (Group 1)

| Parameter | 4-CNAB Dose | | | |
|---|---|---|---|---|
| | 400 mg | 800 mg | 1400 mg | 2000 mg |
| $C_{max}$ (ng/mL) | 22315 ± 11456 | 38011 ± 15804 | 103321 ± 14590 | 135199 ± 86565 |
| $t_{max}$ (h) | 0.50 (0.50-0.50) | 0.50 (0.50-0.75) | 0.75 (0.50-0.77) | 0.75 (0.50-1.50) |
| $AUC_{(0-t)}$ (ng · h/mL) | 22232 ± 6760 | 44343 ± 14478[c] | 143620 ± 33809 | 204136 ± 102850 |
| $AUC_{(0-inf)}$ (ng · h/mL) | 26708 ± 12209 | 49409 ± 15057[b] | 153815 ± 38110 | 192013 ± 37147[a] |

TABLE 8-continued

PK Parameters of 4-CNAB alone (Group 1)

| | 4-CNAB Dose | | | |
|---|---|---|---|---|
| Parameter | 400 mg | 800 mg | 1400 mg | 2000 mg |
| $K_{el}$ (l/h) | 0.11 ± 0.78 | 0.12 ± 0.04[b] | 0.18 ± 0.14 | 0.06 ± 0.03[a] |
| $t_{1/2}$ (h) | 12.0 ± 13.4 | 5.90 ± 1.55[b] | 6.3 ± 4.1 | 15.3 ± 6.9[a] |
| Cl/F (mL/min) | 294 ± 122 | 290 ± 88[b] | 160 ± 38 | 178 ± 32[a] |
| Vd/F (L) | 220 ± 130 | 156 ± 82[b] | 81 ± 50 | 245 ± 131[a] |
| $MRT_{(0-t)}$ (h) | 1.60 ± 0.23 | 1.75 ± 0.22[c] | 1.60 ± 0.20 | 1.73 ± 0.31 |
| $MRT_{(0-inf)}$ (h) | 7.30 ± 11.55 | 2.60 ± 0.53[b] | 3.06 ± 1.71 | 7.45 ± 2.36[a] |

Values are given as Mean ± standard deviation (except $t_{max}$, where median (range) is given) as N = 7 except:
[a] = 3,
[b] = 4 and
[c] = 5

Figure 2:
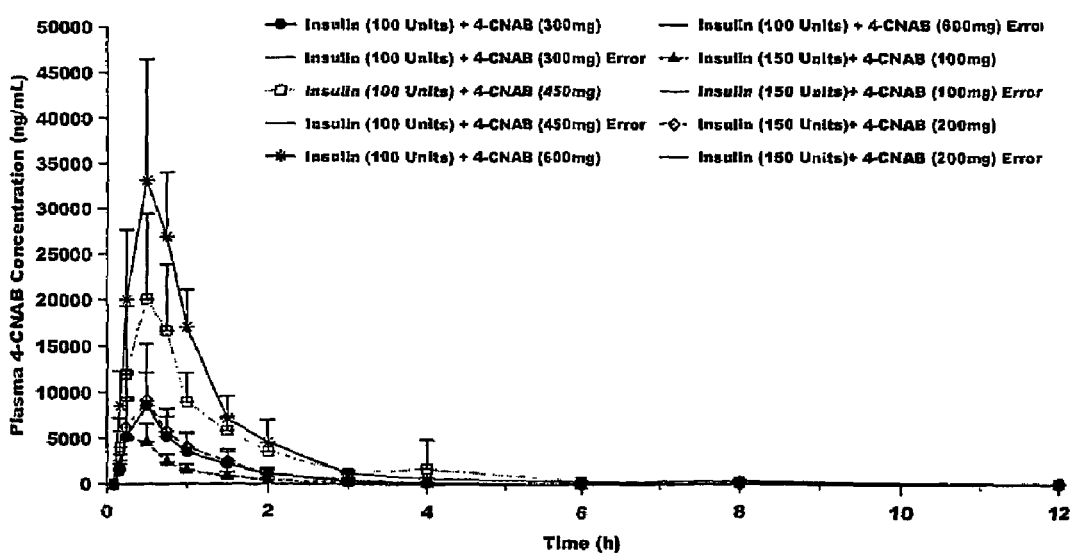
FIG. 2 shows mean (+SD) plasma concentration/time profiles of 4-CNAB following the administration of insulin/4-CNAB capsules to healthy male volunteers.

The Pharmacokinetic parameters of 4-CNAB following the administration of 4-CNAB in combination with insulin (Groups 2 and 3) are summarized in Table 9 below, and mean (+SD) plasma concentration/time profiles for Groups 2 and 3 are shown in FIG. 2.

TABLE 9

PK Parameters of 4-CNAB with Insulin (Groups 2 and 3)

| | Insulin (Units)/4-CNAB(mg) | | | | |
|---|---|---|---|---|---|
| Parameter | 100/300 | 100/450 | 100/600 | 150/100 | 150/200 |
| $C_{max}$ (ng/mL) | 8904 ± 6353 | 23183 ± 7933 | 35790 ± 12291 | 6195 ± 3605 | 10143 ± 5094 |
| $t_{max}$ (h) | 0.50 | 0.50 | 0.50 | 0.50 | 0.50 |
| | (0.27-0.75) | (0.27-4.00) | (0.25-0.77) | (0.25-1.00) | (0.25-0.55) |
| $AUC_{(0-t)}$ (ng · h/Ml) | 8745 ± 5517 | 25988 ± 4408 | 36636 ± 5764 | 4675 ± 1076 | 10018 ± 1894 |
| $AUC_{(0-inf)}$ (ng · h/mL) | 9238 ± 5938 | 26831 ± 4564 | 37571 ± 5432 | 4918 ± 1100 | 10281 ± 2078 |
| $K_{el}$ (l/h) | 0.19 ± 0.12 | 0.1852 ± 0.06 | 0.19 ± 0.06 | 0.22 ± 0.14 | 0.25 ± 0.09 |
| $t_{1/2}$ (h) | 5.3 ± 3.3 | 4.1 ± 1.2 | 4.1 ± 1.2 | 4.8 ± 3.4 | 3.2 ± 1.4 |
| Cl/F (mL/min) | 834 ± 527 | 287 ± 49 | 271 ± 38 | 352 ± 68 | 338 ± 75 |
| Vz/F (L) | 324 ± 239 | 101 ± 35 | 96 ± 35 | 148 ± 102 | 89 ± 35 |
| $MRT_{(0-t)}$ (h) | 1.51 ± 0.16 | 1.79 ± 0.50 | 1.45 ± 0.17 | 1.42 ± 0.56 | 1.59 ± 0.23 |
| $MRT_{(0-inf)}$ (h) | 2.43 ± 0.82 | 2.30 ± 0.46 | 1.90 ± 0.58 | 2.39 ± 1.39 | 1.97 ± 0.39 |

Values are given as Mean ± standard deviation (except $t_{max}$, where median (range) is given).
Mean is of eight subjects.

As can be seen from the mean concentration-time profiles in FIG. 1 and the resulting values of $C_{max}$ and $AUC_{(0-inf)}$ following 4-CNAB alone doses, levels ($C_{max}$) of 4-CNAB and exposure (AUCs) generally increased with 4-CNAB doses, as both $C_{max}$ and AUC values increased in a dose-dependent manner for the 400 mg and 800 mg doses. In the 4-CNAB alone treatment groups, the $C_{max}$ ranged between 22315±11456 ng/mL and 135199±86565 for doses of 400 mg and 2000 mg, respectively. The time of maximum 4-CNAB concentration was consistent across all doses with median values ranging between 0.50-0.75 hours. Mean elimination half-life values for 4-CNAB were variable and ranged between 5.90 and 15.3 hours due to the variability in the terminal elimination phase and difficulty in estimating the elimination rate constants. However, the MRT values were more consistent and ranged from 1.4 to 1.8 hours.

The mean 4-CNAB concentration-time profiles of FIG. 2 and parameters $C_{max}$ and AUC shown in Table 9 above for 4-CNAB following 100 Units Insulin/4-CNAB and 150 Units Insulin/4-CNAB combinations indicate increasing 4-CNAB absorption with increasing 4-CNAB dose. Generally, 4-CNAB absorption increased with increasing dose of 4-CNAB with the exception of the 100 Units Insulin/300 mg 4-CNAB treatment. In the Insulin/4-CNAB combination group, the highest values for $C_{max}$ occurred following 100 Units Insulin/600 mg 4-CNAB (35790±12291 ng/mL) and the lowest following 150 Units Insulin/100 mg 4-CNAB (6195±3605 ng/mL). Mean values of elimination half-life for 4-CNAB were less variable for the combination capsules and ranged between 3.2 hours and 5.3 hours between the dose group.

Table 10 shows a summary of Groups 1, 2 and 3 (average of all subjects in treatment groups), showing $C_{max}$, $t_{max}$ and area under the curve (AUC) of the delivery agent 4-CNAB, based upon unaudited data.

TABLE 10

4-CNAB $C_{max}$ and $t_{max}$

| Group/Treatment | 4-CNAB Dose | $C_{max}$ [ng/mL] | $t_{max}$ [hr](range) | AUC |
|---|---|---|---|---|
| 1/1 | 400 | 22,314.6 ± 11,455.7 | 0.5 (0.5) | 22,373.3 |
| 1/2 | 800 | 32,693.2 ± 16,719.5 | 0.5 (0.5-0.75) | 42,716.6 |
| 1/3 | 1400 | 97,544.6 ± 15,381.2 | 0.5 (0.5-0.75) | 144,017.1 |
| 1/4 | 2000 | 121,937.6 ± 63,321.7 | 0.75 (0.5-1.5) | 212,919.3 |
| 2/1 | None | NA | NA | NA |
| 2/2 | 200 | 9,163.3 ± 2,980.5 | 0.5 (0.25-0.5) | 10,005.2 |
| 2/3 | 600 | 33,184.6 ± 13,303.8 | 0.5 (0.25-0.75) | 36,659.9 |
| 3/1 | 300 | 8,656.9 ± 6,617.9 | 0.5 (0.25-0.75) | 8,738.8 |
| 3/2 | 450 | 20,101.7 ± 9,344.9 | 0.5 (0.25-4.0) | 25,948.0 |
| 3/3 | 100 | 5,168.4 ± 4,332.9 | 0.25 (0.25-1.0) | 4,708.6 |
| 3/4 | None | NA | NA | NA |

Insulin Pharmacokinetics

Individual plasma-concentrations of insulin following all treatments were tabulated. Mean (+SD) plasma insulin concentration/time profiles for non-hypoglycemic subjects following the administration of treatments are shown in FIGS. 3A-C and 4A-B.

Figure 3A:
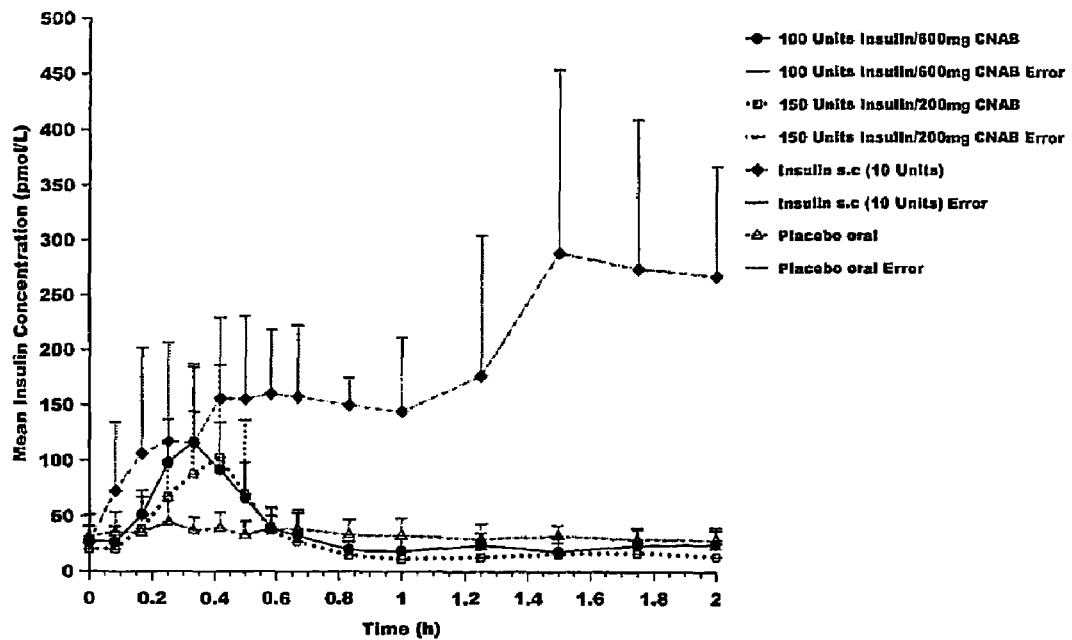
FIGS. 3A, 3B and 3C show mean (+SD) plasma insulin concentration/time profiles following the administration of 150 Units/200 mg (Insulin/4-CNAB), 100 Units/600 mg, 10 Units SC insulin and oral placebo treatment in non-hypoglycemic subjects.
Figure 3B:
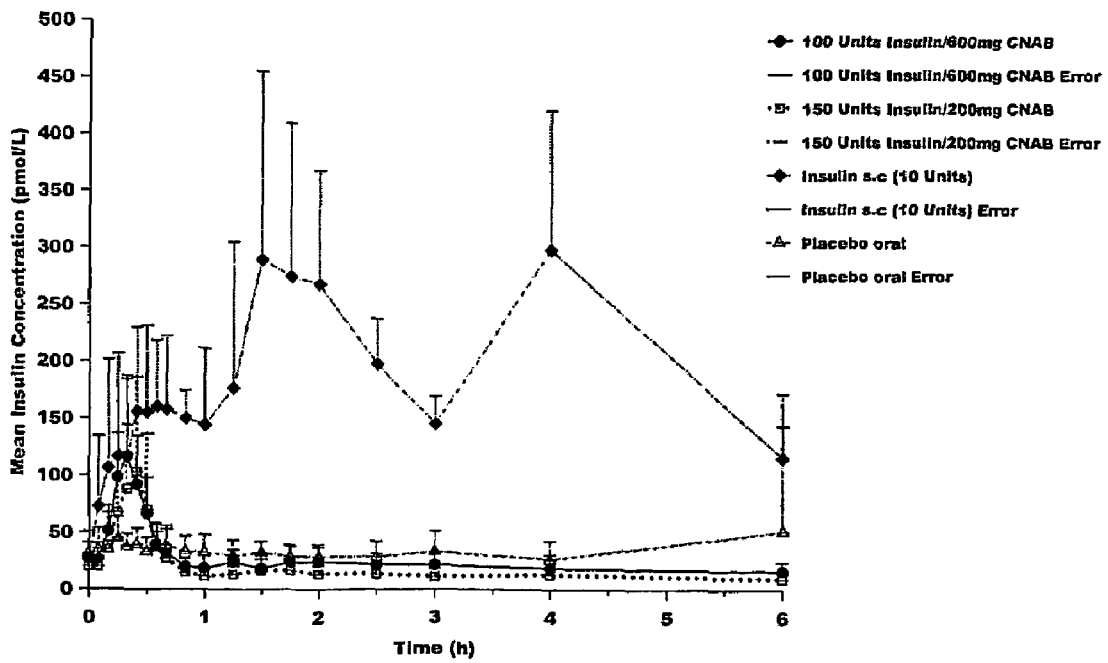
Figure 3C:
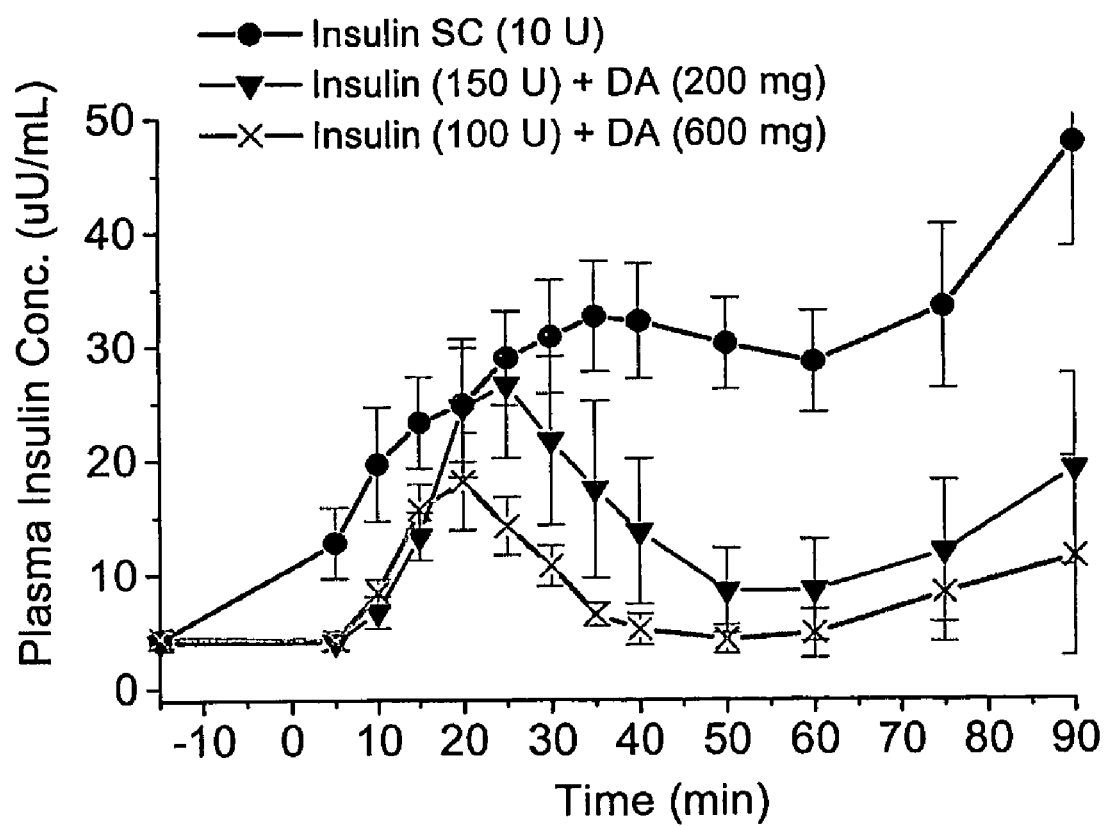
Figure 4A:
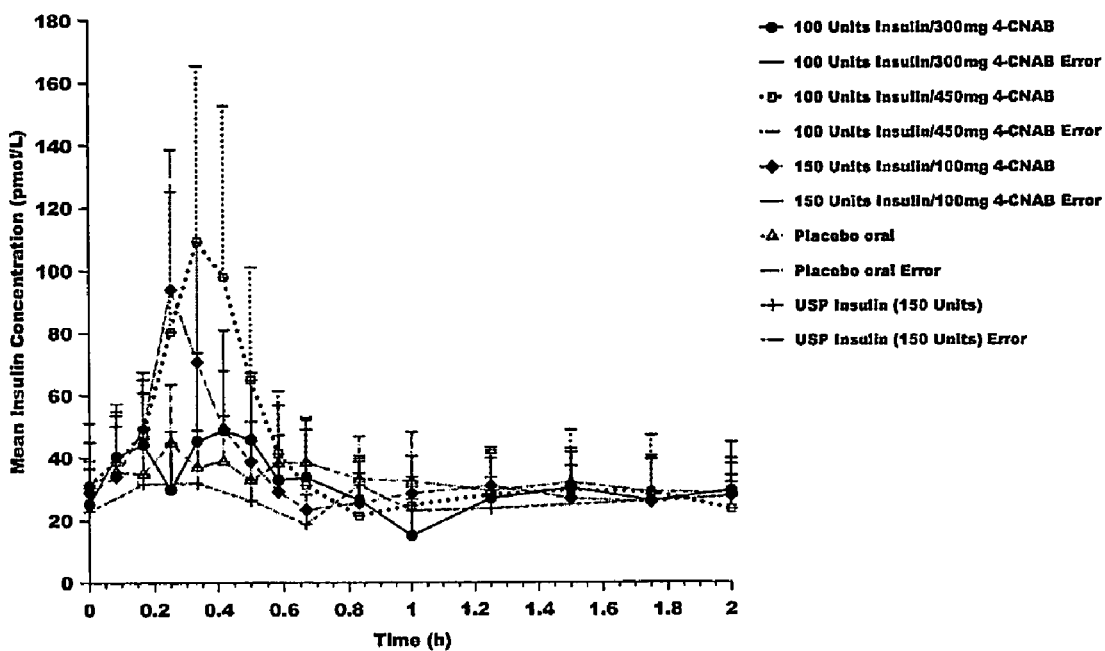
FIGS. 4A and 4B show mean (+SD) plasma insulin concentration/time profiles following the administration of 100 Units/300 mg (Insulin/4-CNAB), 100 Units/450 mg, 150 Units/100 mg, 150 Units USP oral insulin and oral placebo treatment in non-hypoglycemic subjects.
Figure 4B:
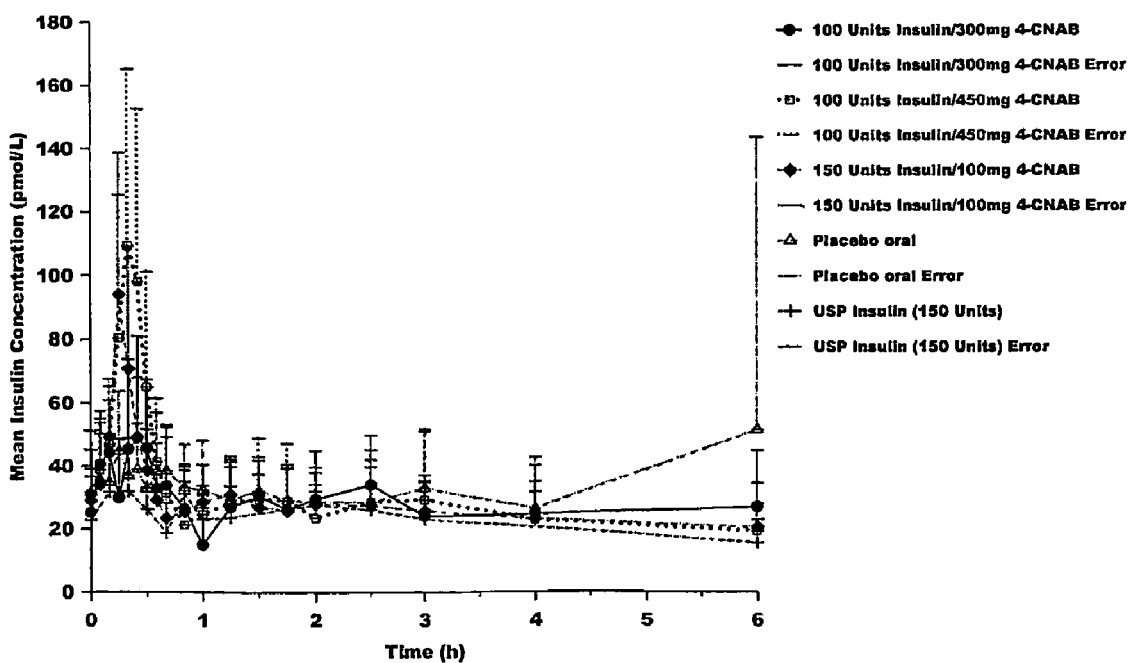

FIGS. 3A, 3B and 3C show mean (+SD) plasma insulin concentration/time profile following the administration of 150 Units/200 mg (Insulin/4-CNAB) (n=5), 100 Units/600 mg (n=7), 10 Units SC insulin (n=8) and oral placebo (n=10) treatment in non-hypoglycemic subjects (Group 2) (FIG. 3C shows this profile using unaudited data). FIGS. 4A and 4B show Mean (+SD) plasma insulin concentration/time profiles following the administration of 100 Units/300 mg (Insulin/4-CNAB) (n=7), 100 Units/450 mg (n=7), 150 Units/100 mg (n=8), 150 Units USP oral insulin (n=8) and oral placebo (n=10) treatment in non-hypoglycemic subjects (Group 3).

Mean insulin concentrations in non-hypoglycemic subjects reached peak levels between 0.4 and 0.6 hours following dosing before declining steeply to return to baseline levels after approximately 1 h. Increases in insulin absorption and exposure were observed with increasing doses (when changing from the 150 Units Insulin/100 mg 4-CNAB treatment to the 150 Units Insulin/200 mg 4-CNAB treatment) as expected. Based on $C_{max}$ and AUC values it was clear that the combined Insulin/4-CNAB treatments enabled insulin absorption significantly compared to 150 Units oral insulin alone and oral placebo. There was no insulin absorption when 150 Units insulin was dosed alone. Following 10 Units SC insulin, the mean profile for insulin concentrations was erratic, with two peak concentrations of approximately 300 pmol/L occurring at around 2 and 4 hours post-dose.

Mean values±SD of insulin PK parameters for all subjects, non-hypoglycemic subjects and hypoglycemic subjects for each treatment are given in the Tables 11 and 12 below.

TABLE 11

PK Parameters of insulin following dosing of subjects in Group 2

| | | Insulin (Units)/4-CNAB (mg) | | | |
|---|---|---|---|---|---|
| | Parameter | 150/200 | 100/600 | 10 Units SC | Oral Placebo[c] |
| All Subjects | N | 8 | 8 | 8 | 11 |
| | $C_{max}^a$ (pmol/L) | 226.9 ± 174.8 | 159.3 ± 125.6 | 374.8 ± 141.7 | 90.7 ± 91.3 |
| | $t_{max}^a$ (h) | 0.42 (0.17-1.75) | 0.33 (0.25-1.50) | 1.88 (1.58-4.00) | 0.50 (0.00-6.00) |
| | $AUC_{(0-2)}$ (pmol · h/L) | 180.68 ± 173.6 | 106.9 ± 101.6 | 414.3 ± 181.5 | 66.0 ± 22.5 |
| | $AUC_{(0-6)}$ (pmol · h/L) | 366.8 ± 367.1 | 212.4 ± 187.0 | 1228.5 ± 378.1 | 222.9 ± 127.4 |
| Non-hypoglycemic Subjects | N | 5 | 7 | — | 10 |
| | $C_{max}^a$ (pmol/L) | 114.6 ± 75.7 | 120.1 ± 64.2 | NA | 77.0 ± 83.5 |
| | $t_{max}^a$ (h) | 0.33 (0.17-0.45) | 0.33 (0.25-0.42) | NA | 0.50 (0.00-6.00) |
| | $AUC_{(0-2)}$ (pmol · h/L) | 57.2 ± 16.5 | 72.5 ± 30.5 | NA | 66.4 ± 23.6 |
| | $AUC_{(0-6)}$ (pmol · h/L) | 103.3 ± 30.9 | 149.7 ± 63.5 | NA | 202.9 ± 114.7 |
| Hypoglycemic Subjects | N | 3 | 1 | 8 | 1 |
| | $C_{max}^a$ (pmol/L) | 414.0 ± 106.7 | NA | 374.8 ± 141.7 | NA |
| | $t_{max}^a$ (h) | 0.58 (0.42-1.75) | NA | 1.88 (1.58-4.00) | NA |
| | $AUC_{(0-2)}$ (pmol · h/L) | 386.6 ± 56.6 | NA | 414.3 ± 181.5 | NA |
| | $AUC_{(0-6)}$ (pmol · h/L) | 805.8 ± 84.6 | NA | 1228.5 ± 378.1 | NA |
| | $C^b$ (pmol/L) | 62.0 ± 25.5 | NA | 168.3 ± 77.5 | NA |
| | $t^b$ (h) | 1.00 (0.62-1.00) | NA | 1.00 (0.75-1.25) | NA |

In Table 11:
values are given as Mean ± SD (except $t_{max}$, where median (range) is given).
[a]Maximum concentration and corresponding time insulin concentration up to 6 hr.
[b]Insulin concentration and corresponding time immediately prior to recovery from hypoglycemia.
[c]Oral placebo values combined for Groups 2 and 3.
NA = not applicable; either 2 subjects or less.

TABLE 12

PK Parameters of insulin following dosing of subjects in Group 3

| | | Insulin (Units)/4-CNAB (mg) | | | | |
|---|---|---|---|---|---|---|
| | Parameter | 100/300 | 100/450 | 150/100 | 150 Oral Insulin Units Alone | Oral Placebo[b] |
| All Subjects | N | 8 | 8 | 8 | 8 | 11 |
| | $C_{max}$[a] (pmol/L) | 91.0 ± 63.4 | 152.5 ± 123.5 | 95.6 ± 43.1 | 38.4 ± 12.8 | 90.7 ± 91.3 |
| | $t_{max}$[a] (h) | 0.29 (0.08-1.53) | 0.38 (0.25-3.02) | 0.25 (0.18-0.28) | 0.43 (0.17-3.00) | 0.50 (0.00-6.00) |
| | $AUC_{(0-2)}$ (pmol · h/L) | 80.5 ± 55.6 | 108.5 ± 91.9 | 69.1 ± 20.5 | 51.8 ± 15.5 | 66.0 ± 22.5 |
| | $AUC_{(0-6)}$ (pmol · h/L) | 182.0 ± 73.3 | 279.2 ± 309.0 | 163.8 ± 56.9 | 135.2 ± 47.1 | 222.9 ± 127.4 |
| Non-Hypoglycemic Subjects | N | 7 | 7 | 8 | 8 | 10 |
| | $C_{max}$[a] (pmol/L) | 69.7 ± 21.4 | 112.4 ± 53.1 | 95.6 ± 43.1 | 38.4 ± 12.8 | 77.0 ± 83.5 |
| | $t_{max}$[a] (h) | 0.25 (0.08-0.42) | 0.33 (0.25-0.42) | 0.25 (0.18-0.28) | 0.43 (0.17-3.00) | 0.50 (0.00-6.00) |
| | $AUC_{(0-2)}$ (pmol · h/L) | 61.3 ± 12.6 | 78.3 ± 36.2 | 69.1 ± 20.5 | 51.8 ± 15.5 | 66.4 ± 23.6 |
| | $AUC_{(0-6)}$ (pmol · h/L) | 167.3 ± 62.3 | 173.4 ± 83.1 | 163.8 ± 56.9 | 135.2 ± 47.1[c] | 202.9 ± 114.7 |

In Table 12:
values are given as Mean ± SD (except $t_{max}$, where median (range) is given).
[a]Maximum concentration and corresponding time insulin concentration up to 6 hr.
[b]Oral placebo values combined for Groups 2 and 3.
[c]Value corresponds to $AUC_{(0-t)}$ for 6 h sampling schedule.
NA = not applicable; either two subjects or less.

Mean $C_{max}$ insulin values in non-hypoglycemic subjects following 100 Units Insulin/300 mg 4-CNAB, 100 Units Insulin/450 mg 4-CNAB and 100 Units Insulin/600 mg 4-CNAB were 69.9±21.4 pmol/L, 112.4±53.1 pmol/L and 120.1±64.2 pmol/L, respectively. The times of peak insulin concentrations ranged between approximately 0.1 and 0.4 h for all Insulin/4-CNAB combined treatments. The insulin concentration was lowest following 150 USP Units oral insulin alone indicating no absorption of insulin when oral administration of insulin alone was administered.

Mean $C_{max}$ insulin values for all subjects (non-hypoglycemic and hypoglycemic subjects) were highly variable. Following 100 Units Insulin/300 mg 4-CNAB, 100 Units Insulin/450 mg 4-CNAB and 100 Units Insulin/600 mg 4-CNAB, mean $C_{max}$ values were 91.0±63.4 pmol/L, 152.5±123.5 pmol/L, and 159.3±125.6 pmol/L, respectively. The median times of peak insulin concentrations ranged between approximately 0.25 and 0.4 h for all Insulin/4-CNAB combined treatments.

Individual C-peptide plasma concentrations following treatments were calculated. Pharmacokinetic parameters of C-peptide corrected insulin following dosing of subjects in Group 2 are summarized below in Table 13.

TABLE 13

PK Parameters of C-peptide corrected insulin (Group 2)

| | | Insulin (Units)/4-CNAB (mg) | | | |
|---|---|---|---|---|---|
| | Parameter | 150/200 | 100/600 | 10 Units SC | Oral Placebo[c] |
| All Subjects | N | 8 | 8 | 8 | 11 |
| | $C_{max}$[a] (pmol/L) | 186.9 ± 137.2 | 118.7 ± 87.7 | 304.5 ± 130.9 | 56.3 ± 90.4 |
| | $t_{max}$[a] (h) | 0.42 (0.17-1.75) | 0.33 (0.33-1.50) | 1.88 (1.50-4.00) | 0.30 (0.00-6.00) |
| | $AUC_{(0-2)}$ (pmol · h/L) | 116.1 ± 126.5 | 50.0 ± 60.15 | 355.2 ± 170.2 | 7.4 ± 25.0 |
| | $AUC_{(0-6)}$ (pmol · h/L) | 146.9 ± 193.0 | 47.4 ± 75.3 | 942.8 ± 333.0 | 53.5 ± 132.5 |
| Non-hypoglycemic Subjects | N | 5 | 7 | — | 10 |
| | $C_{max}$[a] (pmol/L) | 97.5 ± 75.8 | 95.0 ± 61.0 | NA | 46.3 ± 88.7 |
| | $t_{max}$[a] (h) | 0.33 (0.17-0.45) | 0.33 (0.25-0.42) | NA | 0.30 (0.00-6.00) |
| | $AUC_{(0-2)}$ (pmol · h/L) | 25.9 ± 20.0 | 29.4 ± 15.5 | NA | 5.44 ± 25.4 |
| | $AUC_{(0-6)}$ (pmol · h/L) | 11.1 ± 39.2 | 21.8 ± 22.1 | NA | 37.1 ± 127.3 |
| Hypoglycemic Subjects | N | 3 | 1 | 8 | 1 |
| | $C_{max}$[a] (pmol/L) | 335.8 ± 34.16 | NA | 304.5 ± 130.9 | NA |
| | $t_{max}$[a] (h) | 0.58 (0.42-1.75) | NA | 1.88 (1.50-4.00) | NA |

TABLE 13-continued

PK Parameters of C-peptide corrected insulin (Group 2)

| | Insulin (Units)/4-CNAB (mg) | | | |
|---|---|---|---|---|
| Parameter | 150/200 | 100/600 | 10 Units SC | Oral Placebo[c] |
| $AUC_{(0-2)}$ (pmol · h/L) | 266.5 ± 31.0 | NA | 355.2 ± 170.2 | NA |
| $AUC_{(0-6)}$ (pmol · h/L) | 373.4 ± 65.2 | NA | 942.8 ± 333.0 | NA |
| $C^b$ (pmol/L) | 44.2 ± 31.25 | NA | 159.5 ± 75.6 | NA |
| $t^b$ (h) | 1.00 (0.62-1.00) | NA | 1.00 (0.75-1.25) | NA |

In Table 13, values are given as Mean ± SD (except $t_{max}$, where median (range) is given) and
[a]Maximum concentration and corresponding time C-peptide corrected insulin concentration up to 6 hr.
[b]C-peptide corrected Insulin concentration and corresponding time immediately prior to recovery from hypoglycemia.
[c]Oral placebo values combined for Groups 2 and 3.
NA—not applicable; either 2 subjects or less.

Pharmacokinetic parameters of C-peptide corrected insulin following dosing of subjects in Group 3 are summarized below in Table 14:

Mean $C_{max}$ values of C-peptide corrected insulin for all subjects achieved following 150 Units/200 mg and 100 Units/600 mg treatments were 186.9±137.2 pmol/L and 118.7±87.7

TABLE 14

PK Parameters of C-peptide corrected insulin (Group 3)

| | | Insulin (Units)/4-CNAB (mg) | | | | |
|---|---|---|---|---|---|---|
| | Parameter | 100/300 | 100/450 | 150/100 | 150 Oral Insulin Units Alone | Oral Placebo[b] |
| All Subjects | N | 8 | 8 | 8 | 7 | 11 |
| | $C_{max}^a$ (pmol/L) | 63.8 ± 61.1 | 109.4 ± 83.2 | 66.6 ± 41.7 | 16.0 ± 7.5 | 56.3 ± 90.4 |
| | $t_{max}^a$ (h) | 0.42 (0.17-1.53) | 0.38 (0.25-3.02) | 0.25 (0.18-6.02) | 2.00 (0.17-2.50) | 0.30 (0.00-6.00) |
| | $AUC_{(0-2)}$ (pmol · h/L) | 32.9 ± 57.4 | 47.7 ± 64.8 | 15.2 ± 16.2 | 10.8 ± 16.6 | 7.4 ± 25.0 |
| | $AUC_{(0-6)}$ (pmol · h/L) | 49.7 ± 92.2 | 81.5 ± 185.6 | 10.9 ± 35.2 | 21.5 ± 42.0 | 53.5 ± 132.5 |
| Non-Hypoglycemic Subjects | N | 7 | 7 | 8 | 7 | 10 |
| | $C_{max}^a$ (pmol/L) | 45.1 ± 33.5 | 84.1 ± 46.1 | 66.6 ± 41.7 | 16.0 ± 7.5 | 46.3 ± 88.7 |
| | $t_{max}^a$ (h) | 0.42 (0.17-0.50) | 0.33 (0.25-0.50) | 0.25 (0.18-6.02) | 2.00 (0.17-2.50) | 0.30 (0.00-6.00) |
| | $AUC_{(0-2)}$ (pmol · h/L) | 15.4 ± 31.4 | 25.7 ± 19.8 | 15.2 ± 16.2 | 10.8 ± 16.6 | 5.44 ± 25.4 |
| | $AUC_{(0-6)}$ (pmol · h/L) | 37.4 ± 92.2 | 16.8 ± 33.0 | 10.9 ± 35.2 | 21.5 ± 42.0 | 37.1 ± 127.3 |

In Table 14, values are given as Mean ± SD (except $t_{max}$, where median (range) is given) and:
[a]Maximum concentration and corresponding time insulin concentration up to 6 hours.
[b]Oral placebo values combined for Groups 2 and 3.

Figure 5:
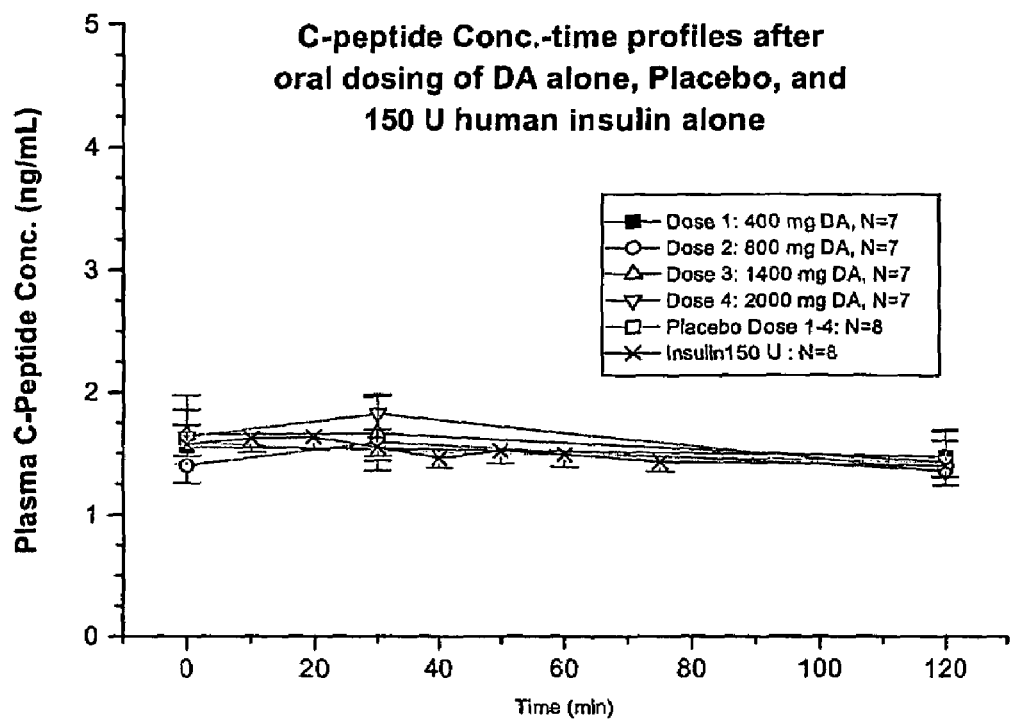
FIG. 5 shows C-peptide concentration versus time after oral dosing of 4-CNAB alone, Placebo and 150 U human insulin alone.
Figure 6:
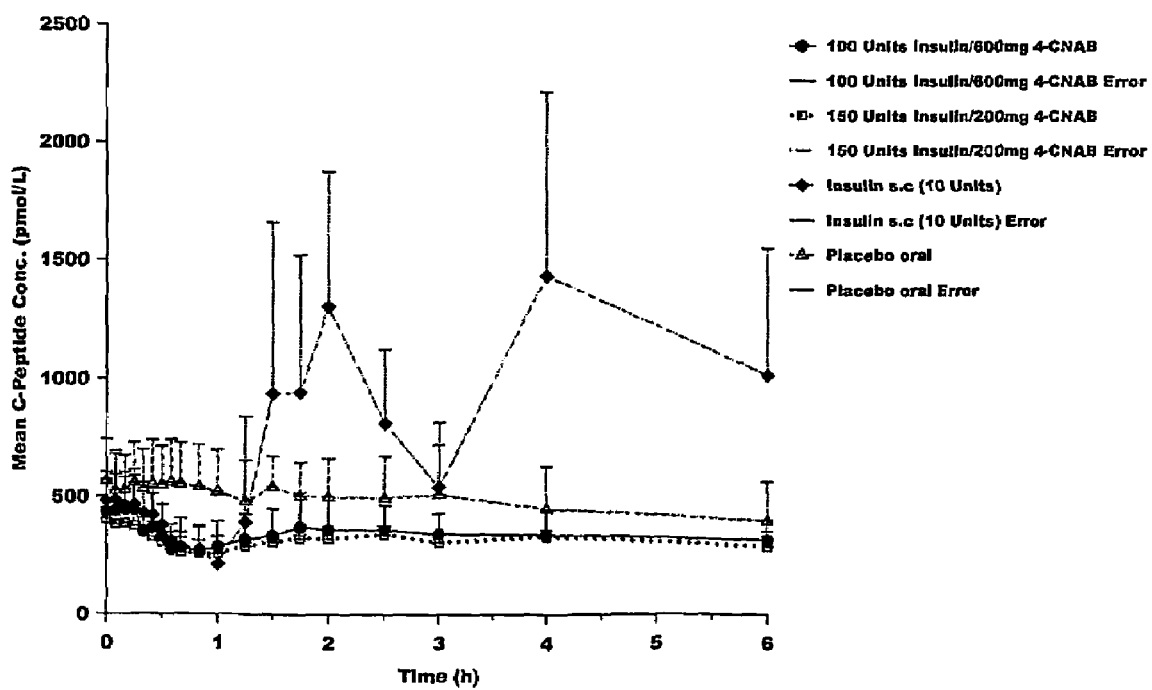
FIG. 6 shows mean (+SD) plasma C-peptide concentration/time profiles following the administration of 150 Units/ 200 mg (Insulin/4-CNAB), 100 Units/600 mg, 10 Units SC insulin and oral placebo treatment in non-hypoglycemic subjects.
Figure 8:
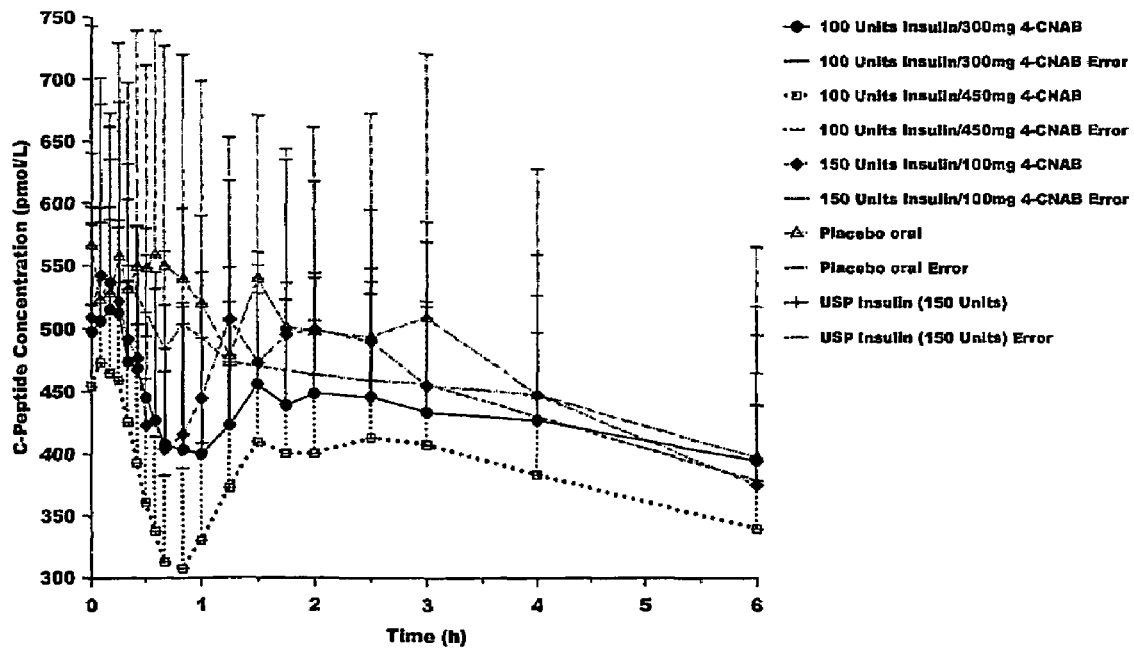
FIG. 8 shows mean (+SD) plasma C-peptide concentration/time profiles following the administration of 100 Units/ 300 mg (Insulin/4-CNAB), 100 Units/450 mg, 150 Units/100 mg, 150 Units USP Insulin and oral placebo treatment profiles in non-hypoglycemic subjects.

FIG. 5 shows the mean (+SD) plasma C-peptide concentration/time profile after oral dosing of 4-CNAB alone, Placebo and 150 U human insulin alone (Group 1). FIG. 6 shows the mean (+SD) plasma C-peptide concentration/time profiles following the administration of 150 Units/200 mg (Insulin/4-CNAB), 100 Units/600 mg, 10 Units SC insulin and oral placebo treatment in non-hypoglycemic subjects (Group 2), except for SC insulin where mean profile is for hypoglycemic subjects. FIG. 8 shows the mean (+SD) plasma C-peptide concentration/time profiles following the administration of 100 Units/300 mg (Insulin/4-CNAB), 100 Units/450 mg, 150 Units/100 mg, 150 Units USP Insulin and oral placebo treatment profiles in non-hypoglycemic subjects (Group 3).

Figure 7:
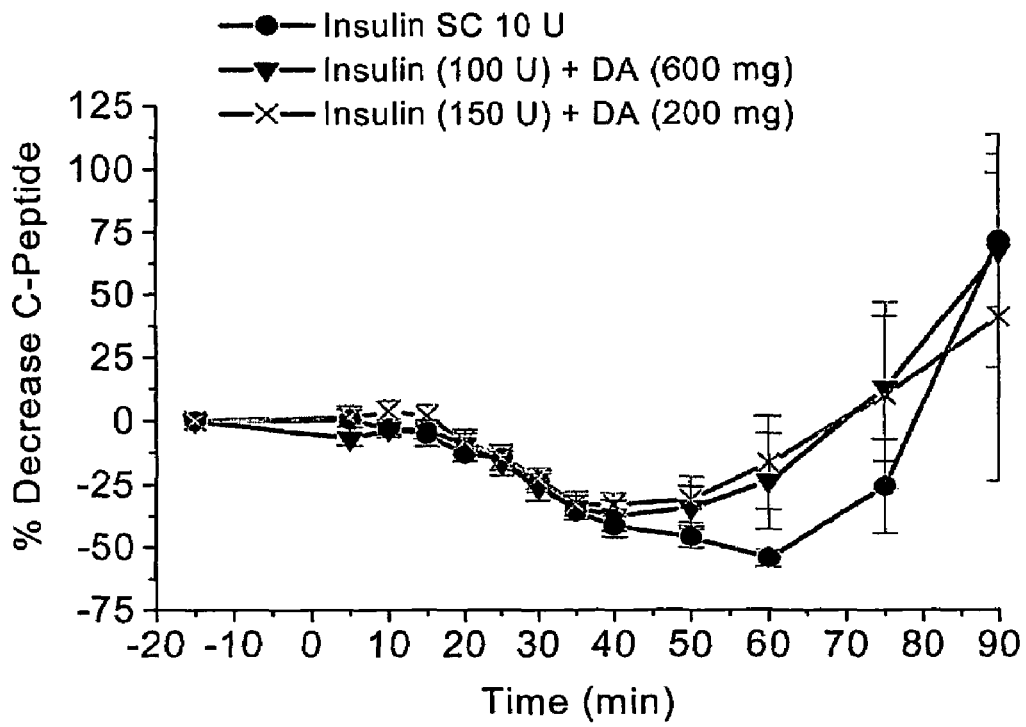
FIG. 7 shows the % decrease in C-peptide versus time after administering insulin subcutaneously and orally in the presence of 4-CNAB.

FIG. 7 shows mean (+SD) C-peptide concentration percent change from baseline/time profiles for subjects Group 2 following the administration of treatments.

pmol/L, respectively. For non-hypoglycemic subjects, following treatments containing 100 Units/300 mg, 100 Units/450 mg and 100/600 mg, there appeared to be a dose-dependent relationship in terms of C-peptide corrected insulin exposure based on $C_{max}$ and $AUC_{0-2}$ values with increasing doses of 4-CNAB. An increase in insulin exposure was also observed when changing from the 150 Units Insulin/100 mg 4-CNAB treatment to the 150 Units Insulin/200 mg 4-CNAB treatment.

Mean C-peptide concentrations declined almost immediately following dosing of the combined Insulin/4-CNAB treatments achieving the greatest decline between 0.5 and 1.0 hours. Concentrations then appeared to return to baseline levels after approximately 2 hours following dosing. Following oral placebo and 150 Units oral insulin alone there was little change in C-peptide concentrations from baseline. The mean profile following 10 Units SC insulin is for subjects who experienced hypoglycemia (8 out of 8 subjects) and were given food/drink in order to increase their blood glucose levels. C-peptide is a byproduct of endogenous insulin excretion. After giving oral insulin, the oral insulin suppresses the production of endogenous insulin, and it leads to decline of c-peptide production. The decrease of the C-peptide levels after oral administration of insulin/4-CNAB, and litter change of C-peptide levels after insulin alone or placebo dosing, clearly demonstrated effective absorption of human insulin in this study.

Following administration of 10 Units of SC insulin, all eight subjects required hypoglycemic recovery with food/drink and hence it was impossible to calculate relative bioavailability and potency for the combined oral Insulin/4-CNAB treatments. Typically, the median times of peak concentrations were around 0.3-0.4 h for all treatments except for 150 USP oral insulin alone and for SC insulin, which had median $t_{max}$ times of approximately 2.00 hours. From these data, it was clear that little of the 150 USP oral insulin was absorbed. The lack of insulin absorbed following 150 USP oral insulin alone compared to the Insulin/4-CNAB treatments indicates the effectiveness of the oral delivery agent 4-CNAB on oral absorption of human insulin.

For the Insulin/4-CNAB combined treatments containing 100 Units insulin, there appeared to be a dose-dependent relationship in terms of C-peptide corrected insulin absorption and exposure based on $C_{max}$ and $AUC_{(0-2)}$ values with increasing doses of 4-CNAB. Increases in insulin absorption and exposure were also observed for the 150 Units insulin doses (when changing from the 150 Units Insulin/100 mg 4-CNAB treatment to the 150 Units Insulin/200 mg 4-CNAB treatment) as expected. Based on $C_{max}$ and AUC values, it was clear that the combined Insulin/4-CNAB treatments enabled significant insulin absorption as compared to 150 Units oral insulin alone and oral placebo.

Based upon the above data, the following pharmacokinetic conclusions can be drawn:

The exposure to 4-CNAB increased with increasing doses of 4-CNAB alone.

The exposure to 4-CNAB appeared to increase with increasing doses of 4-CNAB in the combined Insulin/4-CNAB treatments with the exception of 100 Units Insulin/300 mg 4-CNAB treatment.

The exposure to C-peptide corrected insulin increased with increasing proportions of 4-CNAB as part of the treatment.

There was no absorption of insulin following oral administration of 150 Units oral insulin alone.

Oral absorption of insulin was greatest following administration of the combined treatments containing 150 Units Insulin/200 mg 4-CNAB and 100 Units Insulin/600 mg 4-CNAB.

Pharmacodynamic Results

Figure 9A:
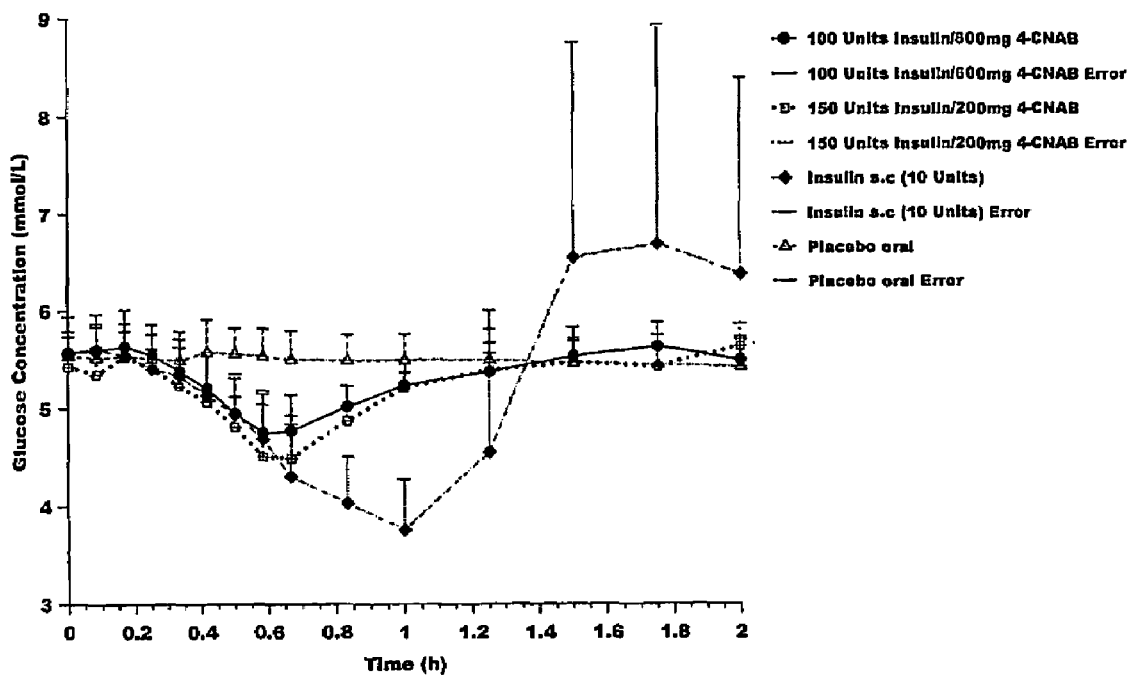
FIGS. 9A and 9B show the mean (+SD) glucose concentration/time profiles following the administration of 150 Units/200 mg (Insulin/4-CNAB), 100 Units/600 mg, 10 Units SC insulin and oral placebo treatment in non-hypoglycemic subjects.
Figure 9B:
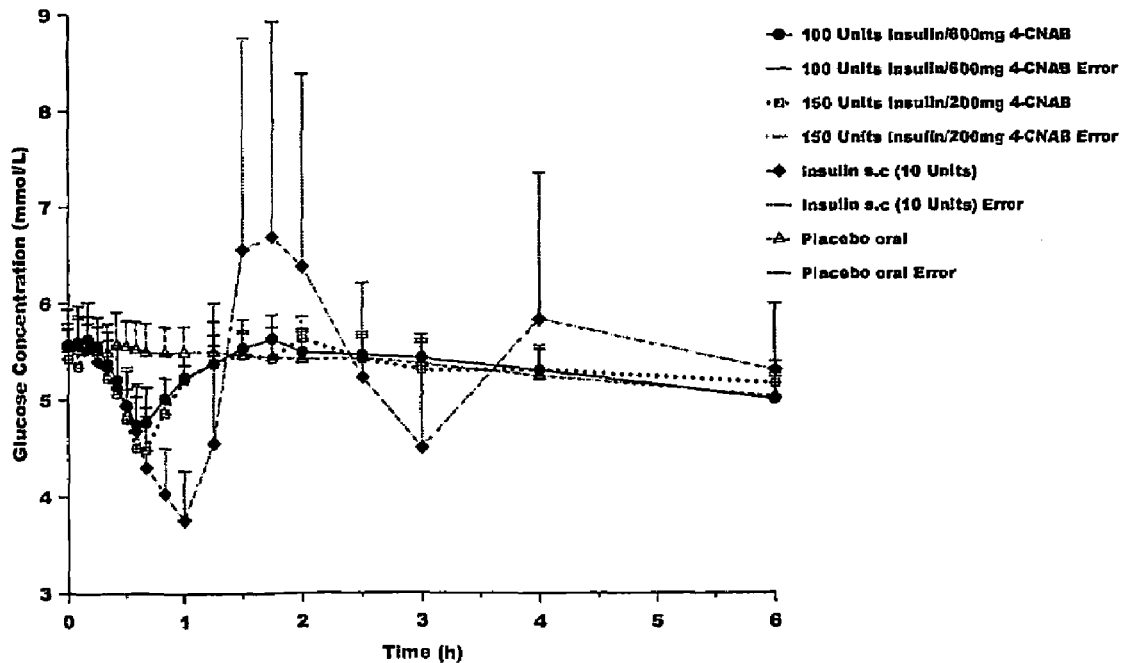
Figure 10A:
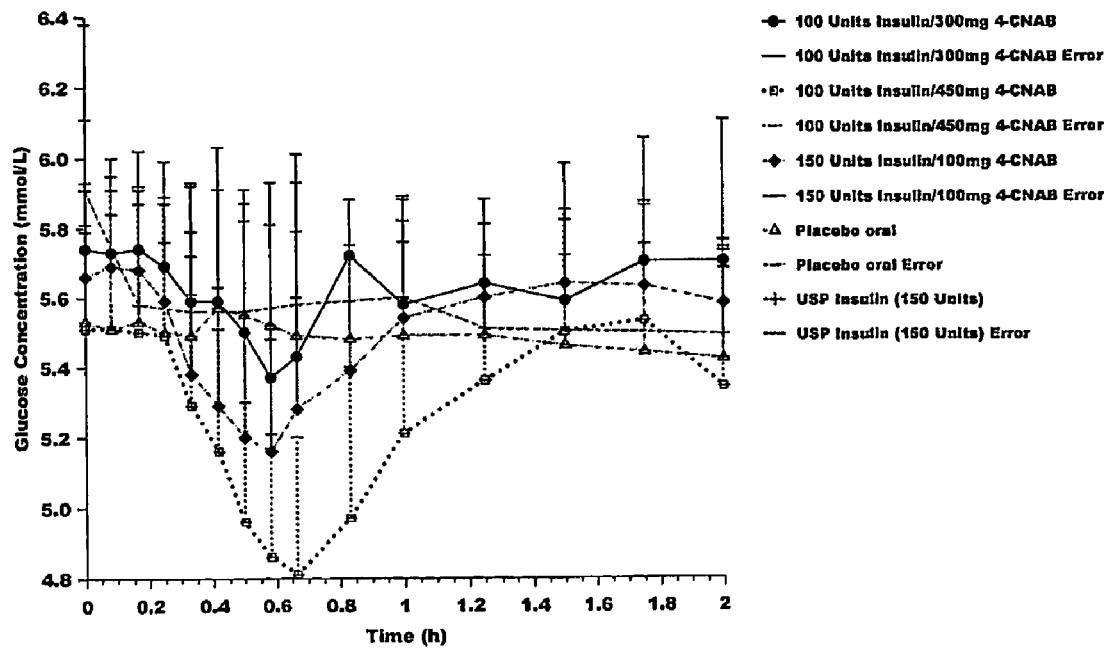
FIGS. 10A and 10B show Fe Mean (+SD) glucose concentration/time profiles following the administration of 100 Units/300 mg (Insulin/4-CNAB), 100 Units/450 mg, 150 Units/100 mg, 150 Units USP oral insulin and oral placebo treatment in non-hypoglycemic subjects.
Figure 10B:
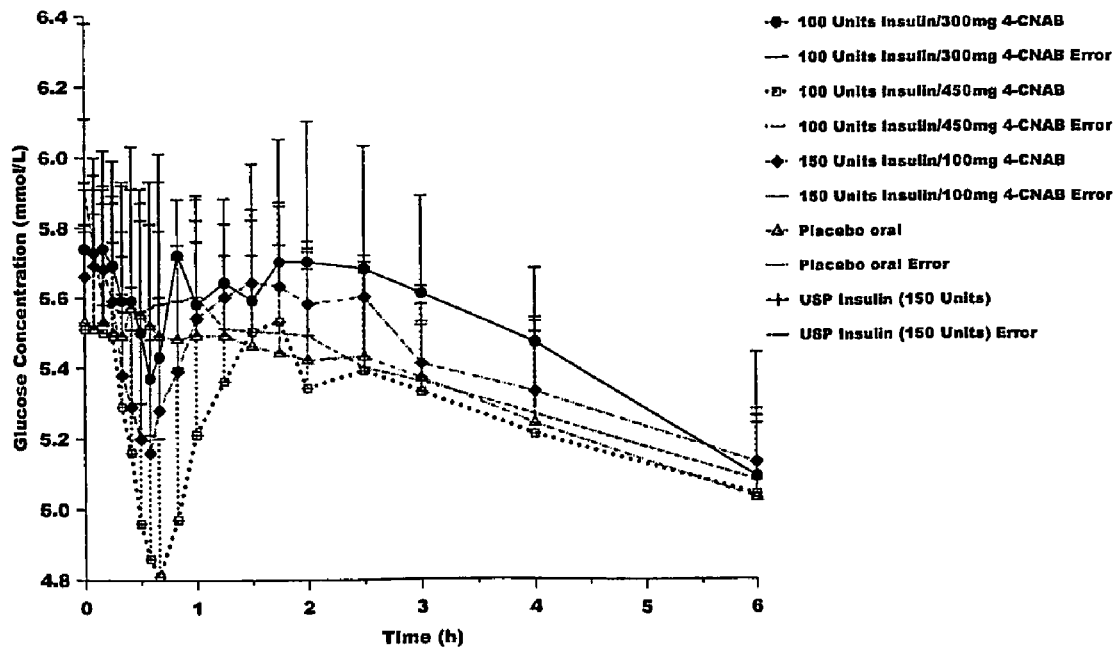

FIGS. 9A and 9B show the mean (+SD) glucose concentration/time profiles following the administration of 150 Units/200 mg (Insulin/4-CNAB) (n=5), 100 Units/600 mg (n=7), 10 Units SC insulin (n=8) and oral placebo (n=10) treatment in non-hypoglycemic subjects (Group 2). FIGS. 10A and 10B show the mean (+SD) glucose concentration/time profiles following the administration of 100 Units/300 mg (Insulin/4-CNAB) (n=7), 100 Units/450 mg (n=7), 150 Units/100 mg (n=8), 150 Units USP oral insulin (n=8) and oral placebo (n=10) treatment in non-hypoglyceric subjects (Group 3).

Mean glucose concentrations began to decline after approximately 0.2 hours following dosing of the combined Insulin/4-CNAB treatments, $R_{max}$ of the combined Insulin/4-CNAB treatments was observed to be between 0.5 and 1.0 hours following dosing. Concentrations then appeared to return to baseline levels after approximately 2 hours following dosing. Following oral placebo and 150 Units oral insulin alone there was only a slight change in glucose concentrations indicating little absorption of insulin. The mean profile following 10 SC Units of insulin is for subjects who experienced hypoglycemia (8 out of 8 subjects) and were given food/drink in order to increase their blood glucose levels.

Individual PD parameters of glucose following all treatments for hypoglycemic and non-hypoglycemic subjects were listed together with descriptive statistics. Individual plasma glucose concentration changes from baseline were tabulated, and individual glucose concentration changes from baseline/time profiles were prepared. Mean values±SD of glucose PD parameters for all subjects, non-hypoglycemic subjects and hypoglycemic subjects for each treatment are given in Tables 15 and 16 below and profiles are shown in FIGS. 9A-B and 10A-B.

TABLE 15

PD Parameters of plasma glucose (Group 2)

| | | Insulin (Units)/4-CNAB (mg) | | | |
|---|---|---|---|---|---|
| | Parameter | 150/200 | 100/600 | 10 Units SC | Oral Placebo[c] |
| All Subjects | N | 8 | 8 | 8 | 11 |
| | $R_{max}^a$ (mmol/L) | 3.95 ± 0.80 | 4.65 ± 0.30 | 3.31 ± 0.42 | 5.03 ± 0.23 |
| | $t_{Rmax}^a$ (h) | 0.63 | 0.58 | 1.00 | 6.0 |
| | | (0.58-3.00) | (0.50-6.00) | (0.67-3.00) | (0.33-6.00) |
| | $AURC_{(0-2)}$ (mmol · h/L) | 11.2 ± 1.8 | 10.85 ± 0.68 | 10.40 ± 1.36 | 11.10 ± 0.72 |
| | $AURC_{(0-6)}$ (mmol · h/L) | 33.3 ± 2.6 | 31.88 ± 1.23 | 32.02 ± 4.66 | 32.55 ± 2.41 |
| Non-hypoglycemic Subjects | N | 5 | 7 | None | 10 |
| | $R_{max}^a$ (mmol/L) | 4.40 ± 0.45 | 4.66 ± 0.32 | NA | 5.02 ± 0.24 |
| | $t_{Rmax}^a$ (h) | 0.58 | 0.58 | NA | 6.0 |
| | | (0.58-3.00) | (0.50-6.00) | | (0.33-6.00) |
| | $AURC_{(0-2)}$ (mmol · h/L) | 10.42 ± 2.19 | 10.66 ± 0.43 | NA | 10.95 ± 0.55 |
| | $AURC_{(0-6)}$ (mmol · h/L) | 31.60 ± 0.87 | 31.78 ± 1.28 | NA | 31.94 ± 1.40 |
| Hypoglycemic Subjects | N | 3 | 1 | 8 | 1 |
| | $R_{max}^a$ (mmol/L) | 3.20 ± 0.69 | NA | 3.31 ± 0.42 | NA |
| | $t_{Rmax}^a$ (h) | 1.00 | NA | 1.00 | NA |
| | | (0.58-1.00) | | (0.67-3.00) | |
| | $AURC_{(0-2)}$ (mmol · h/L) | 12.47 ± 2.81 | NA | 10.40 ± 1.36 | NA |
| | $AURC_{(0-6)}$ (mmol · h/L) | 36.03 ± 1.88 | NA | 32.02 ± 4.66 | NA |

TABLE 15-continued

PD Parameters of plasma glucose (Group 2)

| | Insulin (Units)/4-CNAB (mg) | | | |
|---|---|---|---|---|
| Parameter | 150/200 | 100/600 | 10 Units SC | Oral Placebo[c] |
| $R^b$ (mmol/L) | 3.23 ± 0.75 | NA | 3.45 ± 0.41 | NA |
| $t^b$ (h) | 1.00 | NA | 1.00 | NA |
| | (0.62-1.00) | | (0.75-1.25) | |

In Table 15, values are given as Mean ± SD (except $t_{max}$, where median (range) is given) and
[a]Minimum concentration and corresponding time in blood glucose concentration up to 6 hr post-dose.
[b]Glucose concentration and corresponding time immediately prior to recovery from hypoglycemia.
[c]Oral placebo values combined for Groups 2 and 3.
NA—not applicable; either 2 subjects or less.

TABLE 16

PD Parameters of plasma glucose (Group 3)

| | | Insulin (Units)/4-CNAB (mg) | | | | |
|---|---|---|---|---|---|---|
| | Parameter | 100/300 | 100/450 | 150/100 | 150 Oral Insulin Units Alone | Oral Placebo[b] |
| All Subjects | N | 8 | 8 | 8 | 8 | 11 |
| | $R_{max}^a$ (mmol/L) | 4.93 ± 0.55 | 4.58 ± 0.49 | 5.01 ± 0.20 | 5.08 ± 0.20 | 5.03 ± 0.23 |
| | $t_{Rmax}^a$ (h) | 0.63 | 0.67 | 0.71 | 6.00 | 6.0 |
| | | (0.08-6.00) | (0.50-6.00) | (0.50-6.00) | (0.62-6.00) | (0.33-6.00) |
| | $AURC_{(0-2)}$ (mmol · h/L) | 11.10 ± 0.66 | 10.77 ± 0.81 | 11.02 ± 0.47 | 11.06 ± 0.69 | 11.10 ± 0.72 |
| | $AURC_{(0-6)}$ (mmol · h/L) | 32.6 ± 1.75 | 32.34 ± 2.90 | 32.39 ± 0.92 | 32.15 ± 1.41 | 32.55 ± 2.41 |
| Non-Hypoglycemic Subjects | N | 7 | 7 | 8 | 8 | 10 |
| | $R_{max}^a$ (mmol/L) | 5.07 ± 0.39 | 4.71 ± 0.32 | 5.01 ± 0.20 | 5.08 ± 0.20 | 5.02 ± 0.24 |
| | $t_{Rmax}^a$ (h) | 0.67 | 0.67 | 0.71 | 6.00 | 6.0 |
| | | (0.08-6.00) | (0.50-6.00) | (0.50-6.00) | (0.62-6.00) | (0.33-6.00) |
| | $AURC_{(0-2)}$ (mmol · h/L) | 11.19 ± 0.69 | 10.57 ± 0.64 | 11.02 ± 0.47 | 11.06 ± 0.69 | 10.95 ± 0.55 |
| | $AURC_{(0-6)}$ (mmol · h/L) | 32.91 ± 1.50 | 31.47 ± 1.61 | 32.39 ± 0.92 | 32.15 ± 1.41[c] | 31.94 ± 1.40 |

In Table 16, values are given as Mean ± SD (except $t_{max}$, where median (range) is given) and
[a]Minimum concentration and corresponding time in plasma insulin concentration up to 6 hr post-dose.
[b]Oral placebo values combined for Groups 2 and 3.
[c]Value corresponds to $AURC_{(0-t)}$ for 6 h sampling schedule.

Following the combined Insulin/4-CNAB treatments, plasma glucose concentrations declined rapidly until approximately 0.75 h, then gradually increased to return to baseline levels after about 2.00 hour post-dose. From the profiles above, the maximum glucose concentration change from baseline for the Insulin/4-CNAB combination occurred following 150 Units Insulin/200 mg 4-CNAB. The treatment that had the next greatest effect on glucose appeared to be the 100 Units/600 mg 4-CNAB treatment. These findings correlated well with the peak concentrations of C-peptide corrected insulin levels achieved following these two treatments (See Table 12). Subjects who received 10 Units of SC insulin experienced the greatest decline in glucose concentrations, which hence lead to hypoglycemic response and recovery, by intervention with food/drink intake.

Figure 11A:
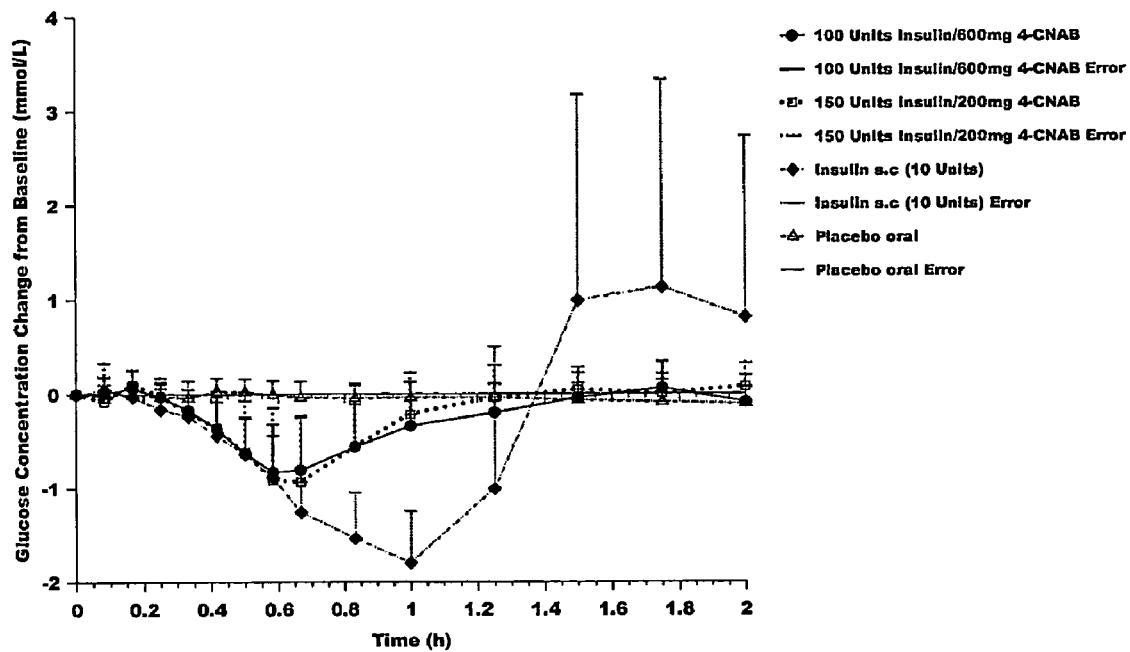
FIGS. 11A, 11B and 11C show mean (+SD) glucose concentration percent change from baseline/time profiles following the administration of 150 Units/200 mg (insulin/4-CNAB), 100 Units/600 mg, 10 Units SC insulin and oral placebo treatment in non-hypoglycemic subjects.
Figure 11B:
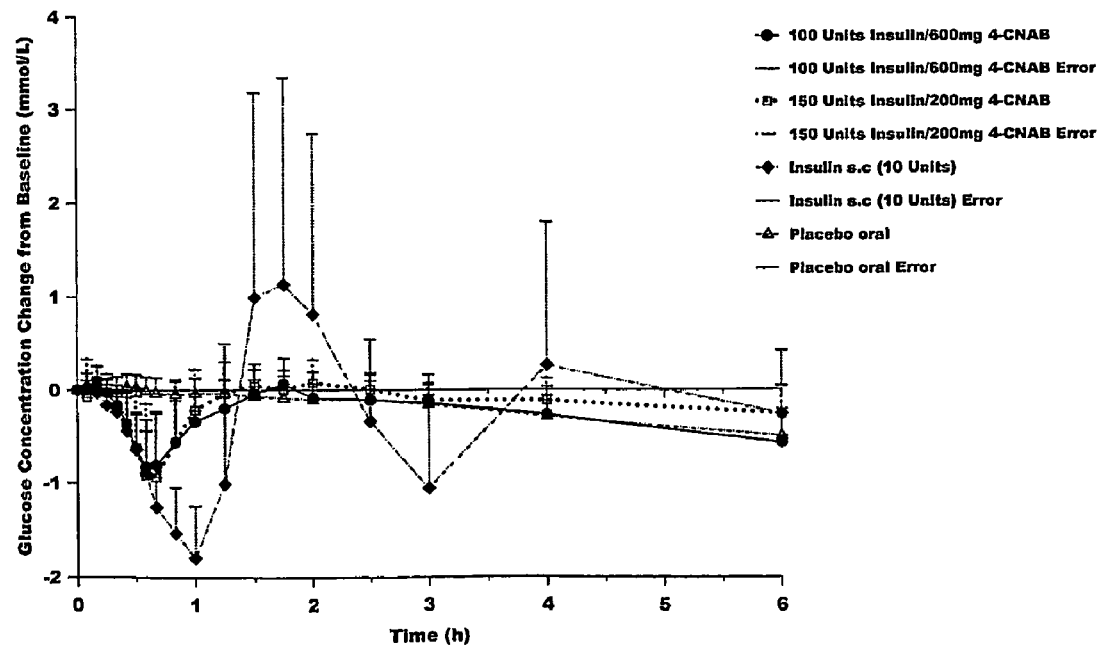
Figure 11C:
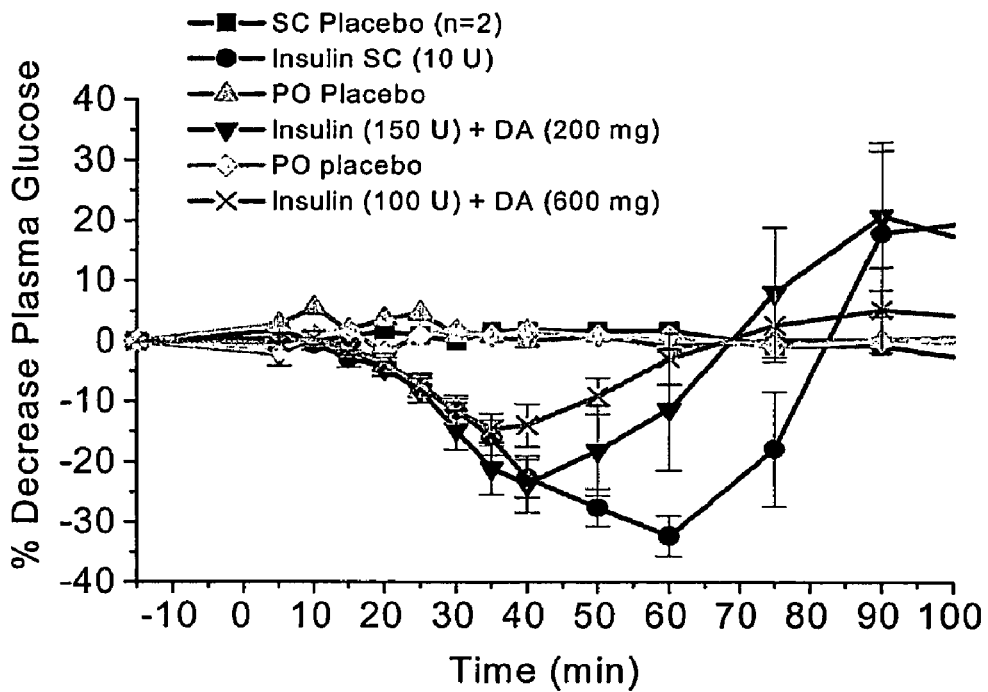
Figure 12:
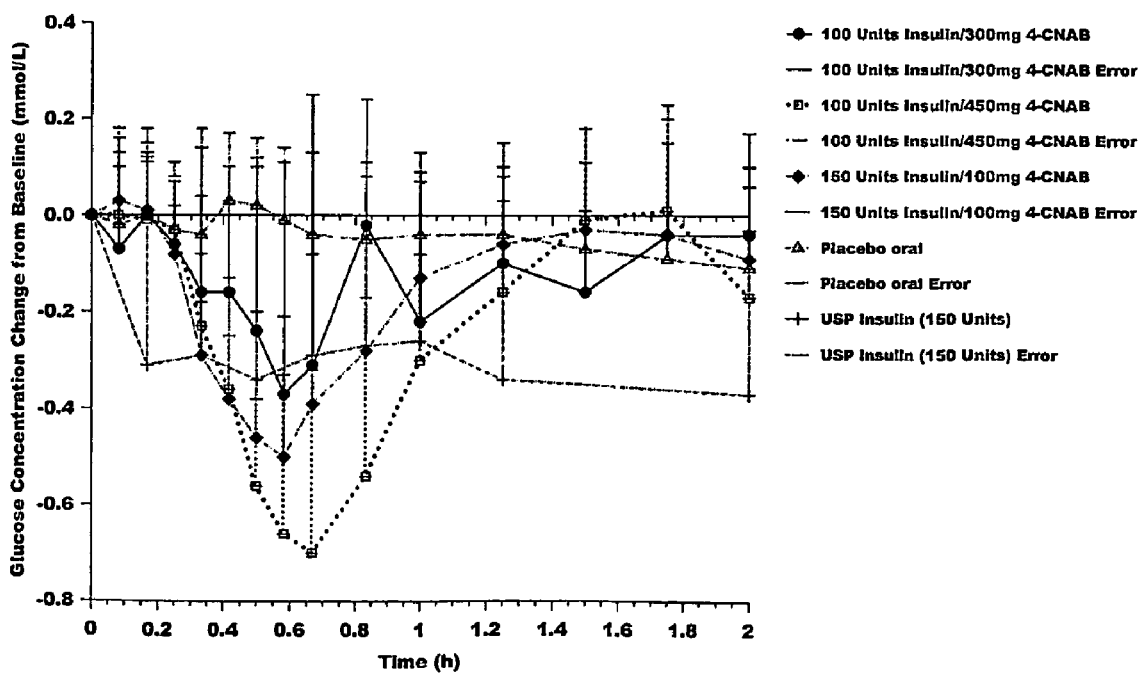
FIG. 12 shows mean (+SD) glucose concentration percent change from baseline/time profiles following the administration of 100 Units/300 mg (Insulin/4-CNAB), 100 Units/450 mg, 150 Units/100 mg, 150 Units USP oral insulin and oral placebo treatment in non-hypoglycemic subjects.

Individual PD parameters for glucose percent changes from baseline following all treatments for hypoglycemic and non-hypoglycemic subjects were tabulated and individual glucose concentration percent changes from baseline-time profiles were created, together with descriptive statistics. Mean values±SD of glucose change from baseline PK parameters for all subjects, non-hypoglycemic subjects and hypoglycemic subjects for treatment Groups 2 and 3 are given in the Tables 17 and 18 below. Mean (+SD) glucose concentration percent change from baseline/time profiles for non-hypoglycemic subjects following the administration of treatments are shown in FIGS. 11A-11C (Group 2) (FIG. 11C shows this profile using unaudited data) and FIG. 12 (Group 3), except for SC insulin where mean profile is for hypoglycemic subjects. In addition, the mean maximum percentage change from baseline up to 6 hours post-dose is also given in these tables below.

TABLE 17

PD Parameters for Change in plasma glucose from baseline (Group 2)

| | | Insulin (Units)/4-CNAB (mg) | | | |
|---|---|---|---|---|---|
| | Parameter | 150/200 | 100/600 | 10 Units SC | Oral Placebo[c] |
| All Subjects | N | 8 | 8 | 8 | 11 |
| | $E_{max}$[a] (mmol/L) | −1.65 ± 1.08 | −0.88 ± 0.48 | −2.28 ± 0.40 | −0.54 ± 0.21 |
| | % Change[b] | −28.64 ± 17.80 | −15.92 ± 7.30 | −39.82 ± 8.26 | −8.05 ± 6.23 |
| | $t_{Emax}$[a] (h) | 0.68 | 0.58 | 1.00 | 6.00 |
| | | (0.58-3.00) | (0.50-0.83) | (0.75-3.00) | (0.33-6.00) |
| | $AUEC_{(0-2)}$ (mmol · h/L) | −0.01 ± 1.59 | −0.25 ± 0.86 | −0.71 ± 1.32 | 0.05 ± 0.52 |
| | $AUEC_{(0-6)}$ (mmol · h/L) | −0.35 ± 1.72 | −2.11 ± 5.24 | −1.40 ± 4.41 | −0.65 ± 2.07 |
| Non-hypoglycemic Subjects | N | 5 | 7 | — | 10 |
| | $E_{max}$[a] (mmol/L) | −1.02 ± 0.70 | −0.89 ± 0.51 | NA | −0.54 ± 0.22 |
| | % Change[b] | −18.34 ± 11.85 | −16.08 ± 7.87 | NA | −9.49 ± 3.67 |
| | $t_{Emax}$[a] (h) | 0.67 | 0.58 | NA | 6.00 |
| | | (0.58-3.00) | (0.50-0.83) | | (0.33-6.00) |
| | $AUEC_{(0-2)}$ (mmol · h/L) | −0.42 ± 0.63 | −0.49 ± 0.59 | NA | −0.09 ± 0.27 |
| | $AUEC_{(0-6)}$ (mmol · h/L) | −0.94 ± 1.37 | −1.66 ± 1.74 | NA | −1.22 ± 0.93 |
| Hypoglycemic Subjects | N | 3 | 1 | 8 | — |
| | $E_{max}$[a] (mmol/L) | −2.70 ± 0.66 | NA | −2.28 ± 0.40 | NA |
| | % Change[b] | −45.80 ± 11.02 | NA | −39.82 ± 8.26 | NA |
| | $t_{Emax}$[a] (h) | 1.00 | NA | 1.00 | NA |
| | | (0.62-1.00) | | (0.75-3.00) | |
| | $AUEC_{(0-2)}$ (mmol · h/L) | −2.70 ± 0.66 | NA | NA | NA |
| | $AUEC_{(0-6)}$ (mmol · h/L) | 1.00 | NA | 1.00 | NA |
| | | (0.62-1.00) | | (0.75-1.25) | |
| | $E^c$ (mmol/L) | 0.67 ± 2.64 | NA | −0.71 ± 1.32 | NA |
| | $t^c$ (h) | 0.63 ± 2.06 | NA | −1.40 ± 4.41 | NA |

In Table 17, values are given as Mean ± SD (except $t_{max}$, where median (range) is given) and:
[a]Maximum change from baseline and corresponding time up to 6 h = (Glucose Concentration − Baseline Concentration).
[b]Maximum % change from baseline up to 6 h = (Glucose Concentration − Baseline Concentration/Baseline Concentration*100).
[c]Glucose concentration change from baseline and corresponding time immediately prior to recovery from hypoglycemia.
[d]Oral placebo values combined for Groups 2 and 3.
NA—not applicable; either 2 subjects or less.

TABLE 18

PD Parameters for Change in glucose concentration baseline (Group 3)

| | | Insulin (Units)/4-CNAB (mg) | | | | |
|---|---|---|---|---|---|---|
| | Parameter | 100/300 | 100/450 | 150/100 | 150 Oral Insulin Units Alone | Oral Placebo[b] |
| All Subjects | N | 8 | 8 | 8 | 7 | 11 |
| | $E_{max}$[a] (mmol/L) | −0.75 ± 0.50 | −0.94 ± 0.46 | −0.66 ± 0.21 | −0.79 ± 0.43 | −0.54 ± 0.21 |
| | % Change[b] | −14.19 ± 9.98 | −16.98 ± 8.28 | −11.62 ± 3.28 | −12.41 ± 6.48 | −8.05 ± 6.23 |
| | $t_{Emax}$[a] (h) | 0.69 | 0.67 | 3.42 | 6.00 | 6.00 |
| | | (0.08-6.02) | (0.50-6.00) | (0.50-6.02) | (0.67-6.00) | (0.33-6.00) |
| | $AUEC_{(0-2)}$ (mmol · h/L) | −0.26 ± 0.41 | −0.26 ± 0.63 | −0.29 ± 0.34 | −0.63 ± 0.77 | 0.05 ± 0.52 |
| | $AUEC_{(0-6)}$ (mmol · h/L) | −1.50 ± 1.41 | −0.73 ± 2.67 | −1.59 ± 1.16 | −3.01 ± 2.44[d] | −0.65 ± 2.07 |
| Non-Hypoglycemic Subjects | N | 7 | 7 | 8 | 7 | 10 |
| | $E_{max}$[a] (mmol/L) | −0.26 ± 0.96 | −0.80 ± 0.27 | −0.66 ± 0.21 | −0.79 ± 0.43 | −0.54 ± 0.22 |
| | % Change[b] | −12.64 ± 9.70 | −14.47 ± 4.60 | −11.62 ± 3.28 | −12.41 ± 6.48 | −9.49 ± 3.67 |
| | $t_{Emax}$[a] (h) | 4.00 | 0.67 | 3.42 | 6.00 | 6.00 |
| | | (0.10-6.00) | (0.50-6.00) | (0.50-6.02) | (0.67-6.00) | (0.33-6.00) |
| | $AUEC_{(0-2)}$ (mmol · h/L) | −0.31 ± 0.41 | −0.46 ± 0.32 | −0.29 ± 0.34 | −0.63 ± 0.77 | −0.09 ± 0.27 |
| | $AUEC_{(0-6)}$ (mmol · h/L) | −1.54 ± 1.51 | −1.61 ± 0.98 | −1.59 ± 1.16 | −3.01 ± 2.44[d] | −1.22 ± 0.93 |

In Table 18:
[a]Maximum change from baseline and corresponding time up to 6 h = (Glucose Concentration − Baseline Concentration).
[b]Maximum % change from baseline up to 6 h = (Glucose Concentration − Baseline Concentration/Baseline Conc).
[c]Oral placebo values combined for Groups 2 and 3.
[d]Value corresponds to $AUEC_{(0-t)}$ for 6 h sampling schedule.

Table 19 below shows a comparison of the effects of the insulin and 4-CNAB combinations in Groups 2 and 3, based upon unaudited data.

TABLE 19

Comparison of Effects of Oral Insulin (Groups 2 and 3)

| Insulin (Units) | Carrier (Mg) | # of Subjects | Basal Insulin (uU/ml) | Insulin $t_{max}$ (Min) | Insulin $C_{max}$ (uU/ml) | % Max Glucose Reduction | % Max C-peptide Reduction |
|---|---|---|---|---|---|---|---|
| 10 (SC) | 0 | 8 | 4.3 ± 2.5 | 105 | 54.5 ± 25.6 | 32.3 ± 9.6 | 54.3 ± 9.8 |
| 150 (PO) | 200 | 8 | 4.1 ± 1.9 | 25 | 26.6 ± 18.2 | 23.7 ± 13.2 | 37.5 ± 16.9 |
| 100 (PO) | 600 | 8 | 4.4 ± 2.3 | 20 | 18.1 ± 11.3 | 14.6 ± 7.5 | 33.1 ± 13.0 |
| 100 (PO) | 300 | 8 | 3.8 ± 3.4 | 25 | 9.5 ± 6.3 | 8.8 ± 10.2 | 21.7 ± 16.2 |
| 100 (PO) | 450 | 8 | 5.1 ± 2.2 | 20 | 19.1 ± 9.0 | 14.5 ± 8.0 | 32.6 ± 12.7 |
| 150 (PO) | 100 | 8 | 4.8 ± 1.8 | 15 | 14.5 ± 7.7 | 8.8 ± 5.1 | 17.9 ± 13.1 |

The greatest change from baseline of glucose based on $E_{max}$ was produced by the 150 Units/200 mg followed by the 100 Units/600 mg and 100 Units/450 mg treatments giving values of −1.0±0.7 mmol/L, −0.9±0.5 mmol/L and −0.8±0.3 mmol/L, respectively in non-hypoglycemic subjects. The effect of insulin on maximum glucose change from baseline appeared to increase with increasing doses of 4-CNAB and plasma concentrations of C-peptide corrected insulin, ranging between −0.3±1.0 mmol/L and −0.9±0.5 mmol/L for 100 Units Insulin/300 mg 4-CNAB and 100 Units Insulin/600 mg 4-CNAB treatments, respectively. In general, there was a good correlation between increasing Insulin/4-CNAB doses and C-peptide corrected plasma insulin concentrations and maximum plasma glucose percent reduction from baseline.

The greatest percent reduction in plasma glucose concentration was achieved after oral dosing of the 150 Units/200 mg treatment followed by the 100 Units/450 mg and 100 Units/600 mg treatments giving maximum percent reduction values of −28.64±17.80%, −16.98±8.28% and −15.92±7.30%, respectively. For these treatments, similar $AUEC_{(0-2)}$ values were observed, all approximately −0.4 mmol.h/L as well as similar $t_{Emax}$ median times of approximately 0.6 h. Maximum % reduction in glucose concentrations from baseline increased with increasing doses of 4-CNAB, with values ranging between −12.6 and −16.1% for the 100 Units Insulin/300 mg 4-CNAB and 100 Units Insulin/600 mg 4-CNAB treatments, respectively.

A similar good correlation was observed between maximum glucose percent change (reduction from baseline) and Insulin/4-CNAB doses and C-peptide corrected insulin concentrations. The greatest percent change (decline) in glucose levels was produced in subjects receiving 10 Units SC insulin (−39.82±8.26%), ($E_{max}$: −2.28±0.5 mmol/L) which led to the need for hypoglycemic recovery, and in subjects receiving oral dose of 150 Units/200 mg (−28.64±17.80

Based upon the above data, the following pharmacodynamic conclusions can be drawn:

The effect of insulin on the mean maximum glucose concentration change from baseline ($E_{max}$) appeared to increase with increasing doses of 4-CNAB as part of the combined treatments.

In general an increasing effect on glucose concentration change from baseline and glucose concentration percent change from baseline were observed with increasing Insulin/4-CNAB doses and C-peptide corrected insulin concentrations.

Based on the mean maximum glucose concentration change from baseline ($E_{max}$), 100 Units Insulin/600 mg 4-CNAB and 150 Units Insulin/200 mg 4-CNAB appeared to elicit a greater PD response compared to oral placebo and 150 Units oral insulin alone, indicating the effectiveness of the deliver agent in delivering insulin.

The effect of any of the oral Insulin/4-CNAB combinations in lowering glucose levels was less than that observed for SC insulin.

Discussion and Overall Conclusions

There were no deaths or serious adverse effects in this study. All subjects passed screening and completed the study, and none withdrew from the study for study drug related reasons. There were no clinically significant abnormal results as assessed by vital signs, ECG, clinical laboratory parameters (except blood glucose) and physical examination. There were 42 adverse effects (AEs) following treatments that were thought to be related to study drug.

Oral administration of 4-CNAB alone was well tolerated. The safety profiles following 4-CNAB alone were very good with very few AEs. Most treatment-related AEs were reported following 150 Units Insulin/200 mg 4-CNAB (n=7) and after 100 Units Insulin/450 mg 4-CNAB (n=6) in addition to sixteen events following 10 Units SC insulin. Forty-one of the total treatment related 42 AEs were classified as mild in severity. The most common treatment-emergent AEs reported during the study were hypoglycemia (26), headache (12) and dizziness (5). During the 26 episodes of hypoglycemia, subjects required rescue treatment on twenty occasions, i.e., food/drink in order to raise their blood glucose, on twenty occasions. Of these, twelve were following 10 Units SC insulin and there were following 150 Units Insulin/200 mg 4-CNAB.

The exposure to 4-CNAB appeared to increase with increasing doses of 4-CNAB when given alone. Oral administration of 4-CNAB alone had no significant effect on plasma glucose levels in human subjects. C-peptide corrected plasma insulin increased with increasing doses of 4-CNAB, demonstrating effective oral delivery and absorption of human insulin.

Mean 4-CNAB peak plasma concentrations and AUC appeared to increase with increasing doses of 4-CNAB either when given alone or as part of the Insulin/4-CNAB treatments, with the exception of the 100 Units Insulin/300 mg 4-CNAB treatment. The median time of maximum 4-CNAB concentration was similar (around 0.6 hours) for 4-CNAB alone and when given as the combined Insulin/4-CNAB treatment. The half-life of 4-CNAB was highly variable when given alone but more consistent with a half-life value of around 4 hours when given with insulin. The variability in the half-life was due to the variable in the terminal elimnation phase and difficulty in estimating the elimination rate constants. However, the MRT values were more consistent and ranged from 1.4 to 1.8 hours for all treatments The oral absorption and exposure of insulin based on $C_{max}$ and $AUC_{(0-2)}$ increased with increasing doses of 4-CNAB, indicating effective absorption of insulin with increasing levels of 4-CNAB. The absorption and exposure to insulin following Insulin/4-CNAB treatments was clearly greater than when given 150 USP oral insulin alone. Based on the mean maximum percent plasma glucose reduction, the treatments 100 Units Insulin/600 mg 4-CNAB and 150 Units Insulin/200 mg 4-CNAB appeared to elicit a greater PD response compared to oral placebo or 150 Units oral insulin alone, indicating the effectiveness of the delivery agent in delivering insulin and producing a subsequent effect.

Mean C-peptide corrected insulin $C_{max}$ ranged between 45.1±33.5 pmol/L, 95.0±61.0 pmol/L, and 97.5±75.8 pmol/L for doses of 100 Units Insulin/300 mg 4-CNAB, 100 Units Insulin/600 mg 4-CNAB, and 150 Units Insulin/200 mg 4-CNAB respectively. Unfortunately, because all eight subjects required rescue with food after 10 Units SC insulin due to hypoglycemia, it was difficult to obtain an accurate measure of insulin relative bioavailability of the Insulin/4-CNAB treatments compared to SC dosing.

Increases in mean $E_{max}$ and $AUEC_{(0-2)}$ were seen with increasing levels of 4-CNAB as part of Insulin/4-CNAB treatments and with increasing plasma concentrations of C-peptide corrected insulin. Mean maximum glucose % reduction from baseline ranged between −12.64±9.7% and −14.47±4.6% for the 100 Units Insulin/300 mg 4-CNAB and 100 Units Insulin/600 mg 4-CNAB treatments, respectively. The values for AUEC(O-2) ranged between −0.31±0.41 mmol.h/L and −0.49±0.59 for the 100 Units Insulin/300 mg 4-CNAB and 100 Units Insulin/600 mg 4-CNAB treatments, respectively.

Thus, the effect of insulin on the mean maximum plasma glucose concentration change from baseline ($E_{max}$) increased with increasing doses of 4-CNAB and was significantly greater than oral insulin alone and placebo for all combined treatments indicating the effectiveness of the delivery agent in delivering insulin. In general, an increasing effect of oral insulin on plasma glucose concentration change from baseline and percent change from baseline was observed with increasing Insulin/4-CNAB doses.

EXAMPLE 6

Comparison of Pharmacodynamic and Pharmacokinetic Properties of Oral Insulin vs. Subcutaneous (Sc) Regular Insulin in Type 2 Diabetic Patients A single-center, open-label, randomized, active controlled, 3-period crossover study was conducted in ten patients with type 2 diabetes in order to compare the pharmacodynamic (PD) and pharmacokinetic (PK) characteristics of an oral insulin formulation with SC regular insulin using the glucose clamp technique and in order to get a first impression about the metabolic effect of oral insulin in the main target population.

The glucose clamp technique was applied to compare the time-action profiles of the orally applied insulin in comparison to SC regular insulin. This method utilizes negative feedback from frequent blood glucose sample values to adjust a glucose infusion to maintain a defined and constant blood glucose level. The glucose infusion rate therefore becomes a measure of the pharmacodynamic effect of any insulin administered.

A primary objective of this study was to compare the PK and PD effect of two doses of an oral insulin capsule formulation (300 U Insulin/400 mg 4-CNAB in 2 capsules, and 150 U Insulin/200 mg 4-CNAB in one capsule) with that of 15 U SC injected regular insulin. Relative bioavailability and biopotency of the two oral formulations vs. SC injection was determined, inter-subject variability was investigated for selected PD and PK parameters.

Male subjects between 35 and 70 years old, inclusive, with type 2 diabetes mellitus as defined by the American Diabetes Association (1998 Diabetes care, 21: S5-S19) for more than one year were chosen. Subjects included in the study had BMI<36 kg/m², had stable glycemic control ($HbA_{1C}$<11%), were off all oral hypoglycemic agents 24 hours prior to each study dosing day and off any investigational drug for at least four (4) weeks prior to Visit 1, refrained from strenuous physical activity beginning 72 hours prior to admission and through the duration of the study, and were confined to the clinical research unit as required by the protocol. Subjects maintained a constant body weight (+/−2 kg).

At Visit 1, the subjects arrived at the clinic in a fasted state (no caloric intake for at least 12 hours). The subjects' height, weight, body mass index (BMI), vital signs and medical history were recorded, and a physical examination was done. An electrocardiogram (ECG) was performed for all subjects as well as local screening laboratory tests.

The oral treatment provided was Insulin/4-CNAB (Monosodium N-(4-chlorosalicyloyl)-4-aminobutyrate (4-CNAB). The insulin used to prepare the capsules was Zinc-Insulin Crystals Human: Proinsulin Derived (Recombinant DNA Origin) USP Quality obtained from Eli Lilly and Company (Indianapolis, Ind.). Each Insulin/4-CNAB capsule contained 150 Insulin Units USP and 200 mg 4-CNAB, and was prepared by AAI Pharma, Inc., Wilmington, N.C. Two tablets were given to those who received the 300 U oral Insulin/400 mg 4-CNAB treatments.

Insulin/4-CNAB capsules were provided in HDPE bottles, each of which contained 40 capsules and a polyester coil. Each bottle had a heat-induction seal and a child-resistant cap, and were stored frozen at or less than minus 10° C. On the day of dosing, the appropriate number of capsules was removed from the freezer and brought to room temperature (between 15 and 30° C.) for about one hour. Capsules were used within four hours of dispensing, and unopened bottles were not left at room temperature for more than four hours.

The SC injection was U-100 human regular insulin (Humulin® R from Eli Lilly and Company), at a dose of 15 U, supplied in 1.5-mL cartridges-100 units/mL, provided by Profil. The Insulin was stored in the refrigerator within a temperature range of 5-8° C.

At Visit 2, each subject was randomized to one of the two possible treatment sequences. Each subject received one of the two treatments during a glucose clamp procedure: an oral treatment (treatment A) of 300 U oral Insulin/400 mg 4-CNAB (in 2 capsules) or one SC treatment (treatment B) of 15 U regular SC insulin.

At Visit 3, the subjects received the alternative treatment A or B, i.e., the one they did not receive in Visit 2, in conjunction with a glucose clamp procedure according to their randomization sequence. Only subjects having received both treatments by the end of Visit 3 were regarded as completers. A final examination (Visit 4) was performed after Visit 3, preferably immediately after the glucose clamp procedures were completed, but no longer than 14 days after Visit 3.

All the subjects were invited to attend a third treatment day (Visit 5), on which they received another oral treatment (treatment C) of a single dose of 150 U of the oral Insulin/200 mg 4-CNAB (one capsule). Eight of ten patients received the treatment C. A "second" final medical examination (Visit 6) was performed after Visit 5, preferably immediately after the glucose clamp procedures were completed, but no longer than 14 days after Visit 5.

The assignment of the treatments within each sequence is described in Table 21 below:

TABLE 21

| Treatment | Treatment Period | | |
|---|---|---|---|
| Sequence | 1 (Visit 2) | 2 (Visit 3) | 3 (Visit 5) |
| 1 | A | B | C (optional) |
| 2 | B | A | C (optional) |

The SC insulin dose of 15 U was selected to fall within a range typical for type 2 diabetic patients. The oral dose of 150 U insulin (combined with 200 mg 4-CNAB) estimated to be equivalent to the SC dose was a 10-fold scale-up compared with the SC dose, based on previous investigational studies. The oral dose of 300 U insulin (combined with 400 mg 4-CNAB) was a 20-fold scale-up compared with the SC dose.

Since the three treatments were single dose administrations, a cross-over design was the most appropriate in order to keep patient numbers low and to reduce data variability. SC injection of 15 U regular insulin is a common standard treatment and was therefore used as control. Two oral insulin doses were chosen to demonstrate a dose dependency of PK and PD parameters and to investigate whether or not the suppressive effect on hepatic glucose production could be seen also at the reduced oral dose of 150 U.

All treatment periods started in the morning after an overnight fast of at least 12 hours. Dosing was performed following a period of 6 hrs of stabilization of the blood glucose by means of the glucose clamp. The subjects received the oral insulin capsules with 200 mL of water in an upright position. For s.c. insulin administration, a 29 gauge needle was inserted perpendicularly into a raised skinfold in the left lower quadrant of the abdominal wall, approximately 10 cm from the umbilicus. For oral insulin administration, the capsules were administered with 200 mL of water to the patients in an upright position. The total administration time did not exceed 2.5 minutes. Subjects remained upright for four hours after taking the study drug.

During each study visit, stabilized individual blood glucose concentrations were maintained after drug administration using a glucose clamp procedure. The glucose clamp technique [DeFronzo, et al. 1979, Glucose Clamp Technique: A Method of Quantifying Insulin Secretion and Resistance, Am. J. Physiol. 237: E214-E223.] was use to compare the time-action profiles of the orally-applied insulin to s.c. insulin. This method utilizes negative feedback from frequent blood glucose sample values to adjust a glucose infusion to maintain euglycemia. The glucose infusion rate becomes a measure of the pharmacodynamic effect of any insulin administered.

The patients' fasting blood glucose concentration at Visit 2 (measured before the baseline insulin infusion was established) was the target level for the glucose clamp experiments. At the following clamps, the fasting blood glucose concentrations were not allowed to differ more than 4 mmol/L (72 mg/dL) from this individualized clamp level, otherwise the visits were postponed for at least 24 hrs.

In each treatment arm, all patients received the same SC or oral insulin dose. The patients' fasting blood glucose concentration, measured before the baseline insulin infusion was established, was the target level for the glucose clamp experiments. During the consecutive glucose clamp experiments, the fasting blood glucose concentration was not allowed to differ more than 4 mmol/L (72 mg/dL) from this individualized clamp level, otherwise the visits were postponed for at least 24 hrs.

The clamp level was adjusted by a variable intravenous (IV) insulin infusion and glucose infusion rate during a 6 hour baseline period before dosing. During the last 2 hours before administration of the study medication, the insulin infusion was set to a rate of 0.2 mU/kg/min, which rate was not changed until the end of the experiment. At t=0 minutes, exogenous insulin was administered by oral administration or by SC injection. The PD response elicited by the study medication was registered for another 6 hours. No food intake was allowed during this period, but water could be consumed as desired.

During each study period, blood samples were collected for the determination of plasma insulin concentrations, plasma C-peptide and plasma glucose concentration. Sampling occurred from 6 hrs before dosing and continued for 6 hrs after the dose was administered. Blood samples were collected via a venous cannula. Blood samples were collected relative to the administration of the study drug (1) prior to study of drug administration at −1 and −0.5 hrs, (2) immediately after study drug administration (time 0), and (3) post administration of the study drug at 10, 20, 30, 40, 50 min, and 1, 1.25, 1.5, 1.75, 2, 2.5, 3, 3.5, 4, 5, and 6 hrs The glucose clamp procedure was performed using a Biostator (glucose controlled insulin infusion system—GCIIS, Life Science Instruments, Elkhart, Ind., USA). A 17-gauge PTFE catheter was inserted into an antecubital vein for blood sampling and kept patent with 0.15 mol/L saline. A dorsal hand vein or lateral wrist vein of the same arm was cannulated in retrograde fashion for insertion of an 18-gauge PTFE double lumen catheter connected to the glucose sensor of the Biostator. The catheterized hand was placed in a hot box and warmed to an air temperature of 55° C. On the contralateral arm, a third vein was cannulated with an 18-gauge PTFE catheter to infuse a glucose solution (20% in water). Into the same vein, an insulin solution (regular human insulin in 0.15 mol/L saline diluted with 2 mL of the patient's blood per 100 mL) was continuously infused by means of a syringe pump (Perfusor Secura FT, Braun, Melsungen, Germany).

Blood samples were collected from each patient during each treatment period for determination of plasma insulin concentrations, plasma C-peptide, and plasma glucose. Glucose infusion rates and blood glucose measurements were measured continuously during the glucose clamp procedure. All treatments were identical in their sample collection and monitoring periods for all visits. After a 6 hours pre-dose baseline period for stabilization of blood glucose concentrations at the desired clamp level, the clamp procedure after study drug administration lasted 6 hours.

The blood samples were centrifuged at 3000 rpm for a period of fifteen minutes at a temperature between 2° C.-8° C., within one hour of sample collection. Using a plastic pipette and without disturbing the red cell layer, the plasma from the collection tube was pipetted in pre-labeled polypropylene tubes for each analysis of plasma insulin, C-peptide, and plasma glucose (approximately 0.3-0.5 µl each). The samples were stored at −20° C. until analysis.

Safety was monitored by vital sign measurements and documentation of adverse events (AE) during all visits throughout the study. No food intake was permitted until the clamp procedure was completed but the patients were allowed to drink water ad libitum. After the last blood sample had been obtained, subjects were provided with a meal.

During the study, insulin therapy and the chronic use of all agents that, in the evaluation of the investigator might have interfered with the interpretation of trial results or were known to cause clinically relevant interference with insulin action, glucose utilization or recovery from hypoglycemia, were prohibited. Intake of all oral hypoglycemic agents was stopped 24 hours prior to each study dosing day and was not resumed until the end of the clamp procedures.

Blood glucose concentration and GIR determinations were made continuously from −6 hrs prior to administration of the study drug up to 6 hrs post-administration of the study drug by the Biostator. These data were recorded at 1-minute intervals throughout the treatment period. Safety assessments included AEs, laboratory data, vital signs, physical examinations and ECGs.

Safety data and pharmacokinetic/pharmacodynamic data were analyzed for all subjects. Pharmacokinetic/pharmacodynamic data were also analyzed for the subset of 8 patients who received the third study treatment. Pharmacokinetic and pharmacodynamic data were statistically analyzed for subjects that received at least the first two treatments (visit 1 to 4) and for subjects who completed all three treatment visits (visit 1 to 6).

The primary PD endpoint of the study was the area under the glucose infusion rate curve ($AUC_{GIR}$) in the first hr after drug administration ($AUC_{GIR\ 0-1h}$). The secondary endpoints for pharmacodynamic assessment were the following parameters: Maximum glucose infusion rate ($GIR_{max}$), time to $GIR_{max}$ ($t_{GIRmax}$), area under the glucose infusion rate curve in defined time-intervals ($AUC_{GIR\ 0-2h}$, $AUC_{GIR\ 0-3h}$, $AUC_{GIR\ 0-4h}$, $AUC_{GIR\ 0-5h}$, $AUC_{GIR\ 0-6h}$), time to early and late half-maximum glucose infusion rate (early and late $T_{GIR\ 50\%}$), and maximum reduction of C-peptide concentrations.

The secondary endpoints for pharmacokinetic assessment were the following parameters: Maximum plasma insulin concentrations ($C_{INSmax}$), time to $C_{INSmax}$ ($t_{INSmax}$), area under the insulin concentration curves in defined time-intervals ($AUC_{INS\ 0-1h}$, $AUC_{INS\ 0-2h}$, $AUC_{INS\ 0-3h}$, $AUC_{INS\ 0-4h}$, $AUC_{INS\ 0-5h}$, $AUC_{INS\ 0-6h}$). Inter-subject variability was investigated for selected PD and PK parameters.

Plasma concentrations of insulin, as shown in Table 23 below, were determined by a good laboratory practice (GLP) validated microparticle enzyme immunoassay (MEIA).

TABLE 22

Summary of Plasma Insulin Concentrations (pmol/L)

| Time Point | 15 U SC | | | 300 U oral | | | 150 U oral | | |
|---|---|---|---|---|---|---|---|---|---|
| | N | Mean | SD | N | Mean | SD | N | Mean | SD |
| Time 0 | 10 | 4.6 | 7.3 | 10 | 9.2 | 9.9 | 8 | 0.3 | 0.9 |
| 10 minutes | 10 | 5.7 | 10.8 | 10 | 50.3 | 62.4 | 8 | 59.6 | 44.7 |
| 20 minutes | 10 | 13.7 | 18.3 | 10 | 429.6 | 474.6 | 8 | 188.3 | 162.6 |
| 30 minutes | 10 | 41.2 | 32.5 | 10 | 409.5 | 268.1 | 8 | 192.5 | 250.6 |
| 40 minutes | 10 | 94.9 | 63.1 | 10 | 366.2 | 258.2 | 8 | 114.3 | 158.9 |
| 50 minutes | 10 | 109.4 | 75.6 | 10 | 214.2 | 185.8 | 8 | 79.8 | 121.7 |
| 60 minutes | 10 | 116.4 | 63.2 | 10 | 122.1 | 108.2 | 8 | 50.2 | 69.5 |
| 75 minutes | 10 | 137.4 | 86.5 | 10 | 48.2 | 37.3 | 8 | 30.3 | 38.6 |
| 90 minutes | 10 | 116.5 | 50.9 | 10 | 20.6 | 28.2 | 8 | 19.5 | 25.9 |
| 105 minutes | 10 | 132.2 | 72.4 | 10 | 7.5 | 12.9 | 8 | 11.5 | 14.9 |
| 120 minutes | 10 | 119.1 | 70.2 | 10 | 19.1 | 22.1 | 8 | 17.1 | 15.7 |
| 150 minutes | 10 | 129.8 | 51.1 | 10 | 10.0 | 14.1 | 8 | 8.3 | 11.6 |
| 180 minutes | 10 | 149.6 | 61.3 | 10 | 9.1 | 13.3 | 8 | 17.0 | 23.4 |

TABLE 22-continued

Summary of Plasma Insulin Concentrations (pmol/L)

| Time Point | 15 U SC | | | 300 U oral | | | 150 U oral | | |
|---|---|---|---|---|---|---|---|---|---|
| | N | Mean | SD | N | Mean | SD | N | Mean | SD |
| 210 minutes | 10 | 146.8 | 71.8 | 10 | 4.9 | 7.0 | 8 | 17.7 | 24.9 |
| 240 minutes | 10 | 138.2 | 64.6 | 10 | 5.1 | 5.9 | 8 | 22.0 | 31.1 |
| 300 minutes | 10 | 129.8 | 42.5 | 10 | 8.1 | 17.2 | 8 | 12.0 | 15.4 |
| 360 minutes | 10 | 87.7 | 56.7 | 10 | 2.4 | 4.5 | 8 | 14.2 | 16.4 |

In Table 22, baseline corrected values were used, i.e., pre-dose baseline values were subtracted, and in case of a negative result, the value was set to zero.

Figure 13:
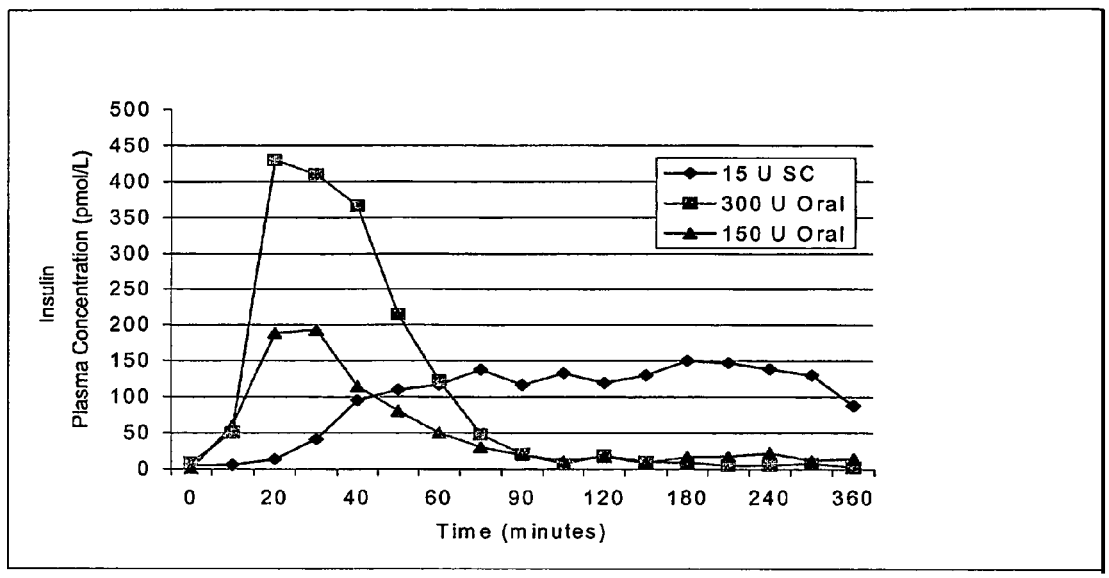
FIG. 13 shows time plots for mean plasma insulin concentrations (baseline corrected) for treatments using 300 U oral insulin/400 mg 4-CNAB, 150 U oral insulin/200 mg 4-CNAB and 15 SC insulin.

FIG. 13 shows time plots for mean plasma insulin concentrations (baseline corrected) for treatments using 300 U oral insulin/400 mg 4-CNAB, 150 U oral insulin/200 mg 4-CNAB and 15 SC insulin.

Table 23 below shows a Summary of C-Peptide Levels (nmol/L):

TABLE 23

Summary of C-Peptide Levels

| Time Point | 15 U SC | | | 300 U oral | | | 150 U oral | | |
|---|---|---|---|---|---|---|---|---|---|
| | N | Mean | SD | N | Mean | SD | N | Mean | SD |
| −60 minutes | 10 | 1.02 | 0.42 | 10 | 0.95 | 0.37 | 8 | 0.86 | 0.33 |
| −30 minutes | 10 | 1.05 | 0.40 | 10 | 0.98 | 0.36 | 8 | 0.86 | 0.30 |
| Time 0 | 10 | 1.04 | 0.39 | 10 | 0.99 | 0.30 | 8 | 0.95 | 0.35 |
| 10 minutes | 10 | 1.05 | 0.42 | 10 | 1.00 | 0.31 | 8 | 1.00 | 0.38 |
| 20 minutes | 10 | 1.07 | 0.47 | 10 | 1.01 | 0.34 | 8 | 1.02 | 0.37 |
| 30 minutes | 10 | 1.09 | 0.46 | 10 | 1.02 | 0.38 | 8 | 1.01 | 0.34 |
| 40 minutes | 10 | 1.11 | 0.47 | 10 | 1.02 | 0.36 | 8 | 0.97 | 0.28 |
| 50 minutes | 10 | 1.05 | 0.43 | 10 | 1.01 | 0.36 | 8 | 0.99 | 0.36 |
| 60 minutes | 10 | 1.04 | 0.39 | 10 | 0.97 | 0.35 | 8 | 1.00 | 0.36 |
| 75 minutes | 10 | 1.07 | 0.45 | 10 | 1.00 | 0.41 | 8 | 0.99 | 0.34 |
| 90 minutes | 10 | 1.03 | 0.44 | 10 | 1.04 | 0.38 | 8 | 0.92 | 0.30 |
| 105 minutes | 10 | 1.01 | 0.43 | 10 | 1.06 | 0.36 | 8 | 0.94 | 0.33 |
| 120 minutes | 10 | 0.99 | 0.45 | 10 | 1.04 | 0.36 | 8 | 0.95 | 0.36 |
| 150 minutes | 10 | 1.01 | 0.50 | 10 | 1.04 | 0.34 | 8 | 1.01 | 0.38 |
| 180 minutes | 10 | 0.99 | 0.44 | 10 | 1.07 | 0.38 | 8 | 1.08 | 0.46 |
| 210 minutes | 10 | 0.97 | 0.40 | 10 | 1.04 | 0.40 | 8 | 1.03 | 0.38 |
| 240 minutes | 10 | 0.94 | 0.31 | 10 | 1.11 | 0.45 | 8 | 1.00 | 0.37 |
| 300 minutes | 10 | 0.96 | 0.36 | 10 | 1.07 | 0.44 | 8 | 0.99 | 0.43 |
| 360 minutes | 10 | 0.92 | 0.34 | 10 | 1.07 | 0.39 | 8 | 0.97 | 0.42 |

Figure 14:
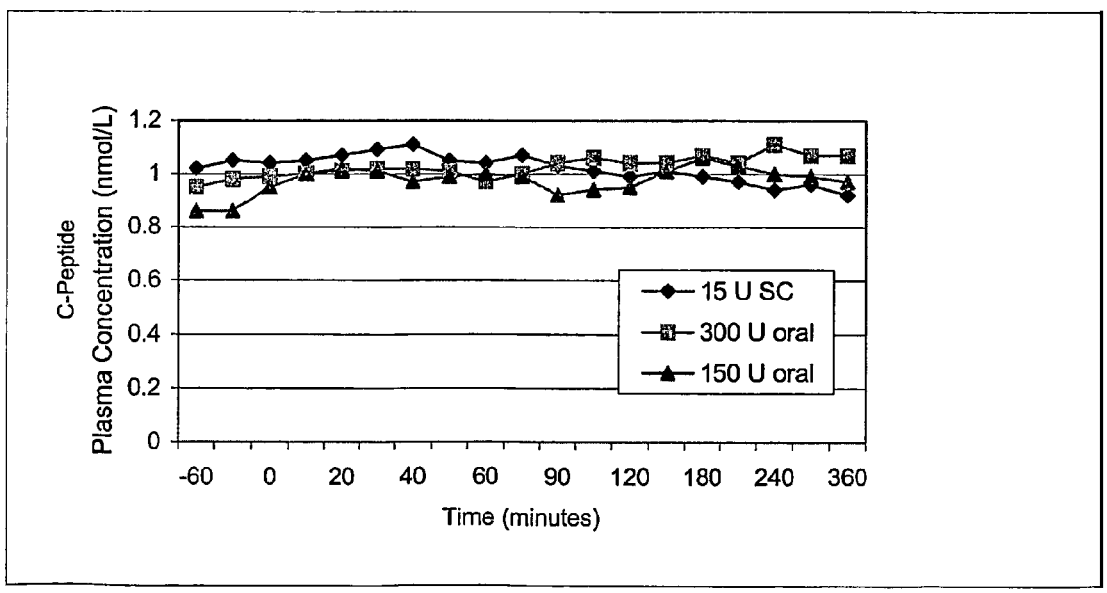
FIG. 14 shows C-peptide measurements for insulin delivered orally and subcutaneously.

FIG. 14 shows a plot of C-peptide [mnol/l] vs. time for 15 IU s.c., 300 IU oral and 150 IU oral. As shown in FIG. 14, C-peptide measurements showed no significant changes during the treatment periods.

The parameters assessed in this study were standard measurements appropriate for comparing the PK and PD properties of insulin absorption after oral administration and SC injection. The use of a glucose clamp with a Biostator minimized the likelihood of the onset of symptomatic hypoglycemia. Calculations based upon the plasma insulin concentrations or glucose infusion rates from the glucose clamp procedure reflect standard PK or PD calculations commonly used for the glucose clamp technique.

The primary PD endpoint of the study was the area under the glucose infusion rate curve ($AUC_{GIR}$) in the first hr after drug administration ($AUC_{GIR\ 0-1h}$)

PK and PD data were statistically analyzed for subjects that received at least the first 2 treatments (Visit 1 to 4) and for subjects who completed all three treatment visits (Visit 1 to 6).

PD parameters used for analysis were the maximum glucose infusion rate after application of the study drugs ($GIR_{max}$), the time to maximum glucose infusion rate ($t_{GIRmax}$), time to half-maximum GIR values before $GIR_{max}$ (early $t_{GIR\ 50\%}$), time to half-maximum GIR values after $GIR_{max}$ (late $t_{GIR\ 50\%}$), and the area under the glucose infusion rate versus time curves from 0 to 60, 120, 180, 240, 300, and 360 min after dosing, and from 180 to 360 min post dose ($AUC_{GIR\ 0-1h}$, $AUC_{GIR\ 0-2h}$, $AUC_{GIR\ 0-3h}$ $AUC_{GIR\ 0-4h}$, $AUC_{GIR\ 0-5h}$, $AUC_{GIR\ 0-6h}$, $AUC_{GIR\ 3-6h}$, respectively). In addition, plasma concentrations of C-peptide and plasma glucose concentrations were used for PD analysis. $GIR_{max}$, $t_{GIRmax}$ and early and late $t_{GIR\ 50\%}$ were calculated by fitting a polynomial function (6th order) to each individual's GIR profile after subtraction of the mean baseline GIR. Areas under the curve (AUCs) were calculated from the raw data using the trapezoidal rule.

PK parameters were calculated using non-compartmental methods. PK parameters determined included the maximum plasma insulin concentration ($C_{INSmax}$), time to maximum insulin concentration ($t_{INSmax}$), and the area under the plasma insulin concentration versus time curves from 0 to 1, 2, 3, 4, 5 and 6 hrs after application of the study drugs ($AUC_{INS\ 0-1h}$, $AUC_{INS\ 0-2h}$, $AUC_{INS\ 0-3h}$, $AUC_{INS\ 0-4h}$, $AUC_{INS\ 0-5h}$ and $AUC_{INS\ 0-6h}$, respectively). The calculation of AUCs from time of dosing until return to baseline concentration ($AUC_{INS\ 0-t'}$) was omitted as in some patients insulin concentrations did not return to baseline measurement within 360 min post dosing.

The PK and PD data obtained were used for comparative analysis of the treatments with 15 U SC insulin and 300 U oral insulin. All tests were performed against a 2-sided alternative hypothesis, with a significance level of 5% ($\alpha$=0.05). The tests were declared statistically significant if the calculated p-value was <0.05. In view of the small sample size and some outliers, a first analysis was done using non-parametric tests only (signed Wilcoxon rank tests and Kruskal-Wallis tests). However, the Kolmogorov-Smirnov test indicated normal distribution for all PK and PD parameters. Therefore, parametric tests paired t-tests and ANOVAs) were performed in addition. Although there were no substantial differences between the results of the non-parametric and the parametric tests, it was decided that the non-parametric results were used for the presentation of the data.

Safety data included AEs, laboratory data, vital signs, physical examinations, and ECGs. Vital signs (systolic and diastolic blood pressure, respiration rate, heart rate, and body temperature) for each treatment group were summarized at baseline (defined as the −30 min time point) and at the end of each study day.

Ten patients with type 2 diabetes were planned (5 patients assigned to each of 2 sequences) with complete data for analysis. One patient dropped out prior to any treatment and was replaced as per protocol. Therefore, the number of enrolled patients was eleven. Ten patients completed the study with the originally planned two treatments. Eight of these ten patients accepted the offer to attend an additional oral treatment of 150 U Insulin/200 mg 4-CNAB due to protocol amendment, and this additional treatment was not performed in random order. PK/PD data were also analyzed for the subset of eight patients who received the second oral study treatment Analysis of Pharmacokinetics and Pharmacodynamics PK and PD data were analyzed for the 10 patients who received the study treatments A and B (oral 300 U Insulin/400 mg 4-CNAB, SC 15 U regular insulin) and had evaluable data. PK and PD data were also analyzed for the amended group of 8 patients who received the second oral study treatment (treatment C: oral 150 U Insulin/200 mg 4-CNAB). All included patients with treatment received at least 2 treatments (one oral and one SC treatment) as planned in the protocol.

The following Table 24 summarizes the pharmacokinetic and pharmacodynamic parameters calculated for the different treatments.

TABLE 24

Comparisons of the PK and PD Parameters

| | Mean ± SD | | |
|---|---|---|---|
| Parameter | Oral 300 U Insulin/ 400 mg 4-CNAB (n = 10) | Oral 150 U Insulin/ 200 mg 4-CNAB (n = 8) | SC 15 U Regular Insulin (n = 10) |
| Insulin | | | |
| $AUC_{0-1h}$ ($\mu U \times mL^{-1} \times min$) | 2559.25 ± 1831.45 | 1099.58 ± 1221.15 | 542.31 ± 296.26 |
| $AUC_{0-2h}$ ($\mu U \times mL^{-1} \times min$) | 2926.58 ± 2104.23 | 1337.14 ± 1407.11 | 1801.97 ± 789.43 |
| $AUC_{0-3h}$ ($\mu U \times mL^{-1} \times min$) | 3046.75 ± 2169.16 | 1463.59 ± 1443.01 | 3122.81 ± 1242.82 |
| $AUC_{0-4h}$ ($\mu U \times mL^{-1} \times min$) | 3106.67 ± 2212.98 | 1649.43 ± 1541.90 | 4576.31 ± 1817.96 |
| $AUC_{0-5h}$ ($\mu U \times mL^{-1} \times min$) | 3172.83 ± 2262.81 | 1819.01 ± 1593.02 | 5916.31 ± 2208.85 |
| $AUC_{0-6h}$ ($\mu U \times mL^{-1} \times min$) | 3225.33 ± 2319.66 | 1949.64 ± 1623.949 | 7003.81 ± 2440.251 |
| $C_{max}$ ($\mu U/mL$) | 93.44 ± 71.18 | 37.90 ± 39.23 | 32.7 ± 10.59 |
| $t_{max}$ (min) | 27.00 ± 9.49 | 22.50 ± 7.0 | 160.5 ± 82.78 |
| Glucose Infusion Rate | | | |
| $AUC_{0-1h}$ (mg/kg) | 172.63 ± 85.54 | 58.08 ± 39.99 | 27.38 ± 32.22 |
| $AUC_{0-2h}$ (mg/kg) | 297.11 ± 142.73 | 102.62 ± 88.94 | 136.54 ± 106.54 |
| $AUC_{0-3h}$ (mg/kg) | 321.19 ± 146.29 | 116.96 ± 78.26 | 271.43 ± 191.04 |
| $AUC_{0-4h}$ (mg/kg) | 343.31 ± 140.47 | 142.00 ± 85.76 | 421.33 ± 264.76 |
| $AUC_{0-5h}$ (mg/kg) | 364.40 ± 135.36 | 160.28 ± 99.64 | 548.83 ± 342.71 |
| $AUC_{0-6h}$ (mg/kg) | 374.10 ± 134.70 | 190.77 ± 133.38 | 650.70 ± 380.16 |
| $GIR_{max}$ (mg/kg/min) | 4.35 ± 2.23 | 2.12 ± 0.89 | 3.57 ± 1.79 |
| $t_{GIRmax}$ (min) | 39.80 ± 16.00 | 131.63 ± 146.04 | 255.30 ± 108.15 |
| Early $t_{50\%}$ (min) | 13.40 ± 6.48 | 103.50 ± 140.90 | 150.40 ± 87.44 |
| Late $t_{50\%}$ (min) | 114.70 ± 78.74 | NA | NA |

The pharmacokinetic and pharmacodynamic parameters discussed here are the averages and standard deviations of the individual values. The oral dose of 300 U Insulin/400 mg 4-CNAB showed a faster and higher rise in plasma insulin concentrations indicating a faster onset of action than the SC treatment ($AUC_{INS\ 0-1h}$ oral 300 U vs. SC 15 U: 2559±1831 vs. 542±296 μU×mL$^{-1}$×min, $p<0.01$; $C_{INS\ max}$ oral 300 U vs. SC 15 U: 93:71 vs. 33±11 μU/mL, $p<0.01$; $t_{INSmax}$ oral 300 U vs. SC 15 U: 27±9 vs. 161±83 min, $p<0.01$).

Figure 15:
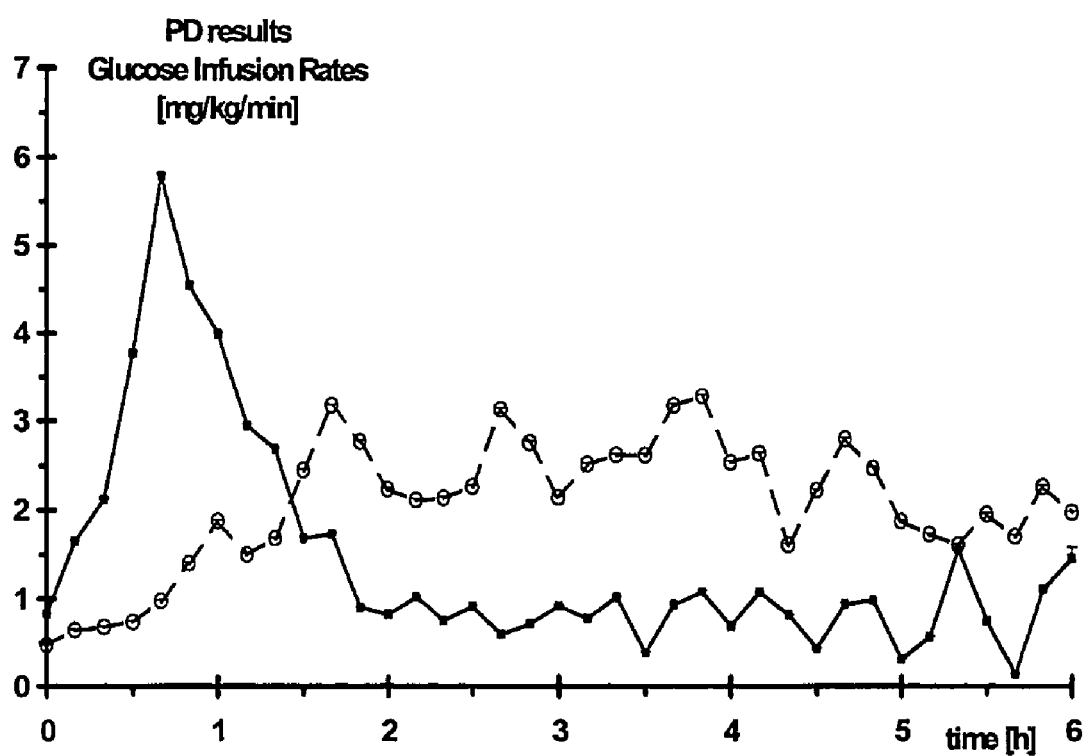
FIG. 15 shows time plots for glucose infusion rates for insulin delivered orally and subcutaneously.

Accordingly, this trend is mirrored in the pharmacodynamic (GIR) results, as expected, with a significantly faster onset of the PD effect after the oral treatment compared to the SC treatment ($AUC_{GIR\ 0-1h}$ oral 300 U vs. SC 15 U: 173±86 vs. 27±32 mg/kg, $p<0.01$; $t_{GIRmax}$ oral 300 U vs. SC 15 U: 40±16 vs. 255±108 min, $p<0.01$; early $t_{50\%}$ oral 300 U vs. SC 15 U: 13±6 vs. 150±87 min, $p<0.01$). The maximum glucose infusion rates, shown in FIG. 15, showed no statistically significant difference, although the initial level of glucose infused was higher from oral insulin than from SC insulin.

Relative bioavailability (based on PK results) and biopotency (based on PD results) of the two oral insulin doses in comparison to the SC administration were calculated as defined hereinabove. Relative bio-availability of oral insulin is listed in the Table 25. Respective values for bio-potency for oral insulin are listed in Table 26.

TABLE 25

Summary of Relative Bioavailability of Insulin

| Time interval | n | Mean | SD | SEM | Max | Min | Median |
|---|---|---|---|---|---|---|---|
| Bioavailability (%): 300 U oral vs. 15 U SC | | | | | | | |
| 0-60 | 10 | 43.7 | 60.5 | 19.1 | 198.2 | 7.2 | 18.3 |
| 0-120 | 10 | 13.0 | 20.1 | 6.4 | 69.1 | 2.9 | 7.0 |
| 0-180 | 10 | 7.8 | 12.7 | 4.0 | 43.5 | 1.8 | 3.9 |
| 0-240 | 10 | 4.9 | 7.3 | 2.3 | 25.4 | 1.3 | 2.6 |
| 0-300 | 10 | 3.4 | 4.1 | 1.3 | 14.6 | 1.0 | 2.1 |
| 0-360 | 10 | 2.7 | 3.0 | 1.0 | 11.0 | 0.8 | 1.8 |
| 180-360 | 10 | 0.3 | 0.3 | 0.1 | 1.1 | 0.0 | 0.1 |
| Bioavailability (%): 150 U oral vs. 15 U SC | | | | | | | |
| 0-60 | 8 | 21.4 | 19.8 | 7.0 | 53.3 | 0.4 | 14.7 |
| 0-120 | 8 | 8.4 | 6.8 | 2.4 | 16.8 | 0.1 | 7.8 |
| 0-180 | 8 | 5.4 | 4.3 | 1.5 | 10.3 | 0.1 | 5.7 |
| 0-240 | 8 | 4.0 | 3.1 | 1.1 | 7.6 | 0.0 | 4.6 |
| 0-300 | 8 | 3.4 | 2.7 | 0.9 | 6.8 | 0.0 | 3.8 |
| 0-360 | 8 | 3.1 | 2.4 | 0.9 | 6.2 | 0.0 | 3.4 |
| 180-360 | 8 | 1.5 | 1.6 | 0.6 | 3.7 | 0.0 | 1.0 |

TABLE 26

Summary of Relative Biopotency of Oral Insulin

| Time interval | n | mean | SD | SEM | Max | Min | Median |
|---|---|---|---|---|---|---|---|
| Biopotency (%): 300 U oral vs. 15 U SC | | | | | | | |
| 0-60 | 7 | 54.90 | 91.93 | 34.74 | 261.44 | 5.54 | 19.90 |
| 0-120 | 9 | 11.70 | 9.21 | 3.07 | 32.76 | 3.65 | 8.12 |
| 0-180 | 9 | 5.76 | 3.41 | 1.14 | 13.56 | 2.03 | 4.85 |
| 0-240 | 10 | 21.14 | 54.94 | 17.37 | 177.45 | 2.19 | 3.56 |
| 0-300 | 10 | 47.53 | 140.38 | 44.39 | 447.03 | 1.56 | 3.12 |
| 0-360 | 10 | 31.01 | 89.44 | 28.28 | 285.54 | 1.10 | 2.69 |
| Biopotency (%): 150 U oral vs. 15 U SC | | | | | | | |
| 0-60 | 5 | 110.86 | 193.40 | 86.49 | 455.95 | 11.74 | 23.52 |
| 0-120 | 7 | 12.86 | 13.59 | 5.14 | 40.76 | 3.23 | 6.94 |
| 0-180 | 7 | 6.66 | 6.17 | 2.33 | 19.53 | 1.58 | 6.28 |
| 0-240 | 8 | 4.03 | 3.56 | 1.26 | 10.67 | 0.00 | 2.86 |
| 0-300 | 8 | 3.55 | 3.22 | 1.14 | 9.74 | 0.00 | 2.52 |
| 0-360 | 8 | 3.15 | 2.77 | 0.98 | 7.93 | 0.00 | 2.40 |

Table 27 shows a comparison of the relative bioavailability and biopotency for oral insulin.

TABLE 27

Comparisons of Relative Bioavailability and Biopotency (Mean ± SD)

| TIME INTERVAL | Oral 300 U Insulin/400 mg 4-CNAB (n = 10) | | Oral 150 U Insulin/200 mg 4-CNAB (n = 8) | |
|---|---|---|---|---|
| | Bioavailability (%) | Biopotency (%) | Bioavailability (%) | Biopotency (%) |
| 0-1 hr | 43.7 ± 60.5 | 54.9 ± 91.9 (n = 7) | 21.4 ± 19.8 | 110.9 ± 193.4 (n = 5) |
| 0-2 hrs | 13.0 ± 20.1 | 11.7 ± 9.2 (n = 9) | 8.4 ± 6.8 | 12.9 ± 13.6 (n = 7) |
| 0-3 hrs | 7.8 ± 12.7 | 5.8 ± 3.4 (n = 9) | 5.4 ± 4.3 | 6.7 ± 6.2 (n = 7) |
| 0-4 hrs | 4.9 ± 7.3 | 21.1 ± 54.9 | 4.0 ± 3.1 | 4.0 ± 3.6 |
| 0-5 hrs | 3.4 ± 4.1 | 47.5 ± 140.4 | 3.4 ± 2.7 | 3.5 ± 3.2 |
| 0-6 hrs | 2.7 ± 3.0 | 31.0 ± 89.4 | 3.1 ± 2.4 | 3.2 ± 2.8 |

Relative biopotency (based on PD results) of 300 U oral Insulin/400 mg 4-CNAB was as high as 54.9±91.9% in the first hr after application, and 31.0±89.4% over 6 hrs. Respective values for bioavailability (based on PK results) were 43.7±60.5%, and 2.7±3.0%. The unexpected increase in mean relative biopotency for the time intervals 0-4, 0-5 and 0-6 hrs accounts for Patient 101 whose values were calculated only for these three time periods and which were up to 100-fold higher than those found for the other patients (177.45%, 447.03%, and 285.54%, respectively).

The oral dose of 150 U Insulin/200 mg 4-CNAB also showed a faster rise in plasma insulin concentrations compared to the SC treatment ($AUC_{INS\ 0-1h}$ oral 150 U vs. SC 15 U: 1100±1221 vs. 542±296 µU×mL$^{-1}$×min; $t_{INSmax}$ oral 300U vs. SC 15U: 23±7 vs. 161±83 min), whereas the observed maximum plasma concentrations were similar for both treatments ($C_{INSmax}$ oral 150 U vs. SC 15 U: 38±39 vs. 33±11 µU/mL).

Accordingly, GIR results for the oral 150 U insulin dose showed a faster onset of the PD effect ($AUC_{GIR\ 0-1h}$ oral 150 U vs. SC 15 U: 58±40 vs. 27±32 mg/kg; $t_{GIRmax}$ oral 150 U vs. SC 15 U: 132±146 vs. 255±108 min; early $t_{50\%}$ oral 150 U vs. SC 15 U: 104±141 vs. 150±87 min). The maximum glucose infusion rate was lower after the oral than after the SC treatment ($GIR_{max}$ oral 150 U vs. SC 15 U: 2.1±0.9 vs. 3.6±1.8 mg/kg/min).

These findings indicate that suppression of hepatic glucose production can be achieved also by the lower dose of 150 U oral insulin.

Relative biopotency of 150 U oral Insulin/200 mg 4-CNAB was 110.9±193.4% in the first hour after application, and 3.2±2.8% over 6 hours. Respective values for bioavailability were 21.4±19.8%, and 3.1±2.4%. The abnormal high mean relative biopotency of 110.9% in the first hour results from an extremely high value of 455.95% found for Patient 102 and the fact that values of only 5 patients were available. Because of the mentioned distortion of the biopotency means, the medians are considered to be a more suitable representation of the data.

Comparison of the PK and PD data of the two oral insulin doses suggests a nearly linear dose relationship of the PK parameters $AUC_{INS}$ and $C_{INS\ max}$. The PD response, as represented by $AUC_{GIR}$ and $GIR_{max}$, also increases with dose but in a less clear fashion.

Pharmacokinetic/Pharmacodynamic Conclusions

This first glucose clamp study demonstrated that orally applied insulin exhibits a pronounced metabolic effect. In view of the presented PD and PK properties, and the advantages of an oral administration (high portal insulin concentrations, convenience of administration), Insulin/4-CNAB seems to be a very attractive candidate for pre-prandial (before meal) insulin therapy in type 1 and type 2 diabetic patients.

All treatments evaluated during the study were safe and well tolerated. No adverse events were observed following oral administration of Insulin/4-CNAB capsules or subcutaneous injection of regular insulin.

EXAMPLE 7

Comparison between Oral Insulin and s.c. Short Acting Postprandial Blood Glucose Excursions A randomized, 3-period crossover, double-blind, double-dummy study was conducted in order to compare the effect (i.e., the postprandial pharmacokinetic and pharmacodynamic profiles) of an oral insulin formulation with that of s.c. administered short acting insulin on postprandial blood glucose excursions in Type 2 Diabetic subjects without any antidiabetic medication.

A primary objective of this study was to compare the effect of an oral insulin formulation (300 U insulin combined with 400 mg 4-CNAB in 2 capsules, each capsule containing 150 U insulin/200 mg 4-CNAB) with that of 12 U subcutaneous (s.c.) injected short acting insulin [Humalog® injection 100 U/ml from Eli Lilly and Company] on postprandial blood glucose excursions. The postprandial blood glucose excursions were assessed after a standardized breakfast intake.

Fifteen male subjects between 35 and 70 years old, inclusive, with type 2 diabetes mellitus as defined by the American Diabetes Association (1998 Diabetes care, 21: S5-S19) for more than one year were chosen. Subjects included in the study had BMI<36 kg/m$^{21}$, had stable glycemic control ($HbA_{1C}$<11%), were off all oral hypoglycemic agents 24 hours prior to each study dosing day and off any investigational drug for at least four (4) weeks prior to Visit 1, refrained from strenuous physical activity beginning 72 hrs prior to admission and through the duration of the study, and were confined to the clinical research unit as required by the protocol. Subjects maintained a constant body weight (+/−2 kg).

All patients received the same oral and SC injection treatments in a randomized sequence. At visit 1, each patient was randomized to one of six possible treatment sequences (see Table 28). On four separate occasions, patients received one of the four possible treatments prior to a standardized breakfast: 300 U oral Insulin/400 mg 4-CNAB (2 capsules, each capsule containing 150 U Insulin/200 mg 4-CNAB), 150 U oral Insulin/200 mg 4-CNAB (one capsule), 12 U SC short-acting insulin (Humalog®), and no supplemental insulin (placebo). During the first three treatment periods, 300 U oral, 12 U SC and placebo insulin were administered in random order and under blinded conditions (double-dummy technique). During the fourth treatment period, the patients received 150 U oral insulin in an open fashion. The overall study design is illustrated in Table 28 below.

TABLE 28

Overall Study Design

| | Randomization ↓ | | | | | | |
|---|---|---|---|---|---|---|---|
| Visit 1 | Visit 2 | Visit 3 | Visit 4 | Visit 5 | Visit 6 | Visit 7 | Visit 8*) |
| Screening | Session 1 | Session 2 | Session 3 | Final Visit | Screening | Session 4 | Final Visit*) |
| | 300 U oral insulin or 12 U SC or placebo | | | | | 150 U oral | |

*)For all patients, Visits 7 and 8 were combined (i.e., final examination was performed at Visit 7, immediately after finishing experimental procedures).

The SC insulin dose of 12 U was selected to fall within a range typical for type 2 diabetic patients. The oral dose of 300 U insulin (in combination with 400 mg 4-CNBA) had been shown to be effective in Example 5 above. The oral dose of 150 U insulin (in combination with 200 mg 4-CNBA) was chosen to investigate whether or not an effect on hepatic glucose production could be achieved also by a lower insulin dose.

The time point of study drug administration (SC injection: 15 minutes prior to meal intake; oral administration: 30 minutes prior to meal intake) was selected in order to match the PK and PD properties of the administered insulin formulations with the postprandial rise of blood glucose. The wash-out period between the first three treatment sessions was 1-20 days. The duration of each session was approximately 8-9 hours, and all experiments were performed after an overnight fast of approx. 12 hours.

At Visit 1 (screening visit), the patients came to the clinical research unit in a fasted state (i.e., not having had any caloric intake for at least 12 hours). The patients' physical statistics, medical history and social habits recorded, and a physical examination performed. Not more than 14 days later, at Visit 2, each patient was randomized to one of six treatment sequences shown in Table 40 below and received either one of the two active treatments (300 U oral Insulin/400 mg 4-CNAB or 12 U short-acting SC insulin) or no supplemental insulin (placebo). Thirty minutes after oral and fifteen minutes after SC drug administration, the patients ate a standardized breakfast, and postprandial blood glucose concentrations were monitored for six hours. Serial blood samples were also collected in regular intervals for measurement of plasma insulin, 4-CNAB, and C-peptide concentrations. The study patients were released from the institute at the end of the treatment session.

At Visits 3 and 4, the study patients returned to the clinical unit to receive the alternative treatments in conjunction with the test meal according to their treatment sequence. All experimental procedures and measurements were identical with those of the preceding treatment days. A final examination (Visit 5) was performed after Visit 4, preferably immediately after the experimental procedures were completed, but no longer than fourteen days after Visit 4.

The patients were invited to attend a fourth treatment session (Visit 7) with a single oral administration of 150 U Insulin/200 mg 4-CNAB thirty minutes prior to a test meal. All experimental procedures and measurements were the same as on the preceding treatment days. Patients attended a screening (Visit 6), no more than twenty days prior to the additional session, as well as a final examination (Visit 8), preferably immediately after the experimental procedures of Visit 7 were completed, but no longer than fourteen days thereafter. Visits 7 and 8 were generally combined (i.e., for all patients final examination was performed at Visit 7, immediately after completion of experimental procedures).

The patients were randomly assigned to one of the following treatment sequences:

TABLE 29

| Treatment Sequence | Treatments Administered | | | |
|---|---|---|---|---|
| | Treatment Period | | | |
| | 1 (Visit 2) | 2 (Visit 3) | 3 (Visit 4) | 4 (Visit 7) |
| 1 | 300 U Oral | 12 U SC | Placebo | 150 U Oral |
| 2 | 300 U Oral | Placebo | 12 U SC | 150 U Oral |
| 3 | 12 U SC | 300 U Oral | Placebo | 150 U Oral |
| 4 | 12 U SC | Placebo | 300 U Oral | 150 U Oral |
| 5 | Placebo | 12 U SC | 300 U Oral | 150 U Oral |
| 6 | Placebo | 300 U Oral | 12 U SC | 150 U Oral |

According to the double-dummy technique, each patient received on the first three treatment sessions (Visits 2-4), in addition to his scheduled treatment administration (oral or SC), the alternative administration (SC or oral) as placebo preparation. On sessions without supplemental insulin, both treatments (oral and SC) were placebo preparations. On the last treatment session (Visit 7), all patients received in an open fashion one oral dose of 150 U Insulin/200 mg 4-CNAB.

Based on the six sequences shown above, the following treatments were administered during the study:

Sequence 1:
Visit 2: Two insulin capsules 30 minutes, one SC placebo injection 15 minutes before meal.
Visit 3: Two placebo capsules 30 minutes, one SC insulin injection 15 minutes before meal
Visit 4: Two placebo capsules 30 minutes, one SC placebo injection 15 minutes before meal
Visit 7: One insulin capsule 30 minutes before meal Sequence 2:
Visit 2: Two insulin capsules 30 minutes, one SC placebo injection 15 minutes before meal.
Visit 3: Two placebo capsules 30 minutes, one SC placebo injection 15 minutes before meal
Visit 4: Two placebo capsules 30 minutes, one SC insulin injection 15 minutes before meal
Visit 7: One insulin capsule 30 minutes before meal Sequence 3:
Visit 2: Two placebo capsules 30 minutes, one SC insulin injection 15 minutes before meal.
Visit 3: Two insulin capsules 30 minutes, one SC insulin injection 15 minutes before meal
Visit 4: Two placebo capsules 30 minutes, one SC placebo injection 15 minutes before meal
Visit 7: One insulin capsule 30 minutes before meal Sequence 4:
Visit 2: Two placebo capsules 30 minutes, one SC insulin injection 15 minutes before meal.
Visit 3: Two placebo capsules 30 minutes, one SC placebo injection 15 minutes before meal
Visit 4: Two insulin capsules 30 minutes, one SC placebo injection 15 minutes before meal
Visit 7: One insulin capsule 30 minutes before meal Sequence 5:
Visit 2: Two placebo capsules 30 minutes, one SC placebo injection 15 minutes before meal.
Visit 3: Two placebo capsules 30 minutes, one SC insulin injection 15 minutes before meal
Visit 4: Two insulin capsules 30 minutes, one SC placebo injection 15 minutes before meal
Visit 7: One insulin capsule 30 minutes before meal Sequence 6:
Visit 2: Two placebo capsules 30 minutes, one SC placebo injection 15 minutes before meal.
Visit 3: Two insulin capsules 30 minutes, one SC placebo injection 15 minutes before meal Visit 4: Two placebo capsules 30 minutes, one SC insulin injection 15 minutes before meal Visit 7: One insulin capsule 30 minutes before meal The 4-CNAB used for the capsules was manufactured under GMP compliance. The Insulin used to prepare the capsules was Zinc-Insulin Crystals Human: Proinsulin Derived (Recombinant DNA Origin) USP Quality obtained from Eli Lilly and Company (Indianapolis, Ind.). The Insulin/4-CNAB capsules contained 150 Insulin Units USP and 200 mg 4-CNAB. The insulin/4-CNAB capsules were prepared by AAI Pharma Inc., Wilmington N.C.

Insulin/4-CNAB capsules were provided in HDPE bottles, each of which contained 40 capsules and a polyester coil. Each bottle had a heat-induction seal and a child-resistant cap, and were stored frozen at or less than minus 10° C. On the day of dosing, the appropriate number of capsules was removed from the freezer and brought to room temperature (between 15 and 30° C.) for about one hour. Capsules were used within four hours of dispensing, and unopened bottles were not left at room temperature for more than four hours.

The subjects ingested the meal fifteen minutes after drug administration. Blood glucose concentrations were monitored for six hours after glucose ingestion, and serial blood samples were collected in regular intervals for measurement of insulin concentration, 4-CNAB concentration, C-peptide, and blood glucose, providing information for pharmacokinetic and pharmacodynamic determinations. Blood glucose concentrations were determined immediately after sample collection and documented. All experiments were identical in their sample collections and monitoring period for all visits. The experimental procedure after the meal intake lasted for six hours (+1 hour baseline period for stabilization of blood glucose concentrations at the desired preprandial blood glucose level).

During each treatment session, blood samples were collected for determination of plasma concentrations of 4-CNAB, insulin and C-peptide, and for blood glucose concentration. Sampling started 1 hour before intake of the test meal and continued until 6 hours thereafter. Blood samples were drawn via a venous cannula and collected related to the start of the test meal at time point 0. The timing of scheduled samples could be adjusted according to clinical needs or needs for pharmacokinetic data. The duration of each session was approximately 8-9 hours. All experiments were performed after an overnight fast of approximately 12 hours.

The studies started in the morning. A 17-gauge PTFE catheter was inserted into an arm vein for blood sampling for measurement of blood glucose, and for plasma insulin, 4-CNAB and C-peptide concentrations. The line was kept patent with 0.15-mol/L (0.9%) sterile saline.

At time-point-15, exogenous insulin was administered by oral insulin administration or by subcutaneous injection at two of the three experimental days. At time point 0, subjects ingested a standardized breakfast at every study day (visits 2-4 and 7). The oral treatments (Insulin/4-CNAB capsules and placebo capsules) were administered 30 minutes, and the injections (short-acting insulin and placebo solution) 15 minutes, before start of meal intake. The pharmacodynamic response elicited was studied by measurements of blood glucose concentrations in 5 minute intervals for another six hours, and no food intake was allowed during this period, although water was consumed as desired.

Blood samples for blood glucose determination (0.25 mL per sample) were taken at −1 min (baseline), 5 minutes after start of meal intake and thereafter in 5 minute intervals until 120 minutes, 10 minute intervals until 240 minutes, and 15 minute intervals until 360 minutes after start of meal intake (45 samples per session). Blood glucose concentrations were measured immediately after sample collection using an automated GOD method (Super GL Ambulance Glucose Analyzer, Ruhrtal Labortechnik, Delecke-Möhnesee, Germany).

Blood samples for determination of 4-CNAB plasma concentrations (2 mL in sodium heparin tube) were drawn 10, 20, 30, 40, 60, 90, 120, 240 and 360 minutes after start of meal intake (9 samples per session). Blood samples for determination of insulin and C-peptide plasma concentrations (5 mL in sodium heparin tube) were drawn at −60 and −30 minutes, at time 0 (start of meal intake), and after 10, 20, 30, 40, 50, 60, 75, 90, 105, 120, 150, 180, 210, 240, 300, and 360 minutes (19 samples per session). Plasma concentrations of insulin were determined by a GLP-validated microparticle enzyme immunoassay (MEIA).

In case of a hypoglycemia (defined as blood glucose concentrations below 60 mg/dl), a blood glucose concentration of 60 mg/dl was maintained by means of a variable-rate intravenous infusion of 20% glucose. The glucose infusion rate was adopted, if necessary, in relation to the blood glucose concentrations measured to maintain this blood glucose level. In case of blood glucose values exceeding 350 mg/dl for more than 60 minutes, the experiments were aborted and the subject was treated with additional s.c. insulin to normalize his blood glucose concentrations.

Blood samples for the determination of plasma insulin concentrations, 4-CNAB and C-peptide were collected at defined intervals, as discussed above. Plasma samples were stored at approximately −20° C. (4-CNAB at −70° C.) until determination by immunoassay is performed. After the end of the sampling period, the study subjects were released from the clinic.

Inter-subject variability for selected pharmacodynamic and pharmacokinetic parameters was assessed. Incidence of postprandial hypoglycemia was assessed for each subject and across the study population.

Blood glucose excursions (i.e., differences between preprandial and postprandial blood glucose concentrations) registered after the ingestion of the meal were used to evaluate pharmacodynamic parameters of the two insulin administration routes and compared with the same data obtained for the study day without any supplemental insulin. From these measurements, the area under the glucose infusion rate versus time curve from 0-6 hours (and other time intervals), the maximal blood glucose excursion ($C_{max}$) and time to the maximal blood glucose excursion ($t_{max}$) were analyzed.

For pharmacodynamic assessment, the following parameters were calculated: Maximal blood glucose excursion ($BG_{max}$), time to $BG_{max}$ ($t_{BG_{max}}$) Area under the blood glucose excursion curve in defined time-intervals ($AUC_{BG\ 0-1h}$, $AUC_{BG\ 0-2h}$, $AUC_{BG\ 0-3h}$, $AUC_{BG\ 0-4h}$, $AUC_{BG\ 0-6h}$), maximal absolute blood glucose concentrations ($BGabs_{max}$), time to $BGabs_{max}$ ($tBGabs_{max}$).

For pharmacokinetic assessment the following parameters were calculated: Maximal plasma insulin concentrations ($INS_{max}$), time to $INS_{max}$ ($t_{INS_{max}}$), Area under the glucose infusion rates in defined time-intervals ($AUC_{Ins\ 0-1h}$, $AUC_{Ins\ 0-2h}$, $AUC_{Ins\ 0-3h}$, $AUC_{Ins\ 0-4h}$, $AUC_{Ins\ 0-6h}$) and maximum reduction of C-peptide concentrations Plasma insulin concentrations were subjected to appropriate pharmacokinetic analyses. Parameters determined include $C_{max}$, $t_{max}$, and the area under the plasma concentration versus time curve from the time of dosing until a return to the baseline measurement ($AUC_{0-t'}$), where t' is the time that the level of plasma insulin concentration returns to the baseline. In addition, other pharmacokinetic parameters, such as $t_{1/2}$, elimination rate constant ($\lambda_z$) and partial AUC values, were calculated, if considered appropriate, for each individual subject enrolled within the study.

Pharmacodynamics

As measurement of a pharmacodynamic effect of oral Insulin/4-CNAB capsules, the blood glucose excursions measured over 6 hours were considered, and the area under the blood glucose excursion vs. time curve in the first two hours after start of meal intake ($AUC_{0-2h}$) was defined as primary pharmacodynamic endpoint.

Figure 16:
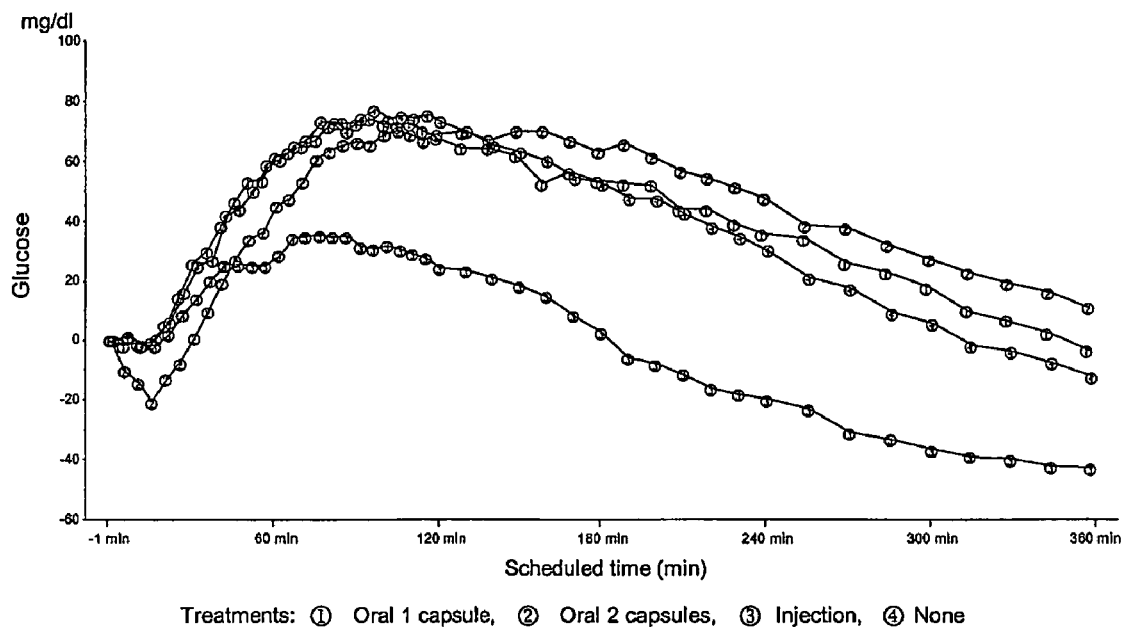
FIG. 16 shows a plot of the arithmetic means of postprandial blood glucose excursions for all subjects.

Based upon individual blood glucose excursion data, the mean time profiles with standard deviation) of the blood glucose excursions per treatment were plotted. FIG. 16 shows a plot of the arithmetic means of postprandial blood glucose excursions (mg/dL) vs. time for all subjects. As indicated in FIG. 16, mean blood glucose excursions of the different treatments reach their maxima between 1 and 2 hours after start of meal intake and then return towards baseline. The time to maximal glucose excursion (median) was 1.3 hours for SC 12 U short-acting insulin, 1.7 hours for placebo, 1.8 hours for oral 150 U Insulin/200 mg 4-CNAB, and 2.2 hours for oral 300 U Insulin/400 mg 4-CNAB.

The lowest overall excursions were achieved with the 12 U SC short-acting insulin injection. Compared to both oral insulin treatments and placebo, blood glucose excursions after SC injection are markedly lower during the period from 45 to 360 minutes and, after crossing the baseline at about 180 minutes, values become increasingly negative until 360 minutes after meal intake.

After oral 300 U Insulin/400 mg 4-CNAB, a sharp decline from baseline can be seen until −20.8 mg/dL at 15 minutes, followed by a return to baseline at 30 minutes. Thus, during approximately the first hour, the dose of 300 U oral Insulin/400 mg 4-CNAB led to lower excursions even when compared to injection. Thereafter, rise and subsequent decline of the curve follows the pattern seen for oral 150 U Insulin/200 mg 4-CNAB dosage and no treatment (placebo). No differences could be seen between 150 U oral Insulin/200 mg 4-CNAB and no treatment (placebo).

Based on the profiles, the parameters, $AUC_{0-1h}$, $AUC_{0-2h}$, $AUC_{0-3h}$, $AUC_{0-4h}$, $AUC_{0-6h}$ and $C_{max}$ were calculated, as presented in Table 30 below.

oral Insulin/200 mg 4-CNAB, all AUCs are more or less equal to those obtained under no treatment. Mean maximum blood glucose excursions ($C_{max}$) after both oral insulin administrations and after no treatment are similar and clearly higher than $C_{max}$ after the SC injection.

The test results can be summarized as follows: When $C_{max}$ and AUCs for 3 hours and more are considered, no statistically significant differences of the oral treatments compared to no treatment (placebo) could be established. On the other hand, both oral treatments differ significantly from SC insulin injection, with oral treatments leading to higher mean values.

With regard to the primary endpoint $AUC_{0-2h}$, a single oral dose of 300 U Insulin/400 mg 4-CNAB, administered 30 minutes prior to a standardized test meal, caused a statistically significant reduction of postprandial blood glucose excursions in comparison to no treatment (placebo). However, the effect was significantly lower than after SC injection of 12 U short-acting insulin. The effect of 150 U oral Insulin/200 mg 4-CNAB was not significantly different from no treatment (placebo).

Pharmacokinetics

From the blood samples taken, the individual plasma concentrations of 4-CNAB, insulin and C-peptide were also determined, and summary concentration vs. time profiles were plotted.

Figure 17:
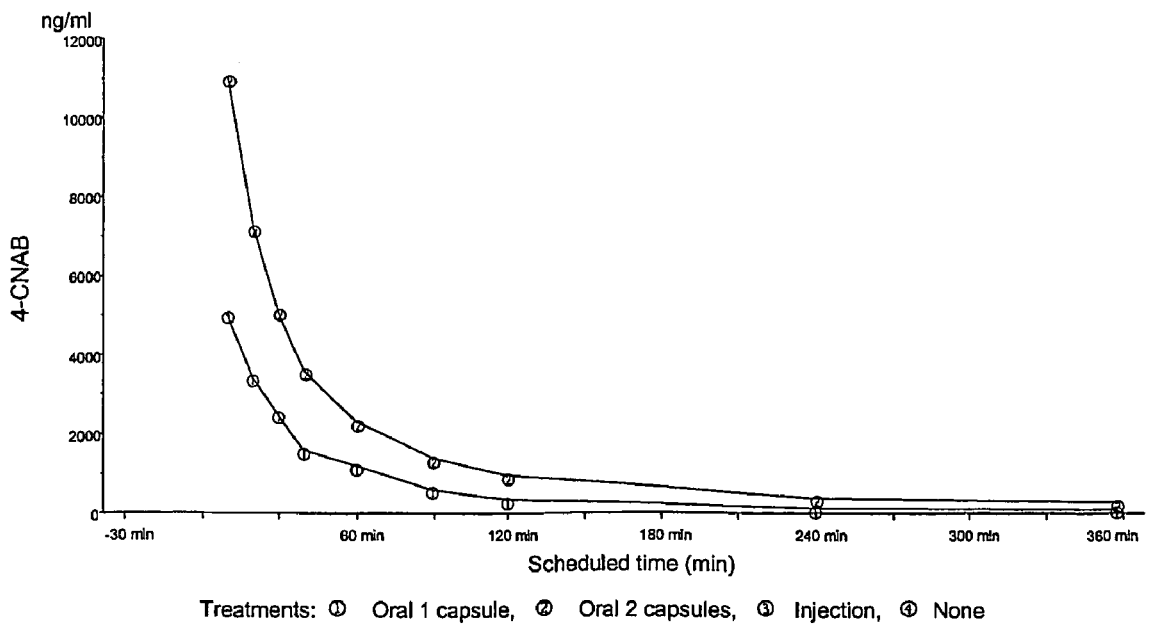
FIG. 17 shows a plot of 4-CNAB plasma concentrations (ng/mL) vs. time (arithmetic means).

FIG. 17 shows profiles of 4-CNAB plasma concentrations (ng/mL) vs. time (arithmetic means). As seen in FIG. 17, plasma 4-CNAB concentrations show a rapid decline within the first two hours after start of meal intake. After 2 hours, concentrations are less than 10% of the levels seen after 10 minutes. The results indicate that markedly higher concentrations might have been be reached in the time between intake of the Insulin/4-CNAB capsules and the first measurement 10 minutes after start of meal intake. Concentrations after intake of 400 mg 4-CNAB are approximately twice as high as after intake of 200 mg.

Figure 18:
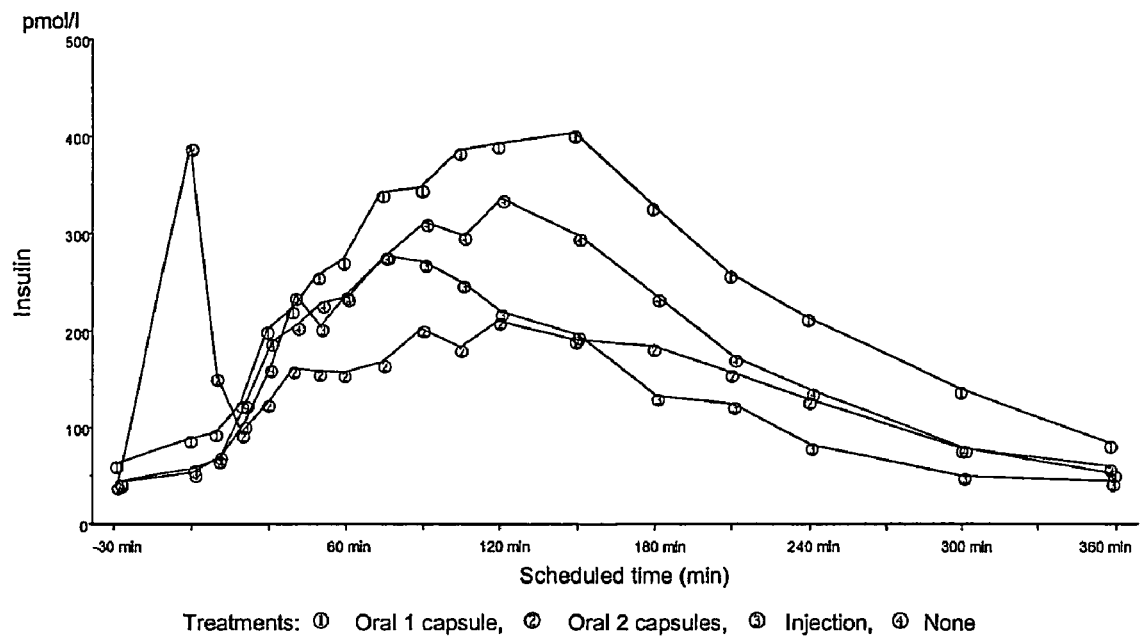
FIG. 18 shows a plot of insulin plasma concentrations (pmol/l) vs. time (arithmetic means).

FIG. 18 shows profiles of insulin plasma concentrations (pmol/l) vs. time (arithmetic means). As shown in FIG. 18, highest mean insulin plasma concentrations are reached after the 150 U oral dose, followed by 300 U oral, placebo, and 12 U SC injection. The curve of oral 300 U Insulin/400 mg

TABLE 30

| | Treatment | | | | | | | |
|---|---|---|---|---|---|---|---|---|
| | Oral 150 U Insulin/ 200 mg 4-CNAB | | Oral 300 U Insulin/ 400 mg 4-CNAB | | SC 12 U Short-acting insulin | | Placebo | |
| Parameter | Mean | STD | Mean | STD | Mean | STD | Mean | STD |
| $AUC_{0-1h}$ (h * mg/dL) | 24.5 | 15.2 | 6.9 | 15.0 | 13.1 | 8.5 | 25.3 | 9.1 |
| $AUC_{0-2h}$ (h * mg/dL) | 94.3 | 46.3 | 69.8 | 38.0 | 44.9 | 32.8 | 97.8 | 28.5 |
| $AUC_{0-3h}$ (h * mg/dL) | 154.1 | 74.1 | 138.2 | 60.4 | 61.4 | 57.5 | 160.2 | 54.0 |
| $AUC_{0-4h}$ (h * mg/dL) | 200.1 | 105.9 | 195.2 | 81.4 | 50.0 | 83.6 | 202.1 | 84.9 |
| $AUC_{0-6h}$ (h * mg/dL) | 233.9 | 164.3 | 250.8 | 140.6 | −21.1 | 119.4 | 214.2 | 143.7 |
| $C_{max}$ (mg/dL) | 90.5 | 38.1 | 85.8 | 28.3 | 50.7 | 25.8 | 88.3 | 27.7 |

This data indicates that $AUC_{0-1h}$ is lowest following the 300 U oral Insulin/400 mg 4-CNAB dosage. Up to 2 hours and 3 hours, the AUCs are still smaller than the AUCs of 150 U oral Insulin/200 mg 4-CNAB and no treatment (placebo), but larger than the AUCs of 12 U SC short-acting insulin. However, for 4 hours and 6 hours, no difference can be seen between the oral applications and no treatment. For 150 U 4-CNAB shows two maxima, the first at 0 min and the second at 120 min. The peak at 0 min is due to one particular patient who contributed with a value of 1803 pmol/L the most to this marked shift of mean insulin concentration. Almost all patients showed a more or less marked isolated increase of insulin concentrations at time 0 but not to such an extent as that patient. In addition, the rise of insulin concentrations under placebo is explained by the patients' endogenous insulin production, induced by the meal intake.

Figure 19:
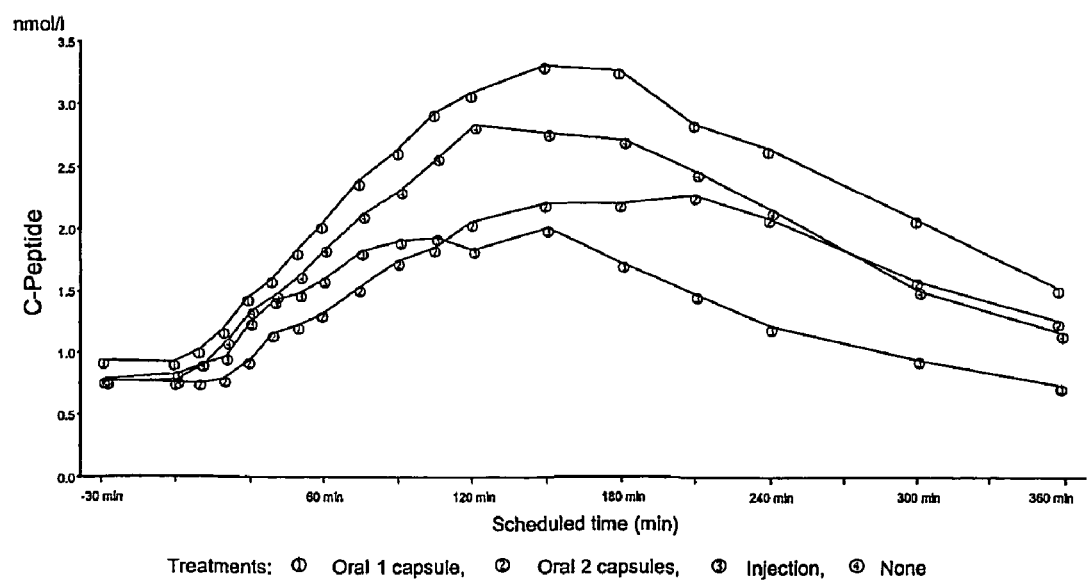
FIG. 19 shows a plot of C-peptide plasma concentrations (nmol/l) vs. time (arithmetic means).

FIG. 19 shows profiles of C-peptide plasma concentrations (nmol/l) vs. time (arithmetic means). Mean plasma concentrations of C-peptide, the indicator of endogenous insulin production, increased after all treatments. Decreasing, or more or less constant C-peptide concentrations, were seen only in a few patients and only after SC injection of short-acting insulin. This may reflect the fact that in most of the patients the ability to produce endogenous insulin was still maintained. As expected, the 150 U oral insulin dose and placebo show the most marked increase, whereas the increases after the 300 U oral dose and the 12 U SC injection are clearly lower.

Based on the insulin concentration vs. time profiles, the parameters $C_{max}$, $t_{max}$ and AUC from time 0 to the time when the baseline insulin level was reached again ($AUC_{0\text{-}t}*$) were calculated, as presented in Table 31 below.

may indicate a rapid onset of action of orally administered 300 U Insulin/400 mg 4-CNAB prior to considerable absorption of carbohydrates from the test meal. Therefore, a time span of 30 minutes between dose administration and start of meal intake might be too long.

Mean fasting blood glucose values at baseline (−1 minute) which served as reference for the calculation of excursions, were 124.38 mg/dL (99.10-172.00) for oral 150 U Insulin/200 mg 4-CNAB, 120.26 mg/dL (72.20-175.00) for oral 300 U Insulin/400 mg 4-CNAB, 143.11 mg/dL (104.00-190.00) for 12 U SC short-acting insulin, and 137.32 mg/dL (93.10-183.00) for placebo. With regard to these baseline values, the four treatments were split into two groups: the two oral treatments with values around 120 mg/dL, and the SC injection together with placebo showing values around 140 mg/dL. This finding may be explained by early action of the oral insulin formulations in the time between dose administration and start of meal intake, which is not covered by the profiles.

TABLE 31

| Treatment | $AUC_{0\text{-}t*}$ (h * pmol/L) | | $C_{max}$ (pmol/L) | | $t_{max}$ (h) | | |
|---|---|---|---|---|---|---|---|
| | Mean | STD | Mean | STD | Median | MIN | MAX |
| Oral 150 U Insulin/200 mg 4-CNAB | 1469.42 | 684.92 | 461.50 | 219.29 | 2.00 | 0.50 | 3.00 |
| Oral 300 U Insulin/400 mg 4-CNAB | 923.06 | 354.59 | 418.53 | 382.46 | 1.50 | 0.00 | 3.50 |
| SC 12 U Short-acting insulin | 791.52 | 417.95 | 315.83 | 155.09 | 1.38 | 0.50 | 3.50 |
| Placebo | 1093.47 | 466.46 | 388.53 | 185.82 | 2.00 | 0.50 | 3.50 | t* denotes time when baseline insulin level is reached again, or last data point (360 min)

This data indicates that mean insulin plasma concentration vs. time profiles showed the highest AUC after 150 U oral insulin, followed by placebo, 300 U oral insulin, and 12 U SC injection. Highest mean $C_{max}$ was reached after 150 U oral insulin, followed by 300 U oral insulin, placebo, and 12 U SC injection. The median time until $C_{max}$ ($t_{max}$) was longest for 150 U oral insulin and placebo, followed by 300 U oral insulin and 12 U SC injection.

Conclusions

The primary objective of this study was to compare the effect of orally administered 300 U Insulin/400 mg 4-CNAB with that of 12 U subcutaneously injected short-acting insulin (Humalog®) on postprandial blood glucose excursions after a standardized breakfast. With respect to $AUC_{0\text{-}2h}$ as main parameter for pharmacodynamic evaluation, the highest effect on blood glucose excursions was found for 12 U SC short-acting insulin, followed by oral 300 U Insulin/400 mg 4-CNAB, oral 150 U Insulin/200 mg 4-CNAB and placebo, and the effects of the two latter appeared more or less equal. However, these results were not consistent for all calculated AUCs. During the first hour, 300 U oral insulin were superior to 12 U SC, and this order changed when the AUCs for more than 2 hours were compared: both oral treatments were no longer significantly different from no treatment (placebo), but the 12 U SC injection showed still a significant difference and clearly smaller AUCs.

After the 300 U oral insulin dose, mean blood glucose excursions turned (until −20.8 mg/dL at 15 minutes after start of meal intake) and returned to baseline at 30 minutes. This transient decline could be seen in most of the patients, but only in one particular with a baseline blood glucose below 80 mg/dL did it lead to a hypoglycemic episode. These findings However, the described non-homogeneity is not considered to impair the quality of the results.

The concentration vs. time profiles for 4-CNAB display only the elimination of the substance from plasma. The absorption phase and the maximum concentrations are missed. In the time between −30 and +10 minutes, a rapid rise followed by a rapid decline can be assumed, and the achieved maximum concentrations should be markedly higher than the values seen at 10 minutes after start of meal intake. Therefore, further investigations of 4-CNAB pharmacokinetics should include an appropriate number of samples from the first hour following dose administration.

The insulin profiles showed the highest AUC after 150 U oral insulin, followed by placebo, 300 U oral insulin, and 12 U SC short-acting insulin. The marked increase of mean plasma insulin concentrations after placebo indicates that the patients' ability of endogenous insulin production, induced by meal intake, was still maintained. Also the high AUC for 150 U oral insulin probably reflects mainly endogenous insulin production, and also the curves of the other treatments may account for a certain amount of endogenous insulin.

The C-peptide plasma concentration profiles confirm this view and also indicate the release of considerable amounts of endogenous insulin. The levels were highest after 150 U oral insulin, followed by placebo, 300 U oral insulin, and 12 U SC short-acting insulin. As expected, the 150 U oral dose and placebo led to the most marked increase, whereas the increase after the 300 U oral dose and the 12 U SC injection was clearly lower, and these findings correlate with the blood glucose lowering effect seen for the different treatments: the lower the effect of the external insulin dose, the higher were the amounts of C-peptide as indicator of endogenous insulin production.

The insulin concentration vs. time profiles seen for both oral doses in this study are considerable different from those obtained in Example 6, where mean insulin concentrations were back to baseline after approximately two hours and where maximum concentrations occurred after about half an hour. These differences might be due to the influence of the meal, stimulating endogenous insulin release and also possibly interfering with the resorption of the oral insulin preparations. In Example 6, patients were fasting during the entire experiment, and endogenous insulin production was suppressed by a constant low-dose insulin infusion. Therefore, the concentration vs. time curves of Example 6 represent more the pure pharmacokinetics of the administered exogenous insulin, whereas in the present study the effects of exogenous and endogenous insulin are overlapping.

No adverse events were reported in this study. There were no treatment related findings of clinical laboratory safety parameters, vital signs, ECG or physical examination. The five hypoglycemic episodes that occurred in four patients remained symptomless due to immediate intervention with intravenous glucose infusion. Only one of the episodes was due to oral 300 U Insulin/400 mg 4-CNAB, and the majority (⅘) occurred after 12 U SC short-acting insulin injection. Accordingly, all study treatments were well tolerated.

Overall, the study results suggest (based on the primary endpoint $AUC_{0-2h}$) that orally administered 300 U Insulin/400 mg 4-CNAB are effective in lowering the postprandial rise of blood glucose in type 2 diabetic patients. However, the effect is smaller than after injection of 12 U SC short-acting insulin, which is significantly superior to both oral administrations. The oral dose of 150 U Insulin/200 mg 4-CNAB is similar effective as no treatment (placebo). At both doses, orally administered Insulin/4-CNAB seems to be well tolerated.

EXAMPLE 8

A single-center, open label, randomized, single dose, 3-way cross-over study was conducted in type 1 diabetes mellitus patients to investigate the effect of food on the absorption and pharmacokinetics of insulin after a single dose of oral 4-CNAB/insulin, and to determine the effect of food on the pharmacodynamics of glucose and C-peptide after a single oral dose of 4-CNAB/insulin.

For the diabetic volunteers, male or postmenopausal female subjects between 18 and 65 years old, inclusive, each with type 1 diabetes mellitus as defined by the American Diabetes Association (1998 Diabetes care, 21: S5-S19) were studied. Subjects had a body mass index of between 18 and 30 kg/m² and had glycemic control HgA1c at screening <10%. Patients also had negative test for antibodies against insulin at screening, fasting blood glucose at screening <12.0 mmol/l, and fasting C-peptide at screening <0.2 nmol/ml. For the healthy control volunteers, male subjects between 18 and 65 years old, inclusive, for more than one year were chosen. Subjects included in the study had between 18 and 30 kg/m².

For diabetic patients, the study consisted of an eligibility screening period, three study periods and a follow-up exam at the conclusion of the last period. The three study periods included the following: administration of single doses of 4-CNAB/insulin followed by fasting (treatment A), followed by an ADA breakfast 20 minutes after dosing (treatment B), and followed by an ADA breakfast 20 minutes after dosing (treatment C). The study was conducted using an open label, randomized, crossover design with an interval of at least 7 days between treatments. The patients fasted overnight. The type 1 diabetics were randomized to treatment A or treatment 3 in periods 1 and 2. In period 3, all diabetics received treatment C. A total of eight type 1 diabetic patients were enrolled. As a control group, two healthy volunteers were enrolled.

For healthy control subjects, the study consisted of an eligibility screening period, one study period and a follow-up exam at the conclusion of the period. The healthy control subjects were not receiving any medication but served as a control for the effect of breakfast on insulin production. Blood sampling and safety assessments followed the same schedule as for the diabetics. The healthy control subjects received the standard ADA breakfast at the same time as the type 1 diabetics in one study period (treatment D).

A typical standard ADA breakfast comprises approximately 30% fat, 50% carbohydrates and 20% protein. Such a breakfast could include, for example, three slices of whole wheat bread, 15 g of low-fast margarine, 15 g of low-caloric jelly, 20 g of 30% fat cheese, 15 g of meat (ham, etc.), 200 ml of 2% fat milk, and coffee tea or water (no sugar).

The study design is presented in Tables 32 and 33 below

TABLE 32

Study design for Type I diabetics

| week −3 to −1 | Treatment A | Treatment B | Treatment C | End of third period |
|---|---|---|---|---|
| Eligibility screening | 4-CNAB/ insulin fasting | 4-CNAB/insulin ADA breakfast 30 min after dosing | 4-CNAB/insulin ADA breakfast 20 min after dosing | follow-up |

TABLE 33

Study Design for Healthy volunteers

| week −3 to −1 | Treatment D | End of period |
|---|---|---|
| Eligibility screening | no dosing ADA breakfast | follow-up |

This study tested the effect of a standard ADA breakfast administered 30 or 20 minutes after dosing on the absorption and pharmacokinetics of 4-CNAB/insulin administered as oral capsules. A control group of healthy subjects received a standard ADA breakfast in one period to measure the amount of insulin produced for this breakfast in healthy control subjects. The type I diabetic patientss were taken off their regular long-acting insulin 24 hrs prior to dosing and their glucose levels were controlled prior to dosing by overnight insulin infusion.

The following treatments were administered to the type 1 diabetics according to the randomization schedule (see below)

a) 400 mg 4-CNAB/300 IU insulin followed by fasting;

b) 400 mg 4-CNAB/300 IU insulin followed by an ADA breakfast 30 minutes after dosing;

c) 400 mg 4-CNAB/300 IU insulin followed by an ADA breakfast 20 minutes after dosing.

Prior to dosing, the patients fasted overnight. The patients received an insulin infusion overnight. The study drug was administered 30 minutes after infusion was stopped (dosing at approximately 9:00 am). In one period, the oral dose was followed by fasting until 3 hours after dosing. In the two other periods, the oral dose is followed by intake of a standard ADA-breakfast 30 or 20 minutes after dosing. On day one of each study period, study medication was administered to subjects. Only an ADA breakfast was administered to the healthy volunteers.

The type I diabetics stopped their regular long acting insulin 24 hrs prior to dosing but were allowed to use their immediate acting insulin up to their entry into the clinic around 3:00 p.m. on day 1. They received 4-6 units (depending on their weight) of regular insulin subcutaneously (s.c.) at approximately 5:30 p.m. on day 1 and a standard dinner thirty minutes after the administration of s.c. insulin. Between 8:30 and 9:00 p.m., the diabetics received a snack. At approximately 9:00 p.m. on day −1, an i.v. infusion of insulin was started at the infusion rate indicated in Table 36. The composition of the insulin infusion and the infusion rate were dependent on the patient's weight and blood glucose concentration, as described in Tables 34 and 35.

TABLE 34

Composition of insulin infusate

| Insulin (U/L) | Patient weight (kg) |
|---|---|
| 80 | 60-65 |
| 88 | 65-70 |
| 96 | 70-75 |
| 104 | 75-80 |
| 112 | 80-85 |
| 124 | 85-90 |
| 140 | 90-95 |
| 180 | >95 |

TABLE 35

Infusion algorithm

| Plasma glucose conc. [mmol/liter (mg/dL)] | Infusion rate (ml/h) |
|---|---|
| <5.5 (<99)[a] | 0 |
| 5.5-6.6 (100-119) | 5 |
| 6.7-7.7 (120-139) | 10 |
| 7.8-8.8 (140-159) | 15 |
| 8.9-9.9 (160-179) | 20 |
| 10-13.3 (180-239) | 40 |
| >13.3 (>240) | 60 |

The infusion rate was adjusted, if necessary, based on the results of blood glucose measurements done every 60 minutes. A blood sample (one drop) for assessment of real-time blood glucose using a Glucocard® was taken from an indwelling cannula, and the blood glucose concentration was adjusted to remain between 6 and 8 mmol/l. The insulin infusion was stopped 30 minutes before drug administration at approximately 9:00 a.m. on day 1. At times when no insulin was needed, only normal saline was administered.

The 4-CNAB (Sodium N-[4-(4-chloro-2-hydroxybenzoyl) amino]butyrate) was manufactured by Emisphere Technologies, Inc. of Tarrytown, N.Y. in 400 mg strength oral capsules. Glucose stablization prior to dosing was done with Actrapid, manufactured by Novo Nordisk and having an active compound of insulin, at 100 U/ml strength, via i.v. infusion. The insulin for subcutaneous injection was also Actrapid, at 100 U/ml strength.

The type I diabetics stopped their regular long acting insulin 24 hrs prior to dosing but were allowed to use their immediate acting insulin up to their entry into the clinic around 3:00 p.m. on day-1. They received 4-6 units of regular insulin s.c. at approximately 5:30 p.m. on day-1 and received a standard dinner thirty minutes after the administration of s.c. insulin. Between 8:30 and 9:00 p.m., the diabetics received a snack and were then were fasted until the next morning. At approximately 9:00 p.m., an i.v. infusion of insulin was started. The insulin infusion was stopped 30 minutes before drug administration at approximately 9:00 a.m. on day 1.

On day 1 of each study period, study medication was administered to subjects in the upright position and was swallowed (not chewed) with 200 mL of water (subjects did not lie down for three hours after dosing). Depending on the treatment given, the patients received a standard ADA breakfast 30 or 20 minutes after dosing or they continued fasting. After the 3 hour blood sample was drawn, patients were allowed to resume their normal pattern of meals and resume using their regular long or immediate acting insulin. Water was allowed ad libitum during the study, except for 1 hour prior to and up to 1 hour after drug administration in each treatment.

The healthy control subjects did not receive any medication but received a standard ADA breakfast at the same time as the diabetics (approximately 9:30 a.m. on day 1) after an overnight fast. The controls resumed normal meals after the 3-hour blood sample was taken.

Study participants did not take any prescription or non prescription medication (with the exception of paracetamol, (acetaminophen) and topical medication) for 14 days prior to entrance into the clinical research facility and for the duration of the study period. The exception to this rule follows: type 1 diabetics continued their insulin therapy and fixed comedication which was used unaltered during the last 6 months. Methylxanthine-containing beverages or food (coffee, tea, coke, chocolate), grapefruit juice, and alcohol were not allowed from 48 hours (2 days) prior to entrance into the clinical research center and during the study.

During each period of the study a series of blood samples were taken for 4-CNAB and insulin pharmacokinetic analyses. The term pre-dose refers to the time that the group of diabetics receives 4-CNAB/insulin. The healthy control subjects do not receive medication.

Blood samples for pharmacokinetic analysis of 4-CNAB and insulin were drawn 30, 15 and 5 minutes prior to and at 10, 20, 30, 40, 50, 60, 75, 90, 105, 120, 150, 180, 210, and 240 minutes after 4-CNAB/insulin administration (17 samples per subject per period). Blood samples for plasma glucose were drawn 30, 15 and 5 minutes prior to and at 10, 20, 30, 40, 50, 60, 75, 90, 105, 120, 150, 180, 210, and 240 minutes after administration (17 samples per subject per period). Blood samples for C-peptide were drawn 30 and 5 minutes prior to and 30, 60, 90, 120, 180 and 240 minutes after administration (8 samples per subject per period).

For healthy control subjects, a blood sample (one drop) was analyzed for real-time at pre-dose of 4-CNAB/insulin to the diabetic patients, 30, 60, 90, 120, 150, 180 and 240 min after each drug administration on day 1 (8 samples per subject per period). Blood samples for pharmacokinetic analysis of 4-CNAB and insulin were drawn 30, 15 and 5 min prior to and at 10, 20, 30, 40, 50, 60, 75, 90, 120, 150, 180, 210, and 240 min after drug administration (16 samples per subject per period). Blood samples for plasma glucose were drawn at 30, 15 and 5 min prior to and at 10, 20, 30, 40, 50, 60, 75, 90, 120, 150, 180, 210, and 240 min after drug administration (16 samples per subject per period). Blood samples for C-peptide were drawn at 30 and 5 min prior to and at 30, 60, 90, 120, 180 and 240 min after drug administration (8 samples per subject per period).

The blood samples (6 mL each) were taken via an indwelling Venflon® catheter or by direct venipuncture into sodium heparin-containing tubes. The blood samples were centrifuged at 1500×g for fifteen minutes at a temperature between 2° C. and 8° C., within one hour of sample collection. The total volume of about 450 mL (type 1 diabetics) or about 180 mL (healthy control subjects) blood was taken during the study.

Diabetic patients received 4-6 units (depending on their weight) of regular insulin subcutaneously (s.c.) at approximately 5:30 p.m. on day 1. Insulin infusion started at 9:00 p.m. on day 1, and the pump stopped 30 min before dosing of 4-CNAB/insulin on day 1 at approximately 9:00 a.m. A blood sample (one drop) was analyzed for real-time glucose every 60 minutes during the time of insulin infusion and at pre-dose, 30, 60, 90, 120, 150, 180 and 240 minutes after each drug administration on day 1 (8 samples per subject per period). The blood samples were taken from the indwelling canula (with obturator), one drop per assessment, and were analyzed for glucose in real time using a Glucocard®.

The pharmacokinetic parameters determined or calculated from the plasma concentration time data for 4-CNAB and insulin were $C_{max}$, $t_{max}$, $K_{el}$, $t_{1/2}$, $AUC_{last}$ (area under the plasma concentration-time curve up to time t, where t is the last time point with concentrations above the lower limit of quantitation (linear trapezoidal rule)), $AUC_{(0-inf)}$, $AUC_{last}$+$C_{last}/K_{el}$, and % $AUC_{extrap}$ (percentage of estimated part for the calculation of $AUC_{(0-inf)}$:$(AUC_{(0-inf)}-AUC_{last})/AUC_{(0-inf)}*100\%$)).

The following pharmacodynamic parameters were computed from the plasma concentration-time data of glucose and C-peptide (both original and baseline subtracted data) using non-compartmental analysis: $E_{max}$, $t_{emax}$, and $AUEC_{last}$ (area under the effect-time curve calculated using linear trapezoidal summation from time zero to time t, where t is the time of the last measurable effect (E).

Pharmacokinetic/Pharmacodynamic Evaluation

In this section, the effect of food on the absorption and pharmacokinetics of 4-CNAB and insulin and on the pharmacodynamics of glucose and C-peptide after a single oral dose of 4-CNAB/insulin is presented.

Figure 20:
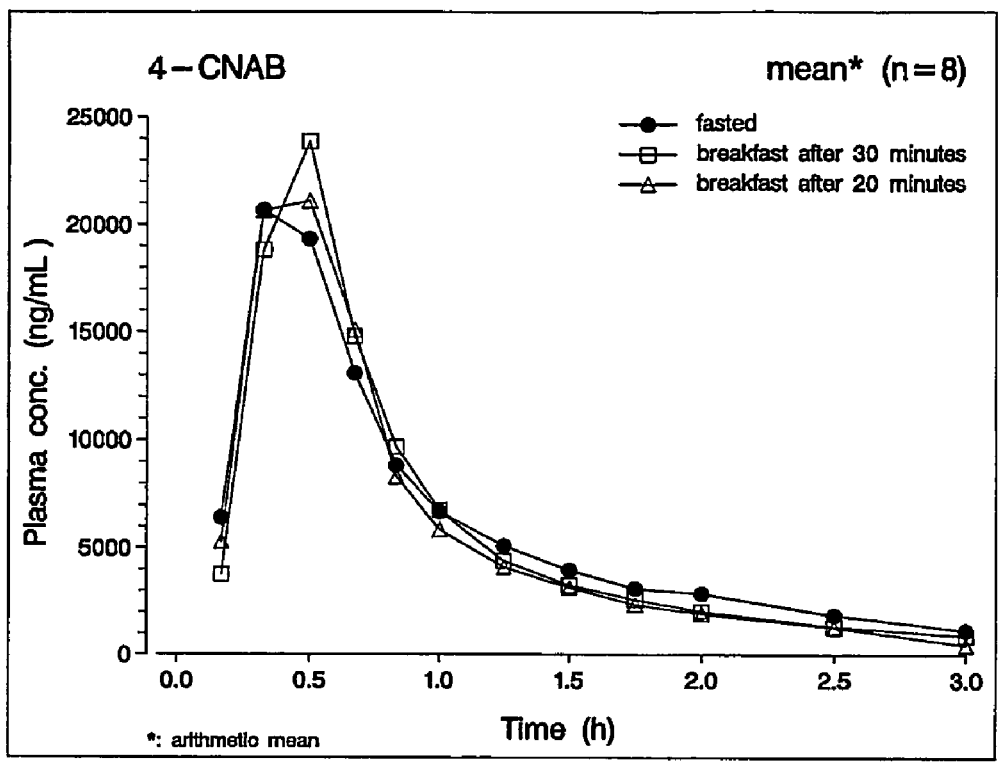
FIG. 20 shows mean concentration/time profiles of 4-CNAB plasma concentration after a single oral dose of 4-CNAB/insulin for three treatment groups (fasting, breakfast 30 or 20 minutes post-dose).

FIG. 20 shows mean profiles of 4-CNAB plasma concentration data for all three treatment groups. As shown in FIG. 20, the concentration-time profiles for the three treatment groups (fasting, breakfast 30 or 20 minutes post-dose) were almost identical.

Individual data under fasting conditions for six out of eight subjects showed a clear 4-CNAB peak around 30 minutes post-dose, while for two subjects (Subjects 106 and 108) the 4-CNAB concentrations did not show a clear peak but a prolonged elevation. When having a breakfast 30 minutes post-dose, seven out of eight subjects showed a clear peak around 30 minutes post-dose, while one subject (Subject 104) showed a flattened peak. When having a breakfast 20 minutes post-dose, all eight subjects showed a clear 4-CNAB peak between 20 and 40 minutes post-dose. In general plasma 4-CNAB was rapidly absorbed and concentration-time profiles were not affected by breakfast at 20 or 30 minutes post-dose.

For insulin, no mean profiles were presented because of the high variability between and within the subjects. With regard to the individual profiles, a slight decrease in insulin concentrations was observed pre-dose, and this was the result of the overnight insulin infusion that was stopped at 30 minutes prior to dosing of study medication.

Under fasting conditions, peak insulin concentrations ranged from 245 to 4450 pmol/L. When subjects had a breakfast 30 minutes post-dose, the peak insulin concentrations ranged from 87 to 2486 pmol/L. When subjects had a breakfast 20 minutes post-dose, the peak insulin concentrations ranged from 84 to 1260 pmol/L. Healthy subjects showed peak insulin concentrations of 254 and 662 pmol/L following breakfast. The majority of insulin peaks, whether high or low, appeared around 20 minutes post-dose. However, in four cases a double insulin peak was observed. In one other case, one late insulin peak was observed, and the late appearing insulin peaks did not correlate with a decrease in glucose.

In general, the insulin peak was accompanied by a slight decrease or stabilization of glucose. However, the height in insulin concentrations reached did not correlate with the extent of glucose lowering.

Each subject showed remarkable intra-individual variation in insulin concentration. The healthy subjects showed a mild (peak insulin: 254 mmol/L for one subject) to moderate (peak insulin 662 mmol/L for one subject) increase of plasma insulin concentrations from around 1 hour after breakfast until 2 hours after breakfast or until 3 hours after breakfast. Due to the considerable variation in insulin plasma concentrations between and within subjects, no effect of food intake on insulin plasma concentration-time profiles could be concluded.

Figure 21:
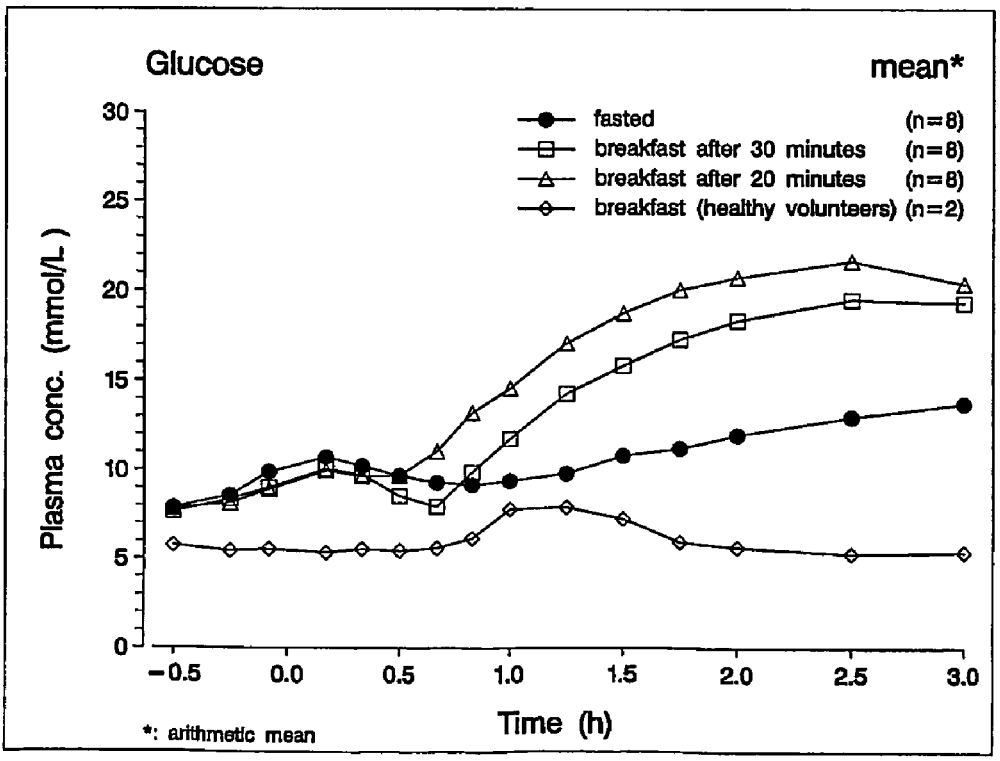
FIG. 21 shows mean concentration/time profiles of plasma glucose concentration after a single oral dose of 4-CNAB/insulin for three treatment groups (fasting, breakfast 30 or 20 minutes post-dose).

FIG. 21 shows mean concentration-time profiles of plasma glucose. In reference to FIG. 21, the majority of patients showed a slight increase of glucose concentration pre-dose, which might be related to the overnight insulin infusion which was stopped 30 minutes prior to dosing of study medication. Under fasting conditions, plasma glucose concentrations showed a slight increase from around 60 minutes post-dose onwards. When patients had a breakfast 20 or 30 minutes post-dose, plasma glucose concentrations increased faster and reached higher values. Under fasting conditions, a very slight dip in glucose between 10 to 60 minutes was observed. When patients had a breakfast 30 minutes post-dose, the dip was slightly more pronounced. When patients had a breakfast 20 minutes post-dose, no clear dip in glucose was observed. The healthy subjects showed a mild increase in glucose between 1 and 2 hours after breakfast.

With regard to C-peptide, for the majority of the samples, the plasma C-peptide concentrations were below the LOQ. Therefore, no descriptive statistics or profiles are shown.

For 4-CNAB pharmacokinetic parameters were calculated as planned. In addition, for three parameters ($C_{max}$, $t_{max}$ and AUC) partial values were calculated for the periods 0-20 minutes post-dose, 0-30 minutes post-dose and 0 3 h post-dose. For Insulin, only $C_{max}$, $t_{max}$ and AUC values for the periods 0-20 minutes post-dose, 0-30 minutes post-dose and 0-3 h post-dose were calculated. No pharmacodynamic parameters for glucose and C-peptide were calculated.

Summary statistics for the PK parameters of 4-CNAB are presented in Table 36 and PK parameters derived for 4-CNAB from the periods 0-20 minutes post-dose, 0-30 minutes post-dose and 0-3 hrs post-dose are presented in Table 37.

TABLE 36

Summary statistics of plasma 4-CNAB pharmacokinetic parameters

| | $C_{max}$ (ng/mL) | $t_{max}$* (h) | $AUC_{0-inf}$ (ng · h/mL) | $t_{1/2}$ (h) |
|---|---|---|---|---|
| Fasting | 21750 (±7506) | 0.42 (0.33-0.67) | 20713 (±7161) | 0.86 (±0.69) |
| Breakfast 30 min post-dose | 24016 (±6700) | 0.50 (0.33-0.67) | 18404 (±3956) | 0.70 (±0.11) |
| Breakfast 20 min post-dose | 24957 (±8047) | 0.42 (0.33-0.67) | 17983 (±4628) | 0.65 (±0.08) |

*Median (min-max)

Under fasting conditions, average $C_{max}$ values were lower compared to fed conditions, while $AUC_{0-inf}$ values showed the opposite. However, the standard deviation for both $C_{max}$, $AUC_{0-inf}$ and $t_{1/2}$ was high. For all treatments, the maximum concentration was reached shortly after dosing, 25 to 30 minutes post-dose. The average half life was slightly shorter under fed conditions compared to the fasting condition.

TABLE 36

Summary statistics of plasma 4-CNAB pharmacokinetic parameters

| | $C_{max}$ (ng/mL) | $t_{max}$ (h) | AUC (ng · h/L) |
|---|---|---|---|
| | 0-20 minutes | | |
| Fasting | 20670 (±7503) | 0.33 (±0) | 2898 (±1476) |
| Breakfast 30 min post-dose | 18809 (±4453) | 0.33 (±0) | 2275 (±669) |
| Breakfast 20 min post-dose | 20642 (±9237) | 0.33 (±0) | 2800 (±1312) |
| | 0-30 minutes | | |
| Fasting | 21533 (±7918) | 0.39 (±0.09) | 6295 (±2657) |
| Breakfast 30 min post-dose | 23973 (±6794) | 0.48 (±0.06) | 5958 (±1515) |
| Breakfast 20 min post-dose | 24554 (±8130) | 0.42 (±0.09) | 6367 (±2300) |
| | 0-3 hours | | |
| Fasting | 21750 (±7506) | 0.44 (±0.13) | 18318 (±3355) |
| Breakfast 30 min post-dose | 24016 (±6700) | 0.50 (±0.09) | 17073 (±3581) |
| Breakfast 20 min post-dose | 24957 (±8047) | 0.46 (±0.15) | 16490 (±4547) |

For the 0-20 minutes period, no differences in $C_{max}$, $t_{max}$ and AUC between the different treatment groups were theoretically to be expected. For $C_{max}$, indeed no clear differences were observed, but for AUC the mean value was lower for the group who received breakfast 30 minutes post-dose compared to the other two treatment groups. If food intake affected the pharmacokinetics of 4-CNAB, it was expected that for the 0-30 minutes period, a difference in $C_{max}$, $t_{max}$ and AUC was observed between the group who received breakfast 20 minutes post-dose and the other two treatment groups. However, this was not observed. For all three treatment groups, $C_{max}$ was reached almost within 30 minutes post-dose; mean $C_{max}$ (0-30 minutes) values were only slightly lower compared to the $C_{max}$ (0-3 hrs).

For insulin, summary statistics for the PK parameters derived from insulin for the periods 0-20 min, 0-30 minutes and 0-3 h post-dose are presented in Table 37.

TABLE 37

Summary statistics of plasma insulin pharmacokinetic parameters

| | | $C_{max}$ (pmol/L) | $t_{max}$ (h) | AUC (pmol · h/L) |
|---|---|---|---|---|
| | | 0-20 minutes | | |
| A | Fasting | 1040 (±1549) | 0.29 (±0.07) | 220 (±325) |
| B | Breakfast 30 min post-dose | 751 (±835) | 0.33 (±0) | 133 (±138) |

TABLE 37-continued

Summary statistics of plasma insulin pharmacokinetic parameters

| | | $C_{max}$ (pmol/L) | $t_{max}$ (h) | AUC (pmol · h/L) |
|---|---|---|---|---|
| C | Breakfast 20 min post-dose | 418 (±439) | 0.31 (±0.06) | 80 (±75) |
| | | 0-30 minutes | | |
| A | Fasting | 1176 (±1527) | 0.31 (±0.11) | 284 (±353) |
| B | Breakfast 30 min post-dose | 751 (±835) | 0.33 (±0) | 227 (±249) |
| C | Breakfast 20 min post-dose | 430 (±430) | 0.33 (±0.09) | 127 (±120) |
| | | 0-3 hours | | |
| A | Fasting | 1332 (±1436) | 0.51 (±0.40) | 472 (±377) |
| B | Breakfast 30 min post-dose | 871 (±808) | 0.39 (±0.18) | 386 (±429) |
| C | Breakfast 20 min post-dose | 430 (±430) | 0.33 (±0.09) | 177 (±120) |

For the 0-20 minutes period, no differences in $C_{max}$, $t_{max}$ and AUC between the different treatment groups were theoretically to be expected. However, clear differences were observed for mean $C_{max}$ and AUC, although considerable variation was reported. $C_{max}$ and AUC values were considerable lower under fed conditions compared to fasting conditions. If food intake affected the pharmacokinetics of insulin it was expected that for the 0-30 minutes period, a difference in $C_{max}$, $t_{max}$ and AUC was observed between the group who received breakfast 20 minutes post-dose and the other two treatment groups. However, this was not observed; the group who had breakfast 30 minutes post-dose showed also a clear difference when compared to fasting, which was not expected.

It appears that there is considerable within subject variation in the absorption of insulin. On basis of the current results, it appears that there is no effect of breakfast on insulin absorption when given at 30 or 20 minutes post-dose. However, in some subjects in fasting condition or having had breakfast 30 minutes post-dose, a late insulin peak was seen whereas this is never seen in subjects having breakfast 20 minutes post-dose. Therefore, an effect of food intake 20 minutes post-dose cannot be excluded.

Conclusions

Absorption of 4-CNAB was rapid, and food intake at 30 and 20 minutes after dosing showed no effect on the pharmacokinetics of 4-CNAB. For all three treatment groups, 4-CNAB-profiles showed a high degree of similarity. In addition, no clear differences between treatment for pharmacokinetic parameters $C_{max}$, $t_{max}$ and AUC derived from 4-CNAB were observed. It could be concluded that food had no effect on 4-CNAB whether breakfast was eaten 20 or 30 minutes post-dose.

Absorption of insulin showed high variety between and within subjects (between treatments), due to which no firm conclusion about the influence of food intake 30 or 20 minutes following dosing could be made. No correlation between 4-CNAB and insulin was observed. This might be related to the time when and the location where insulin is released from its carrier 4-CNAB. Unfortunately, very limited information on this process is available. From the present results it could not be concluded that food affected the pharmacokinetic parameters obtained from plasma insulin concentration data.

Food intake caused an increase in plasma glucose concentrations but did not affect the effect of 4-CNAB/insulin on glucose in Type I diabetic patients. In diabetic patients, plasma glucose concentration data showed a steeper increase after breakfast compared to fasting conditions, which was expected. In general, the insulin peak was accompanied by a slight decrease or stabilization of glucose. However, the height in insulin concentrations reached did not correlate with the extent of glucose lowering.

Plasma C-peptide concentrations were too low to perform any statistical analysis. It is not expected that 4-CNAB/insulin will change these minimal levels. No effect of food intake on C-peptide could be concluded in Type I diabetic patients.

The number of AEs was highest when breakfast was taken 30 minutes after dosing of 4-CNAB/insulin. The majority of AEs was hyperglycemia, which might be expected in Type I diabetic patients. No hypoglycemia was observed, while this was expected. Probably the 4-CNAB/insulin dose was too low, although, high insulin peaks were observed. With regard to vital signs, ECG and clinical chemistry there were no clinical significant observations. Glucose measurements using Glucocard® showed high glucose concentrations, especially following breakfast. Patients received concomitant medication to treat these hyperglycaemic events. A single oral dose of 400 mg 4-CNAB/300 IU insulin in combination with food or under fasting conditions was safe and well tolerated.

EXAMPLE 9

An open-label, single-dose, crossover study was conducted in order to compare the safety, pharmacokinetics, and pharmacodynamics of orally administered 4-CNAB/Insulin in fasting type 2 diabetic patients serving as their own controls, and to compare blood glucose, insulin and C-peptide levels following a standard meal in type 2 patients given their regular medication, with that of blood glucose, insulin and C-peptide levels following a standard meal with 4-CNAB/Insulin.

Twenty-four (24) volunteers, between 46 and 70 years old, each with type 2 diabetes mellitus were studied. Patients had a body mass index of between 21 and 35 and had stable glycemic control (HgA1c ranged from 5.9 to 11.6%). Fifteen patients were on antidiabetic medication (either Metformin or Acarbose), and 9 patients controlled their diabetes by diet alone. All participants who were on medication did not take their antidiabetic drug 24 hours prior to study The diabetic volunteers were divided into two groups—in one group, twelve patients were studied in a fasting state, and in a second group, twelve patients were studied before and during standard meal. Every patient served as his own control and was tested without getting the insulin/4-CNAB mixture.

Figure 22:
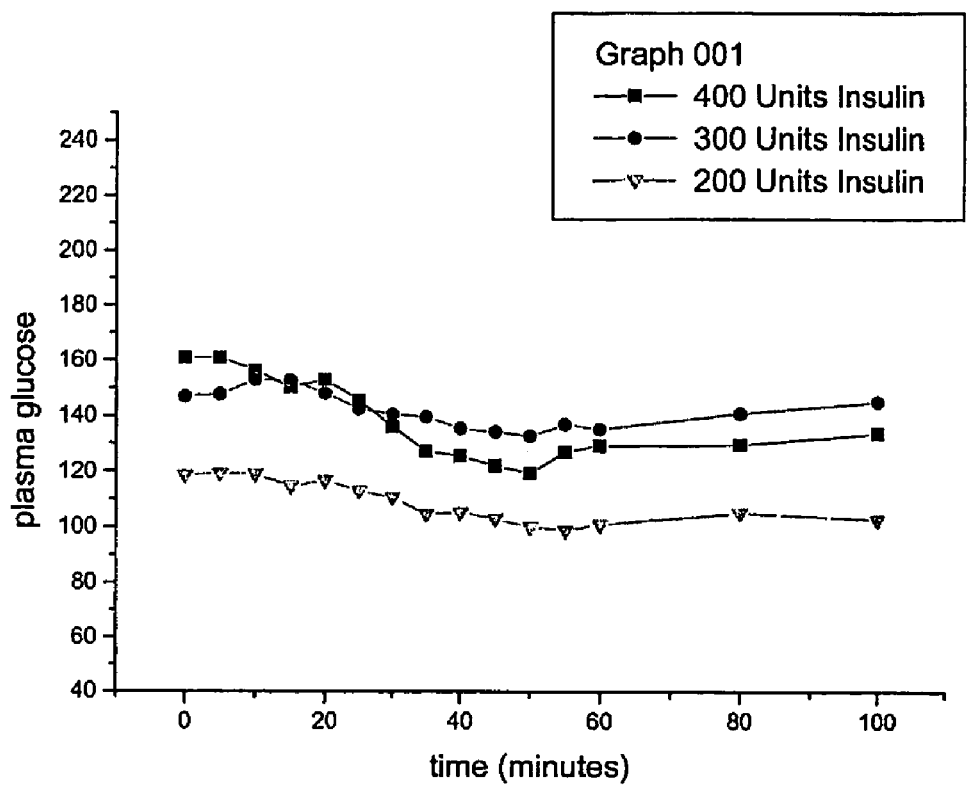
FIG. 22 shows plasma glucose versus time for patients given one capsule containing a mixture of insulin in a stepwise fashion (3 patients received 200 U insulin, 5 patients received 300 U insulin and 4 patients received 400 U insulin) and a fixed dose of 300 mg 4-CNAB.

With respect to Group 1, following a minimum of 8 hour overnight fast, subjects were given one capsule containing a mixture of insulin in a stepwise fashion (3 patients received 200U insulin, 5 patients received 300U insulin and 4 patients received 400U insulin) and a fixed dose of 300 mg 4-CNAB as a delivery agent. In the control session, a placebo was administered to these same patients. See FIG. 22 for a plot of plasma glucose vs. time for Group 1 subjects.

Figure 23:
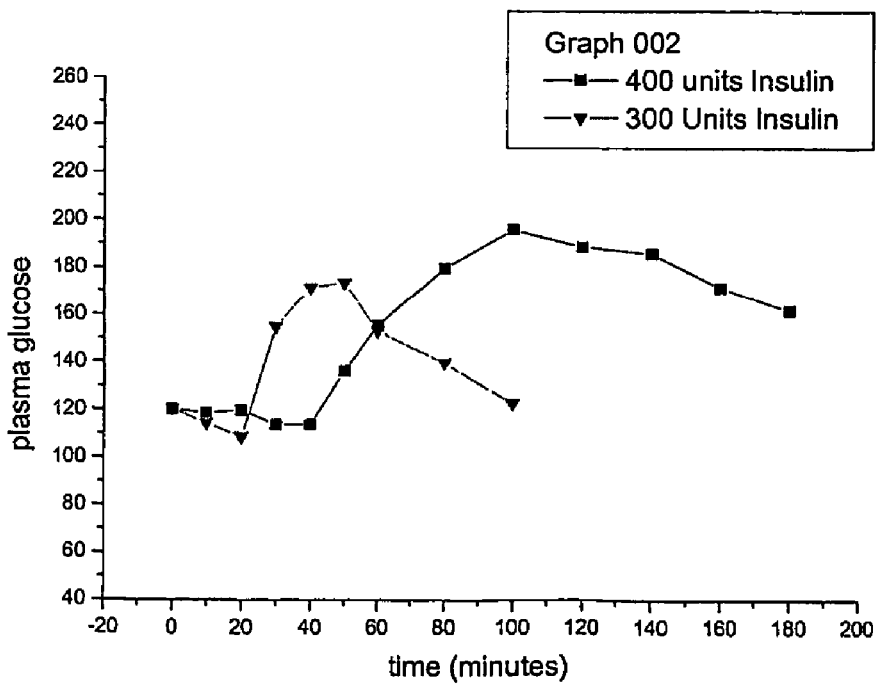
FIG. 23 shows plasma glucose versus time for patients administered a capsule contained 300 U or 400 U insulin and 300 mg of 4-CNAB.

With respect to Group 2, subjects had a standard meal (350 kcal) after a minimum of 8 hour overnight fast. Twenty minutes prior to the ingestion of food, the patients were administered a capsule contained 300U or 400U insulin (six patients received 300U insulin and six patients received 400U of insulin) and 300 mg of 4-CNAB. In the control session, these same patients took their own regular medication, either 850 mg Metformin or 100 mg Acarbose. Subjects who control their diabetes on diet alone had their meal (47 g of carbohydrates (54%) and 350 kcal total calories) without any drug. See FIG. 23 for a plot of plasma glucose vs. time for Group 2 subjects.

Due to the fact that blood glucose level was not reduced by 30% (in average of the first three fasting subjects), the dose was increased to 300U insulin. Then, since the blood glucose level was not reduced by 30% with 300U insulin (in average of the 3 subjects), in both groups (fasting and standard meal), the dose of insulin was increased to 400U insulin.

The delivery agent 4-CNAB was supplied by Emisphere Technologies Inc., of Tarrytown, N.Y., and was stored at room temperature desiccated until use. Recombinant Human Zinc Insulin was shipped directly by Eli Lilly and Company, and was stored at −20 C. Standard capsules were made of gelatin, size 00C.

A catheter was inserted into the antecubital arm vein of each patient. Blood was withdrawn at baseline twice, 5 to 10 minutes apart, and at timed intervals after the administration of the capsule. In group 1, the fasting group, blood was withdrawn during the first hour every 5 minutes and thereafter every 10-20 minutes. In group 2, the standard meal group, blood was withdrawn during the first two hours every 10 minutes and thereafter every 20 minutes. In both groups, blood samples were withdrawn until blood glucose reached basal levels. All plasma samples were analyzed for glucose, insulin, C-peptide and the delivery agent 4-CNAB. Blood glucose levels were measured in real time using two Elite Glucometers (Bayer corporation, Elkhart, Indianapolis, Ind., USA). At the end of the trial, plasma glucose concentrations were measured, using an Enzymatic UV test of Roche Diagnostics (Roche Diagnostics Indianapolis, Ind., USA). Plasma insulin and C-peptide were determined using radio-immunoassay kits produced by Linco Research, Inc., St. Charles, Mo., USA.

Results and Conclusions

While the results were highly variable, there was a clear trend indicating in most subjects the absorption of insulin and its biological effect causing either hypoglycemia or a suppressed elevation of blood glucose, following meals. In the meal session, when the effect of the insulin administered was compared to the effect of the anti-diabetic drug given, there was only a small difference in the blood glucose values, demonstrating the fact that oral insulin was biologically effective even during meals. As in previous examples provided herein employing non-diabetic volunteers, the rise in insulin levels appeared 10-30 minutes after the capsule was swallowed and preceded the drop in blood glucose levels (when there was a drop.)

The C-peptide levels were measured in order to evaluate the extent of enteral absorption of insulin. The absorption of insulin caused a drop in the C-peptide levels, particularly in the standard meal group, indicating a decrease in endogenous insulin secretion due to the absorption of the insulin and the resulting hypoglycemia.

Fasting diabetic type 2 volunteers given increasing dose of insulin (200U to 400U insulin) orally with 300 mg delivery agent 4-CNAB demonstrated a decrease in glucose levels and a moderate increase in insulin levels. In the standard meal group, the insulin capsule caused higher insulin levels and a decrease in C-peptide level. In most cases, following the ingestion of the capsule, there was a decrease in plasma glucose levels, and the nadir appeared after 10-30 minutes in the fast group. In patients with the standard meal who received their regular antidiabetic agent, the 4-CNAB/Insulin capsule "covered" their meal no less than, and sometimes even better than, the Metformin or the Acarbose. In most of the patients in the standard meal group, the C-peptide levels were suppressed, pointing to the fact that the secretion of endogenous hormone was partially abolished.

Plasma insulin levels were elevated in most of the subjects in the fasting group. These levels were not always followed by a reduction in the glucose levels.

No adverse events were detected during the trial or a few weeks later, except for one subject who complained of mild headaches five minutes after ingestion of the capsule, probably not associated with the trial mixture.

It is concluded that this oral insulin preparation is safe and efficient. There is, however, a need for further improvement in absorption of the biologically active insulin.

ADDITIONAL EXAMPLES

In order that the method of reducing the incidence and/or severity of one or more disease states associated with chronic administration of insulin may be better understood, the following examples are set forth. These examples are for the purpose of illustration only and are not to be construed as limiting the scope of the invention in any manner.

The delivery agent 4-CNAB was prepared by Emisphere Technologies, Tarrytown, N.Y. Insulin (Zinc, Human Recombinant) was purchased from Calbiochem (San Diego, Calif.). The Insulin potency was approximately 26 USP units/mg. Insulin was stored as a lyophilized solid at −20° C. In solution, it was stored as frozen aliquots (15 mg/mL) that were subjected to only one freeze-thaw cycle.

An aqueous insulin stock solution was prepared (at pH 7.5) with a final insulin concentration of approximately 15 mg/mL. Delivery agents were dissolved in water with subsequent additions of sodium hydroxide or hydrochloric acid to both dissolve the delivery agent and to titrate the dosing solution to pH 7.5-8.5. The required amount of insulin was added to the delivery agent solution before dosing.

Insulin levels in the rats were assayed using the Insulin ELISA Test Kit [DSL, Webster, Tex. Cat. #DSL-10-1600]. The assay covered the range 3.125 to 250 mU/mL. Blood glucose levels in the rats were measured using a glucometer, One-Touch Basic Blood Glucose Monitoring System, manufactured by Lifescan Inc. (Milpitas, Calif.).

Animal Model

A total of 60 male Sprague-Dawley rats were fasted for 24 hours and then anesthetized with Thorazine (1.5 mg/kg, im) and Ketamine (44 mg/kg, im). They were then divided into the following 5 treatment groups:
1. $H_2O$ (p.o. 1 mL/kg)
2. Carrier (p.o., 1 mL/kg; 200 mg/kg)
3. Insulin (p.o., 1 ml/kg; 0.5 mg/kg)
4. Insulin and Carrier (p.o., 1 ml/kg; 0.5 mg/kg Insulin and 200 mg/kg 1182)
5. Insulin (s.c., 0.05 mg/kg)

There were twelve animals per group, with three being sacrificed at 30, 60, 120 and 180 minutes. For serum insulin and blood glucose monitoring, 0.4 mL of blood was drawn from the tail artery. Following euthanasia, an aorta sample was removed and snap-frozen in liquid nitrogen. All animal studies where conducted in accordance with the IACUC approved protocols.

Animals received streptozotocin (65 mg/kg, iv) after acclimation to the facility. Blood glucose was measured at 24, 48, and 72 hours after injection. Those animals with blood glucose greater than 150 mg/dl were fasted 12 hours and received treatment as described.

Hybridization Sample Preparation

Total RNA was prepared from the frozen tissue sample following the protocol for use of Trizol Reagent (Invitrogen, Inc., Carlsbad, Calif.). The samples were then further cleaned up by use of the Qiagen Midi Kit (Valencia, Calif.). Quality of each RNA sample was assessed using agarose gel electrophoresis and UV absorbance at 260 and 280. Acceptable RNA samples were pooled in equal quantities on a mass basis. This pooled sample was used to prepare cDNA following the protocol provided by Affymetrix. This sample was then used as template in an ii: vitro transcription labeling and amplification reaction using the Enzo BioArray High Yield RNA Transcript Labeling Kit (Affymetrix Inc., Santa Clara, Calif.). 15 µg of labeled transcript was then fragmented and used to prepare a hybridization solution as described in the Affymetrix GeneChip Protocol, Affymetrix, Inc., 2000.

GeneChip Analysis

The samples were hybridized to a Test Array and 5' to 3' ratios, detection limit, and image quality were assessed to ensure the quality of the labeled sample. Acceptable samples were then hybridized to an Affymetrix Rat U34A array. Washing and staining of these arrays was performed using the standard Affymetrix protocols. Array quality was assessed in the same manner as the Test array. Acceptable samples were analyzed both in the expression patterns seen across the group as well as pair wise in the following manner:
1. Group 2 vs. Group 1
2. Group 3 vs. Group 1
3. Group 4 vs. Group 1
4. Group 5 vs. Group 1
5. Group 4 vs. Group 5
6. Group 4 vs. Group 2

EXAMPLE 12

Fold change were determined by the Affymetrix Microarray Suite Software package and values below 2 fold were considered insignificant. This software package analysis compares the individual members of each probe set to determine a Difference Call. In this report all calculated fold changes are used in the figures, however in the results and discussion only those fold changes that received an Increasing or Decreasing call by the Affymetrix software were used to draw conclusions. These data are included in Table 38 below.

TABLE 38

Fold Change Data From Genechip Analysis of Oral and SC Dosing of Insulin

| Time (minutes) | Orally Dosed | | | Subcutaneously Dosed | | | Direct P.O. to S.C. Comparison | | | |
|---|---|---|---|---|---|---|---|---|---|---|
| | 60 | 120 | 180 | 60 | 120 | 180 | 30 | 60 | 120 | 180 |
| 12-LO | 2.7 | −3.4 | −2.1 | 5.8 | 4.3 | −6.4 | −1.6 | −2.2 | −14.3 | 3 |
| 6-Phosphofructo-2-kinase/fructose-2,6-bisphosphatase | 1.2 | 3.3 | 1.8 | 1.2 | 3.2 | 1.4 | −1.3 | −1 | −1.1 | 1.3 |

TABLE 38-continued

Fold Change Data From Genechip Analysis of Oral and SC Dosing of Insulin

| Time (minutes) | Orally Dosed | | | Subcutaneously Dosed | | | Direct P.O. to S.C. Comparison | | | |
|---|---|---|---|---|---|---|---|---|---|---|
|  | 60 | 120 | 180 | 60 | 120 | 180 | 30 | 60 | 120 | 180 |
| a-actin | −1.2 | 1.6 | 3.8 | −1.2 | 1.6 | 3.8 | 1.1 | −1.1 | 1.1 | 2 |
| c-myc | −2.4 | −1.6 | 1.9 | 1 | −1 | 3.8 | −1.1 | −2.6 | −1.6 | 1.1 |
| desmin | −15.7 | −2.8 | 8.4 | −15.7 | −2.8 | 8.4 | −1.4 | −28.2 | 6.6 | −3 |
| Egr-1 | −2.1 | 1.1 | 5.6 | 2.3 | 1.6 | 6.9 | 1.6 | −4.7 | −1.4 | −1.2 |
| Fru-1,6-P | −1.7 | −1.4 | −3.3 | −2.2 | 1 | −2.9 | −1.3 | −1.8 | −1.4 | −2.2 |
| G6Pase | −25.1 | −12.2 | 2.8 | 1.2 | −8.1 | 17.1 | 7.1 | −35 | −6.8 | −8.7 |
| Glycogen Phosphorylase | −14.2 | −4.1 | 1.6 | 4.6 | −33.4 | 1.8 | −1.4 | −57.6 | 10.5 | −1.1 |
| Glycogen synthase | −1.1 | 9.4 | −1.4 | −2.3 | 5.3 | −1.2 | −2.3 | 2.2 | 1.8 | −1.2 |
| gp130 | 3.7 | 1.3 | 1.7 | 3.3 | 1.8 | 1.3 | 1.4 | 1.2 | −1.6 | 1.4 |
| GSK3 beta | −2.5 | −1.4 | 1.5 | −4.2 | −1 | 1.4 | 1.8 | 1.9 | −1.4 | 1.2 |
| Hexokinase II | 1.1 | 9.8 | 2.2 | −1.6 | 5.3 | 1.6 | 2.8 | 2.1 | 2 | 1.2 |
| HO-1 | −4.9 | −1.5 | 2.5 | −1.6 | 5.8 | 1.8 | 1.8 | −3.3 | −6 | 1.4 |
| ICAM-1 | −2.5 | −1.1 | 1.6 | −1.9 | 1.8 | 2.9 | 1.9 | −1.3 | −1.9 | −1.8 |
| IGFBP-1 | 3 | −39.2 | −2 | 2.4 | −3.1 | −1.6 | −1.1 | 1.4 | −6.3 | −1.2 |
| IGFBP-2 | −1.1 | −15.8 | 1.5 | −1.3 | −6.9 | 1.1 | 1.7 | 1.2 | −2.3 | 1.4 |
| IGFBP-3 | −2.5 | 1.4 | 2 | −1.4 | 1.6 | 1.1 | −1.2 | −1.6 | −1.1 | 1.8 |
| IL-6 | −1.7 | 1.9 | −1.7 | −2 | 3.8 | 1.4 | −1.4 | 1.8 | −1.6 | −2.4 |
| Jun B | −6.1 | −6.6 | −2.6 | −1.3 | 1.3 | 1.9 | 1.3 | −3.3 | −4 | −6.5 |
| PAI-1 | −2.6 | 1.5 | −1 | 1.1 | 2.6 | 1.8 | −1.1 | −2.8 | −1.7 | −1.6 |
| PAI-2 | 4.8 | 2.1 | −2 | 2.3 | 2.1 | −1.4 | 2.6 | 2.3 | 1.3 | −1.4 |
| PEPCK | −1.6 | 2.1 | −1.4 | −1.4 | 2.1 | −1.8 | 2.8 | −1.1 | −1 | 1.3 |
| SM22 | 1.1 | 1.1 | 2.1 | 1.1 | 1.1 | 2.1 | −1.5 | 1.1 | 1 | 1.2 |
| vimentin | −1.6 | 3.1 | 1.3 | −1.5 | 2.8 | −1 | −1.1 | −1 | 1.1 | 1.3 |

The numbers in bold in Table 38 indicate values that the Affymetrix Microarray Suite software gave an Increasing or Decreasing call.

EXAMPLE 13

Pharmacokinetics and Pharmacodynamics

Figure 24:
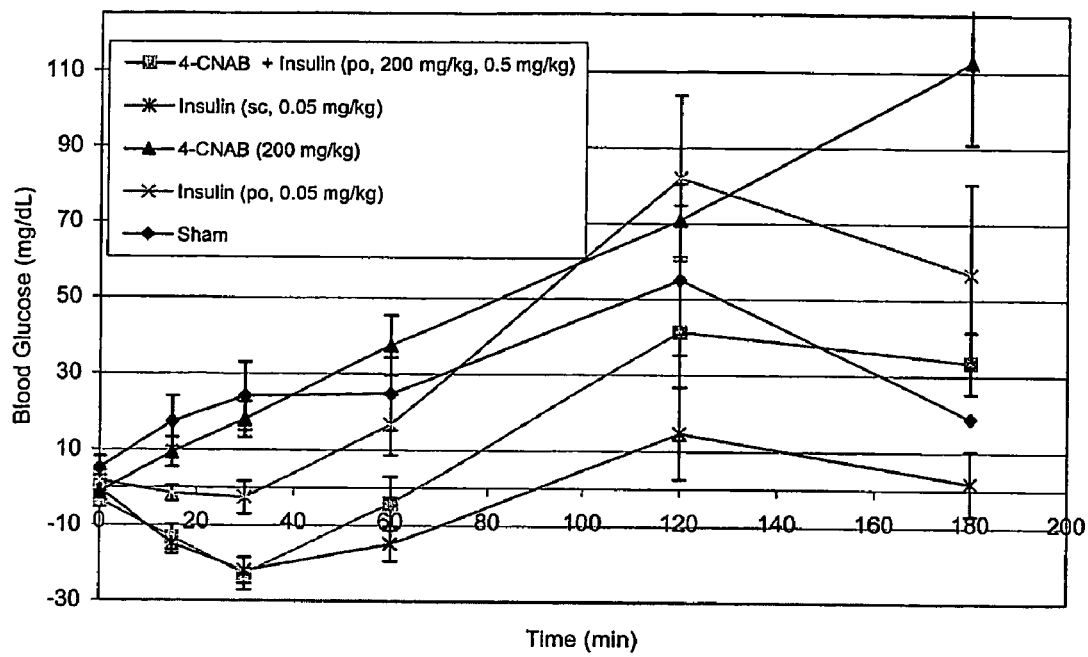
FIG. 24 shows a comparison of blood glucose levels over a time period 180 minutes following single administration of insulin orally and subcutaneously (mean±SE).
Figure 25:
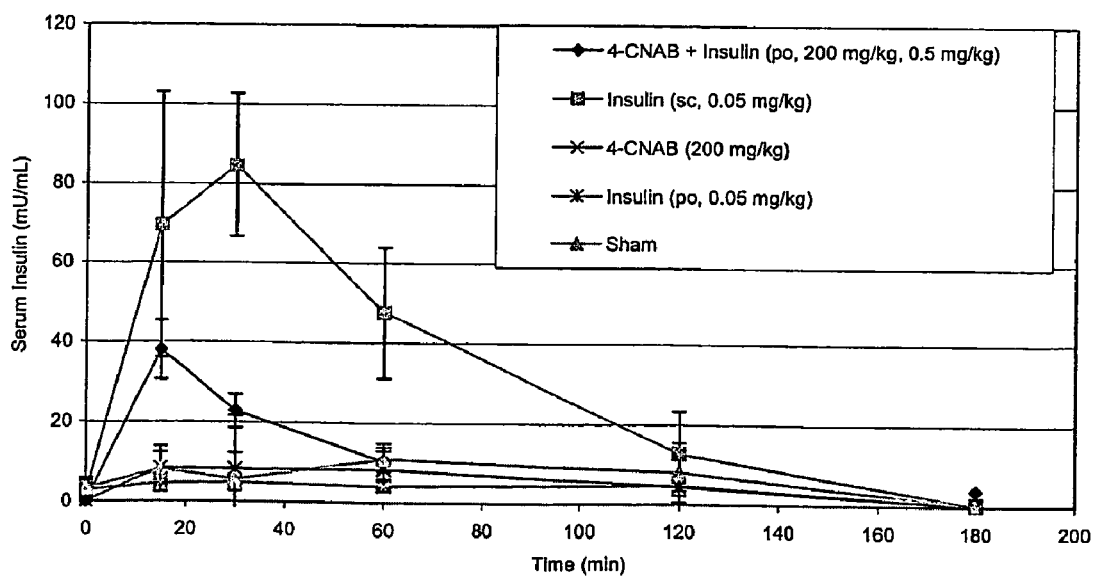
FIG. 25 shows the serum insulin levels over a time period of 180 minutes following single administration orally and subcutaneously (mean±SE).

FIG. 24 shows a graph of blood glucose (mg/mL) over time following a single administration with subcutaneous and oral delivery. This figure shows that the administration of insulin orally, using 4-CNAB as a carrier, yielded approximately 95% of the glucose depression seen with the traditional subcutaneous dosing. However, as shown in FIG. 25, which shows the serum insulin (mU/mL) over time using the administrations of FIG. 24, the serum insulin C required to achieve this depression however, in the orally administered animals was approximately 30% of those receiving subcutaneous injections. The $t_{max}$ was also about 15 minutes later for the subcutaneous sample. The depression in blood glucose was likely eliminated by the continued administration of anesthesia in order to continue blood sampling.

EXAMPLE 14

Glucose Regulation

Glycolysis/Gluconeogenesis occurs through three main cycles that can be driven in both a glycolytic and gluconeogenic direction. From a glycolytic standpoint, the first cycle is the Glu/Glu-6-Pase Cycle, which converts glucose to Glc-6-P. This is followed by the Fru-6-P/Fru-1, 6-P$_2$ Cycle, and the Pyruvate/PEPCK Cycle.

Glu/Glu-6-Pase Cycle

In muscle tissue, glucose is converted to Glc-6-P by hexokinase. See Granner et al., *J Biol Chem* 265, 10173-6 (1990).

Figure 26:
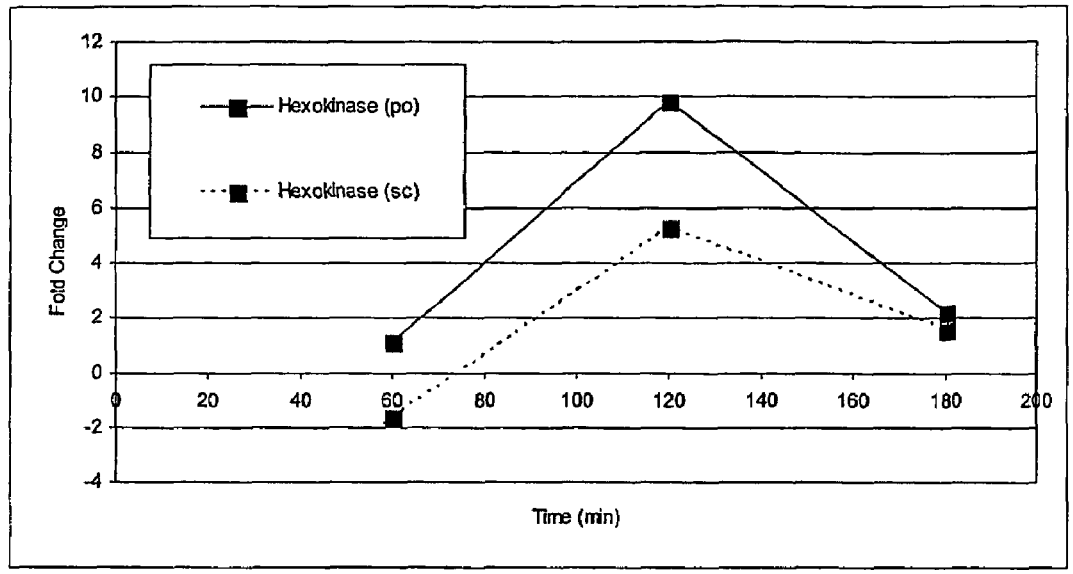
FIG. 26 shows Glucokinase and G6 Pase mRNA expression compared to sham dosing.

In the studies, both subcutaneous and orally administered insulin yielded elevations in the mRNA levels of the enzyme Hexokinase II. FIG. 26 shows Glucokinase and G6 Pase mRNA expression compared to sham dosing. As shown in FIG. 26, despite the lower serum insulin levels, the orally dosed animals showed a 2-fold higher level of hexokinase 11 at 120 minutes. Direct comparison of the arrays from the orally dosed and subcutaneously dosed animals indicates a 2.8-fold higher mRNA level at 30 minutes.

Fru-6-P/Fru-1, 6-P$_2$ Cycle

Figure 27:
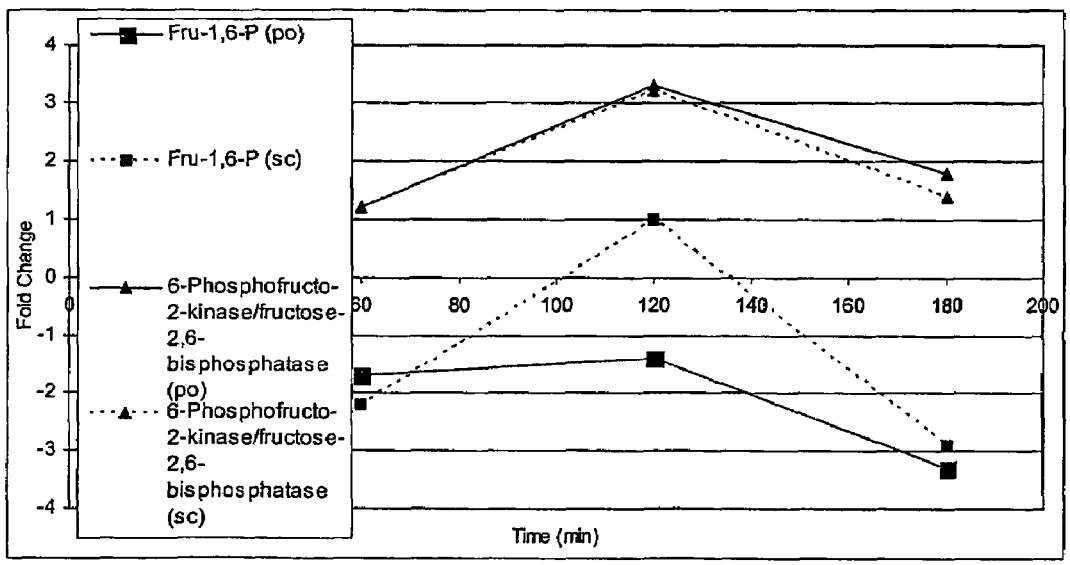
FIG. 27 shows Fru-1, 6-P and 6-Phosphofructo-2-kinase/ fructose-2,6-bisphosphatase mRNA expression compared to sham dosing.

The bi-functional enzyme 6-phosphofructo-2-kinase/fructose 2,6-bisphosphatase serves as a switch between gluconeogenesis and glycolysis. Insulin administration has been shown to drive increases in this enzyme. Granner et al., *J Biol Chem* 265, 10173-6. (1990); Lemaigre et al.,. *Biochem J* 303, 1-14. (1994); Denton. et al., *Adv Enzyme Regul* 36, 183-98 (1996). FIG. 20 shows Fru-1, 6-P and 6-Phosphofructo-2-kinase/fructose-2,6-bisphosphatase mRNA expression compared to sham dosing. In our studies and as shown in FIG. 27, this enzyme showed a nearly identical pattern of expression between the two routes of administration with no significant differences in gene expression being observed.

The enzyme Fructose 1,6-bisphosphatase catalyzes the conversion of Fru-1, 6-P2 to Fru-6-P, the gluconeogenesis side of this cycle. This mRNA is induced by diabetes and starvation and reduced by insulin administration. As shown in FIG. 27 and similar to 6-phosphofructo-2-kinase/fructose 2,6-bisphosphatase, the pattern of expression for this enzyme is nearly identical in both sets of test animals.

Pyruvate/PEP Cycle

Figure 28:
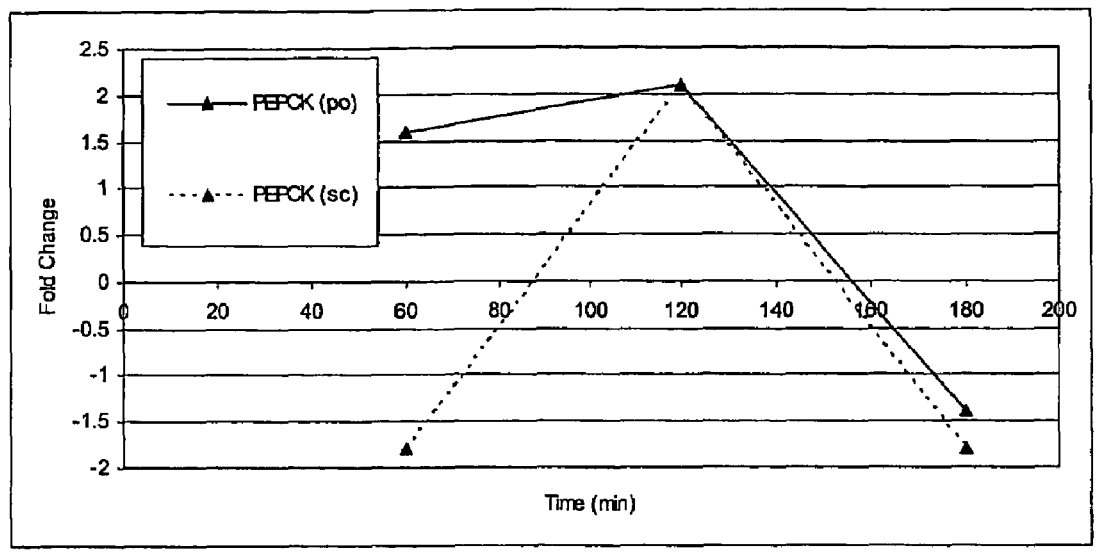
FIG. 28 shows PEPCK mRNA expression compared to sham dosing.

Phosphoenolpyruvate carboxykinase (PEPCK) is a key enzyme in the gluconeogenesis pathway converting oxaloacetate to phosphoenolpyruvate. It is known to be down regulated by insulin. See, for example, Granner et al., *J Biol. Chem.* 265, 10173-6. (1990); Lemaigre et al. *Biochem J*303, 1-14. (1994); Denton, R. M. et al., *Adv Enzyme Regul* 36, 183-98 (1996); Gabbay et al., *J Biol Chem* 271, 1890-7 (1996). FIG. 21 shows PEPCK mRNA expression compared to sham dosing. As shown in FIG. 28, little difference is seen in the expression levels of this mRNA.

Glycogen Synthesis

Insulin is also known to increase the rate of glucose conversion to glycogen. This is performed by linking glucose-1-P molecules into a branched chain. This chain then serves as a store of glucose to be utilized in hypoglycemic states.

Figure 29:
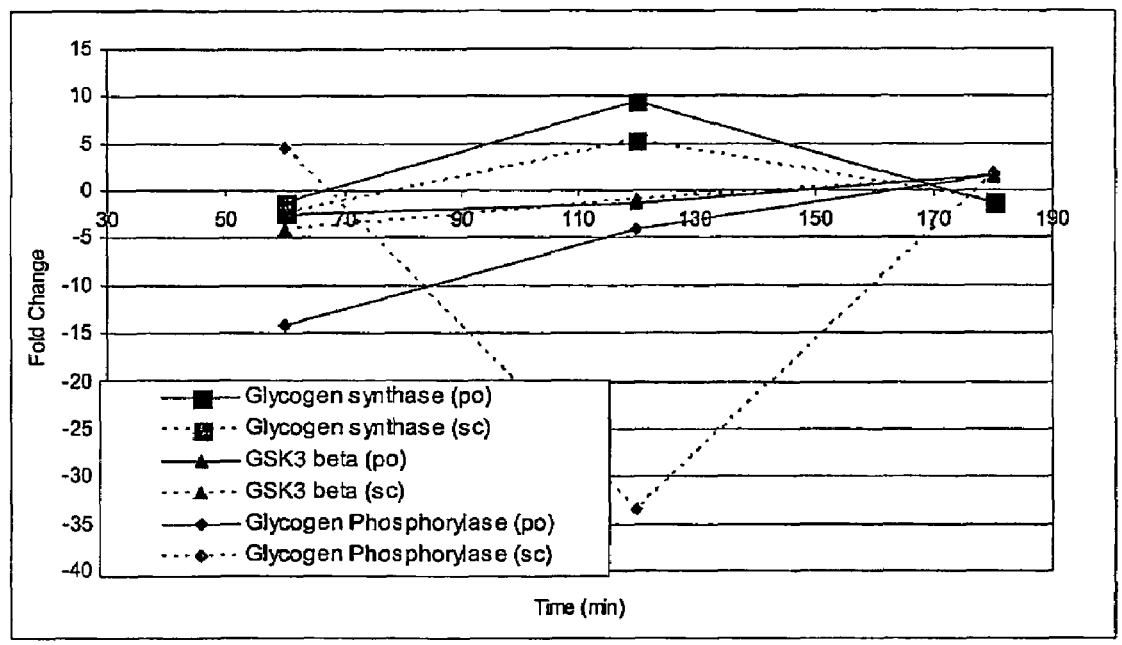
FIG. 29 shows Glycogen synthase mRNA expression compared to sham dosing.

Glycogen Synthase enzyme is responsible for extending the chain of glucose molecules. Administration of insulin is known to up-regulate this enzyme. Vestergaard et al., *Dan Med Bull* 46, 13-34 (1999). FIG. 29 shows glycogen synthase mRNA expression compared to sham dosing. As shown in FIG. 29, oral dosing and subcutaneous dosing produced nearly identical patterns of expression in the levels of this enzyme, with oral dosing yielding nearly twice the increase in mRNA at 120 minutes.

The enzyme Glycogen Synthase Kinase 3 is involved in the inhibition of glycogen synthesis through the phosphorylation of glycogen synthase. As shown in FIG. 29, the expression pattern of this enzyme in the two dosing samples was very similar, exhibiting an initial decrease that returns to sham levels at 120 and 180 minutes. Subcutaneous dosing achieved a slightly stronger down regulation at 60 minutes; however, this difference was not seen in the direct comparison between the two GeneChips.

The enzyme Glycogen Phosphorylase is responsible for the breakdown of the glycogen chain. Insulin is known to normalize phosphorylase levels in diabetic animals. In our studies, as shown in FIG. 29, a dramatic difference in the levels of this enzyme was observed. The oral dosing achieved an immediate decrease in mRNA levels that slowly increased to sham levels at 180 minutes. The subcutaneous dosing yielded an early up regulation that was reversed dramatically at 120 minutes and returned to near sham levels at 180 minutes. The differences seen between the oral and subcutaneous dosings were observed in comparison to sham as well as to each other.

EXAMPLE 15

Vascular Response to Injury

Vascular diseases are commonly described as a response to injury. The vessel is exposed to a stimulus (injury) that leads to a progression of responses designed to repair damage to the vessel wall. This injury may be in several forms, including oxidative stress, mechanical stress, viral infection and changes in shear stress. Though the injury itself is variable, the response to injury has many common aspects. Early response genes are up regulated leading to the transcription of genes for cellular migration and proliferation as well as the recruitment of inflammatory cells to the site of injury. As the response continues, enzymes that lead to matrix remodeling will be expressed. The result is generally the thickening of the arterial wall through smooth muscle proliferation and atherosclerotic plaque formation. The clinical result is the arteriopathies associated with diabetes. In this application, a method for examining the mRNA levels of genes associated with various forms of vascular injury is described.

Vascular diseases are a complex set of processes that involve numerous changes in mRNA levels. While the mRNA markers of vascular injury presented here were seen in this specific study, several others are likely to exist. These include early response genes (i.e. c-myb and c-fos), cytokines (i.e. interleukins, and chemokines), growth factors and their receptors (i.e. fibroblast growth factor, vascular endothelial growth factor, and transforming growth factor beta), adhesion molecules (i.e. selecting, and integrins), extracellular matrix proteins (i.e. collagen and actin), matrix metalloproteinases and their inhibitors, cell cycle proteins (i.e. cyclins and cyclin dependent kinases), and protein kinases (i.e. mitogen activated protein kinases, and protein kinase C), some of which are presented here. This list continues to grow as vascular disease becomes better understood, and which markers are in a particular sample may vary.

Early Response Genes

Figure 30A:
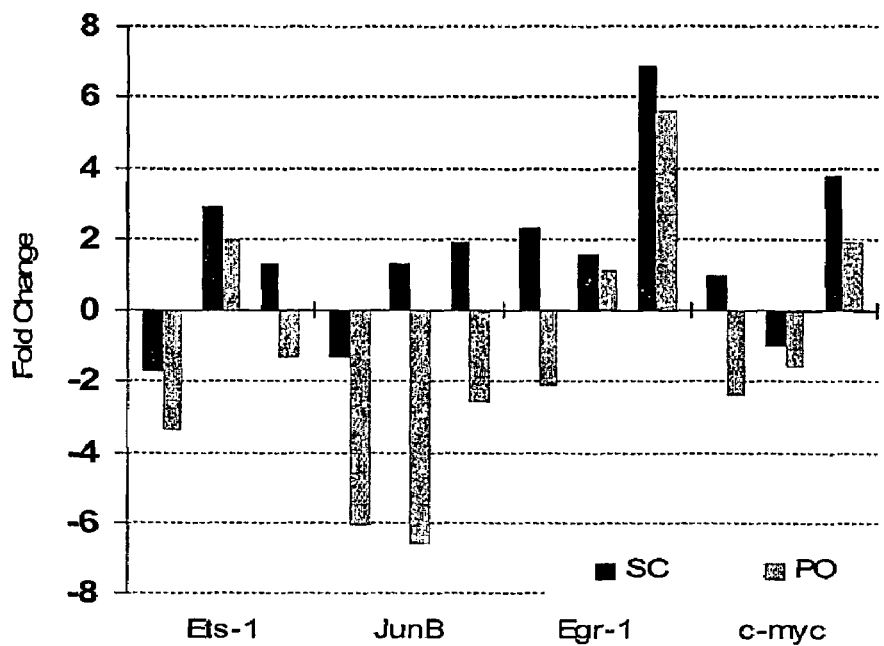
FIGS. 30A and 30B show early response gene mRNA expression compared to sham dosing.
Figure 30B:
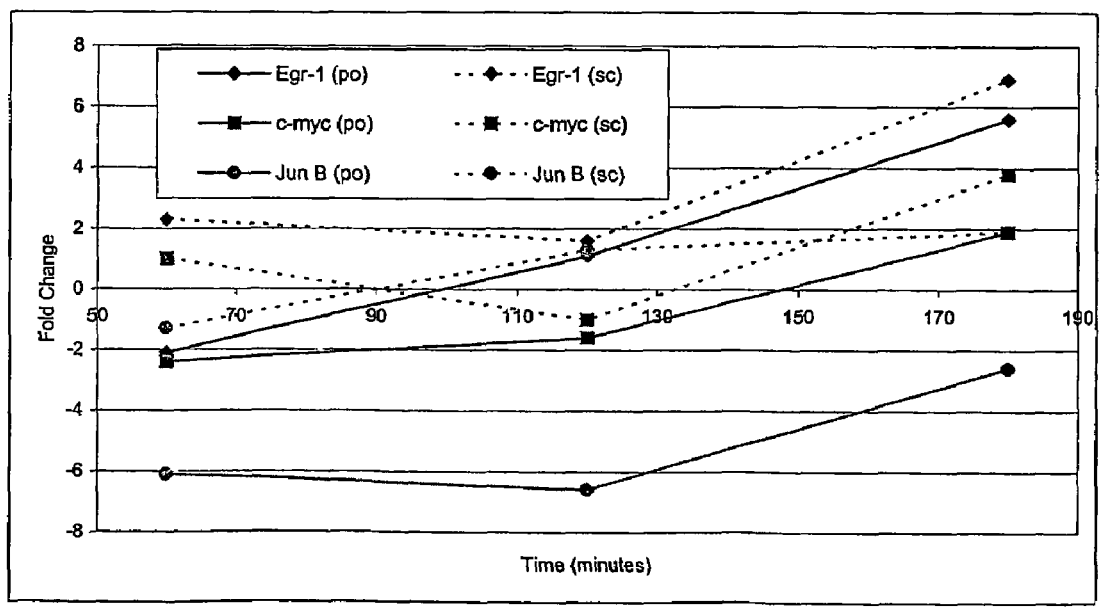

One of the initial markers of arterial injury is the expression of transcription factors in control of the subsequent expression of proteins responsible for potentiating the vascular response to injury. These early response genes include c-myc, c-fos, jun, and Egr-1. FIGS. 30A and 30B show early response gene mRNA expression compared to sham dosing. In our studies, and as shown in FIGS. 30A and 30B, a differential expression in the levels of Egr-1, c-myc, Jun B and Ets-1 was observed.

Egr-1 is associated with several elements of the vascular response to injury. Its expression is very low in uninjured vessels but increases with mechanical or oxidative injury. Egr-1 has been demonstrated to drive increases in mRNA levels of cytokines, adhesion molecules, growth factors and members of the coagulation cascade. In our study and as shown in FIGS. 30A and 30B, Egr-1 is immediately up regulated by subcutaneous insulin administration to a level 4.7-fold higher than with oral. Oral administration does not induce an early increase in Egr-1 mRNA levels. Instead, levels are maintained at near sham levels until at 180 minutes when they are elevated to slightly below that of the subcutaneously animals.

Balloon injury to rat aortae leads to a rapid increase in mRNA for Jun B. Jun and Fos bind to form the heterodimeric transcription factor AP-1. This factor leads to the expression of adhesion molecules, cytokines, and other factors involved in the response to injury. As shown in FIGS. 30A and 30B, Jun B expression remained near sham levels at all time points; however, direct comparison between arrays indicates significantly higher levels in the subcutaneously dosed samples at 120 and 180 minutes. Though both levels are near control at 120 and 180 minutes, a comparison between the two arrays shows a significant decrease in expression in the orally dosed sample.

The switch in the cell cycle state from the dormant Go to the proliferative GI is accompanied by increased levels of c-myc. Vascular damage induces expression of c-myc, and inhibition of c-myc through antisense oligonucleotides prevents intimal hyperplasia following balloon injury in the rat and porcine. It is therefore a critical marker of vascular injury. As shown in FIGS. 30A and 30B, subcutaneous dosing and not oral dosing lead to a significant increase in the mRNA levels of c-myc at 180 minutes. The orally dosed samples remained at near sham levels; however no significant difference between the two dosing routes was seen when compared directly.

Ets-1 mRNA levels for subcutaneous and oral dosing are shown in FIG. 30A.

EXAMPLE 16

Insulin-Like Growth Factor Family

Insulin-like growth factor (IGF) I and II are a single chain polypeptides sharing homology with proinsulin. They play an important role in systemic glucose metabolism but have also been shown to effect cell cycle progression, mitogenesis, cell migration and apoptosis. Much of IGF's function is regulated by IGF-binding proteins (IGFBPs). In general, IGFBPs bind to IGF, preventing its binding to the IGF receptor. IGFBP-3 is the most prevalent in this respect, binding >90% of the IGF in adult serum. Though their primary function is the regulation of IGF, IGFBPs have been shown to have a biological effect at sites of vascular injury. IGFBP-1 stimulates the migration of vascular smooth muscle cells (VSMC) independent of IGF-1. IGFBP-1 to −5 have been shown to be expressed in restenotic tissue suggesting a role in the arterial response to vascular injury.

Figure 31:
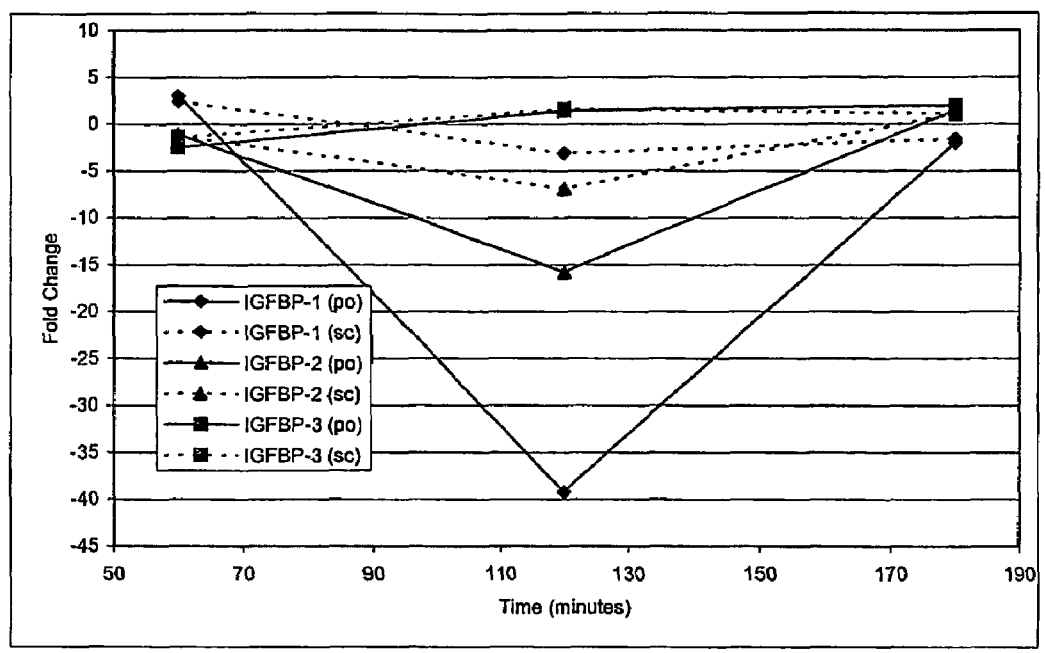
FIG. 31 shows insulin-like Growth Factor Binding Protein mRNA expression compared to sham dosing.

FIG. 31 shows IGFBP mRNA expression compared to sham dosing. As shown in FIG. 31, no significant difference in the expression of IGF-1, IGF-2 or the IGF receptor was seen between the two dosing routes. However, there were drastic differences seen with the IGFBPs. IGFBP-1 was reduced 39-fold as opposed to 3-fold, and IGFBP-2 was reduced 15-fold compared to 6-fold at two hours compared to the sham dosing. In both cases the IGFBP expression is decreased, opposite to the effect seen in vascular injury. The mechanism driving this change may be beyond that of a direct effect of insulin on the VSMC's. Nonetheless, it is clear that the level of IGFBP-1 and -2 expression is higher in the subcutaneously dosed animals and this correlates with an increased response to injury. Little change was observed in IGFBP-3.

EXAMPLE 17

Adhesion Molecules

Figure 32:
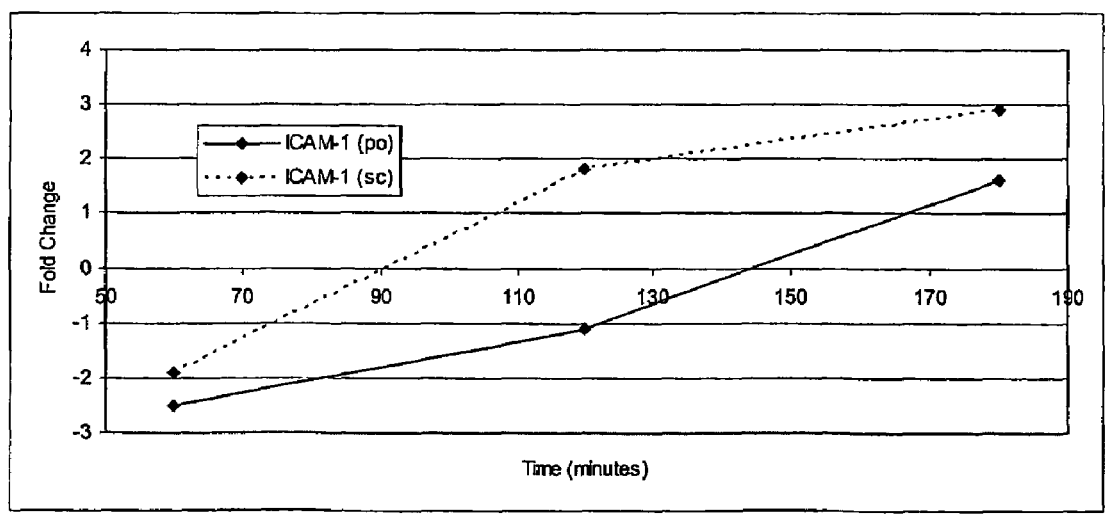
FIG. 32 shows Intracellular Adhesion Molecule—1 mRNA expression compared to sham dosing.

One of the initial steps in arteriopathies is the adhesion of inflammatory cells to the vessel wall. This is mediated by adhesion molecules, such as intercellular adhesion molecule-1 (ICAM-1), vascular cellular adhesion molecule-1 (VCAM-1), the selectins and the integrins. Changes in the levels of mRNA for these genes were examined, and FIG. 32 shows intercellular adhesion molecule-1 mRNA expression compared to sham dosing. As shown in FIG. 32, no significant effect was seen in either dosing group except in the case of ICAM-1. ICAM-1 was increased at 180 minutes in the subcutaneously dosed animals. Increased expression of ICAM-1 is seen in several different forms of vascular injury, and is associated with the recruitment of inflammatory cells to the site of injury. This difference is seen both in the comparison to sham and in the direct comparison of the arrays from the two dosing groups.

EXAMPLE 18

Cytokines

Figure 33A:
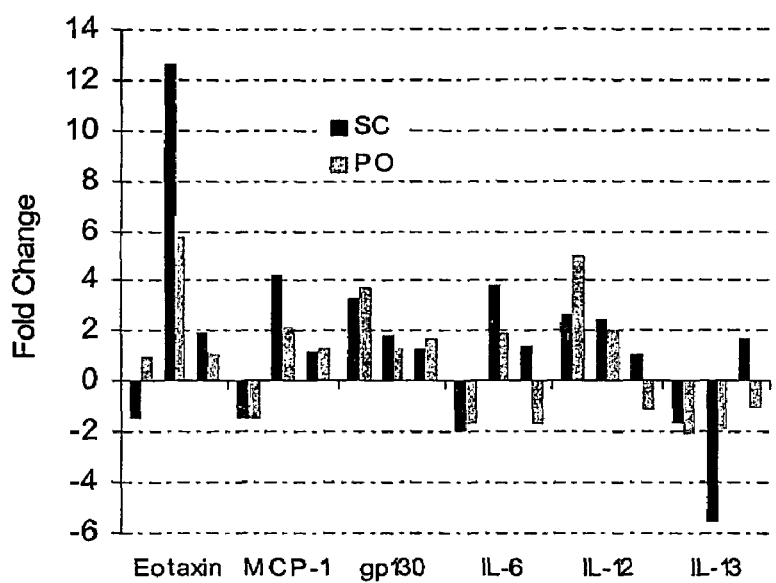
FIGS. 33A and 33B shows Cytokine mRNA expression compared to sham dosing.
Figure 33B:
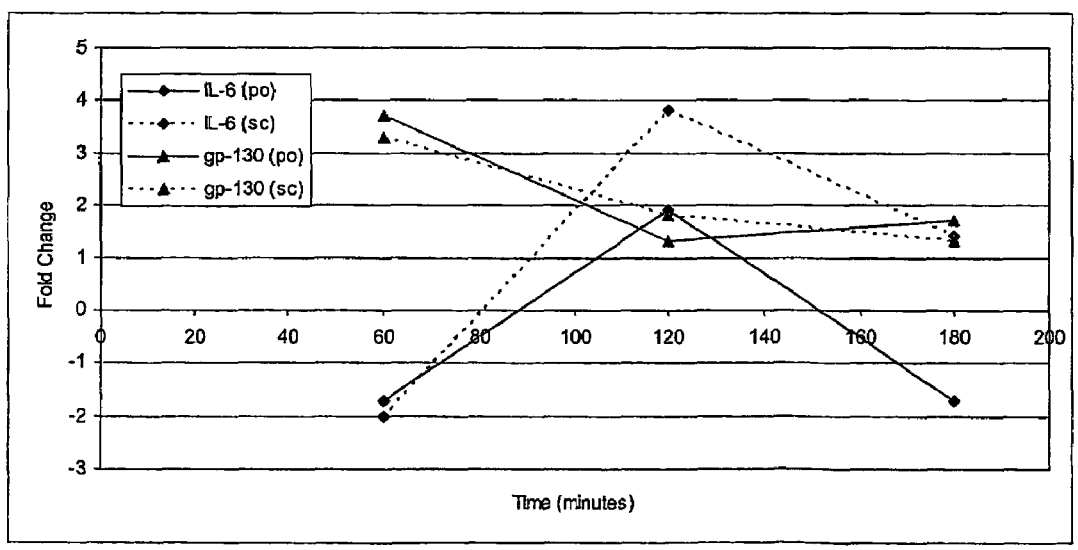

Sites of vascular injury communicate their inflamed state via the expression of pro-inflammatory cytokines that through both autocrine and paracrine effects regulate the expression of growth factors, cytokines, adhesion factors, and matrix metalloproteinases. Of these one found commonly at sites of vascular disease is interleukin-6 (IL-6). VSMCs are not initially susceptible to IL-6 stimulation as they do not express either the IL-6 receptor or glycoprotein 130 (gp130), both of which allow IL-6 signaling. VSMCs are the first cells in which gp130 has been shown to be up regulated. FIGS. 33A and 33B show cytokine mRNA expression compared to sham dosing. In our studies and as shown in FIGS. 33A and 33B, gp130 was seen to be equally increased in both subcutaneously and orally dosed animals. However, a significant increase in IL-6 mRNA was seen only in the subcutaneously dosed group, as shown in FIGS. 33A and 33 This is a critical difference as it shows the aorta of the both groups getting "primed" for a response to injury, but only the subcutaneous dosing actually drives significant production of the expected signal. Cytokine data are represented graphically also for the cytokines Eotaxin, MCP-1, IL-12 and EL-13 in FIG. 33

EXAMPLE 19

Lipid Peroxidation

Several proteins associated with the metabolism of lipids and the oxidation of LDL have been implicated in the progression of atherosclerosis. It has been suggested that the oxidation of LDL produces agents that recruit monocytes, promote their adhesion to the endothelium, and inhibit macrophages from migrating. These steps lead to the formation of foam cells and the fatty streak found in atherosclerotic lesions. 12-lipoxygenase (12-LO) has been demonstrated to drive atherosclerotic lesion formation, and it has also been documented to be significantly up regulated in the vascular response to injury. It therefore is of critical importance in this setting.

Figure 34:
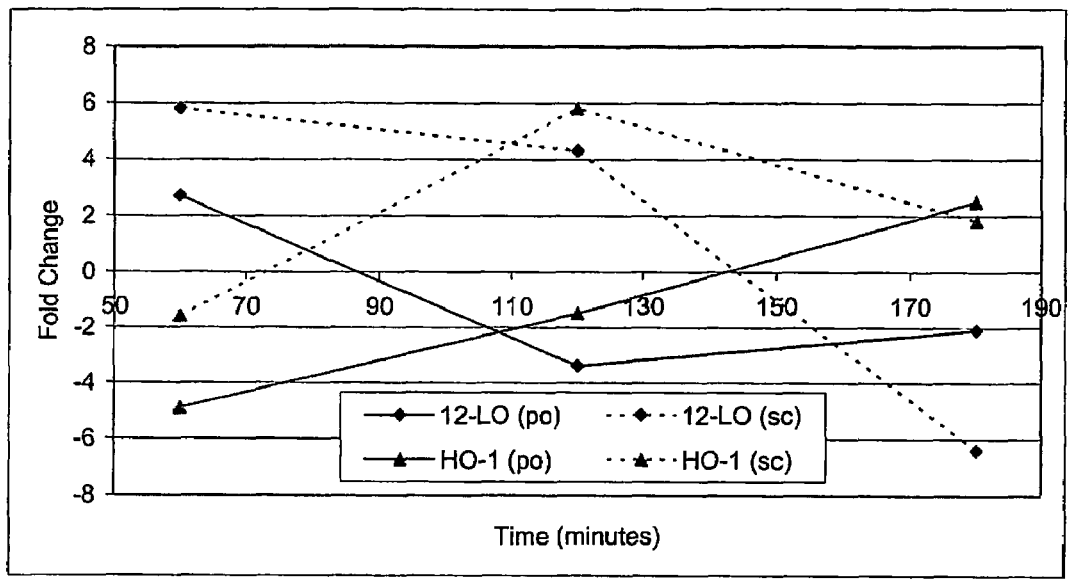
FIG. 34 shows Lipid Peroxidation enzyme mRNA expression compared to sham dosing.

FIG. 34 shows lipid peroxidation mRNA expression compared with sham dosing. As shown in FIG. 34, at 60 minutes, there is a 5.8-fold increase in the subcutaneously dosed samples as compared to a 2.7-fold in the orally dosed. In the orally dosed samples, this up-regulation is reversed at 120 and 180 minutes with 3.4- and 2.1-fold reductions in mRNA levels compared to sham. In the subcutaneously dosed animals, the mRNA levels remain high until 180 minutes, at which time a 6.4-fold decrease is observed. It is important to note that the values at 120 minutes represent greater than 14-fold higher levels of this mRNA in the subcutaneously dosed samples.

Heme Oxygenase-1 (HO-1) is induced by mildly oxidized LDL. It serves a protective antioxidant function through elimination of heme and the further antioxidant capabilities of its reaction products. As shown in FIG. 24, the mRNA levels of this gene are seen to be 6-fold higher in the subcutaneously dosed animals when compared to the orally dosed animals at 60 minutes. Though the function of this enzyme is protective, its up regulation represents a response to injury and may well be in response to the increased levels of 12-LO or its stimulation of LDL oxidation.

EXAMPLE 20

Thrombosis

Figure 35:
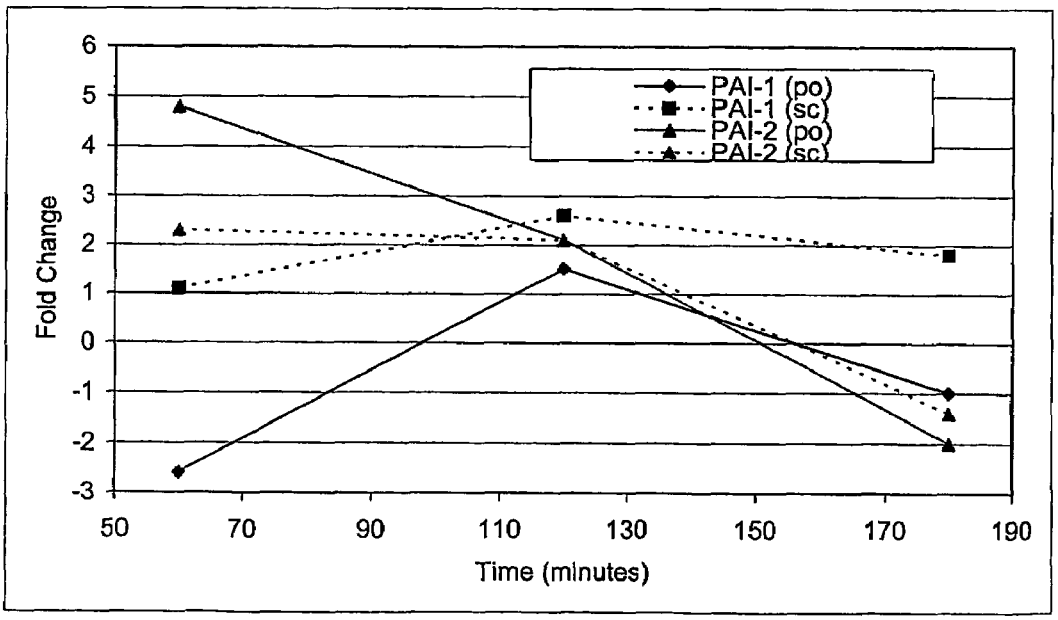
FIG. 35 shows Plasminogen Activator Inhibitors mRNA expression compared to sham dosing.

Fibrin deposition within the arterial wall is believed to play a major role in atherosclerosis. Through their fibrinolytic activity, the plasminogen activators block this from occurring. These protective actions are blocked by the plasminogen activator inhibitors (PAI-1 and -2). FIG. 35 shows plasminogen activator inhibitors mRNA expression compared to sham dosing. In our study, as shown in FIG. 35, PAI-1 levels were elevated in the subcutaneous samples only. A 2.6-fold increase over sham and a 2.8-fold increase over oral were seen at 120 minutes. A 2.6-fold decrease in these levels was seen in the oral samples at 60 minutes, which returned to sham levels at 120 and 180 minutes. PAI-2 expression was similar in both sets of dosing. At 60 minutes, the orally dosed samples exhibited a significantly greater (4.8-fold) level of PAI-2. This elevation is not present at 120 and 180 minutes. There was no significant difference between the two dosing routes for this RNA.

EXAMPLE 21

Figure 36:
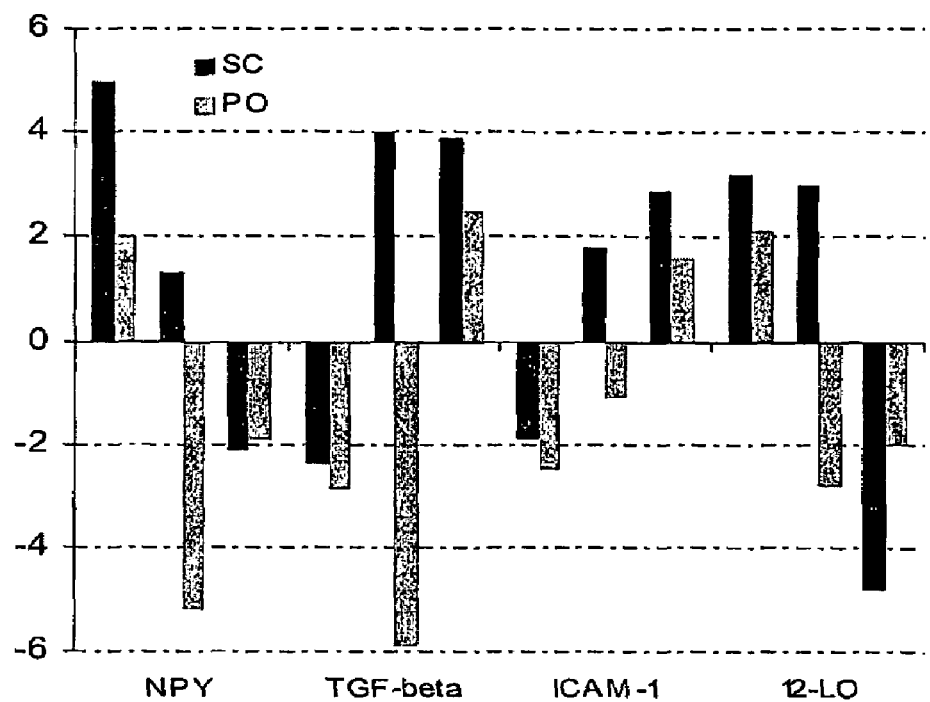
FIG. 36 shows NPY, TGF-beta, ICAM-1 and 12-LO mRNA expression compared to sham dosing.

Additional markers are illustrated in FIG. 36, which compares the effects of subcutaneous delivery of insulin and oral delivery of insulin on the mRNA expression of NPY, TGF-beta, ICAM-1 and 12-LO.

EXAMPLE 22

Figure 37:
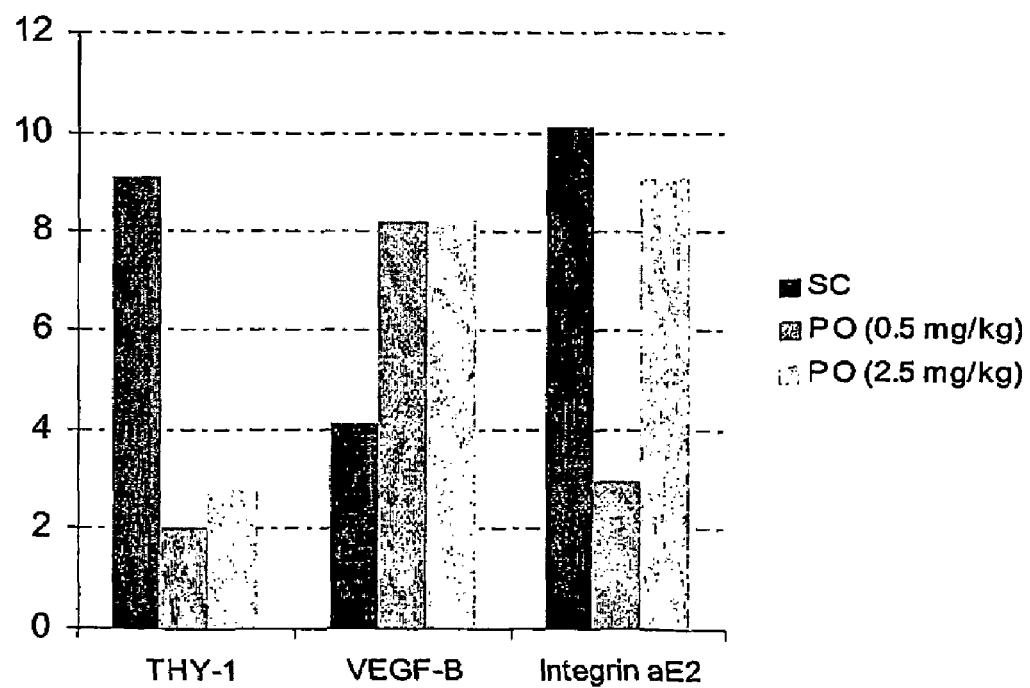
FIG. 37 shows THY-1, VEGF-B and Integrin aE2 mRNA expression compared to sham dosing.

Comparison of mRNA expression between subcutaneous delivery of insulin and oral delivery of insulin are shown for the markers THY-1, VEGF-B and Integrin aE2 in FIG. 37. For the oral delivery data, the effects on mRNA expression of two different dosages are shown.

EXAMPLE 23

Pharmacokinetics and Pharmacodynamics in a Streptozotocin Diabetic Model

Figure 38:
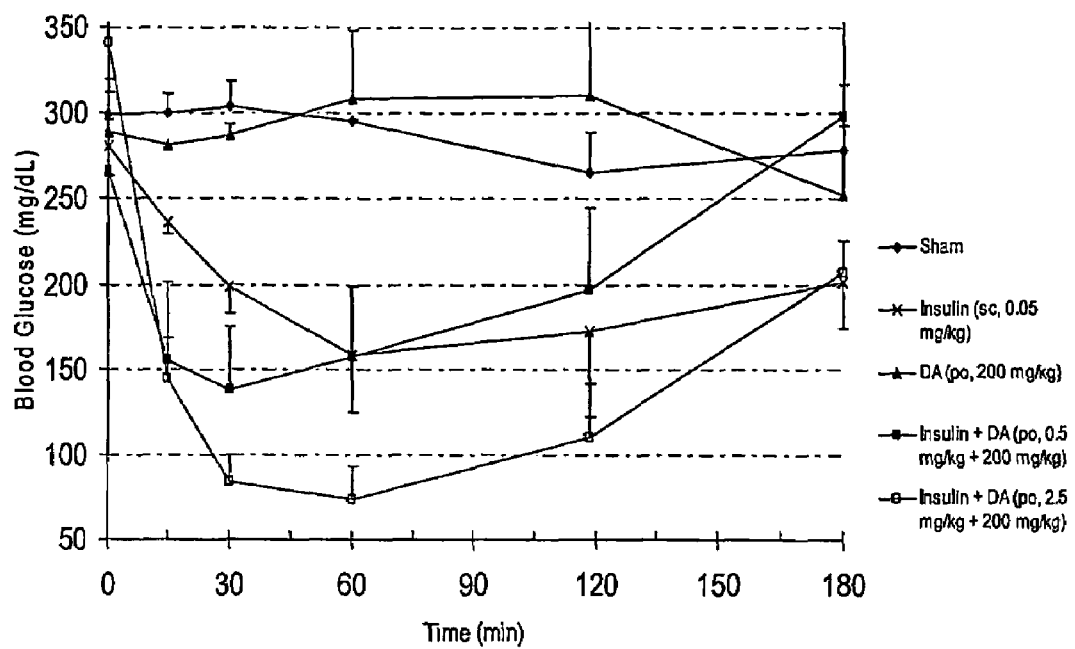
FIG. 38 shows a comparison of blood glucose levels over a time period 180 minutes following single administration of insulin orally and subcutaneously (mean±SE) in a Streptozotocin diabetic model.
Figure 39:
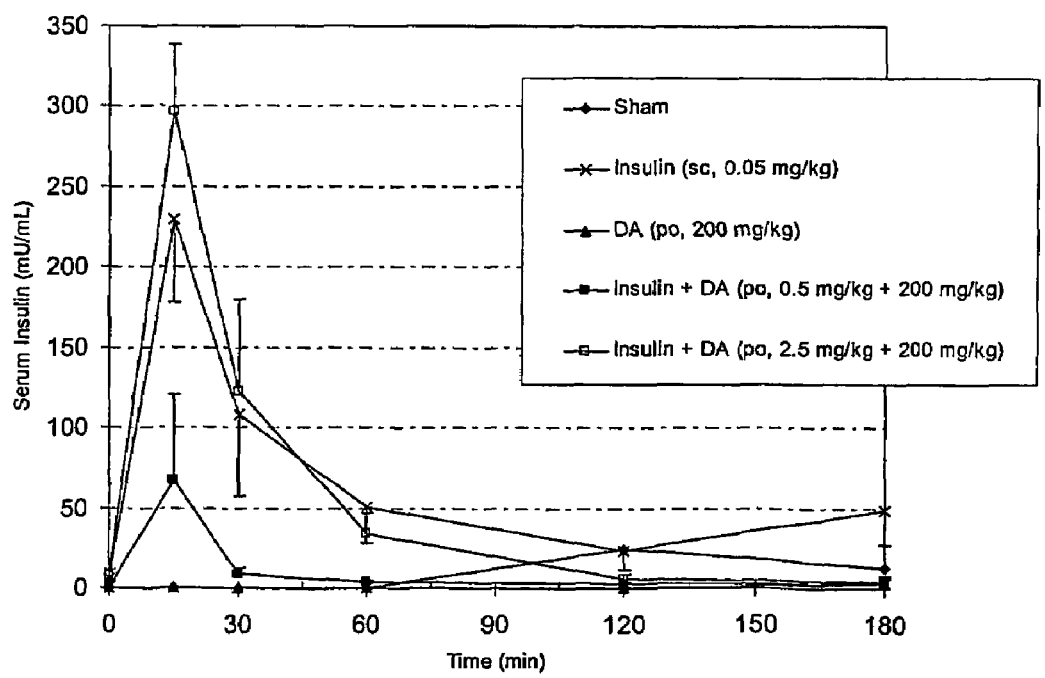
FIG. 39 shows the serum insulin levels over a time period of 180 minutes following single administration orally and subcutaneously (mean±SE) in a Streptozotocin diabetic model.

FIG. 38 shows a graph of blood glucose (mg/mL) over time following a single administration with subcutaneous and oral delivery for a streptozotocin diabetic model. Two different oral dosages of insulin are demonstrated. FIG. 39 shows the serum insulin levels (mU/mL) over time using the administrations of FIG. 38.

Controls for Gene Chip Studies

As control groups, the carrier and insulin were orally administered separately. The results of these GeneChips were analyzed to identify any possible activities of the individual components of the composition. The carrier alone samples generated no consistent and significant changes in mRNA levels in the aorta. The same is true for the insulin alone samples.

Discussion

The examples discussed above demonstrate the ability of an oral composition of insulin to alleviate the undesirable effects on the vasculature of the traditional subcutaneous dosing at the level of messenger RNA regulation, and document changes in glucose metabolism caused by altering the dosing route. The pharmacodynamic data demonstrates the ability of the orally dosed composition to achieve a glucose depression similar to that of the traditional dosing method. Though the pharmacodynamic data is similar, the pharmacokinetic data shows a greatly lower serum insulin level in the orally dosed composition compared with that of the traditional dosing method. The difference in serum insulin level must be a result of direct administration of the insulin to the liver. The liver reacts to the bolus of insulin in two ways. First, it accelerates glycolysis, glycogen synthesis and other mechanisms associated with hyperinsulinemia. Second, first-pass metabolism decreases the level of insulin reaching the systemic circulation. The result is a rapid decrease in blood glucose and a decrease in the level of insulin to which the systemic circulation is exposed. In achieving a similar glucose control as subcutaneous dosing while lowering the exposure of the peripheral circulation to insulin, the undesirable effects of insulin on non-target tissues can be prevented.

Although not considered a major site of glucose metabolism, VSMCs do possess glucose regulatory capacity and therefore yield insight into differences in the peripheral response to changing the dosing route. What is surprising is that despite drastically lower levels of circulating insulin, little difference in the mRNA levels of key enzymes involved in glucose regulation is observed. In fact, the levels seen for hexokinase II and glycogen synthase suggest a stronger response to the oral composition. We conclude that natural regulation of glucose involves the liver controlling peripheral glucose metabolism and utilization through a messenger other than insulin. The fact that higher circulating levels of insulin can compensate for the loss of this natural process may simply be due to the fact that the two proteins bind the same or similar receptors.

The IGF system is a prime candidate for such secondary signaling and is known to exhibit glucose regulatory activity. IGFBP-1 and -2 were down regulated in both sets of data. This is contrary to published data on vascular injury and may not be associated with a vascular injury response so much as playing a role in glucose control. The data previously reported on the liver's response to changes in dosing route of insulin does not demonstrate a differential response in either the IGF's or their binding proteins. This does not rule out this pathway, as no data is available on the proteases responsible for degradation of the IGFBP's. It is quite possible that the liver responds to elevated insulin levels by releasing IGFBP proteases that then degrade IGFBP's freeing IGF to drive a reduction in glucose. Further study is required to determine if this is the case, but the liver and aorta gene array data supports this hypothesis. If correct, this hypothesis supports the use of an oral composition of insulin simply based on its ability to mimic the natural glucose control pathway.

There are numerous disease states related to diabetes, including associated neuropathies, nephropathies and retinopathies. These may be due, at least in part, to the degradation of the microvasculature after chronic dosing of insulin. Because orally administered insulin can achieve a greater glucose depression with a lower systemic level of insulin, a lower incidence of diabetes related disorders results.

Using gene micro-arrays, we were able to monitor numerous areas of the vascular response to injury in animals receiving our oral composition and the traditional subcutaneous insulin. The first step is to assess any effects from administration of the carrier alone. It is believed that, upon entering the systemic circulation, the carrier and insulin no longer interact due to the dilution effect. An exhaustive analysis of the array data from animals receiving the carrier without insulin was performed including adding a second three-hour experiment to try to further identify any response. The analysis yielded no mRNA's whose levels appear to be affected by administration of the carrier. To clarify, any response seen in the carrier alone samples was also seen in the animals receiving insulin orally without carrier suggesting that the effect was due to an experimental parameter not accounted for in the sham dosing. This study is not designed to identify specific genes regulated by the carrier, as such a study would require multiple animals at each time point. Nonetheless, this data supports the view that the carrier has a minimal effect on the vasculature.

The vascular response to injury is a complex set of processes that occur over an extended period of time. Some of these, such as atherosclerotic plaque formation, occur over years or even decades, while the more rapid examples, such as Restenosis, occur on the order of months. Thus, the time scale for studying vascular damage in animal models is on the order of days or weeks and not hours. In this study, we aimed to identify any signs of vascular injury induced by a single dose of insulin and to document any effect changing the route of administration had on these markers. While this may have been a rather optimistic approach, since the type of injury is mild and the time course very short compared to standard models of vascular injury, the results quite remarkably demonstrate qualitatively that oral dosing of insulin beyond simply mimicking the natural route of entry, also attenuates the injury to the vasculature.

It was determined that subcutaneous insulin dosing lead to higher levels of three key early response genes, while a significant increase in only one of these genes was seen with oral dosing. Likewise, elevated levels of IL-6 and ICAM-1 were seen only in the subcutaneously dosed animals. These genes represent the early signs of the cell proliferation as well as the start of an inflammatory response, and their expression can trigger a cascade of events leading to deterioration of the vessel wall. Subcutaneous dosing also generated higher levels of 12-lipoxygenase, PAI-1, PAI-2 and heme oxygenase-1. This second set of genes can be responsible for creating further injury to the vasculature in the form of thrombus and oxidized LDL. Repeated expression of these genes could lead to atherosclerosis and thrombosis. It was found that oral dosing of insulin prevented elevations in all of these genes, except an elevation of PAI-2 that was not significantly different from that seen with subcutaneous dosing. Together, this data suggest the clear advantage of oral dosing of insulin over subcutaneous dosing of insulin of lessened incidence of vascular diseases.

The data from the subcutaneously dosed animals presents a picture of a healthy aorta at the earliest stages of an extended vascular response to injury. The data from the orally dosed animals clearly indicates a dramatic attenuation of this response. By administering insulin orally, elevations in the levels of genes associated with cellular proliferation and migration, inflammatory cell recruitment, and atherosclerotic plaque formation were almost entirely avoided.

It is remarkable that this difference is so clear even following only a single administration of insulin. It was initially believed that multiple dosings would be required before a clear difference in aorta mRNA levels was achieved. In light of this data, it is easy to see how chronic subcutaneous dosing can lead to the increased incidence of vascular diseases and their associated clinical complications. Ongoing studies are currently being conducted which support the increased incidence of vascular disease in chronic subcutaneous dosing. Furthermore, the data suggests that the peripheral glucose metabolism may be similar despite a decrease in circulating insulin levels.

Our results show that returning insulin delivery to its natural site of entry into the circulation and consequently lowering the peripheral insulin levels can achieve a lower incidence of the diseases associated with diabetes. While we have described a number of embodiments of this invention, various modifications of the invention in addition to those shown and described herein will become apparent to those skilled in the art from the foregoing description. Such modifications are intended to fall within the scope of the appended claims.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

While we have hereinbefore described a number of embodiments of this invention, it is apparent that our basic constructions can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

What is claimed is:

1. A method of treating a human patient with diabetes mellitus, comprising orally administering to a human diabetic patient an oral dosage form comprising
a dose of unmodified insulin, and
an effective amount of a delivery agent of the formula or a pharmaceutically acceptable salt thereof:

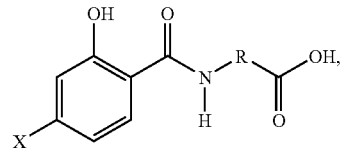

wherein
i. X is hydrogen or halogen; and
ii. R is substituted or unsubstituted C1-C3 alkylene, substituted or unsubstituted C1-C3 alkenylene, substituted or unsubstituted C1-C3 alkyl (arylene), substituted or unsubstituted C1-C3 aryl (alkylene),
wherein said dosage form achieves a therapeutically effective reduction in blood glucose after oral administration to a human diabetic patient as compared to an untreated diabetic patient.

2. The method of claim 1, wherein said oral dosage form achieves a reduction in blood glucose concentration in human diabetic patients comparable to a subcutaneous insulin injection in those patients, while providing a lower plasma concentration of insulin in the peripheral circulation under acute, sub-acute or chronic conditions as compared to the peripheral plasma insulin concentration obtained via subcutaneous insulin injection.

3. The method of claim 2, wherein said lower plasma insulin concentration is at least about 20%.

4. The method of claim 1, wherein said oral dosage form provides a ratio of portal vein to peripheral plasma insulin concentration from about 2.5:1 to about 6:1.

5. The method of claim 1, wherein said oral dosage form is solid.

6. The method of claim 1, wherein the oral dosage form provides a $t_{max}$ for plasma insulin concentration at a time point from about 0.1 to about 1.5 hours after oral administration to said patients.

7. The method of claim 6, wherein at least about 80% of the blood glucose concentration reduction caused by said dose of insulin occurs within about 2 hours after oral administration of said oral dosage form.

8. The method of claim 1, wherein said oral dosage form upon pre-prandial oral administration to human diabetic patients causes the mean blood glucose concentration in said patients to be reduced for the first hour after oral administration relative to a mean baseline fasted blood glucose concentration in said patients.

9. The method of claim 1, wherein said oral dosage form upon pre-prandial oral administration provides a mean blood glucose concentration which does not vary by more than about 40% for the first hour after oral administration, relative to a mean baseline fasted blood glucose concentration in said patients, where a meal is eaten by said patients within about one half hour of oral administration of said dosage form.

10. The method of claim 1, wherein said oral dosage form upon pre-prandial oral administration provides a mean blood glucose concentration which does not vary by more than about 30% for the first hour after oral administration.

11. The method of claim 1, wherein said oral dosage form achieves a $t_{max}$ for plasma insulin concentration at a time point from about 0.25 to about 1.5 hours after oral administration to a human diabetic patient, and upon preprandial administration to the patient provides effective control of blood glucose concentration in response to a meal as manifested by providing a blood glucose concentration which does not vary by more than about 40% for the first hour after oral administration from the baseline fasted blood glucose concentration in the patient, and provides a return to baseline plasma insulin levels in the patient no later than 4 hours after oral administration.

12. The method of claim 11, wherein the insulin is a form of human regular insulin.

13. The method of claim 11, wherein the oral dosage form is solid.

14. The method of claim 1, wherein the oral dosage form is in the form of a tablet or capsule.

15. The method of claim 1, wherein the dose of unmodified insulin contained in the oral dosage form is from about 50 Units to about 600 Units.

16. The method of claim 1, wherein the dose of unmodified insulin contained in the oral dosage form is from about 100 Units to about 400 Units.

17. The method of claim 1, wherein the dose of unmodified insulin is from about 150 Units to about 300 Units.

18. The method of claim 1, which provides a $t_{max}$ for plasma insulin concentration at about 0.1 to about 1.5 hours after oral administration.

19. The method of claim 1, which provides a $t_{max}$ for plasma insulin concentration at about 0.25 to about 0.5 hours after oral administration.

20. The method of claim 1, wherein the oral dosage form begins delivering insulin into the portal circulation to achieve peak levels within about 30 minutes or less.

21. The method of claim 1, wherein said delivery agent is 4-[(4-chloro, 2-hydroxybenzoyl)amino]butanoic acid.

22. The method of claim 1, wherein X is a halogen.

23. The method of claim 22, wherein said halogen is chlorine.

24. The method of claim 1, wherein R is C3 alkylene.

25. The method of claim 1, wherein said peak plasma delivery agent concentration occurs within two hours of oral administration.

26. The method of claim 1, which provides a peak plasma delivery agent concentration that is from about 1,000 to about 100,000 ng/ml within about 0.1 to about 1.5 hours after oral administration.

27. The method of claim 1, which produces a maximal decrease in blood glucose in treated patients from about 0.1 to 1 hour post oral administration.

28. The method of claim 1, which produces a maximal decrease in blood glucose in treated patients at about 40 minutes post oral administration.

29. The method of claim 1, which produces a decreased blood glucose in fasted human patients by at least 10% within one hour post oral administration.

30. The method of claim 1, wherein said effective amount of the pharmaceutically acceptable delivery agent facilitates absorption of said insulin from the gastrointestinal tract of human diabetic patients.

31. The method of claim 30, wherein the effective amount of said delivery agent is from about 1 mg to about 800 mg.

32. The method of claim 30, wherein the effective amount of said delivery agent is from about 100 mg to about 600 mg.

33. A method of treating impaired glucose tolerance, achieving glucose homeostasis, treating early-stage diabetes, or treating late-stage diabetes, comprising administering to a human patient in need thereof an oral dosage form comprising unmodified insulin and an effective amount of a delivery agent of the formula-or a pharmaceutically acceptable salt thereof,

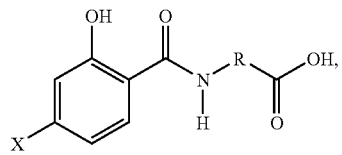

wherein
  i. X is hydrogen or halogen, and
  ii. R is substituted or unsubstituted C1-C3 alkylene, substituted or unsubstituted C1-C3 alkenylene, substituted or unsubstituted C1-C3 alkyl (arylene), substituted or unsubstituted C1-C3 aryl (alkylene)
which oral dosage form achieves a therapeutically effective reduction in blood glucose after oral administration to a human diabetic patient.

34. The method of claim 33, wherein the oral dosage form is administered on a chronic basis.

35. The method of claim 33, wherein the oral dosage form achieves a reduction in blood glucose concentration in human diabetic patients comparable to a subcutaneous insulin injection in those patients, while providing a lower concentration of insulin in the peripheral blood circulation under acute, sub-acute or chronic conditions as compared to the peripheral plasma insulin concentration obtained via the subcutaneous injection.

36. The method of claim 33, wherein the oral dosage form provides a ratio of portal vein to peripheral plasma insulin concentration from about 2.5:1 to about 6:1.

37. The method of claim 33, wherein the dose of unmodified insulin is from about 100 Units to about 400 Units insulin.

38. The method of claim 33, wherein the oral dosage form provides a $t_{max}$ for plasma insulin concentration at about 0.1 to about 1.5 hours after oral administration.

39. The method of claim 33, wherein the oral dosage form provides a $t_{max}$ for plasma insulin concentration at about 0.25 to about 0.5 hours after oral administration.

40. The method of claim 33, wherein the oral dosage form begins delivering insulin into the portal circulation, via absorption through the mucosa of the stomach, to achieve peak levels within about 30 minutes or less.

41. The method of claim 33, wherein said oral dosage form is solid.

42. The method of claim 41, wherein the oral dosage form is in the form of a tablet or capsule.

43. The method of claim 33, wherein said delivery agent is 4-[(4-chloro, 2-hydroxybenzoyl)amino]butanoic acid.

44. The oral solid dosage form of claim 33, wherein X is a halogen.

45. The method of claim 44, wherein said halogen is chlorine.

46. The method of claim 33, wherein R is C3 alkylene.

47. A method of treating a human diabetic patient, comprising orally administering an oral dosage form comprising an effective dose of insulin and a pharmaceutically acceptable delivery agent 4-[(4-chloro, 2-hydroxybenzoyl)amino]butanoic acid pre-prandially to a human diabetic patient, such that an insulin $t_{max}$ at a time point from about 0.25 to about 1.5 hours after oral administration is attained and blood glucose concentration of the patient is effectively controlled in response to the meal as manifested by providing a blood glucose concentration which does not vary by more than about 40% for the first hour after oral administration from the baseline fasted blood glucose concentration in the patient, and which provides a return to baseline plasma insulin levels in the patient no later than 4 hours after oral administration.

48. The method of claim 47, wherein the insulin included in said oral dosage form is a human regular insulin.

49. A method of treating diabetics, comprising orally administering to diabetic patients on a chronic basis an oral insulin treatment comprising a dose of unmodified insulin together with a delivery agent 4-[(4-chloro, 2-hydroxybenzoyl)amino]butanoic acid that facilitates the absorption of the insulin from the gastrointestinal tract to provide a therapeutically effective reduction in blood glucose and a peak blood plasma insulin concentration that is reduced relative to the peak blood plasma insulin concentration of an equivalent therapeutically effective reduction in blood glucose concentration achieved by subcutaneous injection of insulin.

50. The method of claim 49, wherein the method provides a reduced incidence of a disease state associated with chronic insulin administration as compared to the incidence of a disease state associated with chronic insulin administration in a population of patients receiving subcutaneous injection of insulin.

51. The method of claim 49, wherein the method provides a reduced expression of genes associated with vascular disease as compared to the level of expression of genes associated with vascular disease resulting from an equivalent reduction in blood glucose concentration achieved in a population of patients via subcutaneous injection of insulin.

52. The method of claim 51, wherein the genes associated with vascular disease are selected from the group consisting of early response genes, genes associated with cytokines, genes associated with adhesion molecules, genes associated with lipid peroxidation, genes associated with thrombosis and combinations thereof.

53. The method of claim 52, wherein the early response genes are selected from the group consisting of c-myc, jun B, Egr-1, Ets-1 and combinations thereof.

54. The method of claim 49, wherein plasminogen activator inhibitor concentrations resulting from the method are lower as compared to the plasminogen activator inhibitor concentrations resulting from an equivalent therapeutically effective reduction in blood glucose concentration achieved by subcutaneous injection of insulin.

55. The method of claim 49, wherein pro-inflammatory cytokine concentrations resulting from the method are lower as compared to the pro-inflammatory cytokine concentrations resulting from an equivalent therapeutically effective reduction in blood glucose concentration achieved by subcutaneous injection of insulin.

56. A method of treating diabetics comprising orally administering to diabetic patients on a chronic basis an oral insulin treatment comprising a dose of unmodified insulin together with a delivery agent that facilitates the absorption of the insulin from the gastrointestinal tract to provide a therapeutically effective reduction in blood glucose and a peak blood plasma insulin concentration that is reduced relative to the peak blood plasma insulin concentration of an equivalent therapeutically effective reduction in blood glucose concentration achieved by subcutaneous injection of insulin, wherein the delivery agent is a compound having the formula:

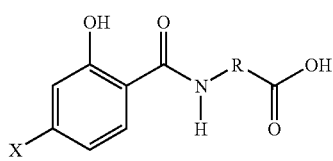

or a pharmaceutically acceptable salt thereof wherein
  i. X is a halogen or hydrogen;
  ii. R is substituted or unsubstituted C1-C12 alkylene, or substituted or unsubstituted C1-C12 alkenylene.

57. The method of claims 49, wherein the insulin is selected from the group consisting of recombinant human insulin, bovine insulin, porcine insulin and functional equivalents thereof.

58. A method of treating diabetes and reducing the incidence and or severity of hyperinsulinemia associated with chronic dosing of insulin, comprising orally administering on a chronic basis to a diabetic patient a dose of insulin and a delivery agent 4-[(4-chloro, 2-hydroxybenzoyl)amino]butanoic acid that facilitates the absorption of the dose of insulin from the gastrointestinal tract to provide therapeutically effective control and/or reduction in blood glucose concentrations, and a mean systemic plasma insulin concentration of the diabetic patient that is reduced relative to the mean systemic plasma insulin concentration provided by subcutaneous injection of insulin in an amount effective to achieve equivalent control and/or reduction in blood glucose concentration in a population of human diabetic patients.

59. A method of reducing the incidence and/or severity of one or more disease states associated with chronic administration of insulin, comprising treating diabetic patients via oral administration on a chronic basis with a therapeutically effective dose of a pharmaceutical composition which comprises insulin and a delivery agent 4-[(4-chloro, 2-hydroxybenzoyl)amino]butanoic acid that facilitates the absorption of insulin from the gastrointestinal tract, such that the pharmaceutical composition provides a therapeutically effective reduction in blood glucose and a peak serum insulin concentration of the diabetic patient that is reduced relative to the peak serum insulin concentration of an equivalent therapeutically effective reduction in blood glucose concentration achieved by subcutaneous injection of insulin.

60. The method of claim 59, wherein the disease state is cardiovascular disease, and wherein the method provides a reduced expression of genes associated with vascular disease as compared to the level of expression of genes associated with vascular disease resulting from an equivalent reduction in blood glucose concentration achieved in a population of patients via subcutaneous injection of insulin.

61. The method of claim 60, wherein the genes associated with vascular disease are selected from the group consisting of early response genes, genes associated with cytokines, genes associated with adhesion molecules, genes associated with lipid peroxidation, genes associated with thrombosis and combinations thereof.

62. The method of claim 61, wherein the early response genes are selected from the group consisting of c-myc, jun B, Egr-1, Ets-1 and combinations thereof.

63. The method of claim 59, wherein the disease state is selected from the group consisting of a neuropathy, a nephropathy, a retinopathy, an arteriopathy, atherosclerosis and combinations thereof.

64. The method of claim 59, wherein the disease state is selected from the group consisting of coronary artery disease, hypertensive cardiomyopathy and congestive heart failure.

65. The method of claim 49, wherein said disease state is vascular diseases.

66. A method of treating diabetes and reducing the incidence and or severity of hyperinsulinemia associated with chronic dosing of insulin, comprising orally administering on a chronic basis to a diabetic patient a dose of insulin and a delivery agent 4-[(4-chloro, 2-hydroxybenzoyl)amino]butanoic acid that facilitates the absorption of the dose of insulin from the gastrointestinal tract to provide a therapeutically effective reduction in blood glucose and a peak serum insulin concentration of the diabetic patient that is reduced relative to the peak serum insulin concentration of an equivalent therapeutically effective reduction in blood glucose concentration achieved by subcutaneous injection of insulin.

67. A method of reducing the exposure of the vasculature of diabetic patients to hyperinsulinemic conditions, comprising orally administering an oral insulin treatment comprising a dose of insulin together with a delivery agent 4-[(4-chloro, 2-hydroxybenzoyl)amino]butanoic acid which facilitates the absorption of said insulin from the gastrointestinal tract on a chronic basis to diabetic patients to reduce blood glucose levels in said diabetic patients by a desired amount, such that the concentration of insulin circulating in the blood of said diabetic patients as a result of insulin treatment is reduced relative to the peak serum insulin concentration of an equivalent therapeutically effective reduction in blood glucose concentration achieved by subcutaneous injection of insulin.

68. A method of treating diabetic patients, comprising orally administering an oral insulin formulation comprising a dose of insulin together with a delivery agent 4-[(4-chloro, 2-hydroxybenzoyl)amino]butanoic acid which facilitates the absorption of said insulin from the gastrointestinal tract on a chronic basis to diabetic patients to reduce blood glucose levels in said diabetic patients by a effective amount, such that the concentration of insulin circulating in the blood of said diabetic patients as a result of said oral insulin treatment is not substantially greater than normal physiological levels.

* * * * *